US009273109B2

(12) United States Patent
Wei et al.

(10) Patent No.: US 9,273,109 B2
(45) Date of Patent: Mar. 1, 2016

(54) CRYSTAL OF RECOMBINANT INTERFERON WITH ALTERED SPATIAL CONFIGURATION, THREE-DIMENSIONAL STRUCTURE AND USES THEREOF

(71) Applicant: Sichuan Huiyang Life Science & Technology Corp., Chengdu, Sichuan (CN)

(72) Inventors: Guangwen Wei, Chengdu (CN); Dacheng Wang, Beijing (CN)

(73) Assignee: Superlab Far East Limited (VG)

( * ) Notice: Subject to any disclaimer, the term of this patent is extended or adjusted under 35 U.S.C. 154(b) by 0 days.

(21) Appl. No.: 14/461,360

(22) Filed: Aug. 15, 2014

(65) Prior Publication Data

US 2014/0356324 A1     Dec. 4, 2014

Related U.S. Application Data

(63) Continuation of application No. 13/516,947, filed as application No. PCT/CN2010/002050 on Dec. 16, 2010, now Pat. No. 8,846,025.

(30) Foreign Application Priority Data

Dec. 18, 2009    (CN) .......................... 2009 1 0259339

(51) Int. Cl.
| | | |
|---|---|---|
| C07K 14/555 | (2006.01) | |
| C07K 14/56 | (2006.01) | |
| A61K 38/00 | (2006.01) | |
| G06F 19/16 | (2011.01) | |
| G06F 19/00 | (2011.01) | |

(52) U.S. Cl.
CPC .............. *C07K 14/555* (2013.01); *C07K 14/56* (2013.01); *G06F 19/703* (2013.01); *A61K 38/00* (2013.01); *C07K 2299/00* (2013.01); *G01N 2500/04* (2013.01); *G06F 19/16* (2013.01); *G06F 19/706* (2013.01)

(58) Field of Classification Search
None
See application file for complete search history.

(56) References Cited

U.S. PATENT DOCUMENTS

| | | | |
|---|---|---|---|
| 4,672,108 A | 6/1987 | Kung et al. | |
| 4,695,623 A | 9/1987 | Stabinsky et al. | |
| 4,897,471 A | 1/1990 | Stabinsky et al. | |
| 5,372,808 A | 12/1994 | Blatt et al. | |
| 5,441,734 A | 8/1995 | Reichert et al. | |
| 5,480,640 A | 1/1996 | Morales et al. | |
| 5,602,232 A | 2/1997 | Reichert et al. | |
| 5,972,331 A | 10/1999 | Reichert et al. | |
| 6,297,021 B1 | 10/2001 | Nienaber et al. | |
| 6,833,256 B1 | 12/2004 | Pontzer et al. | |
| 7,364,724 B2 | 4/2008 | Wei et al. | |
| 7,585,647 B2 | 9/2009 | Wei | |
| 2005/0208019 A1 | 9/2005 | Wei | |
| 2006/0035327 A1 | 2/2006 | Wei | |
| 2015/0031859 A1 | 1/2015 | Wei | |

FOREIGN PATENT DOCUMENTS

| | | |
|---|---|---|
| AU | 2003248419 | 11/2003 |
| CN | 1062565 C | 2/2001 |
| CN | 1740197 A | 3/2006 |
| EP | 0736303 | 10/1996 |
| EP | 1371373 A1 | 12/2003 |
| WO | 83/04053 | 11/1983 |
| WO | 93/21229 | 10/1993 |
| WO | 94/19373 | 9/1994 |
| WO | 02/36627 | 5/2002 |
| WO | WO 02/44197 A2 | 6/2002 |
| WO | WO 02/086156 A2 | 10/2002 |
| WO | 2005/034853 | 4/2005 |
| WO | 2005/067963 | 7/2005 |
| WO | 2006/134497 | 12/2006 |

OTHER PUBLICATIONS

Korn, AP et al., Three-Dimensional Model of a Human Interferon-α Consensus Sequence, Journal of Interferon Research 1994, 14:1-9.
Klein ML, et al., Structural Characterization of Recombinant Consensus Interferon-alpha, Journal of Chromatography, 1988, 454:205-215.
U.S. Office Action, Apr. 27, 2012, Guangwen Wei, U.S. Appl. No. 12/971,956, filed Dec. 17, 2010.
U.S. Office Action, Aug. 22, 2012, Guangwen Wei, U.S. Appl. No. 12/971,956, filed Dec. 17, 2010.
Extended European search report, Jul. 31, 2013, Guangwen Wei, European Application No. 10 836926.5, Filed Jun. 16, 2012.
Chinese Office Action, Aug. 21, 2013, Guangwen Wei, Chinese Application No. 201080057897.1, Filed Jun. 16, 2012.
Chinese Office Action, Aug. 21, 2013, Guangwen Wei, Chinese Application No. 200910259339.2, Filed Dec. 18, 2009.
U.S. Office Action, Oct. 16, 2013, Guangwen Wei, U.S. Appl. No. 13/516,947, filed Aug. 27, 2012.
U.S. Office Action, Nov. 6, 2013, Guangwen Wei, U.S. Appl. No. 13/516,947, filed Aug. 27, 2012.
Wiencek, J. M. Ann. Rev. Biomed. Eng. 1999, 1, 505-534.
Apr. 26, 2011 European Search Report for Huiyangtech (USA), Inc., Application No. EP 10 19 3126.9.

(Continued)

*Primary Examiner* — Nashaat Nashed
(74) *Attorney, Agent, or Firm* — Law Offices of Albert Wai-Kit Chan, PLLC

(57) ABSTRACT

This invention provides crystalline recombinant interferon (rSIFN-co (SEQ ID NO: 1)) having (i) the same amino acid sequence as that of human consensus interferon, and (ii) altered three-dimensional structure as compared to IFN-α2b. The interferon of the present invention exhibits enhanced biological activities. The present invention also provides a structural model of said interferon useful for drug screening and/or drug design, and mimetics of said interferon.

5 Claims, 13 Drawing Sheets

(56) References Cited

OTHER PUBLICATIONS

Jul. 28, 2009 European Office Action, Application No. EP 04809634.1, Filed Mar. 26, 2006.
Dec. 4, 2007 Written Opinion for SG 200601209-0, for Huiyangtech (USA), Inc., Filed Feb. 23, 2006.
Aug. 30, 2006 Taiwanese Office Action for Sichuan Biotechnology Research Center, Taiwanese Application No. 92,123,846, Filed Aug. 28, 2003.
Feb. 27, 2006 International Search Report, Application No. PCT/US2004/028067 for Huiyangtech, Inc., Filed Aug. 26, 2004.
Sep. 20, 2007 Notification Concerning Transmittal of International Preliminary Report on Patentability (Chapter I of the Patent Cooperation Treaty) for PCT/IB2006/002340 for Guangwen Wei, Filed Mar. 9, 2006.
Jul. 23, 2002 International Search Report, Application No. PCT/CN02/00128 for Sichuan Biotechnology Research Center, "Recombination Super Compound Interferon Used as Hepatitis B Surface Antigen and E Antigen Inhibitor," Filed Feb. 28, 2002.
Dec. 12, 2005 Australian Examiner's Report for Sichuan Biotechnology Research Center, Australian Application No. 2003248419, Filed Sep. 26, 2003.
Jun. 1, 2006 Australian Examiner's Report for Sichuan Biotechnology Research Center, Australian Application No. 2003248419, Filed Sep. 26, 2003.
Mar. 1, 2010 Australian Examiner's Report for Sichuan Biotechnology Research Center, Australian Application No. 2004279350, Filed Aug. 26, 2004.
Mar. 27, 2009 Chinese Office Action for 200480031910, Filed Apr. 28, 2006.
Nov. 20, 2009 Chinese Office Action for 200480031910, Filed Apr. 28, 2006.
Oct. 24, 2008 Indian Examination Report for 208/MUM/2004, Filed Mar. 5, 2004.
Mar. 8, 2007 Malaysian Office Action Malaysian Application No. PI 20033246.
Dec. 12, 2008 Taiwan Examination Report for TW 95107930, filed Mar. 9, 2006.
Jan. 6, 2010 U.S. Office Action, U.S. Appl. No. 12/246,153.
Oct. 5, 2011 U.S. Office Action for U.S. Appl. No. 13/019,044, filed Feb. 1, 2011.
Feb. 23, 2012,Supplementary European Search report, European Application No. 06795349.7 Filed Oct. 4, 2007.
May 10, 2010 Indian Office Action, Indian Application No. 1214/MUMNP/2007.
Apr. 19, 2013 Korean Office Action, Korean Application No. 10-2012-7029545, Filed Nov. 12, 2012.
Jun. 4, 2014 Chinese Office Action for 201080057897.1.
Mar. 24, 2011 International search report, PCT Application No. PCT/CN2010/002055, Filed Dec. 16, 2010.
Mar. 24, 2011 Written opinion of the international searching authority, PCT Application No. PCT/CN2010 /002055, Filed Dec. 16, 2010.
Jul. 31, 2013 Extended European search report for 10836926.5, Filed Jun. 16, 2012.
Jul. 9, 2013 U.S. Office Action for U.S. Appl. No. 13/490,719, filed Jun. 7, 2012.
Jul. 16, 2014 PCT International search report and Written opinnion for PCT/CN2014/000019, Filed Jan. 7, 2014).
Jun. 17, 2014 PCT International search report and Written opinion for PCT/CN2014/070212, Filed Jan. 7, 2014).
Mar. 7, 2013 U.S. Office Action for U.S. Appl. No. 12/905,149, filed Oct. 15, 2010.
Sep. 10, 2014 U.S. Office Action, U.S. Appl. No. 13/861,617, filed Apr. 12, 2013.
Blatt, L.M. et al., 1996, "The biological activity and molecular characterization of a novel synthetic interferon-alpha species, consensus interferon," Journal of Interferon and Cytokine Research, 16(7):489-499.
Goldstein D. et al., 1998, "The role of interferon in cancer therapy: A current perspective", CA Cancer J Clin., 38:258-277.
Hu Xue-jun et al., 2006, "Meta-analysis of Maintenance Therapy With Interferon for Small Cell Lung Cancer", Chin J Evid-based Med, 6(11):809-814.
Jin Bo et al., 2006, "Meta-analysis of induction chemotherapy combined with interferon in Advanced Non-small Cell Lung Cancer", Chi J of Evidence-Based Medicine, pp. 370-375.
Jin Bo , et al., 2007, "Meta-analysis of induction chemotherapy combined with interferon in small lung cancer", Chinese Journal of Practical Internal Medicine, 613-616.
Maffezzini M. et al., May 1996, "Salvage immunotherapy with subcutaneous recombinant interleukin 2 (rIL-2) and alpha-interferon (A-IFN) for stage D3 prostate carcinoma failing second-line hormonal treatment." Prostate, 28 (5):282-6.
Melian EB et al., 2001, "Interferon alfacon-1: a review of its pharmacology and therapeutic efficacy in the treatment of chronic hepatitis C.", Drugs. 61(11):1661-91.
Moore, D.H. et al., "A phase I study of intraperitoneal interferon-alpha 2b and intravenous cis-platinum plus cyclophosphamide chemotherapy in patients with untreated state III epithelial ovarian cancer: A gynecologic oncology group pilot study," Gynecologic Oncology, 1995, 59:267-272.
Ozes, O.N. et al., 1992, "A comparison of interferon-con1 with natural recombinant interferons: antiviral, antiproliferative, and natural killer-inducing activities." J. Interferon Res., 12:55-59.
Pfeffer, L.M., 1997, "Biologic activity of natural and synthetic type 1 interferons," Seminars in Oncology, 24(3 suppl. 9):S9-63-S9-69.
Spada S., 2004, Directory of Approved Biopharmaceutic. Prod., 116-117.
Korn, AP et al., Three-Dimensional Model of a Human Interferon-α Consensus Sequence, Journal of Interferon Research 1994,14:1-9.
Rang A. et al. "Effect of interferon alpha on hepatitis B virus replication and gene expression in transiently transfected human hepatoma cells", Nov. 1999, J Hepatol., 31(5):791-9.
Zheng, J. et al. "Effect of Recombinant Super-compound Interferon (rSIFN-co) on Human Breast Cancer Cells in vitro", J Sichuan Univ (Med Sci Edi), Feb. 28, 2010, vol. 41, No. 1, p. 29-34.
Chen, Y. et al. The Growth Inhibition and Apoptosis-promoting Effect of rSIFN-co to the Cervical Carcinoma Cells in vitro, Journal of Practical Obstetrics and Gynecology, Apr. 30, 2009, vol. 25, No. 4, p. 216-219.
Wu JB, et al., "Observation of efficacy of interferon treatment on giant cell tumor of limbs" Modern Journal of Integrated Traditional Chinese and Western Medicine. Dec. 31, 2008, 25(17), p. 3923-3924.
Larmonier N. et al., "An atypical caspase-independent death pathway for an immunogenic cancer cell line", Sep. 5, 2002, Oncogene , 21(39):6091-100.
te Poele RH et al., "DNA damage is able to induce senescence in tumor cells in vitro and in vivo", Mar. 15, 2002, Cancer Res., 62(6):1876-83.

CRYSTAL OF RECOMBINANT INTERFERON WITH ALTERED SPATIAL CONFIGURATION, THREE-DIMENSIONAL STRUCTURE AND USES THEREOF

FIELD OF THE INVENTION

This invention relates in general to crystalline recombinant interferon with altered spatial configuration, its crystallization method and three-dimensional structure thereof, uses of said crystal and its three-dimensional structure, and mimetics of said recombinant interferon.

BACKGROUND OF THE INVENTION

Interferon (IFN) is a kind of soluble protein produced by a variety of cells which has many important biological functions, including anti-viral, anti-tumor, and immunoregulatory functions. Interferons can be divided into type I, type II, and type III interferons according to the differences in the types of producing cells, receptors and biological activities etc. Type I IFNs, which are mostly induced by viruses and synthetic double-stranded RNA, are also known as anti-viral interferons. There are three forms of type I interferons: IFNα, INFβ, IFNω. Type II IFN, also known as immune interferon or IFNγ, is produced by the T cells, and is an important immunoregulatory factor in vivo. Type III interferon is made up of IFN-λ molecules.

In recent years, many companies in the world have engaged in the research of interferon, as exemplified by a number of pertinent patents and disclosure documents. For example, U.S. Pat. Nos. 4,695,623 and 4,897,471 disclosed new types of human interferon polypeptides which have amino acid sequences containing the common or predominant amino acids found in naturally occurring α-interferon polypeptides. That new type of interferon was named IFN-con (consensus interferon α). The disclosed amino acid sequences were named IFN-con1, IFN-con2 and IFN-con3. Genes encoding IFN-cons and gene expression in *Escherichia coli* were also disclosed. Compared with leukocyte interferon or other type I interferons, studies have shown that recombinant IFN-con has higher anti-viral, anti-proliferative and natural killer cell activities in vitro.

U.S. Pat. No. 5,372,808 disclosed the use of human IFN-con in the treatment of diseases. Compared with previous clinically approved α-interferon such as Intron®A (IFN-α2b, SGP) produced by Schering-Plough, recombinant human IFN-con has been shown to have lower side-effects. By the end of 1997, the FDA had approved the use of human IFN-con, which was produced by Amgen and sold under the brand name Infergen® (interferon alfacon-1) (SEQ ID NO: 1), for clinical treatment of hepatitis C.

Both U.S. Pat. No. 7,364,724 and Chinese Patent Publication No. CN1740197A (incorporated in their entirety as references to this application) disclosed a recombinant interferon (hereafter referred to as "rSIFN-co" (SEQ ID NO: 1)) that has enhanced efficacy, fewer side-effects and can be used in high doses. The said recombinant interferon has the same amino acid sequence as Infergen® (SEQ ID NO: 1), but has different spatial structure and biological efficacy. In addition, the above-mentioned Chinese Patent Publication No. CN1740197A also disclosed the crystal form of said recombinant interferon and its crystallization method thereof; however, the crystals were of poor quality, had loose internal structures and an X-ray diffraction resolution as low as 5 Å such that they were not suitable for obtaining useful structural information from further analysis of the protein spatial structure. It is of great interest to obtain good quality crystals of the said recombinant interferon with altered structure and functions at high X-ray diffraction resolution so as to determine the three-dimensional structure of said recombinant interferon, establish its model, and take advantage of said structure and model to perform drug design and to improve the efficacy of known interferons.

SUMMARY OF THE INVENTION

This invention relates to the crystal of the recombinant interferon disclosed by U.S. Pat. No. 7,364,724 and Chinese Patent Publication No. CN1740197A, and this recombinant interferon comprises the amino acid sequence of SEQ ID NO: 1. Further, this invention provides the crystallization method of this recombinant interferon and the composition comprising said crystal. In addition, this invention provides the three-dimensional structure of this recombinant interferon, which is different from the three-dimensional structure of IFN-α2b published in the art and the three-dimensional structure of Infergen® (SEQ ID NO: 1) from Amgen (U.S.) based on computational modelling. Also provided are uses of said three-dimensional structure for identifying the candidate compound interacting with said interferon, designing mimetics of said interferon and performing rational drug design based on computer. Still further, this invention provides mimetics of said recombinant interferon, composition comprising said mimetics and uses of said crystal, mimetics or composition for preparation of medicament for treatment of viral diseases and/or tumors.

| Plot statistics | | |
|---|---|---|
| Residues in most favoured regions [A, B, L] | 240 | 90.6% |
| Residues in additional allowed regions [a, b, l, p] | 24 | 9.1% |
| Residues in generously allowed regions [~a, ~b, ~l, ~p] | 1 | 0.4% |
| Residues in disallowed regions | 0 | 0.0% |
| Number of non-glycine and non-proline residues | 265 | 100.0% |
| Number of end-residues (excl. Gly and Pro) | 127 | |
| Number of glycine residues | 18 | |
| Number of praline reidues | 6 | |
| Total number of residues | 416 | |

Figure 6:
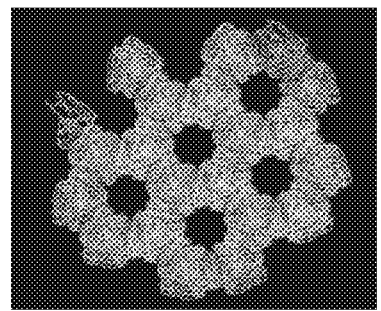

FIG. 6 shows a unit cell packing diagram of rSIFN-co (SEQ ID NO: 1).

Figure 7:
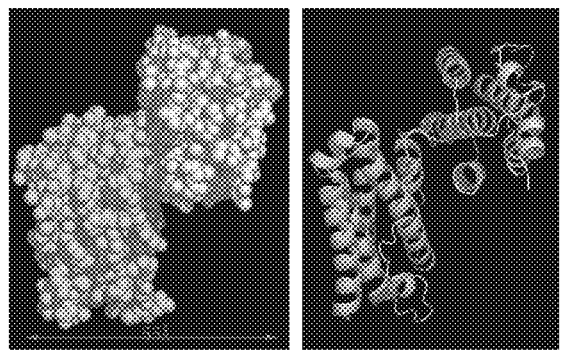

FIG. 7 shows the assembled structure of the rSIFN-co (SEQ ID NO: 1) dimers.

Figure 8:
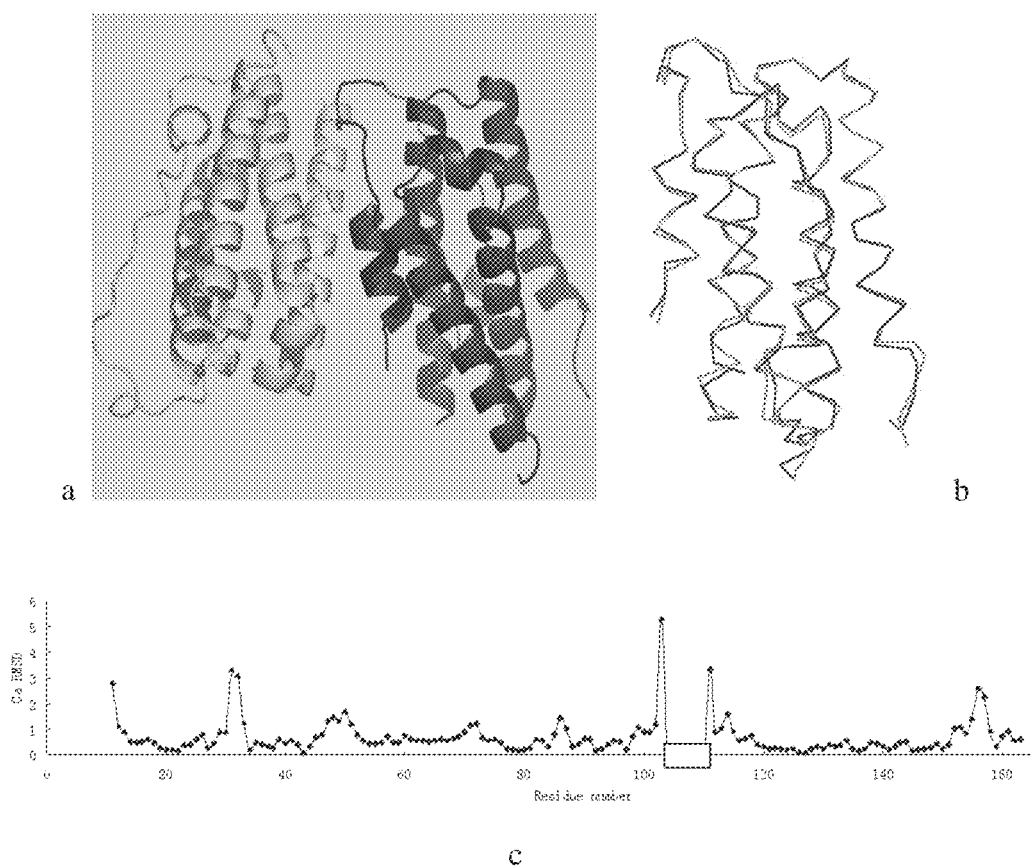

FIG. 8 shows the organization of rSIFN-co (SEQ ID NO: 1) crystallographic dimers (FIG. 8a, FIG. 8b) and the root-mean square deviation (RMSD) of α carbon atoms (the boxes represent missing residues) (FIG. 8c).

Figure 9:
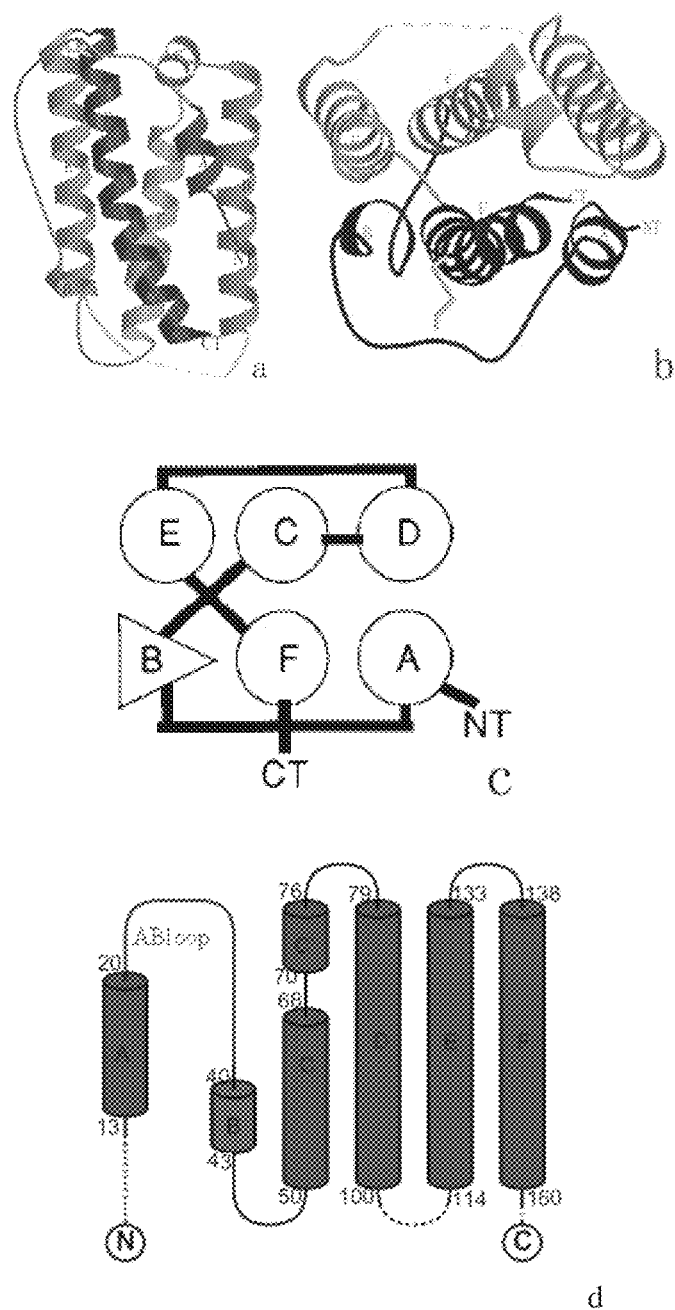

FIG. 9 shows the monomolecular structure of rSIFN-co (SEQ ID NO: 1) (main chain demonstrated only); (A) Side view; (B) Top view; (C) Topology diagram; (D) Topological organization of the secondary structures.

Figure 10:
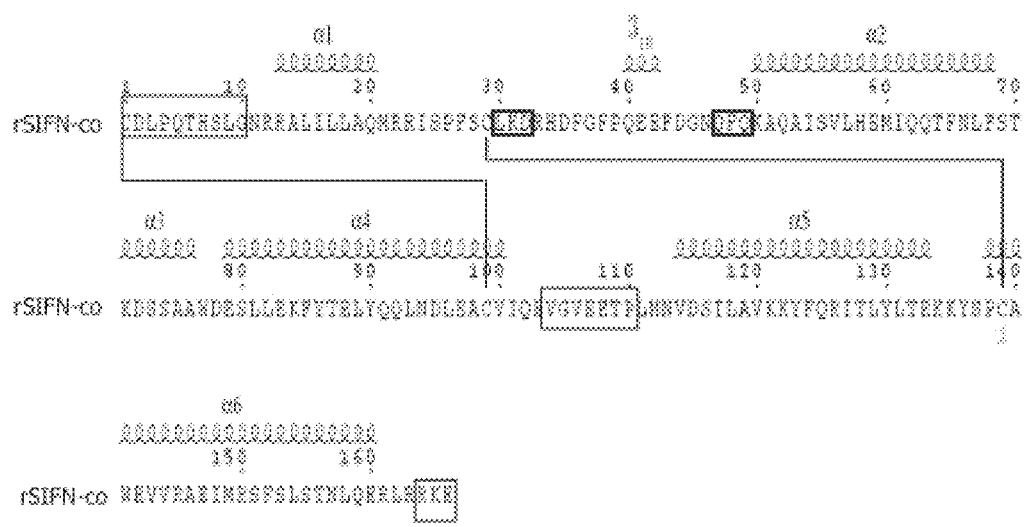

FIG. 10 shows the sequence alignment between the secondary structures of rSIFN-co (SEQ ID NO: 1) and its amino acid sequence; the gray boxes represent amino acid residues that were not set up in the structure; the blue boxes represent amino acid residues which were set up as Ala or Gly. The solid lines represent two pairs of disulfide linkages and the green subscripts represent one disulfide linkage that has been constructed in the structure.

Figure 11:
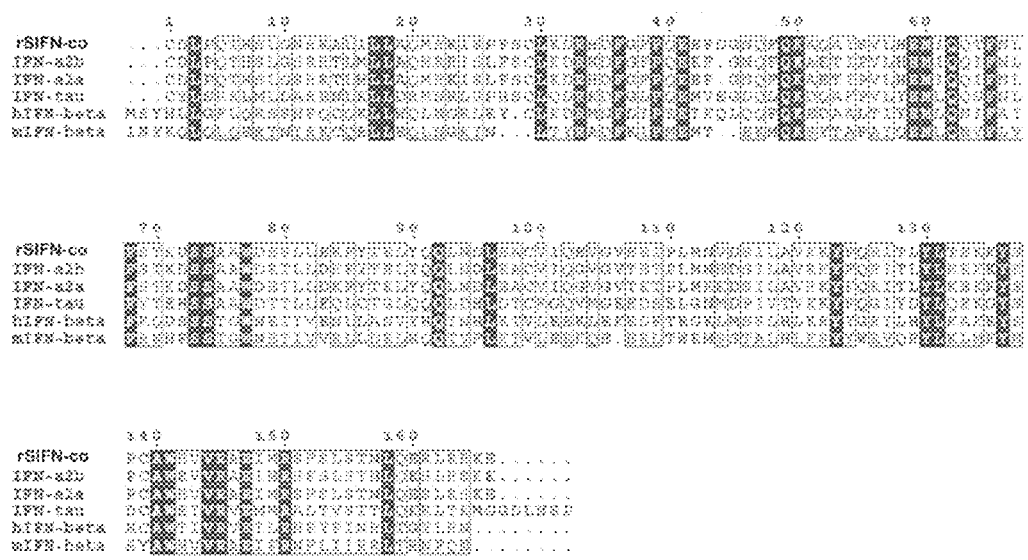

FIG. 11 shows the sequence alignment of rSIFN-co (SEQ ID NO: 1) protein and homologous IFN polypeptides.

Figure 12:
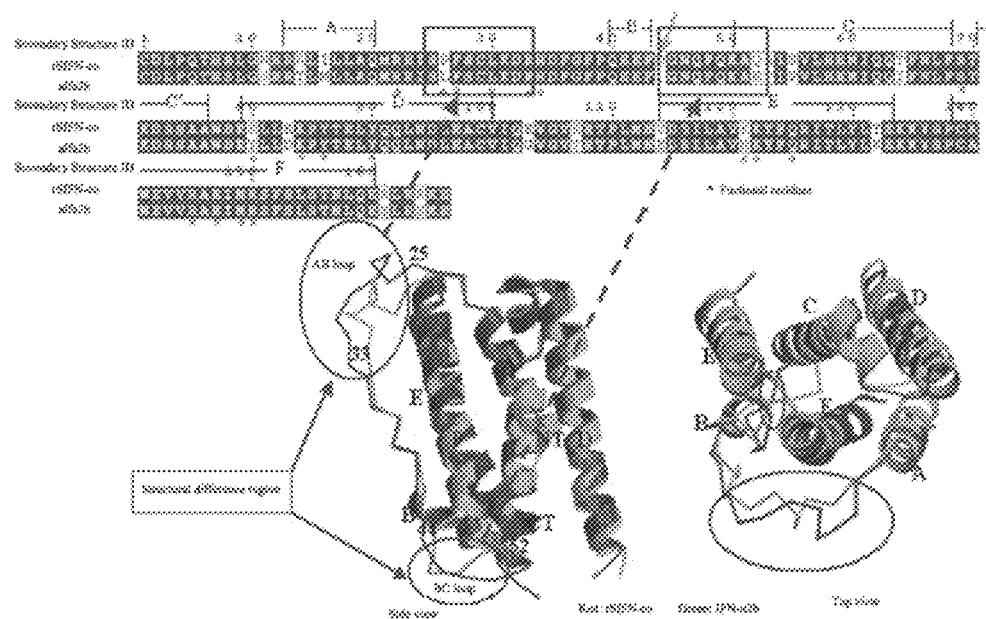

FIG. 12 shows a comparative diagram of the three-dimensional structure of rSIFN-co (SEQ ID NO: 1) and IFN-α2b.

Figure 13:
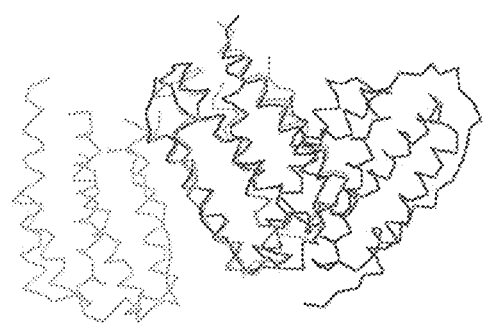

FIG. 13 shows the superimposed image of rSIFN-co (SEQ ID NO: 1) (in red) and IFN-α2b (in yellow).

Figure 14:
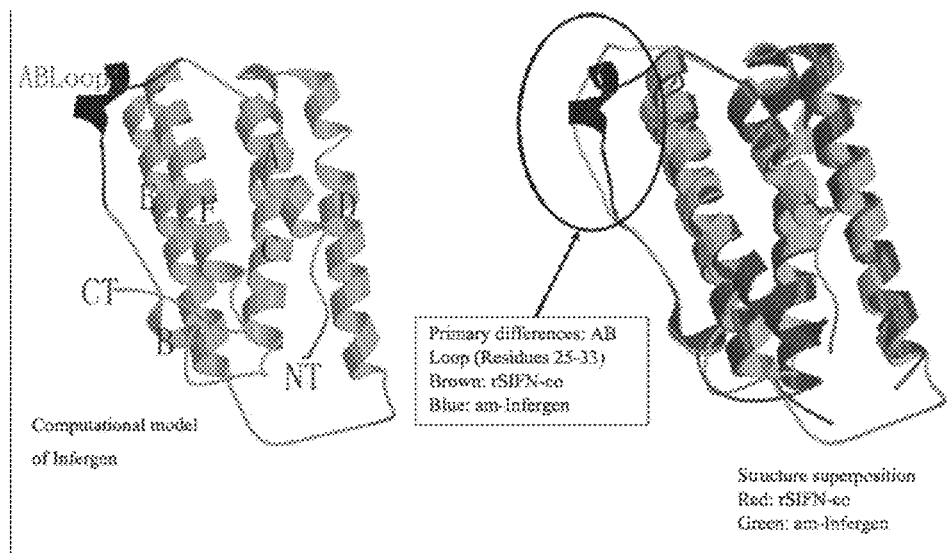

FIG. 14 shows the comparative differences between the three-dimensional structure of rSIFN-co (SEQ ID NO: 1) and the computational model of Infergen® (SEQ ID NO: 1) from Amgen (U.S.).

Figure 15:
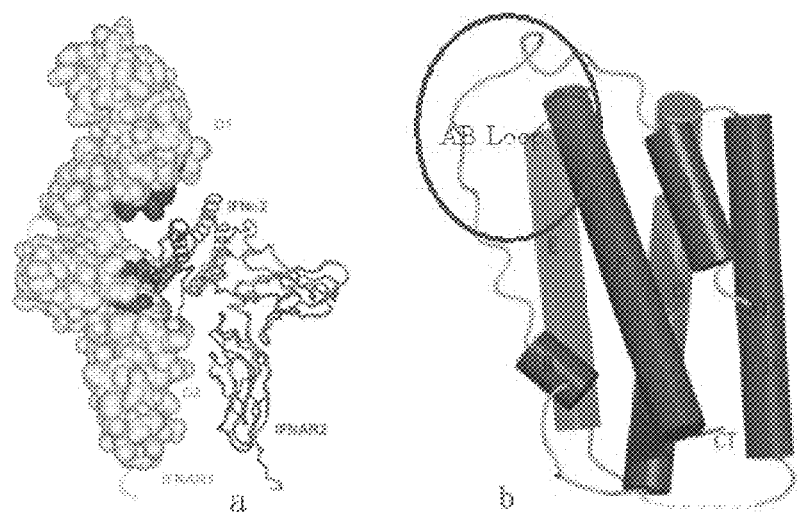

FIG. 15 shows (a) the combined model of protein IFN-α and its receptor; (b) the diagram of the functional domain of protein IFN-α (the important functional domain is illustrated by blue ring).

Figure 16:
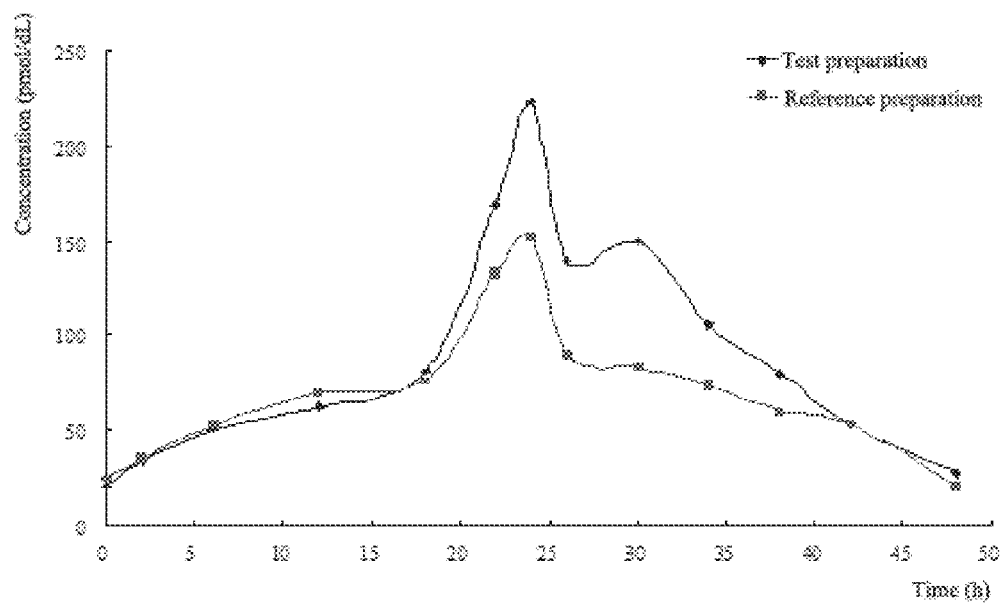

FIG. 16 shows the mean enzyme concentration in blood-time curve after subcutaneous injection of 9 μg rSIFN-co (SEQ ID NO: 1) and 9 μg Infergen® (SEQ ID NO: 1) to 18 subjects.

DETAILED DESCRIPTION OF THE INVENTION

The following is a detailed description of the invention provided to aid those skilled in the art for practicing the present invention.

Recombinant Interferon (rSIFN-co (SEQ ID NO: 1))

The purified recombinant interferon, which has been crystallized in this invention, is obtained from the method disclosed by the examples 1 and 2 of the specification of the U.S. Pat. No. 7,364,724 and/or pages 11-17 of the specification of the Chinese Patent Publication No. CN1740197 Å. The characterization of this recombinant interferon is disclosed in the U.S. Pat. No. 7,364,724 and/or the Chinese Patent Publication No. CN1740197 Å. In one embodiment, the amino acid sequence of the present recombinant interferon, as well as the nucleotide sequence encoding the same, are shown below:

```
            M   C   D   L   P   Q   T   H   S   L   G   N   R   R   A   L   I   L   L   A
  1 ATGTGCGACC TGCCGCAGAC CCACTCCCTG GGTAACCGTC GTGCTCTGAT CCTGCTGGCT
    TACACGCTGG ACGGCGTCTG GGTGAGGGAC CCATTGGCAG CACGAGACTA GGACGACCGA

Q   M   R   I   S   P   F   S   C   L   K   D   R   H   D   F   G   F   P
 61 CAGATGCGTC GTATCTCCCC GTTCTCCTGC CTGAAAGACC GTCACGACTT CGGTTTCCCG
    GTCTACGCAG CATAGAGGGG CAAGAGGACG GACTTTCTGG CAGTGCTGAA GCCAAAGGGC

Q   E   E   F   D   G   N   Q   F   Q   K   A   Q   A   I   S   V   L   H   E
121 CAGGAAGAAT TCGACGGTAA CCAGTTCCAG AAAGCTCAGG CTATCTCCGT TCTGCACGAA
    GTCCTTCTTA AGCTGCCATT GGTCAAGGTC TTTCGAGTCC GATAGAGGCA AGACGTGCTT

M   I   Q   Q   T   F   N   L   F   S   T   K   D   S   S   A   A   W   D   E
181 ATGATCCAGC AGACCTTCAA CCTGTTCTCC ACCAAAGACT CCTCCGCTGC TTGGGACGAA
    TACTAGGTCG TCTGGAAGTT GGACAAGAGG TGGTTTCTGA GGAGGCGACG AACCCTGCTT

S   L   L   E   K   F   Y   T   E   L   Y   Q   Q   L   N   D   L   E   A   C
241 TCCCTGCTGG AAAAATTCTA CACCGAACTG TACCAGCAGC TGAACGACCT GGAAGCTTGC
    AGGGACGACC TTTTTAAGAT GTGGCTTGAC ATGGTCGTCG ACTTGCTGGA CCTTCGAACG

V   I   Q   E   V   G   V   E   E   T   P   L   M   N   V   D   S   I   L   A
301 GTTATCCAGG AAGTTGGTGT TGAAGAAACC CCGCTGATGA ACGTTGACTC CATCCTGGCT
    CAATAGGTCC TTCAACCACA ACTTCTTTGG GGCGACTACT TGCAACTGAG GTAGGACCGA

V   K   K   Y   F   Q   R   I   T   L   Y   L   T   E   K   K   Y   S   P   C
361 GTTAAAAAAT ACTTCCAGCG TATCACCCTG TACCTGACCG AAAAAAAATA CTCCCCGTGC
    CAATTTTTTA TGAAGGTCGC ATAGTGGGAC ATGGACTGGC TTTTTTTTAT GAGGGGCACG
```

```
           A   W   E   V   V   R   A   E   I   M   R   S   F   S   L   S   T   N   L   Q
421 GCTTGGGAAG TTGTTCGTGC TGAAATCATG CGTTCCTTCT CCCTGTCCAC CAACCTGCAG
    CGAACCCTTC AACAAGCACG ACTTTAGTAC GCAAGGAAGA GGGACAGGTG GTTGGACGTC
       E   R   L   R   R   K   E (SEQ ID NO: 1)
481 GAACGTCTGC GTCGTAAAGA ATAA (SEQ ID NO: 2)
    CTTGCAGACG CAGCATTTCT TATT (SEQ ID NO: 3)
```

Moreover, the circular dichroism spectrum (CD) of the present recombinant interferon in ranges of 190-250 nm and 250-320 nm is significantly different from the corresponding CD of INFERGEN® (SEQ ID NO: 1) when determined under the same conditions (see page 3, lines 22-25, example 3 and FIGS. 6A-D of the Chinese Patent Publication No. CN1740197A,).

In addition, the three-dimensional structure of the present recombinant interferon is also different from the three-dimensional structure of IFN-α2b published in the art (see FIG. 12) and the three-dimensional structure of INFERGEN® (SEQ ID NO: 1) based on computational modeling (see KORN, A P et al., Journal of Interferon Research 1994, 14: 1-9). There are obvious differences between the AB loops of the two, and their BC loops also cannot overlap completely (see FIG. 14).

Furthermore, after intramuscular injection of the present recombinant interferon into subjects whose BMI ranged from 18 to 23, the time of blood sample collection was plotted against the concentration of 2-5A oligonucleotidase (also referred to as 2',5'-OAS) in the serum of the subjects. The chart generally shows a two-peak pattern, and the resulting area under the curve of this chart is significantly greater than that of INFERGEN® (SEQ ID NO: 1) after injection under the same conditions. The half-life period of this recombinant interferon is longer than that of INFERGEN® (SEQ ID NO: 1) after injection into the body.

The experimental results have also confirmed that the present recombinant interferon is more effective than any interferon used clinically at present (including INFERGEN® (SEQ ID NO: 1)). For example, for HBV, the recombinant interferon from this invention is capable of not only inhibiting DNA replication of HBV, but also inhibiting secretion of both hepatitis B surface antigen (HBsAg) and hepatitis B e antigen (HBeAg). The efficiency of inhibiting DNA replication of hepatitis B core antigen (HBcAg) by this interferon is about twice that of INFERGEN® (SEQ ID NO: 1). The in vitro pharmacodynamics of the present recombinant interferon shows that it is capable of not only inhibiting the DNA replication of HBV, but also inhibiting secretion of both hepatitis B surface antigen and hepatitis B e antigen. The cytotoxicity of the present recombinant interferon is only ⅛ that of the current clinically used interferons, but its antiviral activity is as much as 5-20 times greater; meanwhile, the biological responses of the present recombinant interferon is more effective, more broad-spectrum and longer lasting in the human body.

Furthermore, with respect to prevention of viral diseases or treatment of tumor, the present recombinant interferon shows higher antiviral activity and less side effects compared with any other interferons (including INFERGEN® (SEQ ID NO: 1)). For example, this recombinant interferon possesses not only an antiviral activity 20 times as great as that of the interferons currently in clinical use, but also a more effective anti-tumor (such as breast cancer and cervical cancer) function compared with recombinant human interferon α (including INFERGEN® (SEQ ID NO: 1)). It also shows greatly reduced toxic side effects and can be safely used in large dosages (each dose >10 million IU), making it possible to treat viral diseases or tumors which require large dosages of interferon.

Thus, the present recombinant interferon has a different spatial configuration, enhanced biologic activities and different pharmacokinetics characteristics as compared with INFERGEN® (SEQ ID NO: 1).

As used herein, the terms 'spatial configuration', 'spatial structure', 'three-dimensional structure' and 'three-dimensional configuration' can be used interchangeably.

Therefore, in one embodiment, the present recombinant interferon comprises the amino acid sequence of SEQ ID NO: 1 and is encoded by the nucleotide sequence comprising SEQ ID NO: 2. Further, the present recombinant interferon has the amino acid sequence of SEQ ID NO: 1, and is encoded by the nucleotide sequence of SEQ ID NO: 2. In comparison with interferons such as INFERGEN® (SEQ ID NO: 1), which has the amino acid sequence of SEQ ID NO: 1 or the same amino acid sequence as the present recombinant interferon, but is not encoded by the nucleotide sequence of SEQ ID NO: 2, the present recombinant interferon has a different spatial configuration and/or enhanced biologic activities and/or different pharmacokinetics characteristics. For example, the present recombinant interferon has a different spatial configuration and enhanced biologic activities, different spatial configuration and different pharmacokinetics characteristics, or enhanced biologic activities and different pharmacokinetics characteristics. Further, said different spatial configuration includes: the circular dichroism spectrum (CD) of the present recombinant interferon at 190-250 nm and/or 250-320 nm is significantly different from the corresponding CD of INFERGEN® (SEQ ID NO: 1) when determined under the same conditions. The enhanced biological activities include: enhanced antiviral activity, enhanced anti-tumor activity, less side effects and/or could be used in large dosages (e.g. each dose >10 million IU). For example, said enhanced biological activities can be enhanced antiviral activity and enhanced anti-tumor activity and the like. Furthermore, said tumors can be breast cancer and cervical cancer. The different pharmacokinetics characteristics include: after intramuscular injection of the recombinant interferon in subjects whose BMI ranged from 18 to 23, the time of blood sample collection was plotted against the concentration of 2-5A oligonucleotidase in the serum of the subjects, and the resulting area under the curve of this chart is significantly greater and/or the half-life of this recombinant interferon in the body is longer than those of INFERGEN® (SEQ ID NO: 1) after injection under the same conditions In another embodiment, the present recombinant interferon can be produced by the method comprising the following steps: introducing a nucleotide sequence comprising SEQ ID NO: 2 that encodes the recombinant interferon into an isolated host cell; culturing the host cell under appropriate condition for expression of the recombinant interferon; and harvesting the recombinant interferon, wherein the recombinant interferon has an amino acid sequence of SEQ ID NO: 1, and the recombinant interferon inhibits secretion of hepatitis B surface antigen (HBsAg) and hepatitis B e antigen (HBeAg) of Hepatitis B Virus. Further, said host cell is *Escherichia coli*, such as *Escherichia coli* LGM 194. Further, the nucleotide sequence comprising SEQ ID NO: 2 is under the control of the promoter $P_{BAD}$. Further, the harvesting step comprises extraction of the interferon from the fermentation broth, collection of the inclusion bodies, denaturation and renaturation of the harvested interferon. Still further, the harvesting step also comprises separation and purification of the recombinant interferon (see the claims of U.S. Pat. No. 7,364, 724).

Crystalline Recombinant Interferon and Crystallization Method Thereof

Crystalline Recombinant Interferon

This invention provides a crystalline recombinant interferon.

In one embodiment, this invention provides a crystalline recombinant interferon comprising the amino acid sequence of SEQ ID NO: 1. Further, this crystal belongs to the trigonal system. In one embodiment, the space group of this crystal is $P3_121$. In some embodiments, the unit cell parameters of this crystal are a=b=77.92 Å, c=125.935 Å, $\alpha=\beta=90°$, $\gamma=120°$, with a variability of at most 5% in all cell parameters. In some embodiments, said crystal contains two molecules in one asymmetric unit. In some embodiments, said crystal comprises covalently or non-covalently bound metal ions. Further, said mental ions can be magnesium ion, zinc ion and the like, these metal ions can mediate the formation of the interferon dimers in the crystal. In some embodiments, said recombinant interferon is encoded by the nucleotide sequence comprising SEQ ID NO: 2.

In a still further embodiment, this invention provides a crystalline recombinant interferon comprising the amino acid sequence of SEQ ID NO: 1, preferably the recombinant interferon having the amino acid sequence of SEQ ID NO: 1, in which the space group of this crystal is $P3_121$, with two molecules in one asymmetric unit, and the unit cell parameters are a=b=77.92 Å, c=125.935 Å, $\alpha=\beta=90°$, $\gamma=120°$, with a variability of at most 5% in all cell parameters. Further, such recombinant interferon is encoded by the nucleotide sequence comprising SEQ ID NO: 2, preferably encoded by the nucleotide sequence of SEQ ID NO: 2.

Crystallization Method

This invention provides a method for preparing or culturing the present crystalline recombinant interferon.

In one embodiment, this invention provides a method for preparing or culturing the present crystalline recombinant interferon, comprising the steps of: concentrating the recombinant interferon to about 3-3.5 mg/ml, and leaving it in the crystallization solution containing $Li_2SO_4$, CAPS (3-(cyclohexylamino)-1-propanesulfonic acid) and $MgCl_2$ for an appropriate period of time to obtain the crystal. Further, said method for culturing crystal is performed at room temperature such as 293K. In some embodiments, this crystal can be cultured by the hanging drop method or the sitting drop method, preferably the hanging drop method (also referred to as hanging drop vapor diffusion method). In some embodiments, said crystallization solution contains about 1.0-about 1.5M $Li_2SO_4$, about 0.05-about 0.15M CAPS (3-(cyclohexylamino)-1-propanesulfonic acid) and about 0.01-about 0.03 M $MgCl_2$. In some embodiments, the pH value of the crystallization solution is in the range of about 10.5-about 12.0, preferably about 11.1. In some embodiments, said crystallization solution contains 1.2M $Li_2SO_4$, 0.1M CAPS (3-(cyclohexylamino)-1-propanesulfonic acid), pH 11.1, 0.02 M $MgCl_2$. In some embodiments, the method for culturing the crystal includes leaving the crystallization solution containing said recombinant interferon to stand for about 1 day to about 2 weeks, preferably about 2 days to about 10 days, more preferably about 3 days to about 1 week, such as 3 days to 1 week.

X-Ray Crystallographic Analysis

Each of the constituent amino acids of interferon disclosed herein is defined by a set of structural coordinates (also known as "atomic coordinates"). The term "structural coordinates" refers to Cartesian coordinates derived from mathematical equations related to the patterns obtained by the diffraction of a monochromatic beam of x-rays by the atoms (scattering centers) of the present interferon in crystalline form. The diffraction data are used to calculate an electron density map of the repeating unit of the crystal. The electron density maps are then used to establish the positions of the individual atoms of the interferon protein or protein/ligand complex.

Slight variations in structural coordinates can be generated by mathematically manipulating the interferon or interferon/ligand structural coordinates. For example, the structural coordinates disclosed herein could be manipulated by crystallographic permutation, fractionalization, addition or subtraction of the entire set, inversion, or any combination of the above. Alternatively, modifications in the crystal structure due to mutations, additions, substitutions, and/or deletions of amino acids, or other changes in any of the components that make up the crystal, could also yield variations in structural coordinates. Such slight variations in the individual coordinates will have little effect on the overall configuration. If such variations are within an acceptable standard error as compared to the original coordinates, the resulting three-dimensional shape is considered to be structurally equivalent.

It should be noted that slight variations in individual structural coordinates of the interferon of the present invention are not expected to significantly alter the nature of the entities such as ligands that could associate with the interferon or portion thereof (e.g. the AB or the BC loop). As used herein, the "AB loop" of the present recombinant interferon means the amino acid residues 25-33 of the present recombinant interferon having the amino acid sequence of SEQ ID NO: 1; namely, the AB loop has the amino acid sequence SPFSCLKDR as shown in SEQ ID NO: 4; and the "BC loop" of the present recombinant interferon means the amino acid residues 44-52 of the present recombinant interferon having the amino acid sequence of SEQ ID NO: 1; namely, the BC loop has the amino acid sequence DGNQFQKAQ as shown in SEQ ID NO: 5. In this context, the phrase "associated with" refers to a condition of proximity between a ligand, or portions thereof, and an interferon molecule or portions thereof. The association may be non-covalent, wherein the juxtaposition is energetically favored by hydrogen bonding, van der Waals forces, or electrostatic interactions, or it may be covalent. Thus, for example, a ligand that binds to the binding pocket or region of an interferon would also be expected to bind to or interact with a structurally equivalent binding pocket or region.

In this invention, any molecule or molecular complex, or any portion thereof, that has a root mean square deviation of conserved residue backbone atoms (e.g. N, Cα, C, O, preferably Cα) of less than about 0.65 Å, when superimposed on the relevant backbone atoms described herein, is considered "structurally equivalent". That is to say, the crystal structures of those portions of the two molecules are substantially identical, within acceptable error. Particularly preferred structurally equivalent molecules or molecular complexes are those that are defined by the entire set of structural coordinates disclosed herein±a root mean square deviation from the conserved backbone atoms of those amino acids of less than about 0.65 Å. More preferably, the root mean square deviation is at most about 0.5 Å, and even more preferably, at most about 0.35 Å. Other embodiments of this invention include a molecular complex defined by the structural coordinates for the AB or the BC loop disclosed herein±a root mean square deviation of less than about 0.65 Å, preferably at most about 0.5 Å, and more preferably at most about 0.35 Å.

The term "root mean square deviation" means the square root of the arithmetic mean of the squares of the deviations. It is a way to express the deviation or variation from a trend or object. In one embodiment, the "root mean square deviation" defines the variation in the backbone of a protein from the backbone of interferon or a portion thereof as defined by the structural coordinates described herein.

X-ray structural coordinates define a unique configuration of points in space. Those skilled in the art would understand that a set of structural coordinates for a protein or a protein/ligand complex, or a portion thereof, defines a relative set of points that, in turn, defines a configuration in three dimensions. A similar or identical configuration can be defined by an entirely different set of coordinates, provided that the distances and angles between coordinates remain essentially the same. In addition, a scalable configuration of points can be defined by increasing or decreasing the distances between coordinates by a scalar factor while keeping the angles essentially the same.

Various computational analyses can be used to determine whether a molecule or a portion thereof is "structurally equivalent", defined in terms of its three-dimensional structure, to the interferon disclosed herein, or part of it. For example, comparisons between different structures, different conformations of the same structure, or different parts of the same structure can be made by various computational analyses. In one embodiment, such analysis can be divided into four steps: (1) load the structures to be compared; (2) define the atom equivalences in these structures; (3) perform a fitting operation; and (4) analyze the results.

Three-dimensional structure of Recombinant Interferon (rSIFN-co (SEQ ID NO: 1))

This invention provides the three-dimensional structure of the present recombinant interferon.

This three-dimensional structure is different from the three-dimensional structure of IFN-α2b published in the art (see FIG. 12) and the structure of the computational model of INFERGEN® (SEQ ID NO: 1) of U.S. Amgen (see FIG. 14), especially in the AB and BC loops.

In one embodiment, the three-dimensional structure of said recombinant interferon contains the atomic coordinates of recombinant interferon as shown in table 7, said atomic coordinates optionally have a variability of root mean square deviation from the conserved backbone atoms, preferably Cα (also referred to as 'α carbon atom'), of less than about 0.65 Å, preferably or about 0.5 Å, and more preferably about 0.35 Å.

In one embodiment, in the above-mentioned three-dimensional structure of the recombinant interferon, each monomer of said recombinant interferon is composed of 6 segments of α-helix, a segment of $3_{10}$ helix, and the connecting peptides between them. The corresponding amino acid residue locations of said 6 segments of the α-helices are 13-20, 50-68, 70-76, 79-100, 114-133, and 138-160; the corresponding amino acid residue location of said segment of $3_{10}$ helix is 40-43. The folding of the monomer structure belongs to the helical cytokine type, having the following characteristics: after superimposition of the Cα-backbone of said recombinant interferon and the Cα-backbone of IFN-α2b protein using least squares method, the location root-mean-square deviation of Cα in the 25-33 residues (AB loop) of said recombinant interferon and Cα in the corresponding residues of IFN-α2b protein is 3.63 Å±5%.

Preferably, the location root-mean-square deviation of Cα at residue 25 of said recombinant interferon and IFN-α2b protein is 3.291 Å±5%, the location root-mean-square deviation of Cα at residue 26 is 4.779 Å±5%; the location root-mean-square deviation of Cα at residue 27 is 5.090 Å±5%; the location root-mean-square deviation of Cα in the 28 residue is 3.588 Å±5%; the location root-mean-square deviation of Cα at residue 29 is 2.567 Å±5%, the location root-mean-square deviation of Cα at residue 30 is 2.437 Å±5%; the location root-mean-square deviation of Cα at residue 31 is 3.526 Å±5%; the location root-mean-square deviation of Cα at residue 32 is 4.820 Å±5%; and the location root-mean-square deviation of Cα at residue 33 is 2.756 Å±5%.

More preferably, the location root-mean-square deviation of Cα at residues 44-52 (BC loop) of said recombinant interferon and Cα in the corresponding residues of IFN-α2b protein is 2.90 Å±5%. Wherein, the location root-mean-square deviation of Cα at residue 44 of both said recombinant interferon and IFN-α2b protein is 1.614 Å±5%; the location root-mean-square deviation of Cα at residue 45 is 1.383 Å±5%; the location root-mean-square deviation of Cα at residue 46 is 2.735 Å±5%; the location root-mean-square deviation of Cα at residue 47 is 2.709 Å±5%; the location root-mean-square deviation of Cα at residue 48 is 5.018 Å±5%; the location root-mean-square deviation of Cα at residue 49 is 4.140 Å±5%; the location root-mean-square deviation of Cα at residue 50 is 3.809 Å±5%; the location root-mean-square deviation of Cα at residue 51 is 2.970 Å±5%; and the location root-mean-square deviation of Cα at residue 52 is 0.881 Å±5%. The "location root-mean-square deviation" listed above are all root-mean-square deviations of the coordinate positions.

In another aspect, this invention provides a selected portion of the three-dimensional structure of the present recombinant interferon, which contains atomic coordinates of one or more amino acid residues from amino acid residues 25-33 and/or 45-52 in table 7. In some embodiments, the "one or more amino acid residues" described herein include 1, 2, 3, 4, 5, 6, 7, 8, 9, 10, 11, 12, 13, 14, 15, 16, 17, 18 amino acid residues. In some embodiments, the "selected portion of said three-dimensional structure" contains the atomic coordinates of the amino acid residues 25-33 and/or 44-52 in table 7. In some embodiments, the "selected portion of the three-dimensional structure" contains the atomic coordinates of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 amino acid residues in table 7. In some embodiments, said atomic coordinates have a variability of root mean square deviation from the conserved backbone atoms (preferably Cα) of less than about 0.65 Å, preferably about 0.5 Å, and more preferably about 0.35 Å.

In another aspect, this invention provides the protein spatial structure model comprising the three-dimensional structure of the present recombinant interferon. In one embodiment, said protein spatial structure model could be an electron density map, a wire-frame model, a chicken-wire model, a space-filling model, a stick-model, a ribbon model and a molecular surface model and the like.

In still another aspect, the present invention provides a scalable three-dimensional configuration of points, wherein at least a portion of said points are derived from the structural coordinates disclosed herein, or from peptides comprising the AB loop or the BC loop of the present recombinant interferon. In one embodiment, the scalable three-dimensional configuration of points is displayed as a holographic image, a stereo diagram, a model, or a computer-displayed image.

The Application of Three-Dimensional Structure Screening/Designing Candidate Substance that could Interact with Recombinant Interferon In one aspect, this invention provides a method for screening/designing candidate compounds that could interact with the present recombinant interferon. Further, said method utilizes the three-dimensional structure of the present recombinant interferon. Still further, said method is based on a computer. In one embodiment, this invention provides a computer-based method for identifying candidate compounds that could interact with recombinant interferon, said method comprises the steps of: (a) providing a three-dimensional structure comprising the atomic coordinates of the recombinant interferon as shown in table 7, said atomic coordinates optionally have a variability of root mean square deviation from the conserved backbone atoms (preferably Cα) of less than about 0.65 Å, preferably about 0.5 Å, and more preferably about 0.35 Å; and (b) selecting a candidate compound that comprises structural features capable of interacting with said three-dimensional structure or selected portion thereof, thereby identifying a candidate compound that could interact with said recombinant interferon. In some embodiments, said structural features are selected from the group consisting of antigenic sites, hydrophilic properties, surface accessibility, and structural motifs. In some embodiments, the selection and identification of candidate compounds in step (b) comprises: (i) generating three-dimensional structures for a plurality of candidate compounds; and (ii) fitting each of the three-dimensional structures of step (i) against the three-dimensional structure of step (a) or selected portion thereof to find the most energetically favorable interaction, thereby identifying a candidate compound that could interact with the recombinant interferon. In some embodiments, said method further comprises the steps of: (c) obtaining or synthesizing the candidate compound; and (d) contacting the candidate compound with said recombinant interferon to determine the ability of the candidate compound to interact with said recombinant interferon. Further, the step of determining the ability of the candidate compound to interact with said recombinant interferon may further comprise measuring the activity of said recombinant interferon when contacted with the candidate compound. Interferon activities to be measured include, for example, antivirus activity, anti-tumor activity, anti-proliferation activity, natural killer cell activation, and immunomodulatory activity. In some embodiments, said candidate compound is a ligand bound to said recombinant interferon or selected portion thereof. For example, said ligand is selected from the group consisting of receptor, modifier, agonist and antagonist, said receptor could be IFNAR1, IFNAR2 or their complex, and said selected portion comprises one or more amino acid residues from the amino acid residues 25-33 (AB loop) and/or 45-52 (BC loop) of said recombinant interferon. Further, said selected portion comprises the amino acid residues 25-33 and/or 44-52 of said recombinant interferon.

In another aspect, the present invention provides a method for determining potential ligands that bind to the present recombinant interferon. In one embodiment, the method includes exposing a crystal disclosed herein to one or more samples comprising potential ligands, and determining whether a ligand-interferon molecular complex is formed.

In another aspect, the present invention provides a method for acquiring structural information to design potential ligands that can form molecular complexes with interferon. In one embodiment, the method includes exposing a crystal disclosed herein to one or more samples comprising potential ligands, and determining whether a ligand-interferon molecular complex is formed.

In another aspect, the present invention provides a computer-assisted method for determining, designing, or making potential modifiers of interferon activity. In one embodiment, the method includes screening a library of chemical or biological entities.

Those skilled in the art can utilize crystallography to screen and identify chemical or biological entities that may become ligands of an interferon (see e.g. in U.S. Pat. No. 6,297,021). For example, a preferred method may include obtaining a crystal of unliganded interferon; exposing the unliganded interferon to one or more test samples that contain potential ligands of the interferon; and determining whether a ligand-interferon molecular complex is formed. The interferon may be exposed to potential ligands by various methods including, but not limited to, soaking an interferon crystal in a solution of one or more potential ligands or co-crystallizing interferon in the presence of one or more potential ligands.

Structural information from said ligand-interferon complexes may preferably be used to design new ligands that bind tighter and more specifically, have desired special biological activities, have better safety profiles or combinations thereof than known ligands. For example, the calculated electron density map directly reveals the binding event, identifies the bound chemical or biological entities, and provides a detailed three-dimensional structure of the ligand-interferon complex. Once a hit is found, a series of analogs or derivatives of the hit may be screened for tighter binding or desired biological activity by traditional screening methods. Optionally, the ligand-interferon complex may be iteratively exposed to additional potential ligands so that two or more hits may preferably be linked together to identify or design a more potent ligand.

Obtaining Structurally Homologous Molecules/Designing Interferon Mimetics

The structural coordinates disclosed herein can be used to aid in obtaining structural information about another crystallized molecule or molecular complex. The method of this invention allows determination of at least a portion of the three-dimensional structure of molecules or molecular complexes which contain one or more structural features that are similar to the structural features of the interferon disclosed herein. These molecules are referred to herein as "structurally homologous". Similar structural features can include, for example, regions of amino acid identity, conserved active site or binding site motifs and similarly arranged secondary structural elements (e.g., α helices and β sheets). In another embodiment, structural homology is determined by aligning the residues of two amino acid sequences to optimize the number of identical amino acids along the lengths of their sequences; gaps in either or both sequences are permitted in making the alignment in order to optimize the number of identical amino acids; however, the amino acids in each sequence must remain in their proper order. Preferably, a structurally homologous molecule is a protein that has an amino acid sequence sharing at least 65% identity with SEQ ID NO:1. More preferably, a protein that is structurally homologous to the interferon of the present invention includes a contiguous stretch of at least 50 amino acids that shares at least 80% amino acid sequence identity with the analogous portion of SEQ ID NO:1. Methods for generating structural information about the structurally homologous molecule or molecular complex are well-known in the art.

The structural coordinates disclosed herein are also useful for solving the crystallographic structures of related interferons, interferon mutants or interferon homologs complexed with a variety of ligands. This approach enables the determination of the optimal sites for interaction between a ligand and an interferon, e.g. between candidate interferon modifiers and interferon. Potential sites for modification within the various binding sites of the molecules can also be identified. This information provides an additional tool for determining the most efficient binding interactions, for example, increased hydrophobic interactions between an interferon and a ligand.

In one embodiment, the present invention also provides a computer-based method for designing a mimetic of the recombinant interferon, comprising the steps of: (a) generating three-dimensional structures for a plurality of mimetics; and (b) fitting each of the three-dimensional structures of step (a) against the three-dimensional structure comprising the atomic coordinates of the recombinant interferon as shown in table 7 or selected portion thereof to find the best fitted mimetic of said recombinant interferon, said atomic coordinates optionally have a variability of root mean square deviation from the conserved backbone atoms (preferably Cα) of less than about 0.65 Å, preferably about 0.5 Å, and more preferably about 0.35 Å.

Rational drug design

Computational techniques can be used to screen, identify, select and/or design chemical entities or ligands capable of associating with interferons or structurally homologous molecules. Knowledge of the structural coordinates of the interferon disclosed herein permits the design and/or identification of synthetic compounds and/or other molecules which have a shape complementary to the conformation of the interferon disclosed herein. In particular, computational techniques can be used to identify or design chemical entities or ligands, such as receptors, modifiers, agonists and antagonists, that associate with the interferon or a portion thereof (e.g. the AB or the BC loop). Potential modifiers may bind to or interfere with all or a portion of an active site of interferon, and can be competitive, non-competitive, or uncompetitive inhibitors; or interfere with dimerization by binding at the interface between the two monomers. Once identified or screened for biological activity, these inhibitors/agonists/antagonists may be used therapeutically or prophylactically to block or enhance interferon activity. Structure-activity data for analogues of ligands that bind to or interfere with interferon can also be obtained computationally.

The term "chemical entity", as used herein, refers to chemical compounds, complexes of two or more chemical compounds, and fragments of such compounds or complexes. Chemical entities that are determined to associate with the interferon of the present invention are potential drug candidates. A graphical three-dimensional representation of the structure of the present interferon or a structurally homologous molecule, as identified herein, or portions thereof may thus be advantageously used for drug discovery. The structural coordinates of the chemical entity are used to generate a three-dimensional image that can be computationally fitted to the three-dimensional image of an interferon or a structurally homologous molecule by one of many computation methods and techniques available in the art.

One embodiment of the method of drug design involves evaluating the potential association of a known chemical entity or ligand with the interferon or a structurally homologous molecule. The method of drug design thus includes computationally evaluating the potential of a selected chemical entity or ligand to associate with any of the molecules or molecular complexes set forth herein. In another embodiment, the method of drug design involves computer-assisted design of chemical entities or ligands that associate with the present interferon, its homologs, or portions thereof. Chemical entities or ligands can be designed in a stepwise fashion, one fragment at a time, or may be designed as a whole or "de novo".

Thus, in one embodiment, the present invention provides a computer-based method of rational drug design, comprising the steps of: (a) providing the three-dimensional structure comprising atomic coordinates of the recombinant interferon as shown in table 7, said atomic coordinates optionally have a variability of root mean square deviation from the conserved backbone atoms (preferably Cα) of less than about 0.65 Å, preferably about 0.5 Å, and more preferably about 0.35 Å; (b) providing a plurality of molecular fragments, and generating three-dimensional structures thereof; (c) fitting each of the three-dimensional structures of step (b) against the three-dimensional structure of step (a) or selected portion thereof; and (d) assembling the selected molecular fragments into a molecule to form a candidate drug. In one embodiment, said method may further comprise the steps of: (e) obtaining or synthesizing the candidate drug; and (f) contacting the candidate drug with said recombinant interferon to determine the ability of the candidate drug to interact with said recombinant interferon.

In some embodiments of this invention, the selected portion of said three-dimensional structure comprises the atomic coordinates of one or more amino acid residues from amino acid residues 25-33 (amino acid sequence as shown in SEQ ID NO: 4) and/or 45-52 (amino acid sequence as shown in SEQ ID NO: 5) in table 7. Further, the selected portion of said three-dimensional structure comprises the atomic coordinates of the amino acid residues 25-33 (amino acid sequence as shown in SEQ ID NO: 4) and/or 45-52 (amino acid sequence as shown in SEQ ID NO: 5) in table 7, said atomic coordinates optionally have a variability of root mean square deviation from the conserved backbone atoms (preferably Cα) of less than about 0.65 Å, preferably about 0.5 Å, and more preferably about 0.35 Å.

Homology Modeling

In one aspect, using homology modeling, a computer model of an interferon homolog can be built or refined without crystallizing the homolog. First, a preliminary model of an interferon homolog is created by sequence alignment, secondary structure prediction, screening of structural libraries, or any combination of these techniques. Computational software may be used to carry out the sequence alignments and secondary structure predictions. Structural incoherencies, e.g., structural fragments around insertions and deletions, can be modeled by screening a structural library for peptides of the desired length and suitable conformation. If the interferon homolog has been crystallized, the final homology model can be used to solve the crystal structure of the homolog by techniques known in the art. Next, the preliminary model is subjected to energy minimization to yield an energy minimized model. The energy minimized model may contain regions where stereochemical restraints are violated; in such cases, these regions are remodeled to obtain a final homology model using one of many techniques known in the art.

In another aspect, the present invention provides a method for obtaining structural information about a molecule or a molecular complex of unknown structure. In one embodiment, the method includes crystallizing the molecule or molecular complex; generating an x-ray diffraction pattern from the crystallized molecule or molecular complex; and applying the x-ray diffraction pattern to at least a portion of the structural coordinates of the interferon disclosed herein to generate a three-dimensional electron density map of at least a portion of said molecule or molecular complex of unknown structure.

In another aspect, the present invention provides a method for modeling an interferon homolog. In one embodiment, the method includes aligning the amino acid sequence of a putative interferon homolog with the amino acid sequence of the present interferon and incorporating the sequence of the putative homolog into a model of interferon formed from the structural coordinates disclosed herein to yield a preliminary model of interferon homolog; subjecting the preliminary model to energy minimization to yield an energy minimized model; and remodeling regions of the energy minimized model where stereochemical restraints are violated to yield a final model of the interferon homolog.

Interferon Mimetics

The present invention provides interferon mimetics.

In one aspect, the present invention provides a peptide comprising a sequence as disclosed herein, or a derivative, active portion, analogue, variant or mimetic, and uses thereof. Thus, in one embodiment, the present invention provides a mimetic of the interferon which comprises the amino acid sequence as shown in SEQ ID NO: 4 and/or SEQ ID NO: 5. In one embodiment, after superimposition of the Cα-backbone of the three-dimensional structure of said recombinant interferon and the Cα-backbone of the three-dimensional structure of IFN-α2b protein using least squares method, the location root-mean-square deviation of Cα at residues 25-33 of said recombinant interferon and Cα in the corresponding residues of IFN-α2b protein is 3.63 Å±5%. In some embodiments, in comparison with the corresponding residues of IFN-α2b, the deviations of α carbons of residues 25-33 of said recombinant interferon are 3.291 Å±5%, 4.779 Å±5%, 5.090 Å±5%, 3.588 Å±5%, 2.567 Å±5%, 2.437 Å±5%, 3.526 Å±5%, 4.820 Å±5% and 2.756 Å±5% respectively. In some embodiments, after superimposition of the Cα-backbone of the three-dimensional structure of said recombinant interferon and the Cα-backbone of the three-dimensional structure of IFN-α2b protein using least squares method, the location root-mean-square deviation of Cα at residues 44-52 of said recombinant interferon and Cα in the corresponding residues of IFN-α2b protein is 2.90 Å±5%. In some embodiments, in comparison with the corresponding residues of IFN-α2b, the deviations of α carbons of residues 44-52 of said recombinant interferon are 1.614 Å±5%, 1.383 Å±5%, 2.735 Å±5%, 2.709 Å±5%, 5.018 Å±5%, 4.140 Å±5%, 3.809 Å±5%, 2.970 Å±5%, and 0.881 Å±5% respectively. In some embodiments, the mimetic is a functional mimetic or a structural mimetic. In some embodiments, the mimetic is a mimetic of the present recombinant interferon (rSIFN-co (SEQ ID NO: 1)). Further, the mimetics do not comprise INFERGEN® (SEQ ID NO: 1). In some embodiments, the three-dimensional structure of said interferon mimetic is similar to that of the present recombinant interferon (rSIFN-co (SEQ ID NO: 1)). In particular, both three-dimensional structures can be the same or essentially the same at the AB and BC loops. Further, the three-dimensional structure of said interferon mimetic comprises the atomic coordinates of amino acid residues 25-33 (AB loop) and/or 44-52 (BC loop) in table 7, said atomic coordinates optionally have a variability of root mean square deviation from the conserved backbone atoms, preferably Cα, of less than about 0.65 Å, preferably about 0.5 Å, and more preferably about 0.35 Å.

The present invention comprises variant peptides in which individual amino acids can be replaced by other closely related amino acids as is understood in the art. For example, individual amino acid may be replaced as follows: any hydrophobic aliphatic amino acid may be replaced by any other hydrophobic aliphatic amino acids; any hydrophobic aromatic amino acid may be replaced by any other hydrophobic aromatic amino acids; any neutral amino acid with a polar side chain may be replaced by any other neutral amino acids with a polar side chain; an acidic amino acid may be replaced by any other acidic amino acids; and a basic amino acid may be replaced by any other basic amino acids. As used herein, "mimetic", "functional/structural mimetic" relate to peptide variants or organic compounds having the same functional/structural activity as the polypeptide disclosed herein. Examples of such mimetic or analogues include chemical compounds or peptides which are modeled to resemble the three-dimensional structure of the interferon disclosed herein (the three-dimensional structure comprise the atomic coordinates of recombinant interferon as shown in table 7), particularly compounds and peptides having the above arrangement of amino acid residues. Thus, as used herein, "mimetic of the present recombinant interferon" refers to a peptide variant or organic compound which has the same function/structure-activity as the present recombinant interferon (rSIFN-co (SEQ ID NO: 1)), especially those having the same AB loop and/or BC loop spatial structure as the present recombinant interferon, but is not the present recombinant interferon When the "mimetic" is a peptide variant, the length of its amino acid sequence is generally similar to that of the present recombinant interferon. For example, said amino acid sequence of the mimetic can comprise about 120-200 amino acid residues, preferably about 140-180 amino acid residues, more preferably about 150-175 amino acid residues, still more preferably about 160-170 amino acid residues; for example, about 164, 165, 166 or 167 amino acid residues. Alternatively, such a "mimetic" can be a peptide variant having a shorter amino acid sequence than the present recombinant interferon but comprising the AB loop and/or BC loop. For example, it can comprise about 10-100 amino acid residues, preferably about 15-80 amino acid residues.

Suitable mimetics or analogues can be generated by modeling techniques generally known in the art. This includes the design of "mimetics" which involves the study of the functional interactions and the design of compounds which contain functional groups arranged in such a manner that they could reproduce those interactions.

The design of mimetics of compounds with known pharmaceutical activity is a known approach based on lead compounds for drug development. This might be desirable where the active compound is difficult or expensive to synthesize or where it is unsuitable for common methods of administration; e.g. polypeptides are not well suited as active agents for oral compositions as they tend to be quickly degraded by proteases in the alimentary canal Mimetic design, synthesis and testing may be used to avoid randomly screening a large number of molecules for a target property.

There are several steps commonly taken in the design of a mimetic from a compound/peptide having a given target property. Firstly, determine the particular parts of the compound/peptide that are critical and/or important in determining the target property. In the case of a peptide, this can be done by systematically varying the amino acid residues in the peptide, e.g. by replacing each residue in turn. These parts or residues constituting the active region of the compound are known as its "pharmacophore".

Once the pharmacophore has been identified, its structure can be modeled according to its physical properties, e.g. stereochemistry, bonding, size and/or charge, using data from a range of sources, e.g. spectroscopic techniques, X-ray diffraction and NMR data. Computational analysis, similarity mapping (which models the charge and/or volume of a pharmacophore, rather than the bonding between atoms) and other techniques can be used in this modeling process. In a variant of this approach, the three-dimensional structures of the ligand and its binding partner are modeled. This can be especially useful where the ligand and/or binding partner change conformation on binding, allowing further consideration of the model while designing the mimetic.

Afterwards, select a template molecule onto which chemical groups that mimic the pharmacophore can be grafted. The template molecule and the chemical groups to be grafted can be conveniently selected so that the mimetic, besides maintaining the biological activities of the lead compound, would be easy to synthesize, likely be pharmacologically acceptable, and not degrade in vivo. The mimetics found by this approach can then be screened to see whether they have the target property, or to what extent they exhibit it. Further optimization or modification can then be carried out to arrive at one or more final mimetics for in vivo or clinical testing.

In another aspect, the present invention provides an unliganded molecule including at least a portion of the interferon disclosed herein, e.g. the unliganded molecule may comprise SEQ ID NO:4 or SEQ ID NO:5 (the sequence of the AB loop and the BC loop respectively of the interferon described herein). Further, the unliganded molecule has sequence as shown in SEQ ID NO:4 or SEQ ID NO:5.

Composition and Therapeutic Application

The present invention provides a composition comprising a crystalline form of the present recombinant interferon or a mimetic of the present recombinant interferon. In one embodiment, the composition is a pharmaceutical composition. In one embodiment, said pharmaceutical composition further comprises a pharmaceutically acceptable carrier.

Whether it is a polypeptide, antibody, peptide, nucleic acid molecule, small molecule, mimetic or other pharmaceutically useful compounds according to the present invention that is to be administered to an individual, the preferred dosage is a "prophylactically effective amount" or a "therapeutically effective amount" (although prophylaxis may be considered a therapy), this dosage being sufficient to provide its beneficial effects to the individual. The actual amount, frequency and time-course of administration will depend on the nature and severity of the disease being treated. Prescription of treatment, e.g. decisions on dosage etc., is within the responsibility of medical doctors and other medical workers. Depending on the circumstances, pharmaceutical compositions may be administered alone or in combinations.

Pharmaceutical compositions according to the present invention, and those for use with the present invention, may include, in addition to the active ingredient, a pharmaceutically acceptable excipient, carrier, buffer, stabilizer or other materials well known to those skilled in the art. Such materials should be non-toxic and should not interfere with the efficacy of the active ingredient. The exact nature of the carrier or other materials will depend on the route of administration, which may be oral or by injection, e.g. cutaneous, subcutaneous or intravenous. Examples of techniques and protocols mentioned above can be found in Remington's Pharmaceutical Sciences, 16th edition, Osol, A. (ed.), 1980.

In some embodiments, said pharmaceutical composition can be formulated into the following dosage forms, including: tablets, capsules, oral liquids, patches, injections, sprays, suppositories, and solution preparations. The recommended dosage form is injection, such as subcutaneous or intravenous injection, and the carrier in the pharmaceutical composition may be any acceptable drug carrier, including binders, disintegrating agents, lubricants, fillers, solubilizers, buffers, preservatives, thickeners, chelating agents and other adjuvants.

On the basis of the different purposes of this invention, "pharmaceutically acceptable carriers" may be any of the standard pharmaceutical carriers. For example, known appropriate carriers include, but are not limited to, phosphate buffered saline and various wetting agents. Other carriers may include additives used for tablets, granules, and capsules. Typical carriers often contain: starch, emulsion, sugar, cellulose, certain types of clay, gelatin, stearic acid and its salts such as magnesium stearate or calcium stearate, talc, plant oils, gums, glycol or other known excipients. Such carriers may also include flavorings and color additives or other ingredients. The composition of these carriers can be formulated using known methods.

Furthermore, since the mimetics of the present recombinant interferon have the AB loop and/or BC loop structures (such as the above specific AB loop and/or BC loop space structures) of the present recombinant interferon, they are expected to be capable of treating viral diseases and/or tumor similar to the present recombinant interferon.

Therefore, in another aspect, the present invention provides a use of the crystal of the present recombinant interferon, an interferon mimetic or a composition comprising said crystal or mimetic for the preparation of medicament for treating viral diseases and/or tumors.

In another aspect, the present invention provides a method for the treatment of viral diseases and/or tumors, said method comprises administering to a subject an effective amount of the crystal of the present recombinant interferon, an interferon mimetic or a composition comprising said crystal or mimetic.

In another aspect, the present invention also provides a pharmaceutical composition for the treatment of viral diseases and/or tumors, comprising an effective amount of the crystal of the present recombinant interferon, an interferon mimetic or a composition comprising said crystal or mimetic.

In some embodiments, said viral diseases may include: hepatitis A, hepatitis B, hepatitis C, other types of hepatitis, viral infections caused by Epstein-Barr virus, human immunodeficiency virus (HIV), Ebola virus, severe acute respiratory syndrome (SARS) virus, influenza virus, cytomegalovirus, herpes simplex virus, or other type of herpes virus, papovavirus, pox virus, picornavirus, adenovirus, rhinovirus, human T-cell leukemia viruses type I, or human T-cell leukemia viruses type II, or human T-cell leukemia virus type III.

In some embodiments, said tumor is cancer or solid tumors, and said tumors may include: skin cancer, basal cell carcinoma and malignant melanoma, renal cell carcinoma, liver cancer, thyroid cancer, nasopharyngeal cancer, solid tumors, prostate cancer, stomach/abdominal cancer, esophageal cancer, rectal cancer, pancreatic cancer, breast cancer, ovarian cancer, superficial bladder cancer, hemangioma, epidermoid cancer, cervical cancer, non-small cell lung cancer, small cell lung cancer, glial stromal tumors, leukemia, acute leukemia, chronic leukemia, chronic myelogenous leukemia, hairy cell leukemia, lymphadenoma, multiple myeloma, polycythemia, Kaposi's sarcoma.

This invention will be described in details using the following examples which are included merely for the purpose of illustrating certain aspects and embodiments of the present invention, and are not intended to limit the scope of this invention. Modifications may be made to the invention described herein without deviating from the scope of the invention.

All publications, patents and patent applications cited herein are incorporated by reference in their entireties, both individually and collectively, into this application.

EXAMPLES

Example 1

Production of Recombinant Interferon rSIFN-co
(SEQ ID NO: 1)

This example describes the preparation of recombinant interferon rSIFN-co (SEQ ID NO: 1) (stock solution). (Refer to Examples 1 and 2 of U.S. Pat. No. 7,364,724, and pages 11-17 of the specification of Chinese Patent publication No. CN1740197A.)
1. Gene Cloning Based on the published encoding DNA sequence and deduced amino acid sequence of INFERGEN® (SEQ ID NO: 1) (Klein M L, et al., Structural characterization of recombinant consensus interferon-alpha. Journal of Chromatography, 1988; 454: 205-215), the DNA encoding sequence was redesigned using *E. Coli* codon usage (The Wisconsin Package, by Genetics Computer Group, Inc. Copyright 1992, Medison, Wis., USA) under conditions that preserve the amino acid sequence, and then the full-length cDNA of rSIFN-co (SEQ ID NO: 1) was synthesized.
rSIFN-Co (SEQ ID NO: 1) cDNA Sequence Synthesis
Synthesis of the rSIFN-Co (SEQ ID NO: 1) cDNA 5'-Terminus and 3'-Terminus Partial Molecules PCR was used to directly synthesize the 5'-terminus 280 bp (fragment I) and 3'-terminus 268 bp (fragment II) partial molecules of the rSIFN-co (SEQ ID NO: 1) cDNA. There was a 41-bp overlap of the complementary nucleotide sequences between the 3' end of fragment I and the 5' end of fragment II.

(1) Chemical synthesis of oligodeoxynucleotide fragment
Oligomer A:
(SEQ ID NO: 6)
5'ATGTGCGACCTGCCGCAGACCCACTCCCTGGGTAACCGTCGTGCTCTG

ATCCTGCTGGCTCAGATGCGTCGTATCTCCCCGTTCTCCTGCCTGAAAGA

CCGTCACGAC3'

Oligomer B:
(SEQ ID NO: 7)
5'CTGAAAGACCGTCACGACTTCGGTTTCCCGCAGGAAGAATTCGACGGT

AACCAGTTCCAGAAAGCTCAGGCTATCTCCGTTCTGCACGAAATGATCCA

GCAGACCTTC3'

Oligomer C:
(SEQ ID NO: 8)
5'GCTGCTGGTACAGTTCGGTGTAGAATTTTTCCAGCAGGGATTCGTCCC

AAGCAGCGGAGGAGTCTTTGGTGGAGAACAGGTTGAAGGTCTGCTGGATC

ATTTC3'

Oligomer D:
(SEQ ID NO: 9)
5'ATCCCTGCTGGAAAAATTCTACACCGAACTGTACCAGCAGCTGAACGA

CCTGGAAGCTTGCGTTATCCAGGAAGTTGGTGTTGAAGAAACCCCGCTGA

TGAAC3'

Oligomer E:
(SEQ ID NO: 10)
5'GAAGAAACCCCGCTGATGAACGTTGACTCCATCCTGGCTGTTAAAAAA

TACTTCCAGCGTATCACCCTGTACCTGACCGAAAAAAAATACTCCCCGTG

CGCTTGGG3'

Oligomer F:
(SEQ ID NO: 11)
5'TTATTCTTTACGACGCAGACGTTCCTGCAGGTTGGTGGACAGGGAGAA

GGAACGCATGATTTCAGCACGAACAACTTCCCAAGCGCACGGGGAGTATT

TTTTTTCGGTCAGG3'

(2) PCR

PCR I for synthesizing rSIFN-co (SEQ ID NO: 1) 5'-terminus partial molecule: using oligodeoxynucleotide fragment B (SEQ ID NO: 7) as a template, oligodeoxynucleotide fragments A (SEQ ID NO: 6) and C (SEQ ID NO: 8) as primers, the rSIFN-co (SEQ ID NO: 1) 5'-terminus partial molecule with a length of 280 bp was synthesized by PCR.

| The PCR I reaction mixture is as follows: | (units: µl) (Total volume: 50 µl) |
|---|---|
| sterilized distilled water without nuclease | 39 |
| 10x Pfu buffer (Stratagene, La Jolla, CA, USA) | 5 |
| dNTP mixture (2.5 mmol/L for each dNTP) | 2 |
| Oligomer A primer (25 µmol/L) (SEQ ID NO: 6) | 1 |
| Oligomer C primer (25 µmol/L) (SEQ ID NO: 8) | 1 |
| Oligomer B template (1 µmol/L) (SEQ ID NO: 7) | 1 |
| Pfu DNA polymerase (Stratagene, La Jolla, CA, USA) (25 U/µl) | 1 |

PCR I reaction cycle: 95° C. 2 min→(95° C. 45 s→65° C. 1 min→72° C. 1 min) × 25 cycles→72° C. 10 min→4° C.

PCR II for synthesizing rSIFN-co (SEQ ID NO: 1) 3'-terminus partial molecule: using oligodeoxynucleotide fragment E (SEQ ID NO: 10) as a template, oligodeoxynucleotide fragments D (SEQ ID NO: 9) and F (SEQ ID NO: 11) as primers, the rSIFN-co (SEQ ID NO: 1) 3'-terminus partial molecule with a length of 268 bp was synthesized by PCR.

| The PCR II reaction mixture is as follows: | (units: µl) (Total volume: 50 µl) |
|---|---|
| sterilized distilled water without nuclease | 39 |
| 10x Pfu buffer (Stratagene, La Jolla, CA, USA) | 5 |
| dNTP mixture (2.5 mmol/L for each dNTP) | 2 |
| Oligomer D primer (25 µmol/L) (SEQ ID NO: 9) | 1 |
| Oligomer E primer (25 µmol/L) (SEQ ID NO: 10) | 1 |
| Oligomer F template (1 µmol/L) (SEQ ID NO: 11) | 1 |
| Pfu DNA polymerase (Stratagene, La Jolla, CA, USA) (25 U/µl) | 1 |

PCR II reaction condition and cycle: same as PCR I

Assembling of Full-Length rSIFN-Co (SEQ ID NO: 1) cDNA

Fragments I and II were assembled together to give the complete full-length cDNA sequence of rSIFN-co (SEQ ID NO: 1) using the overlapping and extending PCR method. Restriction enzyme sites Nde I and Pst I were introduced to the 5'-terminus and 3'-terminus of the sequence respectively, so that the rSIFN-co (SEQ ID NO: 1) cDNA sequence can be cloned into the plasmid.

(1) Chemically synthesized primers
Oligomer G:
                               (SEQ ID NO: 12)
5'ATCGGCCATATGTGCGACCTGCCGCAGACCC3'

Oligomer H:
                                 (SEQ ID NO: 13)
5'ACTGCCAGGCTGCAGTTATTCTTTACGACGCAGACGTTCC3'

(2) Overlapping and Extending PCR

| PCR reaction mixture | (units: μl)<br>(Total volume: 50 μl) |
|---|---|
| sterilized distilled water without nuclease | 38 |
| 10x Pfu buffer (Stratagene, La Jolla, CA, USA) | 5 |
| dNTP mixture (2.5 mmol/L for each dNTP) | 2 |
| primer G (25 μmol/L) (SEQ ID NO: 12) | 1 |
| primer H (25 μmol/L) (SEQ ID NO: 13) | 1 |
| *fragment I PCR product (1 μmol/L) | 1 |
| *fragment II PCR product (1 μmol/L) | 1 |
| Pfu DNA polymerase (Stratagene, La Jolla, CA, USA) (25 U/μl) | 1 |

*Separating and purifying the PCR product with STRATAPREP PCR purification kit produced by Stratagene (La Jolla, CA), then dissolving the PCR product into sterilized distilled water. PCR reaction condition and cycle: same as PCR I.

rSIFN-Co (SEQ ID NO: 1) Gene Cloning and Sequence Analysis

The pLac T7 plasmid was used as vector for cloning rSIFN-co (SEQ ID NO: 1) cDNA. The pLac T7 plasmid was reconstructed from the pBLUESCRIPT II KS(+) plasmid produced by Stratagene (La Jolla, Calif., USA).

PCR product containing rSIFN-co (SEQ ID NO: 1) full-length cDNA was purified with STRATAPREP PCR purification kit produced by Stratagene (La Jolla, Calif.), followed by digestion with Nde I and Pst I. At the same time, the pLac T7 plasmid was double digested with Nde I and Pst I. These double-digested DNA fragments were separated using 1% agarose gel electrophoresis followed by recovery and purification of a 507-bp rSIFN-co (SEQ ID NO: 1) DNA fragment and a 2.9-kb plasmid DNA fragment with Wizard DNA purification kit produced by Promega (Fitchburg, Wis., USA). These fragments were ligated by T4 DNA ligase to form a recombinant plasmid. DH5α competent cells (Gibco) were transformed with the recombinant plasmid. After culturing overnight at 37° C., the positive recombinant colony, named as pHY-1, was identified.

DNA sequencing was performed with SEQUITHERM™ Cycle Sequencing Kit following instruction provided by the manufacturer (Epicentre Technologies Ltd, Madison, Wis., USA) using the universal primer T7 and T3. The DNA sequencing result showed that the sequence was consistent with the theoretical design.

The sixteen N-terminus amino acids and four C-terminus amino acids of the purified recombinant rSIFN-co (SEQ ID NO: 1) were sequenced. The results were shown below:

N-terminus:
                                (SEQ ID NO: 14)
Cys-Asp-Leu-Pro-Gln-Thr-His-Ser-Leu-Gly-Asn-Arg-
Arg-Ala-Leu- MET at N-terminus was resected in mature protein.

C-terminus:
                               (SEQ ID NO: 15)
Arg-Arg-Lys-Glu-COOH

Full-length nucleotide sequence of rSIFN-co (SEQ ID NO: 1) is shown as SEQ ID NO:2 and the amino sequence is shown as SEQ ID NO:1.

Construction, Transformation, Enzyme Digestion and Identification, and Hereditary Stability of Expression Vector
Construction and Transformation of Expression Vector E. Coli expression vector pBAD18 was digested with Nde I and linearized, then fully digested with Xba I. Electrophoresis with 1% agarose gel and purification with QIAEX II kit (QIAGEN) were performed to give a 4.8-kb fragment from pBAD18 having been digested with Nde I and Xba I.

At the same time, the pHY-1 plasmid was double digested with NdeI and Xba I and, after separation with 1% agarose gel electrophoresis, a 715-bp fragment was purified. This fragment was ligated with the above 4.8-kb fragment from pBAD18 using T4 DNA ligase to produce the recombinant plasmid. The recombinant plasmid was used to transform DH5α-competent cells. The transformed cells were spread on LB-Amp agar plate, and then cultured overnight at 37° C.

Screening for Positive Clones

E. Coli. colonies from the above LB-plate were randomly chosen, and clones containing recombinant plasmid with full length rSIFN-co (SEQ ID NO: 1) cDNA were screened using endonuclease digestion and PCR analysis. One of the PCR positive recombinant plasmid was named pHY-5, and the strain containing pHY-5 plasmid was named PVIII. PVIII was amplified and stored at −80° C. with glycerol freezing medium for future use.

High Expression of rSIFN-Co (SEQ ID NO: 1) Gene in E. Coli LMG194

In the pHY-5 plasmid, rSIFN-co (SEQ ID NO: 1) gene was under the control of the strong promoter $P_{BAD}$ which is regulated by the AraC protein. AraC is a protein encoded by the AraC gene located in the same plasmid. In the absence of arabinose, the dimer of AraC binds to $O_2$ and $I_2$ forming a 210-bp loop. This conformation leads to a complete inhibition of transcription. In the presence of arabinose, the dimer of AraC is released from $O_2$ and binds to $I_1$ and $I_2$ eliminating the inhibition on transcription. Arabinose binding deactivates, represses and even activates the transcription of $P_{BAD}$ promoter, which stimulates $P_{BAD}$ to mediate high expression of rSIFN-co (SEQ ID NO: 1). rSIFN-co (SEQ ID NO: 1) expression level is more than 50% of the total bacterial protein.

2. Separation and Purification
(1) Preparation of Producing Strains

The E. coli strain LMG194 with expression vector pHY-5 was inoculated in LB culture medium, then shaken at 200 rpm overnight (about 18 h) at 37° C. To the medium was added 50% of 30% glycerine. After mixing, the medium was stored at −20° C. in 1 ml aliquots for use as the producing strain;

(2) Preparation of Grade-I Seed Strain

The producing strain was inoculated in LB culture medium (1 L containing Tryptone 10 g, Yeast extracts 5 g and NaCl 10 g) at a ratio of 1%, then shaken at 200 rpm overnight (about 18 h) at 37° C., for use as grade-I seed strain;

(3) Fermentation and Collection of the Strain

Grade-I seed strain was added to RM media (1 L containing Casein 20 g, $MgCl_2$ 1 mmol/L (0.203 g), $Na_2HPO_4$ 4 g, $KH_2PO_4$ 3 g, NaCl 0.5 g and $NH_4Cl$ 1 g) at a ratio of 10% and cultured at 37° C., pH 7.0. Fermentation was carried out until OD$_{600}$ reached about 2.0, then arabinose (20% solution) was added until a final concentration of 0.02% as an inductor; after 4 hours, the strain was collected and centrifuged to give a pellet;

(4) Preparation of Inclusion Bodies

The strain pellet was re-suspended with an appropriate amount of buffer A (100 mmol/L Tris-HCl, pH 7.5, 10 mmol/L EDTA, 100 mmol/L NaCl), and kept at −20° C. overnight. The strain was thawed and broken by a homogenizer, then centrifuged. The pellet was washed with buffer B (50 mmol/L Tris-HCl, pH 7.5, 1 mol/L Urea, 10 mmol/L EDTA, 0.5% Triton X-100), buffer C (50 mmol/L Tris-HCl, pH 7.5, 2 mol/L Urea, 10 mmol/L EDTA, 0.5% Triton X-100) and then precipitated; this was repeated once, and the pellet was then washed once with distilled water to give inclusion bodies.

(5) Renaturation Treatment

The inclusion body was dissolved in 6 mol/L Guanidine-HCl (or urea) to obtain a slightly cloudy denaturation solution, which was then centrifuged at a speed of 10000 rpm. The supernatant was collected and used to determine the protein concentration. The denaturation solution was added in three portions into a renaturation buffer (0.5 mol/L Arg, 150 mmol/L Tris-HCl, pH 7.5, 0.2 mmol/L EDTA) and then stirred continuously at 4° C. overnight (about 18 h). The solution was dialyzed sequentially with ten times its volume of 10 mol/L phosphate buffer (PB), 5 mol/L PB buffer and distilled water; After dialysis, the pH was adjusted with 2 mol/L HAc-NaAc (pH 5.0). The solution was left to stand and then filtered.

(6) HS Cation Column Chromatography

A column was prepared with 20 mmol/L HOAc-NaOAc (pH 5.0), loaded with the renaturation product obtained from step (5) at a speed of 30 ml/min, washed with 20 column volumes (CV) of 20 mmol/L HOAc-NaOAc (pH 5.0) to remove other proteins; washed with 5 CV of 20 mmol/L HOAc-NaOAc (pH 5.0) containing 0.15 mol/L NaCl to remove other proteins; then washed with 3 CV of 20 mmol/L HOAc-NaOAc (pH 5.0) containing 0.18 mol/L NaCl to remove other proteins. Finally, 20 mmol/L HOAc-NaOAc (pH 5.0) containing 0.25 mol/L NaCl was used to elute the target protein, thereby obtaining an HS-eluted protein solution.

(7) Copper Ion Affinity Chromatography (Chelating SEPHAROSE™ FAST FLOW)

The HS-eluted protein solution was added into PB buffer of 0.2 mol/L (pH 6.6). 4 mol/L NaCl was added to adjust the NaCl concentration to 1 mol/L and pH to 6.0, and the solution was ready for loading. A column was prepared with 50 mmol/L Na$_2$HPO$_4$ (pH 5.5) containing 1 mol/L NaCl, and loaded at a rate of 1 ml/min. The column was washed with 50 mmol/L Na$_2$HPO$_4$ (pH 5.0) to remove other proteins, then washed with 50 mmol/L Na$_2$HPO$_4$ (pH 4.0) to remove other proteins. Finally, 50 mmol/L Na$_2$HPO$_4$ (pH 3.6) was used to elute the target protein to obtain the chelating column-eluted target protein solution.

(8). HS Column Chromatography

The protein solution eluted from the chelating column was diluted 30 folds and its pH adjusted to 5.0, then loaded onto an HS column which was eluted with PB buffer, pH 7.0, containing 0.5 mol/L NaCl to give the recombinant interferon (Protein Stock Solution).

Example 2

Preparation of Recombinant Interferon

| Lyophilized injection formula (lyophilized powder) | |
|---|---|
| rSIFN-co (SEQ ID NO: 1) stock solution of the present invention | 34.5 µg/ml |
| phosphate buffer, pH 7.0 | 10 mmol/L |
| glycine | 0.4 mol/L |

Preparation Method:

Materials were weighed according to the formula, dissolved in sterile and pyrogen-free water for injection, sterilized by filtration through a membrane with 0.22 µm pores, and then stored at 6-10° C. Samples passed the sterility test and pyrogen test, before aliquoted into vials. Every vial contained a single dose of 0.3-0.5. All the aliquoted samples were lyophilized in a lyophilization machine.

| Aqueous injection formula | |
|---|---|
| rSIFN-co (SEQ ID NO: 1) stock solution of the present invention | 34.5 µg/ml |
| phosphate buffer, pH 7.0 | 25 mmol/L |
| NaCl | 0.4 mol/L |

Preparation Method:

Materials were weighed according to the formula, dissolved in sterile and pyrogen-free water for injection, sterilized by filtration through a membrane with 0.22 µm pores, and then stored at 6-10° C. Samples passed the sterility and pyrogen test before aliquoted into vials. Every vial contained a single dose of 0.3-0.5. Final products were stored in the dark at 2-10° C.

Example 3

In Vitro Study of rSIFN-Co (SEQ ID NO: 1) and INFERGEN® (SEQ ID NO: 1) Against Human Breast Cancer Cells This example describes the in vitro study of rSIFN-co (SEQ ID NO: 1) and INFERGEN® (SEQ ID NO: 1) against human breast cancer cells.

The present recombinant interferon (rSIFN-co (SEQ ID NO: 1)) and INFERGEN® (SEQ ID NO: 1) produced by Amgen (U.S.) were used as test drugs to study their effects on cell proliferation, apoptosis and expression of oncogenes in MCF-7 and resistant strain MCF-7/ADR.

A. Methods

1. Cell Culture

Human breast cancer cell line MCF-7 and adriamycin resistant strain MCF-7 (MCF-7/ADR) were cultured in 25 cm$^2$ or 75 cm$^2$ flasks respectively. After the cells covered the bottom of the flasks, they were trypsinized with 0.25% trypsin. Cells in the logarithmic growth phase were harvested for experiments.

2. Detecting the Effects of Different Concentrations of rSIFN-Co (SEQ ID NO: 1) on Cell Proliferation with the MTT Colorimetric Assay Experimental grouping: each cell strain was divided into 3 groups (with 11 small groups in total): rSIFN-co (SEQ ID NO: 1) group (0.02, 0.078, 0.313, 1.25, 5.0 μg/ml), INFERGEN® (SEQ ID NO: 1) group (0.02, 0.078, 0.313, 1.25, 5.0 μg/ml) and blank control group (RPMI1640 medium containing 10% fetal bovine serum (Sigma, America), also known as RPMI1640 complete medium). rSIFN-co (SEQ ID NO: 1) and INFERGEN® (SEQ ID NO: 1) were diluted into the desired concentrations (final ethanol concentration <1%) with the RPMI1640 complete medium, and stored at 4° C.

MCF-7 cells and MCF27/ADR cells in the logarithmic growth phase were diluted with RPMI1640 medium containing 10% fetal bovine serum to $1.25 \times 10^5$/ml cell suspension. Trypan blue method was used to ensure >95% cell viability. The cells were seeded in 96-well culture plates, 100 μL per well. 24 h, 48 h, 72 h after drugs were added according to the groupings mentioned above, conventional MTT assay was used to detect cell proliferation (absorbance detected with microplate reader at the wavelength of 490 nm). Each group had two wells as parallel samples. The experiment was repeated three times. The effects of different drug concentrations at different time on cell growth inhibition were calculated according to the following formula:

Cell Growth Inhibition Rate (%)=(Value of A in control group−Value of A in experimental group)/Value of A in control group×100%

3. Apoptosis Detection with Flow Cytometry (FCM)

Experimental grouping: each cell strain was divided into 3 groups: rSIFN-co (SEQ ID NO: 1) group (5 μg/mL), INFERGEN® (SEQ ID NO: 1) group (5 μg/mL), and blank control group (containing 10% calf serum RPMI1640 culture medium).

FCM detection: the cells were collected 48 h after drugs were added, then the cells were suspended as single cells and dyed with propidium iodide (PI). The apoptosis rate was assayed with the Elite Esp-based flow cytometer (Coulter, USA), and the results were analyzed with the software supplied with the equipment. These experiments were repeated 3 times.

4. Immunohistochemical Detection of Cellular Oncogene Expression

Experimental Grouping:

Each cell strain was divided into 3 groups. rSIFN-co (SEQ ID NO: 1) (5 μg/mL), INFERGEN® (SEQ ID NO: 1) (5 μg/mL), and RPMI1640 containing 10% fetal bovine serum were added to the medium of MCF-7 cell cultures. And rSIFN-co (SEQ ID NO: 1) (5 μg/mL), INFERGEN® (SEQ ID NO: 1) (5 μg/mL) and RPMI1640 containing 10% fetal bovine serum were also added to the medium of MCF-7/ADR cell cultures.

Immunohistochemical Detection of P53, Bcl-2, CerbB-2 Expression:

The coverslips were treated with acid, washed and sterilized under high pressure, and then placed in 6-well culture plates. The MCF-7 and MCF-7/ADR cells in logarithmic growth phase were digested into single cell suspensions with 0.25% trypsin. The cells were inoculated into 6-well plates, each well $1 \times 10^5$, and cultured at 37° C. in a $CO_2$ incubator for 24 h. After the cells adhered to the walls, drugs were added to each group. After 48 h, the coverslips were removed. Conventional immunohistochemical SABC staining was performed, all concentrations at 1:100.

Criteria for Evaluation of Results:

Staining results were determined according to the methods of Volm (Volm M, et al., European Journal of Cancer, 1997, 33 (3), 691-693), wherein yellow or brown particles appearing in cell nucleus (P53), cytoplasm (Bcl-2) or membrane (CerbB-2) were taken as positive results. Five fields of view (FOV) on each slide under high magnification (400×) were randomly selected, counting 200 cells per field. Two factors determined if there was expression in each group of cells. Scoring was done according to the intensity of staining for each cell, 0 point for no coloring, 1 point for light yellow, 2 points for brown, 3 points for tan. The average would be the average staining intensity for a group of cells. Percentage of positive cells: no 0 point for no staining; 1 point for <25% stained cells; 2 points for 25%-50%; 3 points for >50%. Sum of the two scores: 0 means negative expression; 2-4 means positive; 4-6 means strongly positive. These experiments were double blind (stainers and observers both do not know the grouping of the slides).

B. Statistical Methods

Statistical Analysis of Experimental Data:

All the experimental data were tested with the t test, variance analysis and rank correlation analysis using the SPSS 11.5 statistical package. P value <0.05 means that the difference was statistically significant.

C. Results

1. Effects on the Proliferation of MCF-7 and MCF-7/ADR Cells (1) MCF-7 Cells rSIFN-co (SEQ ID NO: 1) could inhibit the proliferation of MCF-7 cells. Each cell group treated with 0.02, 0.078, 0.313, 1.25, 5.0 μg/mL of rSIFN-co (SEQ ID NO: 1) and INFERGEN® (SEQ ID NO: 1) showed a significant decrease in its absorbance (OA) compared with the blank control groups. The inhibitory effects of rSIFN-co (SEQ ID NO: 1) and INFERGEN® (SEQ ID NO: 1) showed no significant differences at the early stages (24 h, 48 h) (P>0.05). After over 72 h of treatment, the % inhibition of rSIFN-co (SEQ ID NO: 1) was higher than that of INFERGEN® (SEQ ID NO: 1) at the same concentrations except at the lowest concentration of 0.02 μg/mL, the differences were statistically significant (P<0.05) (shown in Table 1-1).

TABLE 1-1

In vitro growth inhibition of the MCF-7 cells (%, n = 6)

| Dose (μg/mL) | | 24 h | 48 h | 72 h |
|---|---|---|---|---|
| INFERGEN® | 0.02 | 8.59 ± 2.26 | 8.28 ± 2.27 | 10.43 ± 3.59 |
| (SEQ ID NO: 1) | 0.078 | 13.84 ± 1.96 | 7.80 ± 2.01 | 9.47 ± 2.48 |
| | 0.312 | 15.53 ± 1.51 | 9.30 ± 3.28 | 13.39 ± 4.37 |
| | 1.25 | 17.58 ± 0.62 | 12.76 ± 1.63 | 14.41 ± 0.83 |
| | 5.0 | 19.98 ± 5.22 | 26.69 ± 3.47 | 24.93 ± 2.53 |
| rSIFN-co | 0.02 | 7.78 ± 4.32 | 11.60 ± 0.77 | 12.53 ± 0.70 |
| (SEQ ID NO: 1) | 0.078 | 15.71 ± 3.68 | 13.03 ± 3.27 | 16.77 ± 2.22* |
| | 0.312 | 17.49 ± 1.34 | 14.80 ± 2.40 | 22.73 ± 6.06* |
| | 1.25 | 20.07 ± 1.01 | 24.65 ± 2.18 | 27.62 ± 1.81* |
| | 5.0 | 24.79 ± 4.01 | 30.77 ± 3.09 | 44.75 ± 2.32* |

*P < 0.05, vs. INFERGEN® (SEQ ID NO: 1)

(2) MCF-7/ADR Cells rSIFN-co (SEQ ID NO: 1) could inhibit the proliferation of MCF-7/ADR cells. Each cell group treated with 0.02, 0.078, 0.313, 1.25, 5.0 μg/mL of rSIFN-co (SEQ ID NO: 1) and INFERGEN® (SEQ ID NO: 1) showed a significant decrease in its absorbance (OA) compared with the control groups. The inhibitory effect of rSIFN-co (SEQ ID NO: 1) was higher than that of INFERGEN® (SEQ ID NO: 1) at the same concentrations except at the lowest concentration of 0.02 μg/mL as shown by analysis of variance, the differences were statistically significant (P <0.05) (shown in Table 1-2).

TABLE 1-2

In vitro growth inhibition of MCF-7/ADR (%, n = 6)

| Dose (µg/mL) | | 24 h | 48 h | 72 h |
|---|---|---|---|---|
| INFERGEN® | 0.02 | 16.36 ± 0.96 | 24.97 ± 0.33 | 28.87 ± 6.20 |
| (SEQ ID | 0.078 | 23.01 ± 2.11 | 28.04 ± 0.85 | 30.90 ± 3.34 |
| NO: 1) | 0.312 | 26.69 ± 2.49 | 29.64 ± 2.78 | 43.02 ± 2.11 |
| | 1.25 | 31.64 ± 1.17 | 49.87 ± 1.74 | 46.68 ± 2.42 |
| | 5.0 | 37.61 ± 0.96 | 57.24 ± 0.80 | 62.52 ± 4.01 |
| rSIFN-co | 0.02 | 16.24 ± 2.30 | 34.20 ± 1.80 | 34.80 ± 1.38 |
| (SEQ ID | 0.078 | 29.70 ± 1.40* | 33.92 ± 1.35* | 48.71 ± 1.04* |
| NO: 1) | 0.312 | 33.46 ± 1.04* | 41.52 ± 5.27* | 47.71 ± 0.40* |
| | 1.25 | 38.80 ± 2.16* | 52.50 ± 0.73* | 52.70 ± 1.01* |
| | 5.0 | 48.36 ± 6.52* | 67.65 ± 4.40* | 69.44 ± 0.95* |

*P < 0.05, vs. INFERGEN ® (SEQ ID NO: 1)

2. Effect on Apoptosis of MCF-7 and MCF-7/ADR Cells

Compared with the control group, 5 µg/mL of rSIFN-co (SEQ ID NO: 1) and INFERGEN® (SEQ ID NO: 1) induced apoptosis of MCF-7 and MCF-7/ADR cells after treatment for 48 h, the differences were statistically significant (P<0.01). rSIFN-co (SEQ ID NO: 1) showed stronger apoptosis-inducing activities on MCF-7 and MCF-7/ADR than INFERGEN® (SEQ ID NO: 1) at the same concentrations, the differences were statistically significant (P<0.01) (shown in Table 1-3).

TABLE 1-3

The % apoptosis of MCF-7 after 48 h treatment (%, n = 6)

| | Blank control | INFERGEN ® (SEQ ID NO: 1) | rSIFN-co (SEQ ID NO: 1) |
|---|---|---|---|
| MCF-7 | 7.27 ± 1.19 | 19.67 ± 0.95* | 23.10 ± 0.80*▲ |
| MCF-7/ADR | 8.40 ± 0.70 | 34.80 ± 3.20* | 65.63 ± 4.60*▲ |

*P < 0.01, vs. control;
▲P < 0.01, vs. INFERGEN ® (SEQ ID NO: 1)

3. Effect on Expression of P53, CerbB-2 and Bcl-2 in Each Cell Group rSIFN-co (SEQ ID NO: 1) down-regulated the expression of P53 in MCF-7 cells compared with the control group, the difference was statistically significant (P<0.05). Although INFERGEN® (SEQ ID NO: 1) decreased the expression of P53, the decrease was not significantly different (P >0.05) compared with the control group. Both rSIFN-co (SEQ ID NO: 1) and INFERGEN® (SEQ ID NO: 1) down-regulated the expression of P53 in MCF-7/ADR compared with the control group, the difference was statistically significant (P<0.05), but rSIFN-co (SEQ ID NO: 1) and INFERGEN® (SEQ ID NO: 1) at the same concentration showed no significant difference between them (P >0.05).

rSIFN-co (SEQ ID NO: 1) down-regulated the expression of CerbB-2 in both MCF-7 and MCF-7/ADR as compared with the control group, the difference was statistically significant (P<0.01). CerbB-2 expression was decreased after INFERGEN (SEQ ID NO: 1) treatment; however, the decrease was not significantly different (P >0.05) compared with the control group.

rSIFN-co (SEQ ID NO: 1) and INFERGEN® (SEQ ID NO: 1) both up-regulated the expression of Bcl-2 in MCF-7 compared with the control group, the difference was statistically significant (P<0.01), but rSIFN-co (SEQ ID NO: 1) showed stronger activities than INFERGEN® (SEQ ID NO: 1) at the same concentration, the difference was statistically significant (P=0.001). rSIFN-co (SEQ ID NO: 1) and INFERGEN® (SEQ ID NO: 1) both up-regulated the expression of Bcl-2 in MCF-7/ADR compared with the control group, the difference was statistically significant (P<0.01). Results are shown in Table 1-4.

TABLE 1-4

Effect on the expression of P53, CerbB-2 and Bcl-2 in MCF-7 48 h after treatment (n = 5).

| | Groups | Blank control | INFERGEN ® (SEQ ID NO: 1) | rSIFN-co (SEQ ID NO: 1) |
|---|---|---|---|---|
| P53 | MCF-7 | 4.17 ± 0.0120 | 3.78 ± 0.0851 | 2.62 ± 0.0208★ |
| | MCF-7/ADR | 4.09 ± 0.0361 | 2.68 ± 0.0100★ | 2.60 ± 0.0089★ |
| CerbB-2 | MCF-7 | 4.08 ± 0.0322 | 3.15 ± 0.3469 | 2.61 ± 0.0120* |
| | MCF-7/ADR | 4.06 ± 0.0030 | 3.82 ± 0.0404 | 3.70 ± 0.0291* |
| Bcl-2 | MCF-7 | 2.59 ± 0.0153 | 3.93 ± 0.0306* | 4.02 ± 0.0252* |
| | MCF-7/ADR | 3.64 ± 0.0252 | 3.93 ± 0.0176* | 4.02 ± 0.0145* |

★P < 0.05,
*P < 0.01, vs. control.

Example 4

In Vitro Study of rSIFN-Co (SEQ ID NO: 1) and INFERGEN® (SEQ ID NO: 1) Against Cervical Cancer Cell This example describes the in vitro study of rSIFN-co (SEQ ID NO: 1) and INFERGEN® (SEQ ID NO: 1) in inhibiting the growth and inducing apoptosis of cervical cancer cell.

The present recombinant interferon (rSIFN-co (SEQ ID NO: 1)) and INFERGEN® (SEQ ID NO: 1) produced by Amgen (U.S.) were used as test drugs to study their effects on growth inhibition and apoptosis induction of cervical cancer Caski cells (HPV16+).

A. Methods

1. Caski Cells Growth Inhibition Test 1.1 Cell Culture and Grouping

Drug samples were diluted with RPMI-1640 culture medium containing 10% fetal bovine serum. Cervical cancer Caski cells were cultured in a 96-well plate. Cells were prepared as single cell suspension using culture medium with a cell concentration of $1 \times 10^5$/ml. To each well was added 100 µl of cell suspension. rSIFN-co (SEQ ID NO: 1) and INFERGEN® (SEQ ID NO: 1) were added to the plate at a concentration gradient of 0.156 µg/ml, 0.625 µg/ml, 2.5 µg/ml and 10 µg/ml. RPMI-1640 medium containing 10% fetal bovine serum was used as control group. Each concentration was triplicated. The cells were cultured at 37° C. with 5% $CO_2$ in an incubator for 72 h.

1.2 Cell Growth Inhibition Test by MTT Method

MTT reagent (Sigma Company, U.S.) was prepared at 5 mg/ml, and 10 µl MTT reagent was added to each well. The plate was shaken gently to homogenize the reagent, incubated at 37° C. with 5% $CO_2$ for 4 h, whereupon blue crystals could be seen at the bottom of the wells. The supernatant was removed, and 100 µl of DMSO were added to each well, then the absorbance at 570 nm was measured with a microplate reader after the blue crystals dissolved at room temperature.

1.3 Calculation of Cell Growth Inhibition $$\text{Cell growth inhibition} = \left(1 - \frac{OD \text{ value of sample well}}{OD \text{ value of control well}}\right) \times 100\%$$

2. Apoptosis Test on Caski Cells

2.1 Cell Culture and Grouping

The Caski cells were divided into 7 groups and cultured in RPMI-1640 medium containing 10% inactivated fetal bovine serum in a 96-well plate. Group 1 was cultured for 72 h as control group. Groups 2-4 were cultured with different concentrations of rSIFN-co (SEQ ID NO: 1): 0.156 µg/ml, 0.625 µg/ml, 2.5 µg/ml. Groups 5-7 were cultured with different concentrations of INFERGEN® (SEQ ID NO: 1): 0.156 µg/ml, 0.625 µg/ml, 2.5 µg/ml.

2.2 Apoptosis Rate of Caski Cells Determined by Flow Cytometry (FCM)

Each group of cells were centrifuged at 1000 r/min for 5 min. The supernatant was removed, and the cells were tested for apoptosis with Annexin V/PI double dying method. Each specimen containing $1 \times 10^6$ viable cells was washed once with incubation buffer and centrifuged at 1000 r/min for 5 min. The cells were re-suspended with 100 µl marker solution, incubated at room temperature for 15 min in the dark, and centrifuged at 1000 r/min for 5 min to precipitate the cells. The cells were washed once with an incubation buffer, triturated with a fluorescent solution, then incubated at 4° C. for 20 min. in the dark, while shaken frequently, before being tested with FCM.

B. Statistical Analysis

All quantitative analysis data were expressed as $\bar{x} \pm s$. Variance analysis was used to analyze the variance between different drugs and different concentrations, and the statistical analysis was performed with the SPSS 14.0 software package.

C. Results

1. Caski Cells Growth Inhibition Test

Both rSIFN-co (SEQ ID NO: 1) and INFERGEN® (SEQ ID NO: 1) inhibited the growth of Caski cells, and this effect increased with increasing concentrations of interferons. The effect of rSIFN-co (SEQ ID NO: 1) was greater than that of INFERGEN® (SEQ ID NO: 1) in groups of 0.625, 2.5 and 10 µg/ml. The differences displayed in Table 2-1 showed statistical significance (P<0.01):

TABLE 2-1

Inhibitory effect on Caski cells ($\bar{x} \pm s$)

| Drug concentration (µg/ml) | Cell growth inhibition rate | |
|---|---|---|
| | rSIFN-co (SEQ ID NO: 1) | INFERGEN® (SEQ ID NO: 1) |
| 0.156 | 8.6 ± 2.1 | 7.3 ± 2.2 |
| 0.625 | 17.6 ± 3.3[1] | 7.4 ± 4.0 |
| 2.5 | 42.7 ± 1.5[1] | 9.7 ± 1.6 |
| 10 | 67.3 ± 4.4[1] | 53.0 ± 5.8 |

[1]Compared with INFERGEN® (SEQ ID NO: 1) at the same concentration, P < 0.01

2. Inducing Apoptosis in Caski Cells

Both rSIFN-co (SEQ ID NO: 1) and INFERGEN® (SEQ ID NO: 1) induced apoptosis in Caski cells, and the effect was positively correlated with increasing concentrations of interferons. The effect of rSIFN-co (SEQ ID NO: 1) at low concentration (0.156 µg/ml) was higher than that of INFERGEN® (SEQ ID NO: 1). The difference displayed in Table 2-2, showed statistical significance (P<0.01):

TABLE 2-2

Apoptotic effect on Caski cells ($\bar{x} \pm s$)

| Drug concentration (µg/ml) | Cell growth inhibition rate | |
|---|---|---|
| | rSIFN-co (SEQ ID NO: 1) | INFERGEN® (SEQ ID NO: 1) |
| 0 | 21.3 ± 3.9 | 21.3 ± 3.9 |
| 0.156 | 53.5 ± 4.6[1,2] | 47.6 ± 3.1[1] |
| 0.625 | 64.9 ± 3.3[1] | 67.1 ± 3.6[1] |
| 2.5 | 74.4 ± 1.3[1] | 72.0 ± 2.6[1] |

[1]Compared with controls, P < 0.01.
[2]Compared with INFERGEN® (SEQ ID NO: 1) at the same concentration, P < 0.01.

Example 5

Study of the Pharmacokinetics and Bioequivalence of rSIFN-Co (SEQ ID NO: 1) and INFERGEN® (SEQ ID NO: 1)

This example describes the research work on the pharmacokinetics and bioequivalence between rSIFN-co (SEQ ID NO: 1) and INFERGEN® (SEQ ID NO: 1). The present recombinant interferon rSIFN-co (SEQ ID NO: 1) and INFERGEN® (SEQ ID NO: 1) produced by Amgen (U.S.) were taken as test drugs to compare their pharmacokinetics and bioequivalence.

It is difficult to undertake pharmacokinetics study of interferon in healthy people. As the level of medicinal interferon in blood plasma is very low after injection, enzyme-linked immunosorbent assay (ELISA) or virus cytopathic inhibition assay can hardly measure it directly in the serum of healthy adults. Currently, the detection marker for pharmacokinetics study of interferon is generally 2',5'-OAS (2-5A oligonucleotidase), which is a product induced by interferon, and also an indicator of its efficacy.

A. Subject and Method

1. Subject

There were 18 healthy male volunteers with an average age of 22.8±1.4, height of 170±5.0 cm, BMI of 20.5±2.4, and body weight of 59.4±7.2 kg. Subjects were determined to be normal by a comprehensive physical examination, laboratory tests (including hematology, urine, liver and kidney functions) and electrocardiogram. The subjects did not use any drugs within 4 weeks prior to the test, and did not use any drugs known to damage the organs within 3 months prior to the test. They had no history of allergy to the test drugs; and they volunteered for the test and signed an informed agreement.

2. Method

The experimental scheme was approved by the Medical Ethics Committee of West China Hospital, Sichuan University, operated in accordance with relevant guidelines of GCP of the PRC.

2.1 Materials

Reagents:

Lyophilized powder of recombinant interferon for injection (Test preparations, i.e. the recombinant interferon rSIFN-co (SEQ ID NO: 1) of the present invention, 9 μg/vial). Comparison preparation: INFERGEN® (SEQ ID NO: 1) injection (compare reagent, 9 μg/vial) produced by Amgen (U.S.).

2-5A Kit: Eiken' Radioimmunoassay Kit was supplied by Eiken Chemical Co., LTD. The Kit includes: (1) $I^{125}$-labelled 2',5'-OAS, (2) Anti-2',5'-OAS serum, (3) 2',5'-OAS Standard vial (each contains 0, 10, 30, 90, 270 or 810 pmol/dL 2',5'-OAS), (4) Buffer, (5) Blank serum, (6) Poly(I)-poly(C) agarose gel, (7) ATP, (8) Mercaptoethanol, and (9) Quality control serum.

2.2 Experimental Design and Dosing Methods

Using the randomized controlled crossover trial, 18 subjects were randomly divided into A and B groups, nine in each group, separate subcutaneous injections of 9 μg rSIFN-co (SEQ ID NO: 1) and 9 μg INFERGEN® (SEQ ID NO: 1) was made alternately in two cycles, one week of wash period.

Fast from 8 pm the day before the test until 2 h after dose the next morning, subcutaneous injection was taken in brachial deltoid muscle at 7:00 am. All the subjects were required to have standard meals (food without high fat), and forbidden to smoke, drink alcohol, tea, coffee beverages, and refrain from strenuous exercises. All other drugs were banned during the tests.

2.3 Collecting and Testing of Blood Samples 4 ml of blood samples were drawn before dosing, while 3.5 ml of blood samples were drawn from the elbow vein opposite the injection site at 2, 6, 12, 18, 22, 24, 26, 30, 34, 38, 42 and 48 hours after the injection; the samples were centrifuged immediately, and the resulting serum preserved at −20° C. until they were tested for the 2',5'-OAS concentration.

3. Statistical Methods

Using the DAS ver1.0 statistical software, test Test preparation and compare preparation were compared by the paired t test using the statistical software DAS ver1.0.

B. Results

According toBased on the measured serum 2',5'-OAS concentration of the blood samples, the mean enzyme concentration-time curves were plotted in FIG. 16.

As shown in FIG. 16, after subcutaneous injection with 9 μg of rSIFN-co (SEQ ID NO: 1) or 9 μg of INFERGEN® (SEQ ID NO: 1), the two enzyme concentration-time curves had basically the same trend; but after subcutaneous injection of rSIFN-co (SEQ ID NO: 1), the concentration at the peak of the enzyme concentration-time curve was significantly higher than that of INFERGEN® (SEQ ID NO: 1).

The relative bioavailability (F) of test preparation (rSIFN-co (SEQ ID NO: 1)) compared to the compare preparation (INFERGEN® (SEQ ID NO: 1)) was calculated by the following formula:

$$F = \left(\frac{AUC_{test\ preparation}}{AUC_{compare\ preparation}}\right) \times \left(\frac{compare\ preparation\ dosage}{test\ preparation\ dosage}\right) \times 100\%$$

The results showed that the relative bioavailability of rSIFN-co (SEQ ID NO: 1) (F0~48) was 125.4%. The Tmax difference between test preparation and compare preparation was not statistically significant (t=1.458, P=0.163). The difference between AUC0-48 and Cmax was statistically significant (t=2.730, P=0.014; t=2.347, P=0.031), and test preparation was higher than the compare preparation.

In addition, the INFERGEN® (SEQ ID NO: 1) group was more severe than the rSIFN-co (SEQ ID NO: 1) group in terms of the incidence, extent and duration of the adverse reactions that were compared.

C. Conclusion (1) After subcutaneous injection, both rSIFN-co (SEQ ID NO: 1) and INFERGEN® (SEQ ID NO: 1) induced the production of 2',5'-OAS. The pharmacokinetics curves of the two drugs were of the same trend, and the main pharmacokinetics parameters showed no statistical difference.

(2) Both the $C_{max}$ and $AUC_{0-48}$ of 2',5'-OAS induced by rSIFN-co (SEQ ID NO: 1) were higher than that of INFERGEN® (SEQ ID NO: 1), indicating that the efficacy of rSIFN-co (SEQ ID NO: 1) might be better than INFERGEN® (SEQ ID NO: 1) under the same dosage.

(3) The INFERGEN® (SEQ ID NO: 1) group was more severe than the rSIFN-co (SEQ ID NO: 1) group in the incidence, extent and duration of the adverse reactions that were compared.

(4) It was discovered, after plotting the mean enzyme concentration-time curves based on the the serum 2',5' oligoadenylate synthase (2',5'-OAS) concentration measured at different times, the 2',5'-OAS concentration induced by rSIFN-co (SEQ ID NO: 1) generally had double peaks and the area under the curve was significantly greater than that obtained by INFERGEN® (SEQ ID NO: 1) when each was separately injected under the same conditions. An increment in the area under the curve was not correlated to an increase in the incidence and/or the occurrence degree of the adverse reactions.

Example 6

Crystallization of Recombinant Interferon

The preparation of high-quality rSIFN-co (SEQ ID NO: 1) protein monocrystal is a prerequisite for determining its crystal structure. The rSIFN-co (SEQ ID NO: 1) used for crystal growth was derived from the said rSIFN-co (SEQ ID NO: 1) of the present invention. The preparation method, technical process, crystallization conditions and crystallographic parameters of the rSIFN-co (SEQ ID NO: 1) monocrystal were as follow.

lyophilized powder of the rSIFN-co (SEQ ID NO: 1) in the present invention was dissolved in pure water and stored under −20° C. at an initial protein concentration of 0.42 mg/ml. Prior to crystallization, the rSIFN-co (SEQ ID NO: 1) protein samples were concentrated to 3-3.5 mg/ml and immediately used for the crystal growth experiments. The hanging drop vapor diffusion method was used for the crystallization process held at room temperature (293K).

Figure 1:
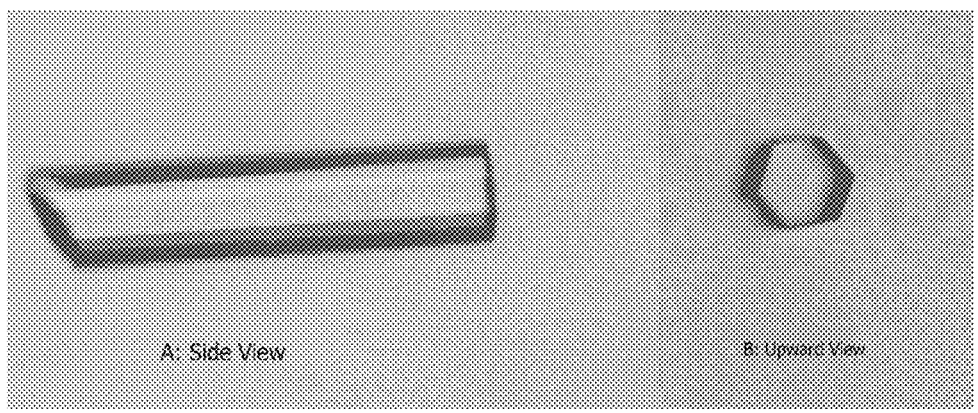
FIG. 1 shows a monocrystal of the recombinant interferon (rSIFN-co (SEQ ID NO: 1)) of the present invention used in crystal structure analysis.

In the initial crystallization studies, microcrystalline rSIFN-co (SEQ ID NO: 1) appeared under different sets of conditions, but it was difficult to obtain high-quality monocrystal that could be used for X-ray diffraction analysis of sufficient resolution. After optimization of a large number of crystallization conditions, it was found that the best quality crystals were obtained using the crystallization solution made up of the following: 1.2 M LiSO$_4$, 0.1 M CAPS (3-(cyclohexylamino)-1-propanesulfonic acid), pH 11.1 and 0.02 M MgCl$_2$. A good monocrystal of rSIFN-co (SEQ ID NO: 1) protein was obtained after the crystallization solution prepared with this formula was left standing for 3 days to 1 week. The monocrystal was of the tripartite crystal type, and had a size of 0.42×0.08×0.08 mm. The rSIFN-co (SEQ ID NO: 1) protein crystal used in the X-ray diffraction analysis of the crystal structure is shown in FIG. 1.

Example 7

Analysis of the Crystal X-Ray Diffraction Data

Figure 2:
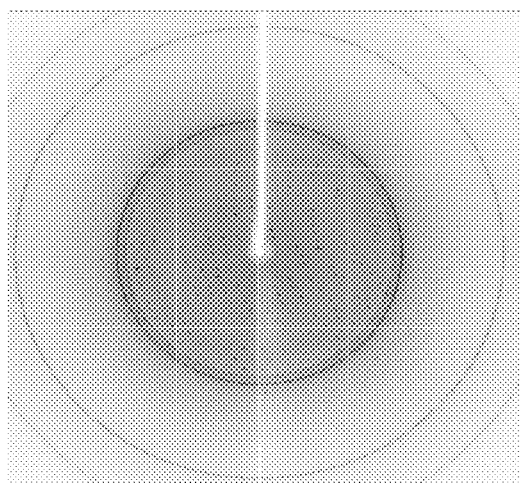
FIG. 2 shows an X-ray diffractogram of the rSIFN-co (SEQ ID NO: 1) crystal (2.6 Å resolution).

Collection of Crystal Diffraction Data:

Data collection was conducted under low temperature condition (100K) using the synchrotron radiation from beamline BL5A at a photon factory in Tsukuba, Japan. The crystal diffraction data was collected using the following steps:

(1) Under a microscope, a crystal placement tool was carefully used for transferring a crystal from the mother liquor to a loop at the top part of the tool;

(2) Employing the Flash-Cooling technique, the loop containing the crystal was quickly soaked in paraffin oil (Hampton Research, U.S.), which acted as an antifreeze reagent, for several seconds and quickly transferred to the goniometer head of the diffraction apparatus. At this time, the crystal will be instantaneously in a low-temperature nitrogen stream (100K) such that data collection was conducted under the low temperature of 100K;

(3) Data collection was started after setting the required parameters; the light source wavelength was 1.0 Å, the detector was a ADSC Quantum 315 CCD (charge-coupled device) and the crystal-to-detector distance was 310 mm. The data was collected using the oscillation method, and for every image the oscillation angle was 1°, the exposure time was 12 seconds, and a total of 110 images were collected (FIG. 2).

Processing and Analysis of the Diffraction Data:

The complete set of diffraction data collected had to be processed and analyzed using the CCP4 program package before the set of intuitional diffraction images (FIG. 2) originally obtained in the diffraction experiment could be used for quality assessment of the diffraction data and structural analysis of the crystal. This process consisted of: 1) indexing: transforming the diffraction data to crystallography index (h, k, l), and calculating unit cell parameters and space group; 2) parameter modification: refining parameters such as the unit cell parameters, crystal-to-detector distance and angle, and degree of mosaicity etc; 3) integration: obtaining the intensity information from the diffraction spots; 4) merging data: merging all the diffraction spots that arose due to symmetry or are duplicated to generate a complete set of data with only independent diffraction spots; 5) transforming the intensity data into structure amplitudes. The details on the collection of rSIFN-co (SEQ ID NO: 1) crystal diffraction data and results of the analysis are shown in Table 3.

TABLE 3

RDetails on the collection of rSIFN-co (SEQ ID NO: 1) crystal diffraction data and results of the analysis

| Data acquisition conditions | |
| --- | --- |
| X-ray source | PF, BL-5A |
| Wavelength (Å) | 1.0 |
| Detector | ADSC Quantum 315 CCD |
| Distance (mm) | 310 |
| Temperature (K) | 100 |
| Data acquisition statistics | |
| Space group (number of molecules/asymmetric unit) | P3$_1$21(2) |
| Cell parameters | |
| a = b (Å) | 77.920 |
| c (Å) | 125.935 |
| α = β = 90°, γ = 120° | |
| Solvent content (%) | 56.7 |
| Resolution coverage (Å) | 67.58-2.60 |
| Diffraction spots (I/σ (I) > 0) | 86556 |
| Unique diffraction spot (I/σ (I) > 0) | 14052 |
| Outermost shell | 2.74-2.60 |
| Symmetry related diffraction spot quality factor R (%): | |
| Overall, (Outermost shell) | 7.1 (25.8) |
| Signal to noise ratio | 21.2 (4.5) |
| Intigrity(%): overall, (Outermost shell) | 99.5 (100.0) |
| Redundancy: overall, (Outermost shell) | 6.2 (6.5) |

Example 8

Analysis of the Crystal Structure

Determination of the Crystal Diffraction Phase and Construction of the rSIFN-Co (SEQ ID NO: 1) Initial Molecular Structural Model The molecular replacement method was adopted to solve for the rSIFN-co (SEQ ID NO: 1) crystal structure; the crystal structure (PDB number 1B5L) of sheep INF-τ (54% sequence homology to rSIFN-co (SEQ ID NO: 1)) was selected as the homologous structural model. The software program PHASER was used for computing its rotation function and translation function which was then used to presume the location and orientation of the rSIFN-co (SEQ ID NO: 1) molecule in a unit cell. Based on the Laue groups and the systematic absence law, its space group was determined to be P3$_1$21 and the molecular model was correspondingly modified (viz. preserving residues 13-25, 37-69, 79-101, 114-151 in the 1B5L structure); results calculated from this model were as follow: Z-score was 15.71, IL-gain was 307.79, Clash was 0. The molecules heaped up reasonably in a unit cell, and IL-gain gradually rose during the process of molecular replacement. This indicated that an exact solution was obtained and the initial phase of each diffraction point had been determined. In turn, the mtz generated by PHASER, possessing the initial phases, was used for building the electron density map using FFT. The initial molecular structural model obtained was well-matched to the electron density map, demonstrating that the exact phase solution of all the diffraction points of rSIFN-co (SEQ ID NO: 1) had been obtained. Based on the results above, the rSIFN-co (SEQ ID NO: 1) initial molecular structural model was built.

Rectification of the rSIFN-Co (SEQ ID NO: 1) Structural Model

With the aim of obtaining an accurate rSIFN-co (SEQ ID NO: 1) molecular structural model, the coordinates and temperature factors of all the non-hydrogen atoms in the rSIFN-co (SEQ ID NO: 1) initial molecular structural model underwent iterative refinement by using molecular modeling techniques and a computerized optimization program.

program CNS1.1 was used for structural refinement using phaseless population data; 10% of these data was randomly extracted for use as the testing set, and the same randomly extracted testing set was kept throughout. All the atoms in the structural model participated in the refinement, and each atom possessed 4 refining parameters, including coordinates (x, y, z) and isotropic temperature factor B. Computerized automatic refinement and manual adjustment or building of the model (using software O) took place alternately during the entire refinement process. Restrictive NCS was used at the beginning of the refinement, and was disused once the structural adjustment was basically accomplished. When $R_{work}$ factor (<0.30) and $R_{free}$ factor practically stopped descending, water and solvent molecules were added to the structure to complete the structure rectification. The major indices for the rectification were a $R_{work}$ value of 0.250 and a $R_{free}$ value of 0.286. The major indices of the final rSIFN-co (SEQ ID NO: 1) structure rectification are listed in Table 4. The resulting atomic coordinates of rSIFN-co (SEQ ID NO: 1) are shown in Table 7.

TABLE 4

Major parameter indices and qualitative statistical results of rSIFN-co (SEQ ID NO: 1) molecular structure

| | |
|---|---|
| Resolution ratio range(outermost shell) (Å) | 20.0-2.6 |
| Cutoff point of signal-to-noise | 0.0 |
| Crystallographic incongruent indexes (outermost shell) (%) | 25.0 (36.3) |
| Free incongruent indexes[1] (outermost shell) (%) | 28.6 (40.5) |
| Component of asymmetric unit | |
| Number of all the residues | 293 |
| Number of A chain residues (unbuilt residues) | 146 (20) |
| Number of B chain residues (unbuilt residues) | 147 (19) |
| Molecular number of water and solvent | 123 |
| Root mean square deviation[2] | |
| Bond length (Å) | 0.007 |
| Bond angle (°) | 1.379 |
| Dihedral angle (°) | 19.234 |
| Unfit angle (°) | 0.844 |
| Wilson temperature factor (Å$^2$) | 70.7 |
| Average temperature factor (Å$^2$) | |
| Number of all the atoms (2403) | 61.76 |
| Atomic number of protein (2254) | 61.11 |
| A chain of protein (1120) | 58.39 |
| B chain of protein (1134) | 63.79 |
| water and solvent (149) | 68.21 |
| Statistics of Ramachandran plot (%)[3] | |
| Optimal regions | 90.6 |
| Additionally allowed regions | 9.1 |
| common allowed regions | 0.4 |
| Disallowed regions | 0.0 |

[1]Free incongruent indices were calculated using 10% of the total diffraction points unmodified;
[2]Root mean square deviation was calculated using relative standard bond length/bond angle;
[3]Statistics of Ramachandran plot used software PROCHECK.

Example 9

Figure 3:
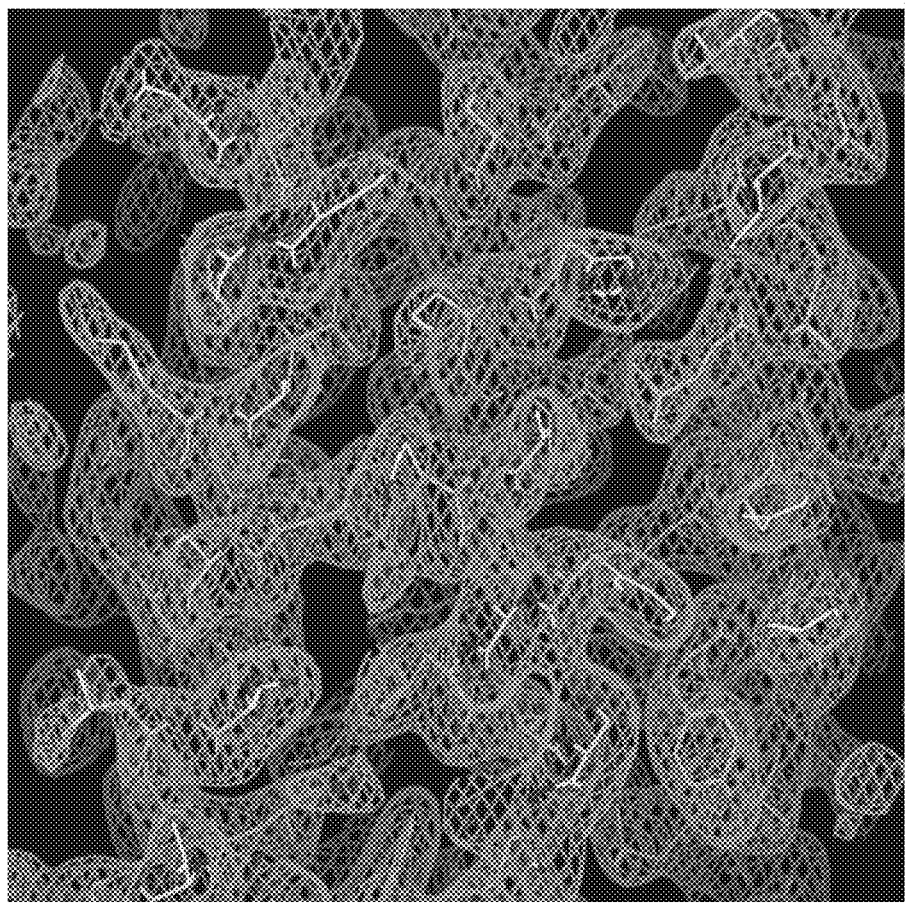
FIG. 3 shows a partial 1.0σ electron-density map of 2Fo-Fc format within the crystal structure of rSIFN-co (SEQ ID NO: 1).

Quality Characterization of the Quality of the rSIFN-Co (SEQ ID NO: 1) Molecular Structural Model Quality Characterization of the Quality of the rSIFN-Co (SEQ ID NO: 1) Molecular Structural Model The model: rSIFN-co (SEQ ID NO: 1) was displayed intuitively, clearly and accurately. FIG. 3 is a typical electron density map matching to the structure of the amino acid residues in a rSIFN-co (SEQ ID NO: 1) molecule; the spatial location and orientation of each amino acid residue could be clearly identified.

Figure 4:
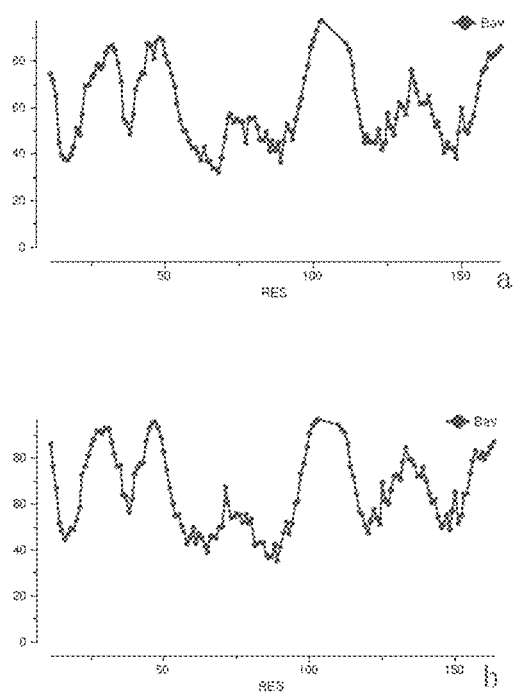
FIG. 4 shows a distribution map of the average temperature factors along the amino acid residues for all the atoms of rSIFN-co (SEQ ID NO: 1). (a) A chain; (b) B chain.

(2) Distribution map of the average temperature factors associated with the amino acid residues. (FIG. 4)

Figure 5:
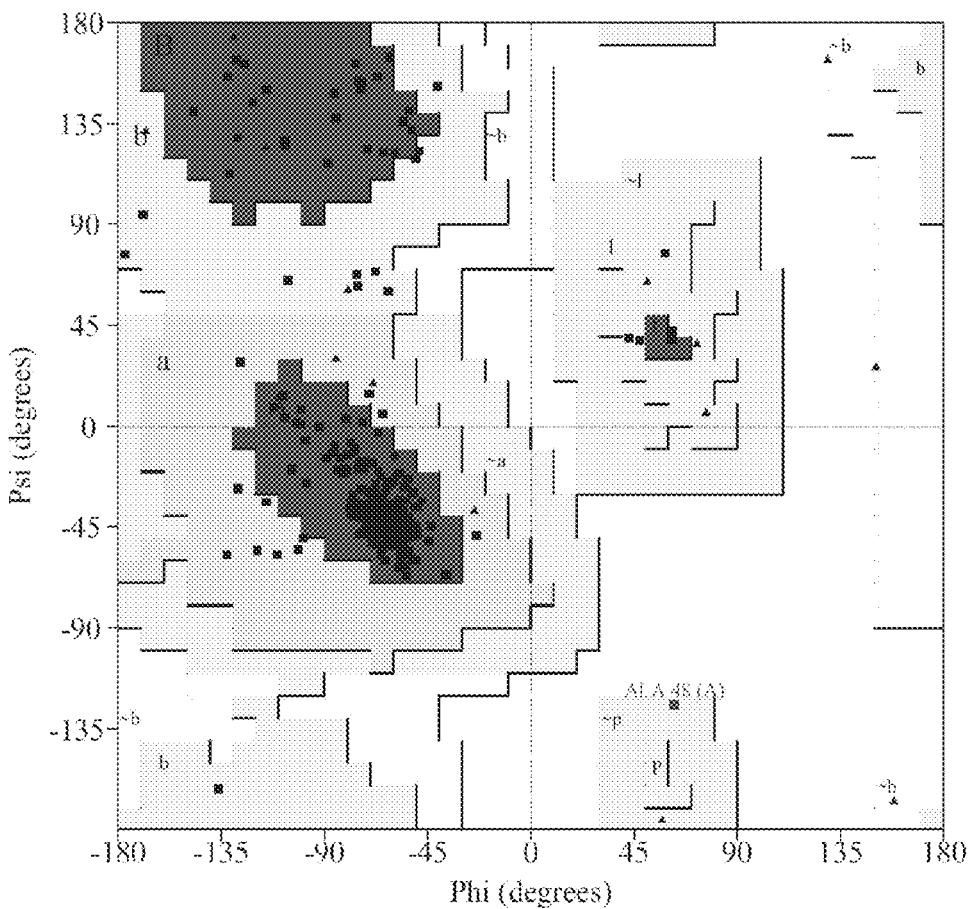
FIG. 5 shows the (Φ, Ψ) value distribution on the Ramachandran plot of all the amino acid residues in the model of the rSIFN-co (SEQ ID NO: 1) protein molecular structure. Based on an analysis of 118 structures with resolution of at least 2.0 Å and R-factor no greater than 20%, a good quality model would be expected to have over 90% in the most favoured regions; the statistical data as follows.

(3) Stereochemical rationality of the rSIFN-co (SEQ ID NO: 1) molecule was characterized in the Ramachandran conformational plot (FIG. 5), and showed that 90.6% of its amino acid residues were located in the optimal allowed regions, 9.1% were in the allowed regions, 0.4% were in the common allowed regions. This demonstrated that the rSIFN-co (SEQ ID NO: 1) molecular structural model was stereochemically rational.

Example 10

Crystal Structure Characteristics of the Crystal Structure of the rSIFN-Co (SEQ ID NO: 1) Molecule Stacking and Global Assignment of the rSIFN-Co (SEQ ID NO: 1) Molecule in a Crystal FIG. 6 shows the stacking manner of the rSIFN-co (SEQ ID NO: 1) molecule in an unit cell. An asymmetric unit in the rSIFN-co (SEQ ID NO: 1) crystal structure was made of two protein molecules (called crystallographic dimers) (FIG. 7). The embedding area between the dimers was 1033.3 Å$^2$ with each monomer contributing 516.6 Å$^2$. This only accounted for 6.4% of the total area in the monomer. The A, B, F sides of the A chain in the dimer corresponded to the C, D, E sides of the B chain (see FIG. 9). Using the software VADAR, the folding free energies of the monomer and dimer were calculated as −126.9 and −257.1 respectively, which meant that the folding free energy of the dimer was quite close to the free energy of the two isolated monomers (−126.9×2). This demonstrated that the interaction between the dimers was relatively weak and there were only two weak hydrogen bonds between them A12(ARG) NH2 . . . NH2 B71(Arg), 3.05 Å; A145(Arg) NH1 . . . OH B90 (Tyr), 3.14 Å.

The purification process showed that rSIFN-co (SEQ ID NO: 1) existed as monomers in solution; the current biochemical function experiments showed that the functional unit of the likes of IFN-α should be monomeric. Therefore, this dimer might be formed from the stacking of crystals.

Dimer Structure of the Dimers

Two single rSIFN-co (SEQ ID NO: 1) molecules in an asymmetric unit form one dimer. FIG. 8 shows the crystallographic dimeric organization of rSIFN-co (SEQ ID NO: 1). Chain A consisted of residues 11-103 and 111-163 (residues 1-10, 104-110 and 164-166, were not involved in building of this crystal structure since they were not shown in the electron density map); chain B consisted of residues 11-103 and 110-163 (residues 1-10, 104-109, and 164-166, were not involved in building of this crystal structure since they were not shown in the electron density map). In the crystal structure of each monomer, it was observed that the Cys29 and Cys139 formed an intramolecular disulfide bond; the intramolecular disulfide bond from Cys1 and Cys99 was not shown because Cys1 was not involved in building of this crystal structure. Besides, since the density of the side chains were not shown, residues 30-33, 47-49 of chain A and residues 30-33, 48-50 of chain B were mainly constructed as Ala or Gly. The structures of the two monomers were roughly the same and were linked by non-crystallographic symmetry (from B to A, polar angles Omega, Phi, Kappa were 170.64, 94.56, 118.35, respectively; tx, ty, tz were −1.061, −0.225, 0.155 respectively.). The two monomers were superimposed and compared; apart from the regional flexibility of a few loops on the molecular surface, most of the residues superimposed completely. The distribution of the RMSD of all the Cα associated with the amino acid residues are shown in FIG. 8c; 127 residues (13-30, 34-44, 53-101, 115-163) had a RMSD of 0.64 Å for all Cα. The difference in the local structure might be a result of the comparatively large flexibility of this protein and the differences in the environment where the crystal stacked.

Structure of a Single Molecule

Each monomer was made up of six α-helices (A, C, C', D, E, F) and one 310 helix (B), which were connected to each other by the connecting peptides between them; the fold of the monomer structure belonged to the helical cytokines (FIG. 9).

comparison between rSIFN-co (SEQ ID NO: 1) and IFN-α2b was carried out only at the Cα level. The overall RMSD of all the Cα of the two molecules was 1.577 Å; but in the AB loop and BC loop, the RMSD was 3.63 Å and 2.9 Å, which were 2.5 times and 2 times that of the total average, respectively. Besides, rSIFN-co (SEQ ID NO: 1) contained two molecules in the asymmetric unit of its crystal structure while IFN-α2b had six protein molecules, composed of 3 dimers, in its asymmetric unit. Obviously, the dimeric organization of rSIFN-co (SEQ ID NO: 1) was distinctly different from IFN-α2b (FIG. 13).

TABLE 5

The determined structures of IFNs

| Protein name | Source | Method | Resolution (Å) | PDB code | Identify of rSIFN-co (SEQ ID NO: 1) |
|---|---|---|---|---|---|
| rSIFN-co (SEQ ID NO: 1) | Synthesis | X-ray | 2.6 | This invention | |
| IFN-α 2b | Human | X-ray | 2.9 | 1RH2 (Only Cα) | 89% |
| IFN-α 2a | Human | NMR | | 1ITF | 88% |
| IFN-τ | Human | X-ray | 2.1 | 1B5L | 54% |
| IFN-β | Human | X-ray | 2.2 | 1AU1 | 30% |
| IFN-β | Mouse | X-ray | 2.2 | 1RMI | 23% |

The amino-acid residues which corresponded to the six α-helices (A, C, C', D, E, F) were 13-20, 50-68, 70-76, 79-100, 114-133, and 138-160, respectively. Residues 40-43 corresponded to the 310 helix (B). The distribution and organization of these secondary structures are shown clearly in FIG. 9. The corresponding relationship between the secondary structures and the amino acid sequence is shown in FIG. 10.

Example 11

The Three Dimensional Structure of rSIFN-Co (SEQ ID NO: 1) and IFN-α2b

Based on their receptors, IFN can broadly be divided into two types: type I and type II. Type I can further be sub-divided into α, β, ω, etc. IFN-α, in turn, contains approximately fifteen different sub-types; the different IFN-α subtypes have sequence homologies of above 80% yet they exhibit diversity in their functions. rSIFN-co (SEQ ID NO: 1) is considered to be an unnatural and artificially designed protein. To date, there are only six 3-D structures of type I IFNs (Table 5) and their sequence homology can be seen in the aligned sequences shown in FIG. 11.

From the comparative analysis shown in Table 5 and FIG. 11, the crystal structure of IFN-α2b showed the highest similarity to that of rSIFN-co (SEQ ID NO: 1) (FIG. 12). It was found, by comparing their sequences, that rSIFN-co (SEQ ID NO: 1) had one more Asp (D) than IFN-α2b at residue 45; and, by comparing their 3D structures, rSIFN-co (SEQ ID NO: 1) differed markedly from IFN-α2b with respect to the conformation of the AB loop (residues 25-33) and the BC loop (residues 44-52). The crystal structure of IFN-α2b had been determined at a resolution of 2.9 Å; however, except for the Cα, the coordinates of all other atoms were absent in the Protein Data Bank (PDB code: 1RH2) such that structural It is known that IFN, as a cytokine, first binds with specific receptors on the cell membrane to activate several signal transduction pathways that will generate biological effects in the body, such as antivirus and antitumor effects. rSIFN-co (SEQ ID NO: 1) is a type of IFN-α. Since its receptor on the cell membrane is made up of IFNAR1 and IFNAR2, a 3D model of receptor binding with IFN-α was constructed (FIG. 15a). A series of molecular biology experiments were conducted based on this model and the results suggested that IFN-α-like proteins interacted with IFNAR1 and IFNAR2 in a sandwich structure (FIG. 15a), i.e., sides A, B and F interacted with IFNAR2, and the opposite sides C, D, and E interacted with IFNAR1. Meanwhile, site-directed mutagenesis revealed that the AB loop, which interacted with IFNAR2, was the main constituent of the active site of IFN-α-like proteins (FIG. 15). Structural comparison showed that the structure of this important region was distinctly different between rSIFN-co (SEQ ID NO: 1) and IFN-α2b (FIG. 12, Table 6). Structural differences in this important region may trigger different physiological or pharmacological effects as a result of changes in the binding characteristics with receptors.

Apparently, although the molecular skeleton of rSIFN-co (SEQ ID NO: 1) was similar to that of IFN-α2b, they differed markedly in the structure of their active sites. Therefore, judging from the local structure closely related to the pharmacological activities of the molecules, it was found that rSIFN-co (SEQ ID NO: 1) was a new type of IFN different from IFN-α2b, and their structural differences had led to distinctly different biological and pharmacological characteristics. Based on the differences in the specific key region of its three dimension structure, rSIFN-co (SEQ ID NO: 1) might produce unique physiological and pharmacological effects.

TABLE 6

Root-Mean-Square Deviation (RMSD) of Cα between AB Loop and BC Loop of rSIFN-co (SEQ ID NO: 1) and IFN-α2b (unit: Å)

| Residue number of AB Loop | RMSD (Å) | Residue number of BC Loop | RMSD (Å) |
|---|---|---|---|
| 25 | 3.291 | 44 | 1.164 |
| 26 | 4.779 | 45 | 1.383 |
| 27 | 5.090 | 46 | 2.735 |
| 28 | 3.588 | 47 | 2.709 |
| 29 | 2.567 | 48 | 5.018 |
| 30 | 2.437 | 49 | 4.140 |
| 31 | 3.526 | 50 | 3.809 |
| 32 | 4.820 | 51 | 2.970 |
| 33 | 2.756 | 52 | 0.881 |
| Average RMSD of AB Loop | 3.63 | Average RMSD of BC Loop | 2.90 |
| RMSD of all Cα atoms | | | 1.60 |

TABLE 7

Atomic coordinates of rSIFN-co (SEQ ID NO: 1)

| CRYST1 | 77.920 | 77.920 | 125.935 | 90.00 90.00 120.00 P 31 2 1 | | | | | |
|---|---|---|---|---|---|---|---|---|---|
| ATOM | 1 | CB | ASN | A | 11 | −36.673 | 14.399 | −31.951 | 1.00 79.36 A |
| ATOM | 2 | CG | ASN | A | 11 | −37.660 | 14.647 | −33.090 | 1.00 81.91 A |
| ATOM | 3 | OD1 | ASN | A | 11 | −37.274 | 14.829 | −34.245 | 1.00 85.24 A |
| ATOM | 4 | ND2 | ASN | A | 11 | −38.947 | 14.622 | −32.764 | 1.00 82.54 A |
| ATOM | 5 | C | ASN | A | 11 | −34.980 | 16.273 | −31.802 | 1.00 76.68 A |
| ATOM | 6 | O | ASN | A | 11 | −34.061 | 16.507 | −31.007 | 1.00 76.57 A |
| ATOM | 7 | N | ASN | A | 11 | −34.283 | 13.985 | −31.533 | 1.00 78.32 A |
| ATOM | 8 | CA | ASN | A | 11 | −35.239 | 14.843 | −32.283 | 1.00 77.86 A |
| ATOM | 9 | N | ARG | A | 12 | −35.760 | 17.226 | −32.307 | 1.00 74.41 A |
| ATOM | 10 | CA | ARG | A | 12 | −35.635 | 18.622 | −31.899 | 1.00 69.90 A |
| ATOM | 11 | CB | ARG | A | 12 | −35.404 | 19.525 | −33.115 | 1.00 72.01 A |
| ATOM | 12 | CG | ARG | A | 12 | −34.052 | 19.300 | −33.792 | 1.00 77.29 A |
| ATOM | 13 | CD | ARG | A | 12 | −33.757 | 20.318 | −34.894 | 1.00 79.77 A |
| ATOM | 14 | NE | ARG | A | 12 | −32.967 | 21.461 | −34.430 | 1.00 83.05 A |
| ATOM | 15 | CZ | ARG | A | 12 | −31.669 | 21.635 | −34.679 | 1.00 84.53 A |
| ATOM | 16 | NH1 | ARG | A | 12 | −30.994 | 20.740 | −35.390 | 1.00 85.41 A |
| ATOM | 17 | NH2 | ARG | A | 12 | −31.049 | 22.721 | −34.235 | 1.00 84.48 A |
| ATOM | 18 | C | ARG | A | 12 | −36.917 | 19.021 | −31.174 | 1.00 65.99 A |
| ATOM | 19 | O | ARG | A | 12 | −37.334 | 20.177 | −31.210 | 1.00 65.41 A |
| ATOM | 20 | N | ARG | A | 13 | −37.530 | 18.037 | −30.521 | 1.00 61.78 A |
| ATOM | 21 | CA | ARG | A | 13 | −38.757 | 18.209 | −29.750 | 1.00 58.49 A |
| ATOM | 22 | CB | ARG | A | 13 | −39.049 | 16.937 | −28.963 | 1.00 61.57 A |
| ATOM | 23 | CG | ARG | A | 13 | −40.120 | 16.061 | −29.535 | 1.00 66.89 A |
| ATOM | 24 | CD | ARG | A | 13 | −40.996 | 15.577 | −28.414 | 1.00 69.61 A |
| ATOM | 25 | NE | ARG | A | 13 | −42.336 | 16.134 | −28.518 | 1.00 72.80 A |
| ATOM | 26 | CZ | ARG | A | 13 | −43.253 | 16.035 | −27.562 | 1.00 75.39 A |
| ATOM | 27 | NH1 | ARG | A | 13 | −42.964 | 15.403 | −26.425 | 1.00 74.38 A |
| ATOM | 28 | NH2 | ARG | A | 13 | −44.462 | 16.555 | −27.748 | 1.00 76.67 A |
| ATOM | 29 | C | ARG | A | 13 | −38.720 | 19.378 | −28.767 | 1.00 54.28 A |
| ATOM | 30 | O | ARG | A | 13 | −39.709 | 20.098 | −28.625 | 1.00 54.11 A |
| ATOM | 31 | N | ALA | A | 14 | −37.597 | 19.555 | −28.075 | 1.00 48.77 A |
| ATOM | 32 | CA | ALA | A | 14 | −37.481 | 20.645 | −27.116 | 1.00 45.39 A |
| ATOM | 33 | CB | ALA | A | 14 | −36.082 | 20.689 | −26.526 | 1.00 44.44 A |
| ATOM | 34 | C | ALA | A | 14 | −37.816 | 21.984 | −27.762 | 1.00 43.36 A |
| ATOM | 35 | O | ALA | A | 14 | −38.656 | 22.723 | −27.262 | 1.00 42.76 A |
| ATOM | 36 | N | LEU | A | 15 | −37.169 | 22.287 | −28.879 | 1.00 40.93 A |
| ATOM | 37 | CA | LEU | A | 15 | −37.402 | 23.542 | −29.568 | 1.00 39.71 A |
| ATOM | 38 | CB | LEU | A | 15 | −36.364 | 23.730 | −30.669 | 1.00 39.82 A |
| ATOM | 39 | CG | LEU | A | 15 | −34.952 | 23.714 | −30.072 | 1.00 40.23 A |
| ATOM | 40 | CD1 | LEU | A | 15 | −33.913 | 23.928 | −31.151 | 1.00 39.64 A |
| ATOM | 41 | CD2 | LEU | A | 15 | −34.850 | 24.800 | −29.005 | 1.00 40.94 A |
| ATOM | 42 | C | LEU | A | 15 | −38.802 | 23.667 | −30.130 | 1.00 40.00 A |
| ATOM | 43 | O | LEU | A | 15 | −39.372 | 24.751 | −30.100 | 1.00 39.95 A |
| ATOM | 44 | N | ILE | A | 16 | −39.364 | 22.572 | −30.638 | 1.00 40.32 A |
| ATOM | 45 | CA | ILE | A | 16 | −40.730 | 22.601 | −31.179 | 1.00 40.64 A |
| ATOM | 46 | CB | ILE | A | 16 | −41.213 | 21.189 | −31.637 | 1.00 43.33 A |
| ATOM | 47 | CG2 | ILE | A | 16 | −42.605 | 21.283 | −32.231 | 1.00 41.37 A |
| ATOM | 48 | CG1 | ILE | A | 16 | −40.257 | 20.590 | −32.673 | 1.00 44.72 A |
| ATOM | 49 | CD1 | ILE | A | 16 | −40.190 | 21.342 | −33.941 | 1.00 46.03 A |
| ATOM | 50 | C | ILE | A | 16 | −41.682 | 23.087 | −30.080 | 1.00 41.12 A |
| ATOM | 51 | O | ILE | A | 16 | −42.425 | 24.051 | −30.271 | 1.00 41.43 A |
| ATOM | 52 | N | LEU | A | 17 | −41.662 | 22.411 | −28.930 | 1.00 40.37 A |
| ATOM | 53 | CA | LEU | A | 17 | −42.516 | 22.794 | −27.812 | 1.00 41.00 A |
| ATOM | 54 | CB | LEU | A | 17 | −42.303 | 21.837 | −26.640 | 1.00 42.66 A |
| ATOM | 55 | CG | LEU | A | 17 | −42.835 | 20.411 | −26.850 | 1.00 43.03 A |

TABLE 7-continued

Atomic coordinates of rSIFN-co (SEQ ID NO: 1)

| ATOM | 56 | CD1 | LEU | A | 17 | −42.045 | 19.434 | −25.983 | 1.00 | 39.82 | A |
|---|---|---|---|---|---|---|---|---|---|---|---|
| ATOM | 57 | CD2 | LEU | A | 17 | −44.328 | 20.368 | −26.526 | 1.00 | 40.26 | A |
| ATOM | 58 | C | LEU | A | 17 | −42.257 | 24.233 | −27.359 | 1.00 | 40.48 | A |
| ATOM | 59 | O | LEU | A | 17 | −43.187 | 25.022 | −27.212 | 1.00 | 39.35 | A |
| ATOM | 60 | N | LEU | A | 18 | −40.986 | 24.574 | −27.161 | 1.00 | 40.86 | A |
| ATOM | 61 | CA | LEU | A | 18 | −40.594 | 25.909 | −26.718 | 1.00 | 40.17 | A |
| ATOM | 62 | CB | LEU | A | 18 | −39.073 | 25.973 | −26.597 | 1.00 | 40.05 | A |
| ATOM | 63 | CG | LEU | A | 18 | −38.378 | 26.953 | −25.641 | 1.00 | 42.40 | A |
| ATOM | 64 | CD1 | LEU | A | 18 | −37.548 | 27.948 | −26.430 | 1.00 | 42.15 | A |
| ATOM | 65 | CD2 | LEU | A | 18 | −39.393 | 27.657 | −24.767 | 1.00 | 43.03 | A |
| ATOM | 66 | C | LEU | A | 18 | −41.094 | 26.966 | −27.698 | 1.00 | 40.88 | A |
| ATOM | 67 | O | LEU | A | 18 | −41.230 | 28.137 | −27.345 | 1.00 | 39.41 | A |
| ATOM | 68 | N | ALA | A | 19 | −41.373 | 26.539 | −28.929 | 1.00 | 41.87 | A |
| ATOM | 69 | CA | ALA | A | 19 | −41.861 | 27.432 | −29.975 | 1.00 | 44.08 | A |
| ATOM | 70 | CB | ALA | A | 19 | −41.536 | 26.866 | −31.358 | 1.00 | 42.64 | A |
| ATOM | 71 | C | ALA | A | 19 | −43.359 | 27.594 | −29.830 | 1.00 | 46.35 | A |
| ATOM | 72 | O | ALA | A | 19 | −43.905 | 28.665 | −30.090 | 1.00 | 47.47 | A |
| ATOM | 73 | N | GLN | A | 20 | −44.017 | 26.517 | −29.417 | 1.00 | 48.12 | A |
| ATOM | 74 | CA | GLN | A | 20 | −45.462 | 26.519 | −29.224 | 1.00 | 50.49 | A |
| ATOM | 75 | CB | GLN | A | 20 | −45.986 | 25.075 | −29.111 | 1.00 | 51.83 | A |
| ATOM | 76 | CG | GLN | A | 20 | −45.540 | 24.097 | −30.195 | 1.00 | 53.52 | A |
| ATOM | 77 | CD | GLN | A | 20 | −46.151 | 22.712 | −29.999 | 1.00 | 55.01 | A |
| ATOM | 78 | OE1 | GLN | A | 20 | −45.806 | 21.745 | −30.693 | 1.00 | 52.54 | A |
| ATOM | 79 | NE2 | GLN | A | 20 | −47.069 | 22.614 | −29.046 | 1.00 | 56.71 | A |
| ATOM | 80 | C | GLN | A | 20 | −45.855 | 27.284 | −27.941 | 1.00 | 51.19 | A |
| ATOM | 81 | O | GLN | A | 20 | −47.024 | 27.634 | −27.745 | 1.00 | 51.17 | A |
| ATOM | 82 | N | MET | A | 21 | −44.874 | 27.541 | −27.080 | 1.00 | 49.97 | A |
| ATOM | 83 | CA | MET | A | 21 | −45.110 | 28.204 | −25.802 | 1.00 | 48.63 | A |
| ATOM | 84 | CB | MET | A | 21 | −44.002 | 27.808 | −24.822 | 1.00 | 46.02 | A |
| ATOM | 85 | CG | MET | A | 21 | −44.097 | 26.374 | −24.330 | 1.00 | 43.96 | A |
| ATOM | 86 | SD | MET | A | 21 | −42.595 | 25.764 | −23.516 | 1.00 | 47.28 | A |
| ATOM | 87 | CE | MET | A | 21 | −42.353 | 27.001 | −22.206 | 1.00 | 42.84 | A |
| ATOM | 88 | C | MET | A | 21 | −45.272 | 29.723 | −25.809 | 1.00 | 49.74 | A |
| ATOM | 89 | O | MET | A | 21 | −45.696 | 30.303 | −24.807 | 1.00 | 49.63 | A |
| ATOM | 90 | N | ALA | A | 22 | −44.950 | 30.375 | −26.922 | 1.00 | 51.41 | A |
| ATOM | 91 | CA | ALA | A | 22 | −45.075 | 31.828 | −26.978 | 1.00 | 53.11 | A |
| ATOM | 92 | CB | ALA | A | 22 | −44.641 | 32.362 | −28.341 | 1.00 | 52.27 | A |
| ATOM | 93 | C | ALA | A | 22 | −46.517 | 32.196 | −26.716 | 1.00 | 53.84 | A |
| ATOM | 94 | O | ALA | A | 22 | −47.428 | 31.552 | −27.227 | 1.00 | 52.97 | A |
| ATOM | 95 | N | ARG | A | 23 | −46.719 | 33.225 | −25.904 | 1.00 | 56.56 | A |
| ATOM | 96 | CA | ARG | A | 23 | −48.064 | 33.683 | −25.581 | 1.00 | 59.73 | A |
| ATOM | 97 | CB | ARG | A | 23 | −48.367 | 33.484 | −24.094 | 1.00 | 60.59 | A |
| ATOM | 98 | CG | ARG | A | 23 | −48.309 | 32.059 | −23.604 | 1.00 | 62.22 | A |
| ATOM | 99 | CD | ARG | A | 23 | −48.845 | 31.998 | −22.183 | 1.00 | 66.26 | A |
| ATOM | 100 | NE | ARG | A | 23 | −50.250 | 32.397 | −22.143 | 1.00 | 70.17 | A |
| ATOM | 101 | CZ | ARG | A | 23 | −50.744 | 33.339 | −21.345 | 1.00 | 71.62 | A |
| ATOM | 102 | NH1 | ARG | A | 23 | −49.946 | 33.985 | −20.504 | 1.00 | 71.69 | A |
| ATOM | 103 | NH2 | ARG | A | 23 | −52.035 | 33.652 | −21.405 | 1.00 | 72.49 | A |
| ATOM | 104 | C | ARG | A | 23 | −48.242 | 35.158 | −25.921 | 1.00 | 61.02 | A |
| ATOM | 105 | O | ARG | A | 23 | −49.334 | 35.584 | −26.284 | 1.00 | 62.43 | A |
| ATOM | 106 | N | ALA | A | 24 | −47.171 | 35.937 | −25.799 | 1.00 | 61.98 | A |
| ATOM | 107 | CA | ALA | A | 24 | −47.236 | 37.366 | −26.080 | 1.00 | 63.61 | A |
| ATOM | 108 | CB | ALA | A | 24 | −46.139 | 38.093 | −25.319 | 1.00 | 62.75 | A |
| ATOM | 109 | C | ALA | A | 24 | −47.139 | 37.676 | −27.570 | 1.00 | 65.56 | A |
| ATOM | 110 | O | ALA | A | 24 | −46.450 | 36.983 | −28.322 | 1.00 | 65.76 | A |
| ATOM | 111 | N | SER | A | 25 | −47.848 | 38.724 | −27.984 | 1.00 | 67.91 | A |
| ATOM | 112 | CA | SER | A | 25 | −47.865 | 39.157 | −29.373 | 1.00 | 69.93 | A |
| ATOM | 113 | CB | SER | A | 25 | −49.175 | 39.887 | −29.698 | 1.00 | 71.12 | A |
| ATOM | 114 | OG | SER | A | 25 | −50.227 | 38.952 | −29.909 | 1.00 | 72.49 | A |
| ATOM | 115 | C | SER | A | 25 | −46.663 | 40.064 | −29.610 | 1.00 | 71.13 | A |
| ATOM | 116 | O | SER | A | 25 | −46.236 | 40.806 | −28.726 | 1.00 | 71.22 | A |
| ATOM | 117 | N | PRO | A | 26 | −46.109 | 40.027 | −30.825 | 1.00 | 71.97 | A |
| ATOM | 118 | CD | PRO | A | 26 | −46.787 | 39.560 | −32.046 | 1.00 | 72.50 | A |
| ATOM | 119 | CA | PRO | A | 26 | −44.938 | 40.842 | −31.165 | 1.00 | 73.26 | A |
| ATOM | 120 | CB | PRO | A | 26 | −44.887 | 40.767 | −32.702 | 1.00 | 73.01 | A |
| ATOM | 121 | CG | PRO | A | 26 | −45.664 | 39.526 | −33.023 | 1.00 | 72.89 | A |
| ATOM | 122 | C | PRO | A | 26 | −45.008 | 42.284 | −30.673 | 1.00 | 74.39 | A |
| ATOM | 123 | O | PRO | A | 26 | −43.979 | 42.872 | −30.322 | 1.00 | 74.28 | A |
| ATOM | 124 | N | PHE | A | 27 | −46.212 | 42.856 | −30.653 | 1.00 | 75.25 | A |
| ATOM | 125 | CA | PHE | A | 27 | −46.375 | 44.245 | −30.222 | 1.00 | 75.22 | A |
| ATOM | 126 | CB | PHE | A | 27 | −47.502 | 44.910 | −30.995 | 1.00 | 75.78 | A |
| ATOM | 127 | CG | PHE | A | 27 | −47.305 | 44.909 | −32.463 | 1.00 | 77.48 | A |
| ATOM | 128 | CD1 | PHE | A | 27 | −47.573 | 43.765 | −33.204 | 1.00 | 79.44 | A |
| ATOM | 129 | CD2 | PHE | A | 27 | −46.788 | 46.029 | −33.106 | 1.00 | 77.96 | A |
| ATOM | 130 | CE1 | PHE | A | 27 | −47.347 | 43.738 | −34.579 | 1.00 | 80.53 | A |
| ATOM | 131 | CE2 | PHE | A | 27 | −46.557 | 46.022 | −34.472 | 1.00 | 79.57 | A |
| ATOM | 132 | CZ | PHE | A | 27 | −46.826 | 44.870 | −35.215 | 1.00 | 80.89 | A |
| ATOM | 133 | C | PHE | A | 27 | −46.635 | 44.449 | −28.737 | 1.00 | 74.52 | A |

TABLE 7-continued

Atomic coordinates of rSIFN-co (SEQ ID NO: 1)

| ATOM | 134 | O | PHE | A | 27 | −46.415 | 45.540 | −28.218 | 1.00 | 74.03 | A |
|---|---|---|---|---|---|---|---|---|---|---|---|
| ATOM | 135 | N | ALA | A | 28 | −47.097 | 43.411 | −28.052 | 1.00 | 74.01 | A |
| ATOM | 136 | CA | ALA | A | 28 | −47.394 | 43.532 | −26.637 | 1.00 | 73.15 | A |
| ATOM | 137 | CB | ALA | A | 28 | −47.812 | 42.175 | −26.080 | 1.00 | 73.48 | A |
| ATOM | 138 | C | ALA | A | 28 | −46.241 | 44.112 | −25.822 | 1.00 | 73.09 | A |
| ATOM | 139 | O | ALA | A | 28 | −46.460 | 44.586 | −24.707 | 1.00 | 74.58 | A |
| ATOM | 140 | N | CYS | A | 29 | −45.030 | 44.090 | −26.383 | 1.00 | 72.82 | A |
| ATOM | 141 | CA | CYS | A | 29 | −43.820 | 44.598 | −25.713 | 1.00 | 73.33 | A |
| ATOM | 142 | C | CYS | A | 29 | −42.968 | 45.450 | −26.659 | 1.00 | 74.96 | A |
| ATOM | 143 | O | CYS | A | 29 | −43.340 | 45.648 | −27.812 | 1.00 | 75.82 | A |
| ATOM | 144 | CB | CYS | A | 29 | −42.967 | 43.432 | −25.217 | 1.00 | 71.43 | A |
| ATOM | 145 | SG | CYS | A | 29 | −43.896 | 42.126 | −24.366 | 1.00 | 69.57 | A |
| ATOM | 146 | N | GLY | A | 30 | −41.814 | 45.931 | −26.192 | 1.00 | 76.71 | A |
| ATOM | 147 | CA | GLY | A | 30 | −40.990 | 46.756 | −27.065 | 1.00 | 79.56 | A |
| ATOM | 148 | C | GLY | A | 30 | −39.496 | 46.977 | −26.848 | 1.00 | 81.04 | A |
| ATOM | 149 | O | GLY | A | 30 | −38.987 | 47.036 | −25.725 | 1.00 | 80.04 | A |
| ATOM | 150 | N | GLY | A | 31 | −38.800 | 47.111 | −27.976 | 1.00 | 83.09 | A |
| ATOM | 151 | CA | GLY | A | 31 | −37.365 | 47.369 | −27.994 | 1.00 | 86.03 | A |
| ATOM | 152 | C | GLY | A | 31 | −36.448 | 46.384 | −27.283 | 1.00 | 86.91 | A |
| ATOM | 153 | O | GLY | A | 31 | −36.097 | 45.330 | −27.822 | 1.00 | 87.85 | A |
| ATOM | 154 | N | GLY | A | 32 | −36.030 | 46.767 | −26.078 | 1.00 | 86.34 | A |
| ATOM | 155 | CA | GLY | A | 32 | −35.161 | 45.949 | −25.244 | 1.00 | 85.69 | A |
| ATOM | 156 | C | GLY | A | 32 | −34.216 | 44.887 | −25.810 | 1.00 | 84.42 | A |
| ATOM | 157 | O | GLY | A | 32 | −34.386 | 43.694 | −25.541 | 1.00 | 84.88 | A |
| ATOM | 158 | N | GLY | A | 33 | −33.200 | 45.298 | −26.562 | 1.00 | 82.49 | A |
| ATOM | 159 | CA | GLY | A | 33 | −32.247 | 44.327 | −27.076 | 1.00 | 81.23 | A |
| ATOM | 160 | C | GLY | A | 33 | −31.315 | 43.958 | −25.929 | 1.00 | 80.18 | A |
| ATOM | 161 | O | GLY | A | 33 | −30.199 | 44.473 | −25.846 | 1.00 | 79.67 | A |
| ATOM | 162 | N | HIS | A | 34 | −31.768 | 43.066 | −25.048 | 1.00 | 79.01 | A |
| ATOM | 163 | CA | HIS | A | 34 | −30.984 | 42.654 | −23.881 | 1.00 | 76.91 | A |
| ATOM | 164 | CB | HIS | A | 34 | −31.932 | 42.245 | −22.742 | 1.00 | 76.85 | A |
| ATOM | 165 | CG | HIS | A | 34 | −31.313 | 42.323 | −21.381 | 1.00 | 76.31 | A |
| ATOM | 166 | CD2 | HIS | A | 34 | −31.596 | 43.113 | −20.319 | 1.00 | 76.73 | A |
| ATOM | 167 | ND1 | HIS | A | 34 | −30.249 | 41.534 | −20.995 | 1.00 | 76.92 | A |
| ATOM | 168 | CE1 | HIS | A | 34 | −29.905 | 41.835 | −19.756 | 1.00 | 76.89 | A |
| ATOM | 169 | NE2 | HIS | A | 34 | −30.707 | 42.791 | −19.322 | 1.00 | 77.36 | A |
| ATOM | 170 | C | HIS | A | 34 | −29.992 | 41.525 | −24.168 | 1.00 | 74.89 | A |
| ATOM | 171 | O | HIS | A | 34 | −30.383 | 40.450 | −24.635 | 1.00 | 75.01 | A |
| ATOM | 172 | N | ASP | A | 35 | −28.716 | 41.783 | −23.869 | 1.00 | 71.97 | A |
| ATOM | 173 | CA | ASP | A | 35 | −27.631 | 40.823 | −24.089 | 1.00 | 69.11 | A |
| ATOM | 174 | CB | ASP | A | 35 | −26.366 | 41.561 | −24.542 | 1.00 | 71.02 | A |
| ATOM | 175 | CG | ASP | A | 35 | −25.270 | 40.617 | −25.018 | 1.00 | 73.48 | A |
| ATOM | 176 | OD1 | ASP | A | 35 | −25.490 | 39.904 | −26.022 | 1.00 | 76.44 | A |
| ATOM | 177 | OD2 | ASP | A | 35 | −24.183 | 40.591 | −24.398 | 1.00 | 74.76 | A |
| ATOM | 178 | C | ASP | A | 35 | −27.318 | 40.010 | −22.837 | 1.00 | 66.06 | A |
| ATOM | 179 | O | ASP | A | 35 | −26.862 | 40.554 | −21.830 | 1.00 | 66.03 | A |
| ATOM | 180 | N | PHE | A | 36 | −27.558 | 38.705 | −22.900 | 1.00 | 61.83 | A |
| ATOM | 181 | CA | PHE | A | 36 | −27.282 | 37.853 | −21.757 | 1.00 | 57.75 | A |
| ATOM | 182 | CB | PHE | A | 36 | −28.283 | 36.698 | −21.674 | 1.00 | 57.18 | A |
| ATOM | 183 | CG | PHE | A | 36 | −29.696 | 37.146 | −21.442 | 1.00 | 56.02 | A |
| ATOM | 184 | CD1 | PHE | A | 36 | −30.556 | 37.357 | −22.505 | 1.00 | 55.11 | A |
| ATOM | 185 | CD2 | PHE | A | 36 | −30.148 | 37.415 | −20.159 | 1.00 | 56.96 | A |
| ATOM | 186 | CE1 | PHE | A | 36 | −31.847 | 37.827 | −22.296 | 1.00 | 56.30 | A |
| ATOM | 187 | CE2 | PHE | A | 36 | −31.441 | 37.889 | −19.939 | 1.00 | 56.70 | A |
| ATOM | 188 | CZ | PHE | A | 36 | −32.289 | 38.097 | −21.010 | 1.00 | 56.38 | A |
| ATOM | 189 | C | PHE | A | 36 | −25.870 | 37.326 | −21.835 | 1.00 | 55.62 | A |
| ATOM | 190 | O | PHE | A | 36 | −25.367 | 36.747 | −20.882 | 1.00 | 55.22 | A |
| ATOM | 191 | N | GLY | A | 37 | −25.233 | 37.534 | −22.982 | 1.00 | 53.97 | A |
| ATOM | 192 | CA | GLY | A | 37 | −23.859 | 37.103 | −23.163 | 1.00 | 52.66 | A |
| ATOM | 193 | C | GLY | A | 37 | −23.589 | 35.614 | −23.171 | 1.00 | 52.31 | A |
| ATOM | 194 | O | GLY | A | 37 | −22.627 | 35.140 | −22.572 | 1.00 | 52.88 | A |
| ATOM | 195 | N | PHE | A | 38 | −24.439 | 34.868 | −23.856 | 1.00 | 52.34 | A |
| ATOM | 196 | CA | PHE | A | 38 | −24.272 | 33.428 | −23.960 | 1.00 | 53.26 | A |
| ATOM | 197 | CB | PHE | A | 38 | −25.329 | 32.873 | −24.925 | 1.00 | 50.67 | A |
| ATOM | 198 | CG | PHE | A | 38 | −25.161 | 31.424 | −25.244 | 1.00 | 48.53 | A |
| ATOM | 199 | CD1 | PHE | A | 38 | −25.352 | 30.457 | −24.264 | 1.00 | 47.04 | A |
| ATOM | 200 | CD2 | PHE | A | 38 | −24.793 | 31.023 | −26.529 | 1.00 | 47.77 | A |
| ATOM | 201 | CE1 | PHE | A | 38 | −25.177 | 29.110 | −24.559 | 1.00 | 47.91 | A |
| ATOM | 202 | CE2 | PHE | A | 38 | −24.615 | 29.676 | −26.834 | 1.00 | 46.88 | A |
| ATOM | 203 | CZ | PHE | A | 38 | −24.806 | 28.719 | −25.850 | 1.00 | 48.21 | A |
| ATOM | 204 | C | PHE | A | 38 | −22.863 | 33.114 | −24.478 | 1.00 | 54.82 | A |
| ATOM | 205 | O | PHE | A | 38 | −22.481 | 33.579 | −25.547 | 1.00 | 55.48 | A |
| ATOM | 206 | N | PRO | A | 39 | −22.071 | 32.327 | −23.724 | 1.00 | 56.41 | A |
| ATOM | 207 | CD | PRO | A | 39 | −22.373 | 31.704 | −22.422 | 1.00 | 56.33 | A |
| ATOM | 208 | CA | PRO | A | 39 | −20.711 | 31.982 | −24.158 | 1.00 | 57.36 | A |
| ATOM | 209 | CB | PRO | A | 39 | −20.084 | 31.414 | −22.889 | 1.00 | 55.84 | A |
| ATOM | 210 | CG | PRO | A | 39 | −21.234 | 30.702 | −22.266 | 1.00 | 56.06 | A |
| ATOM | 211 | C | PRO | A | 39 | −20.705 | 30.974 | −25.318 | 1.00 | 59.32 | A |

TABLE 7-continued

Atomic coordinates of rSIFN-co (SEQ ID NO: 1)

| ATOM | 212 | O | PRO | A | 39 | −20.292 | 29.824 | −25.153 | 1.00 | 59.38 | A |
|---|---|---|---|---|---|---|---|---|---|---|---|
| ATOM | 213 | N | GLN | A | 40 | −21.159 | 31.428 | −26.487 | 1.00 | 61.42 | A |
| ATOM | 214 | CA | GLN | A | 40 | −21.235 | 30.616 | −27.710 | 1.00 | 63.86 | A |
| ATOM | 215 | CB | GLN | A | 40 | −21.539 | 31.520 | −28.911 | 1.00 | 65.01 | A |
| ATOM | 216 | CG | GLN | A | 40 | −21.996 | 30.776 | −30.148 | 1.00 | 67.78 | A |
| ATOM | 217 | CD | GLN | A | 40 | −22.372 | 31.713 | −31.297 | 1.00 | 70.50 | A |
| ATOM | 218 | OE1 | GLN | A | 40 | −22.885 | 32.818 | −31.079 | 1.00 | 70.05 | A |
| ATOM | 219 | NE2 | GLN | A | 40 | −22.135 | 31.262 | −32.528 | 1.00 | 69.96 | A |
| ATOM | 220 | C | GLN | A | 40 | −19.979 | 29.797 | −28.011 | 1.00 | 64.05 | A |
| ATOM | 221 | O | GLN | A | 40 | −20.064 | 28.709 | −28.577 | 1.00 | 62.19 | A |
| ATOM | 222 | N | GLU | A | 41 | −18.821 | 30.329 | −27.630 | 1.00 | 66.08 | A |
| ATOM | 223 | CA | GLU | A | 41 | −17.537 | 29.667 | −27.854 | 1.00 | 68.16 | A |
| ATOM | 224 | CB | GLU | A | 41 | −16.405 | 30.478 | −27.216 | 1.00 | 68.78 | A |
| ATOM | 225 | CG | GLU | A | 41 | −16.575 | 31.993 | −27.302 | 1.00 | 71.65 | A |
| ATOM | 226 | CD | GLU | A | 41 | −17.599 | 32.538 | −26.309 | 1.00 | 71.91 | A |
| ATOM | 227 | OE1 | GLU | A | 41 | −17.436 | 32.289 | −25.095 | 1.00 | 70.55 | A |
| ATOM | 228 | OE2 | GLU | A | 41 | −18.558 | 33.220 | −26.742 | 1.00 | 72.43 | A |
| ATOM | 229 | C | GLU | A | 41 | −17.514 | 28.249 | −27.276 | 1.00 | 69.40 | A |
| ATOM | 230 | O | GLU | A | 41 | −16.971 | 27.327 | −27.884 | 1.00 | 70.02 | A |
| ATOM | 231 | N | GLU | A | 42 | −18.107 | 28.081 | −26.098 | 1.00 | 70.37 | A |
| ATOM | 232 | CA | GLU | A | 42 | −18.134 | 26.784 | −25.437 | 1.00 | 70.92 | A |
| ATOM | 233 | CB | GLU | A | 42 | −18.816 | 26.907 | −24.073 | 1.00 | 70.33 | A |
| ATOM | 234 | CG | GLU | A | 42 | −18.096 | 27.839 | −23.108 | 1.00 | 70.66 | A |
| ATOM | 235 | CD | GLU | A | 42 | −16.674 | 27.387 | −22.810 | 1.00 | 71.66 | A |
| ATOM | 236 | OE1 | GLU | A | 42 | −15.901 | 28.192 | −22.245 | 1.00 | 71.99 | A |
| ATOM | 237 | OE2 | GLU | A | 42 | −16.329 | 26.228 | −23.134 | 1.00 | 70.35 | A |
| ATOM | 238 | C | GLU | A | 42 | −18.817 | 25.703 | −26.263 | 1.00 | 72.31 | A |
| ATOM | 239 | O | GLU | A | 42 | −18.658 | 24.515 | −25.982 | 1.00 | 71.27 | A |
| ATOM | 240 | N | PHE | A | 43 | −19.565 | 26.115 | −27.285 | 1.00 | 74.43 | A |
| ATOM | 241 | CA | PHE | A | 43 | −20.279 | 25.169 | −28.142 | 1.00 | 77.01 | A |
| ATOM | 242 | CB | PHE | A | 43 | −21.801 | 25.343 | −27.982 | 1.00 | 73.77 | A |
| ATOM | 243 | CG | PHE | A | 43 | −22.266 | 25.393 | −26.551 | 1.00 | 70.14 | A |
| ATOM | 244 | CD1 | PHE | A | 43 | −22.212 | 26.580 | −25.829 | 1.00 | 69.12 | A |
| ATOM | 245 | CD2 | PHE | A | 43 | −22.728 | 24.249 | −25.916 | 1.00 | 69.47 | A |
| ATOM | 246 | CE1 | PHE | A | 43 | −22.608 | 26.627 | −24.498 | 1.00 | 66.90 | A |
| ATOM | 247 | CE2 | PHE | A | 43 | −23.126 | 24.287 | −24.579 | 1.00 | 68.62 | A |
| ATOM | 248 | CZ | PHE | A | 43 | −23.065 | 25.480 | −23.873 | 1.00 | 67.55 | A |
| ATOM | 249 | C | PHE | A | 43 | −19.904 | 25.329 | −29.620 | 1.00 | 80.52 | A |
| ATOM | 250 | O | PHE | A | 43 | −19.615 | 24.350 | −30.312 | 1.00 | 80.71 | A |
| ATOM | 251 | N | GLY | A | 44 | −19.917 | 26.571 | −30.093 | 1.00 | 84.43 | A |
| ATOM | 252 | CA | GLY | A | 44 | −19.594 | 26.849 | −31.483 | 1.00 | 87.53 | A |
| ATOM | 253 | C | GLY | A | 44 | −18.109 | 26.912 | −31.796 | 1.00 | 89.96 | A |
| ATOM | 254 | O | GLY | A | 44 | −17.397 | 27.829 | −31.367 | 1.00 | 89.88 | A |
| ATOM | 255 | N | GLY | A | 45 | −17.642 | 25.933 | −32.564 | 1.00 | 91.49 | A |
| ATOM | 256 | CA | GLY | A | 45 | −16.243 | 25.889 | −32.936 | 1.00 | 93.11 | A |
| ATOM | 257 | C | GLY | A | 45 | −15.734 | 24.468 | −33.038 | 1.00 | 94.05 | A |
| ATOM | 258 | O | GLY | A | 45 | −16.213 | 23.577 | −32.333 | 1.00 | 93.98 | A |
| ATOM | 259 | N | GLY | A | 46 | −14.767 | 24.255 | −33.925 | 1.00 | 94.77 | A |
| ATOM | 260 | CA | GLY | A | 46 | −14.195 | 22.935 | −34.098 | 1.00 | 95.42 | A |
| ATOM | 261 | C | GLY | A | 46 | −13.231 | 22.606 | −32.972 | 1.00 | 95.90 | A |
| ATOM | 262 | O | GLY | A | 46 | −12.194 | 21.976 | −33.199 | 1.00 | 96.10 | A |
| ATOM | 263 | N | GLY | A | 47 | −13.570 | 23.040 | −31.759 | 1.00 | 95.61 | A |
| ATOM | 264 | CA | GLY | A | 47 | −12.726 | 22.778 | −30.606 | 1.00 | 95.48 | A |
| ATOM | 265 | C | GLY | A | 47 | −12.428 | 21.298 | −30.455 | 1.00 | 95.42 | A |
| ATOM | 266 | O | GLY | A | 47 | −11.319 | 20.921 | −30.073 | 1.00 | 95.45 | A |
| ATOM | 267 | N | GLY | A | 48 | −13.425 | 20.466 | −30.760 | 1.00 | 94.95 | A |
| ATOM | 268 | CA | GLY | A | 48 | −13.272 | 19.023 | −30.674 | 1.00 | 93.55 | A |
| ATOM | 269 | C | GLY | A | 48 | −12.943 | 18.541 | −29.279 | 1.00 | 93.16 | A |
| ATOM | 270 | O | GLY | A | 48 | −12.016 | 19.041 | −28.649 | 1.00 | 94.44 | A |
| ATOM | 271 | N | ALA | A | 49 | −13.705 | 17.566 | −28.796 | 1.00 | 91.77 | A |
| ATOM | 272 | CA | ALA | A | 49 | −13.507 | 17.000 | −27.463 | 1.00 | 90.57 | A |
| ATOM | 273 | CB | ALA | A | 49 | −13.219 | 18.103 | −26.449 | 1.00 | 90.50 | A |
| ATOM | 274 | C | ALA | A | 49 | −14.771 | 16.245 | −27.069 | 1.00 | 89.91 | A |
| ATOM | 275 | O | ALA | A | 49 | −15.801 | 16.855 | −26.774 | 1.00 | 90.84 | A |
| ATOM | 276 | N | GLY | A | 50 | −14.690 | 14.919 | −27.068 | 1.00 | 88.13 | A |
| ATOM | 277 | CA | GLY | A | 50 | −15.844 | 14.113 | −26.727 | 1.00 | 86.16 | A |
| ATOM | 278 | C | GLY | A | 50 | −16.495 | 14.504 | −25.416 | 1.00 | 85.07 | A |
| ATOM | 279 | O | GLY | A | 50 | −17.671 | 14.870 | −25.387 | 1.00 | 84.82 | A |
| ATOM | 280 | N | ALA | A | 51 | −15.721 | 14.442 | −24.335 | 1.00 | 83.62 | A |
| ATOM | 281 | CA | ALA | A | 51 | −16.211 | 14.753 | −22.992 | 1.00 | 81.83 | A |
| ATOM | 282 | CB | ALA | A | 51 | −15.276 | 14.138 | −21.955 | 1.00 | 82.10 | A |
| ATOM | 283 | C | ALA | A | 51 | −16.424 | 16.235 | −22.685 | 1.00 | 79.92 | A |
| ATOM | 284 | O | ALA | A | 51 | −17.409 | 16.602 | −22.049 | 1.00 | 79.80 | A |
| ATOM | 285 | N | ALA | A | 52 | −15.504 | 17.088 | −23.115 | 1.00 | 77.79 | A |
| ATOM | 286 | CA | ALA | A | 52 | −15.655 | 18.511 | −22.852 | 1.00 | 76.55 | A |
| ATOM | 287 | CB | ALA | A | 52 | −14.469 | 19.286 | −23.424 | 1.00 | 76.24 | A |
| ATOM | 288 | C | ALA | A | 52 | −16.965 | 19.027 | −23.450 | 1.00 | 75.56 | A |
| ATOM | 289 | O | ALA | A | 52 | −17.473 | 20.072 | −23.037 | 1.00 | 76.89 | A |

TABLE 7-continued

Atomic coordinates of rSIFN-co (SEQ ID NO: 1)

| ATOM | 290 | N | ALA | A | 53 | −17.510 | 18.288 | −24.416 | 1.00 | 72.47 | A |
|---|---|---|---|---|---|---|---|---|---|---|---|
| ATOM | 291 | CA | ALA | A | 53 | −18.756 | 18.677 | −25.080 | 1.00 | 68.45 | A |
| ATOM | 292 | CB | ALA | A | 53 | −18.737 | 18.220 | −26.532 | 1.00 | 69.53 | A |
| ATOM | 293 | C | ALA | A | 53 | −19.980 | 18.108 | −24.374 | 1.00 | 64.99 | A |
| ATOM | 294 | O | ALA | A | 53 | −21.033 | 18.738 | −24.329 | 1.00 | 63.06 | A |
| ATOM | 295 | N | ILE | A | 54 | −19.838 | 16.903 | −23.841 | 1.00 | 62.13 | A |
| ATOM | 296 | CA | ILE | A | 54 | −20.926 | 16.269 | −23.119 | 1.00 | 59.68 | A |
| ATOM | 297 | CB | ILE | A | 54 | −20.601 | 14.793 | −22.815 | 1.00 | 59.54 | A |
| ATOM | 298 | CG2 | ILE | A | 54 | −21.606 | 14.224 | −21.820 | 1.00 | 60.50 | A |
| ATOM | 299 | CG1 | ILE | A | 54 | −20.611 | 13.993 | −24.117 | 1.00 | 59.64 | A |
| ATOM | 300 | CD1 | ILE | A | 54 | −20.368 | 12.518 | −23.930 | 1.00 | 59.00 | A |
| ATOM | 301 | C | ILE | A | 54 | −21.164 | 17.028 | −21.813 | 1.00 | 57.90 | A |
| ATOM | 302 | O | ILE | A | 54 | −22.290 | 17.095 | −21.327 | 1.00 | 57.31 | A |
| ATOM | 303 | N | SER | A | 55 | −20.097 | 17.601 | −21.259 | 1.00 | 55.70 | A |
| ATOM | 304 | CA | SER | A | 55 | −20.184 | 18.370 | −20.023 | 1.00 | 54.92 | A |
| ATOM | 305 | CB | SER | A | 55 | −18.793 | 18.751 | −19.519 | 1.00 | 55.15 | A |
| ATOM | 306 | OG | SER | A | 55 | −18.065 | 17.604 | −19.145 | 1.00 | 57.20 | A |
| ATOM | 307 | C | SER | A | 55 | −20.984 | 19.640 | −20.247 | 1.00 | 53.44 | A |
| ATOM | 308 | O | SER | A | 55 | −22.026 | 19.837 | −19.627 | 1.00 | 55.68 | A |
| ATOM | 309 | N | VAL | A | 56 | −20.494 | 20.502 | −21.127 | 1.00 | 50.22 | A |
| ATOM | 310 | CA | VAL | A | 56 | −21.178 | 21.752 | −21.415 | 1.00 | 50.34 | A |
| ATOM | 311 | CB | VAL | A | 56 | −20.418 | 22.574 | −22.478 | 1.00 | 50.53 | A |
| ATOM | 312 | CG1 | VAL | A | 56 | −19.161 | 23.152 | −21.878 | 1.00 | 50.53 | A |
| ATOM | 313 | CG2 | VAL | A | 56 | −20.078 | 21.697 | −23.668 | 1.00 | 51.00 | A |
| ATOM | 314 | C | VAL | A | 56 | −22.610 | 21.528 | −21.894 | 1.00 | 49.62 | A |
| ATOM | 315 | O | VAL | A | 56 | −23.516 | 22.293 | −21.567 | 1.00 | 49.30 | A |
| ATOM | 316 | N | LEU | A | 57 | −22.812 | 20.475 | −22.673 | 1.00 | 49.64 | A |
| ATOM | 317 | CA | LEU | A | 57 | −24.136 | 20.154 | −23.190 | 1.00 | 49.65 | A |
| ATOM | 318 | CB | LEU | A | 57 | −24.032 | 18.974 | −24.152 | 1.00 | 51.00 | A |
| ATOM | 319 | CG | LEU | A | 57 | −25.034 | 18.931 | −25.301 | 1.00 | 52.21 | A |
| ATOM | 320 | CD1 | LEU | A | 57 | −25.250 | 20.322 | −25.881 | 1.00 | 52.24 | A |
| ATOM | 321 | CD2 | LEU | A | 57 | −24.488 | 17.992 | −26.361 | 1.00 | 54.20 | A |
| ATOM | 322 | C | LEU | A | 57 | −25.054 | 19.800 | −22.027 | 1.00 | 47.55 | A |
| ATOM | 323 | O | LEU | A | 57 | −26.140 | 20.356 | −21.870 | 1.00 | 46.60 | A |
| ATOM | 324 | N | HIS | A | 58 | −24.592 | 18.862 | −21.216 | 1.00 | 46.31 | A |
| ATOM | 325 | CA | HIS | A | 58 | −25.319 | 18.415 | −20.043 | 1.00 | 45.33 | A |
| ATOM | 326 | CB | HIS | A | 58 | −24.482 | 17.375 | −19.301 | 1.00 | 46.40 | A |
| ATOM | 327 | CG | HIS | A | 58 | −25.242 | 16.619 | −18.263 | 1.00 | 46.64 | A |
| ATOM | 328 | CD2 | HIS | A | 58 | −25.757 | 15.368 | −18.275 | 1.00 | 46.79 | A |
| ATOM | 329 | ND1 | HIS | A | 58 | −25.582 | 17.164 | −17.044 | 1.00 | 46.24 | A |
| ATOM | 330 | CE1 | HIS | A | 58 | −26.275 | 16.280 | −16.352 | 1.00 | 48.22 | A |
| ATOM | 331 | NE2 | HIS | A | 58 | −26.397 | 15.180 | −17.076 | 1.00 | 46.23 | A |
| ATOM | 332 | C | HIS | A | 58 | −25.649 | 19.590 | −19.118 | 1.00 | 43.94 | A |
| ATOM | 333 | O | HIS | A | 58 | −26.783 | 19.724 | −18.663 | 1.00 | 42.85 | A |
| ATOM | 334 | N | GLU | A | 59 | −24.664 | 20.442 | −18.847 | 1.00 | 41.52 | A |
| ATOM | 335 | CA | GLU | A | 59 | −24.896 | 21.585 | −17.979 | 1.00 | 41.77 | A |
| ATOM | 336 | CB | GLU | A | 59 | −23.600 | 22.326 | −17.702 | 1.00 | 43.24 | A |
| ATOM | 337 | CG | GLU | A | 59 | −23.694 | 23.232 | −16.489 | 1.00 | 47.79 | A |
| ATOM | 338 | CD | GLU | A | 59 | −24.197 | 22.493 | −15.249 | 1.00 | 49.54 | A |
| ATOM | 339 | OE1 | GLU | A | 59 | −23.853 | 21.304 | −15.074 | 1.00 | 49.34 | A |
| ATOM | 340 | OE2 | GLU | A | 59 | −24.928 | 23.107 | −14.442 | 1.00 | 52.72 | A |
| ATOM | 341 | C | GLU | A | 59 | −25.882 | 22.536 | −18.619 | 1.00 | 41.87 | A |
| ATOM | 342 | O | GLU | A | 59 | −26.719 | 23.135 | −17.942 | 1.00 | 41.28 | A |
| ATOM | 343 | N | MET | A | 60 | −25.770 | 22.677 | −19.935 | 1.00 | 42.94 | A |
| ATOM | 344 | CA | MET | A | 60 | −26.662 | 23.542 | −20.692 | 1.00 | 42.22 | A |
| ATOM | 345 | CB | MET | A | 60 | −26.290 | 23.512 | −22.165 | 1.00 | 43.31 | A |
| ATOM | 346 | CG | MET | A | 60 | −27.230 | 24.305 | −23.017 | 1.00 | 45.06 | A |
| ATOM | 347 | SD | MET | A | 60 | −27.202 | 26.008 | −22.511 | 1.00 | 51.70 | A |
| ATOM | 348 | CE | MET | A | 60 | −27.674 | 26.784 | −24.033 | 1.00 | 51.65 | A |
| ATOM | 349 | C | MET | A | 60 | −28.096 | 23.052 | −20.545 | 1.00 | 42.26 | A |
| ATOM | 350 | O | MET | A | 60 | −29.039 | 23.839 | −20.450 | 1.00 | 40.80 | A |
| ATOM | 351 | N | ILE | A | 61 | −28.245 | 21.733 | −20.534 | 1.00 | 40.98 | A |
| ATOM | 352 | CA | ILE | A | 61 | −29.548 | 21.123 | −20.418 | 1.00 | 40.78 | A |
| ATOM | 353 | CB | ILE | A | 61 | −29.504 | 19.681 | −20.995 | 1.00 | 42.85 | A |
| ATOM | 354 | CG2 | ILE | A | 61 | −30.790 | 18.936 | −20.694 | 1.00 | 41.14 | A |
| ATOM | 355 | CG1 | ILE | A | 61 | −29.312 | 19.763 | −22.518 | 1.00 | 42.64 | A |
| ATOM | 356 | CD1 | ILE | A | 61 | −29.143 | 18.421 | −23.214 | 1.00 | 43.13 | A |
| ATOM | 357 | C | ILE | A | 61 | −30.060 | 21.159 | −18.984 | 1.00 | 39.56 | A |
| ATOM | 358 | O | ILE | A | 61 | −31.195 | 21.558 | −18.744 | 1.00 | 39.81 | A |
| ATOM | 359 | N | GLN | A | 62 | −29.224 | 20.781 | −18.026 | 1.00 | 39.29 | A |
| ATOM | 360 | CA | GLN | A | 62 | −29.639 | 20.793 | −16.627 | 1.00 | 38.51 | A |
| ATOM | 361 | CB | GLN | A | 62 | −28.488 | 20.338 | −15.726 | 1.00 | 39.26 | A |
| ATOM | 362 | CG | GLN | A | 62 | −28.827 | 20.246 | −14.242 | 1.00 | 39.53 | A |
| ATOM | 363 | CD | GLN | A | 62 | −30.002 | 19.321 | −13.941 | 1.00 | 40.52 | A |
| ATOM | 364 | OE1 | GLN | A | 62 | −31.042 | 19.758 | −13.438 | 1.00 | 39.54 | A |
| ATOM | 365 | NE2 | GLN | A | 62 | −29.840 | 18.040 | −14.248 | 1.00 | 39.51 | A |
| ATOM | 366 | C | GLN | A | 62 | −30.102 | 22.189 | −16.221 | 1.00 | 38.93 | A |
| ATOM | 367 | O | GLN | A | 62 | −31.106 | 22.348 | −15.522 | 1.00 | 37.04 | A |

TABLE 7-continued

Atomic coordinates of rSIFN-co (SEQ ID NO: 1)

| ATOM | 368 | N | GLN | A | 63 | −29.383 | 23.204 | −16.683 | 1.00 | 39.52 | A |
|---|---|---|---|---|---|---|---|---|---|---|---|
| ATOM | 369 | CA | GLN | A | 63 | −29.741 | 24.578 | −16.353 | 1.00 | 40.38 | A |
| ATOM | 370 | CB | GLN | A | 63 | −28.644 | 25.543 | −16.797 | 1.00 | 41.37 | A |
| ATOM | 371 | CG | GLN | A | 63 | −27.350 | 25.361 | −16.049 | 1.00 | 42.32 | A |
| ATOM | 372 | CD | GLN | A | 63 | −27.523 | 25.576 | −14.563 | 1.00 | 46.04 | A |
| ATOM | 373 | OE1 | GLN | A | 63 | −26.881 | 24.907 | −13.753 | 1.00 | 47.35 | A |
| ATOM | 374 | NE2 | GLN | A | 63 | −28.386 | 26.526 | −14.192 | 1.00 | 46.16 | A |
| ATOM | 375 | C | GLN | A | 63 | −31.062 | 25.006 | −16.957 | 1.00 | 40.51 | A |
| ATOM | 376 | O | GLN | A | 63 | −31.837 | 25.685 | −16.286 | 1.00 | 43.32 | A |
| ATOM | 377 | N | THR | A | 64 | −31.313 | 24.625 | −18.215 | 1.00 | 39.04 | A |
| ATOM | 378 | CA | THR | A | 64 | −32.564 | 24.972 | −18.904 | 1.00 | 37.15 | A |
| ATOM | 379 | CB | THR | A | 64 | −32.539 | 24.536 | −20.398 | 1.00 | 36.84 | A |
| ATOM | 380 | OG1 | THR | A | 64 | −31.493 | 25.233 | −21.084 | 1.00 | 35.39 | A |
| ATOM | 381 | CG2 | THR | A | 64 | −33.872 | 24.834 | −21.077 | 1.00 | 32.91 | A |
| ATOM | 382 | C | THR | A | 64 | −33.714 | 24.265 | −18.181 | 1.00 | 37.88 | A |
| ATOM | 383 | O | THR | A | 64 | −34.827 | 24.791 | −18.061 | 1.00 | 37.95 | A |
| ATOM | 384 | N | PHE | A | 65 | −33.438 | 23.061 | −17.700 | 1.00 | 37.24 | A |
| ATOM | 385 | CA | PHE | A | 65 | −34.435 | 22.326 | −16.951 | 1.00 | 37.39 | A |
| ATOM | 386 | CB | PHE | A | 65 | −33.934 | 20.930 | −16.625 | 1.00 | 37.39 | A |
| ATOM | 387 | CG | PHE | A | 65 | −34.874 | 20.159 | −15.749 | 1.00 | 40.42 | A |
| ATOM | 388 | CD1 | PHE | A | 65 | −35.967 | 19.503 | −16.292 | 1.00 | 39.82 | A |
| ATOM | 389 | CD2 | PHE | A | 65 | −34.706 | 20.155 | −14.370 | 1.00 | 40.52 | A |
| ATOM | 390 | CE1 | PHE | A | 65 | −36.871 | 18.861 | −15.485 | 1.00 | 40.75 | A |
| ATOM | 391 | CE2 | PHE | A | 65 | −35.611 | 19.511 | −13.556 | 1.00 | 40.34 | A |
| ATOM | 392 | CZ | PHE | A | 65 | −36.697 | 18.867 | −14.115 | 1.00 | 40.24 | A |
| ATOM | 393 | C | PHE | A | 65 | −34.756 | 23.070 | −15.639 | 1.00 | 36.83 | A |
| ATOM | 394 | O | PHE | A | 65 | −35.918 | 23.289 | −15.317 | 1.00 | 37.76 | A |
| ATOM | 395 | N | ASN | A | 66 | −33.730 | 23.450 | −14.880 | 1.00 | 35.91 | A |
| ATOM | 396 | CA | ASN | A | 66 | −33.950 | 24.177 | −13.633 | 1.00 | 34.39 | A |
| ATOM | 397 | CB | ASN | A | 66 | −32.631 | 24.485 | −12.935 | 1.00 | 32.13 | A |
| ATOM | 398 | CG | ASN | A | 66 | −31.851 | 23.238 | −12.606 | 1.00 | 34.28 | A |
| ATOM | 399 | OD1 | ASN | A | 66 | −32.418 | 22.153 | −12.512 | 1.00 | 37.35 | A |
| ATOM | 400 | ND2 | ASN | A | 66 | −30.545 | 23.380 | −12.424 | 1.00 | 33.10 | A |
| ATOM | 401 | C | ASN | A | 66 | −34.678 | 25.481 | −13.900 | 1.00 | 34.39 | A |
| ATOM | 402 | O | ASN | A | 66 | −35.582 | 25.851 | −13.163 | 1.00 | 35.59 | A |
| ATOM | 403 | N | LEU | A | 67 | −34.299 | 26.172 | −14.963 | 1.00 | 34.07 | A |
| ATOM | 404 | CA | LEU | A | 67 | −34.937 | 27.440 | −15.292 | 1.00 | 34.52 | A |
| ATOM | 405 | CB | LEU | A | 67 | −34.189 | 28.135 | −16.434 | 1.00 | 31.74 | A |
| ATOM | 406 | CG | LEU | A | 67 | −34.902 | 29.382 | −16.972 | 1.00 | 32.77 | A |
| ATOM | 407 | CD1 | LEU | A | 67 | −34.922 | 30.487 | −15.907 | 1.00 | 29.39 | A |
| ATOM | 408 | CD2 | LEU | A | 67 | −34.216 | 29.848 | −18.259 | 1.00 | 31.96 | A |
| ATOM | 409 | C | LEU | A | 67 | −36.417 | 27.335 | −15.655 | 1.00 | 34.13 | A |
| ATOM | 410 | O | LEU | A | 67 | −37.185 | 28.238 | −15.362 | 1.00 | 35.27 | A |
| ATOM | 411 | N | PHE | A | 68 | −36.824 | 26.236 | −16.280 | 1.00 | 36.35 | A |
| ATOM | 412 | CA | PHE | A | 68 | −38.218 | 26.081 | −16.690 | 1.00 | 37.11 | A |
| ATOM | 413 | CB | PHE | A | 68 | −38.284 | 25.620 | −18.150 | 1.00 | 33.91 | A |
| ATOM | 414 | CG | PHE | A | 68 | −38.023 | 26.708 | −19.133 | 1.00 | 31.92 | A |
| ATOM | 415 | CD1 | PHE | A | 68 | −36.724 | 26.985 | −19.563 | 1.00 | 33.37 | A |
| ATOM | 416 | CD2 | PHE | A | 68 | −39.071 | 27.494 | −19.607 | 1.00 | 30.01 | A |
| ATOM | 417 | CE1 | PHE | A | 68 | −36.469 | 28.045 | −20.466 | 1.00 | 31.57 | A |
| ATOM | 418 | CE2 | PHE | A | 68 | −38.835 | 28.553 | −20.504 | 1.00 | 30.12 | A |
| ATOM | 419 | CZ | PHE | A | 68 | −37.534 | 28.830 | −20.932 | 1.00 | 28.79 | A |
| ATOM | 420 | C | PHE | A | 68 | −39.128 | 25.186 | −15.845 | 1.00 | 39.17 | A |
| ATOM | 421 | O | PHE | A | 68 | −40.318 | 25.067 | −16.131 | 1.00 | 39.72 | A |
| ATOM | 422 | N | SER | A | 69 | −38.592 | 24.558 | −14.806 | 1.00 | 41.24 | A |
| ATOM | 423 | CA | SER | A | 69 | −39.424 | 23.709 | −13.969 | 1.00 | 41.35 | A |
| ATOM | 424 | CB | SER | A | 69 | −38.721 | 22.398 | −13.704 | 1.00 | 39.74 | A |
| ATOM | 425 | OG | SER | A | 69 | −37.509 | 22.664 | −13.042 | 1.00 | 40.54 | A |
| ATOM | 426 | C | SER | A | 69 | −39.790 | 24.355 | −12.635 | 1.00 | 42.76 | A |
| ATOM | 427 | O | SER | A | 69 | −40.328 | 23.687 | −11.772 | 1.00 | 45.46 | A |
| ATOM | 428 | N | THR | A | 70 | −39.508 | 25.642 | −12.459 | 1.00 | 44.33 | A |
| ATOM | 429 | CA | THR | A | 70 | −39.839 | 26.316 | −11.201 | 1.00 | 47.21 | A |
| ATOM | 430 | CB | THR | A | 70 | −39.038 | 27.630 | −10.990 | 1.00 | 47.32 | A |
| ATOM | 431 | OG1 | THR | A | 70 | −39.366 | 28.565 | −12.031 | 1.00 | 49.98 | A |
| ATOM | 432 | CG2 | THR | A | 70 | −37.547 | 27.364 | −10.977 | 1.00 | 45.16 | A |
| ATOM | 433 | C | THR | A | 70 | −41.307 | 26.709 | −11.179 | 1.00 | 50.70 | A |
| ATOM | 434 | O | THR | A | 70 | −42.001 | 26.617 | −12.195 | 1.00 | 50.43 | A |
| ATOM | 435 | N | ARG | A | 71 | −41.777 | 27.164 | −10.018 | 1.00 | 53.44 | A |
| ATOM | 436 | CA | ARG | A | 71 | −43.164 | 27.594 | −9.908 | 1.00 | 55.27 | A |
| ATOM | 437 | CB | ARG | A | 71 | −43.576 | 27.847 | −8.449 | 1.00 | 57.92 | A |
| ATOM | 438 | CG | ARG | A | 71 | −43.186 | 26.760 | −7.454 | 1.00 | 61.59 | A |
| ATOM | 439 | CD | ARG | A | 71 | −41.834 | 27.104 | −6.805 | 1.00 | 64.19 | A |
| ATOM | 440 | NE | ARG | A | 71 | −40.663 | 26.474 | −7.420 | 1.00 | 58.72 | A |
| ATOM | 441 | CZ | ARG | A | 71 | −39.469 | 27.046 | −7.453 | 1.00 | 55.24 | A |
| ATOM | 442 | NH1 | ARG | A | 71 | −39.304 | 28.250 | −6.929 | 1.00 | 52.89 | A |
| ATOM | 443 | NH2 | ARG | A | 71 | −38.435 | 26.399 | −7.964 | 1.00 | 55.93 | A |
| ATOM | 444 | C | ARG | A | 71 | −43.298 | 28.891 | −10.697 | 1.00 | 53.94 | A |
| ATOM | 445 | O | ARG | A | 71 | −44.382 | 29.232 | −11.171 | 1.00 | 53.96 | A |

TABLE 7-continued

Atomic coordinates of rSIFN-co (SEQ ID NO: 1)

| ATOM | 446 | N | ASP | A | 72 | −42.196 | 29.619 | −10.832 | 1.00 | 52.47 | A |
|---|---|---|---|---|---|---|---|---|---|---|---|
| ATOM | 447 | CA | ASP | A | 72 | −42.232 | 30.857 | −11.588 | 1.00 | 53.16 | A |
| ATOM | 448 | CB | ASP | A | 72 | −40.896 | 31.592 | −11.491 | 1.00 | 55.60 | A |
| ATOM | 449 | CG | ASP | A | 72 | −40.517 | 31.929 | −10.069 | 1.00 | 56.39 | A |
| ATOM | 450 | OD1 | ASP | A | 72 | −39.627 | 31.244 | −9.517 | 1.00 | 57.77 | A |
| ATOM | 451 | OD2 | ASP | A | 72 | −41.114 | 32.874 | −9.510 | 1.00 | 56.32 | A |
| ATOM | 452 | C | ASP | A | 72 | −42.524 | 30.523 | −13.050 | 1.00 | 52.84 | A |
| ATOM | 453 | O | ASP | A | 72 | −43.402 | 31.114 | −13.672 | 1.00 | 51.84 | A |
| ATOM | 454 | N | SER | A | 73 | −41.780 | 29.569 | −13.592 | 1.00 | 51.97 | A |
| ATOM | 455 | CA | SER | A | 73 | −41.980 | 29.169 | −14.971 | 1.00 | 52.26 | A |
| ATOM | 456 | CB | SER | A | 73 | −40.981 | 28.062 | −15.347 | 1.00 | 51.52 | A |
| ATOM | 457 | OG | SER | A | 73 | −41.246 | 27.525 | −16.629 | 1.00 | 48.35 | A |
| ATOM | 458 | C | SER | A | 73 | −43.416 | 28.674 | −15.134 | 1.00 | 53.10 | A |
| ATOM | 459 | O | SER | A | 73 | −44.097 | 29.008 | −16.107 | 1.00 | 54.40 | A |
| ATOM | 460 | N | SER | A | 74 | −43.882 | 27.893 | −14.165 | 1.00 | 53.63 | A |
| ATOM | 461 | CA | SER | A | 74 | −45.231 | 27.342 | −14.222 | 1.00 | 53.33 | A |
| ATOM | 462 | CB | SER | A | 74 | −45.484 | 26.414 | −13.041 | 1.00 | 51.87 | A |
| ATOM | 463 | OG | SER | A | 74 | −45.620 | 25.076 | −13.494 | 1.00 | 53.40 | A |
| ATOM | 464 | C | SER | A | 74 | −46.320 | 28.389 | −14.274 | 1.00 | 52.78 | A |
| ATOM | 465 | O | SER | A | 74 | −47.411 | 28.125 | −14.771 | 1.00 | 54.19 | A |
| ATOM | 466 | N | ALA | A | 75 | −46.021 | 29.579 | −13.770 | 1.00 | 51.42 | A |
| ATOM | 467 | CA | ALA | A | 75 | −46.990 | 30.662 | −13.755 | 1.00 | 50.95 | A |
| ATOM | 468 | CB | ALA | A | 75 | −46.727 | 31.573 | −12.556 | 1.00 | 48.85 | A |
| ATOM | 469 | C | ALA | A | 75 | −46.927 | 31.473 | −15.041 | 1.00 | 50.90 | A |
| ATOM | 470 | O | ALA | A | 75 | −47.774 | 32.319 | −15.292 | 1.00 | 52.54 | A |
| ATOM | 471 | N | ALA | A | 76 | −45.923 | 31.213 | −15.860 | 1.00 | 49.86 | A |
| ATOM | 472 | CA | ALA | A | 76 | −45.769 | 31.969 | −17.080 | 1.00 | 49.41 | A |
| ATOM | 473 | CB | ALA | A | 76 | −44.334 | 32.491 | −17.168 | 1.00 | 50.92 | A |
| ATOM | 474 | C | ALA | A | 76 | −46.122 | 31.192 | −18.341 | 1.00 | 49.59 | A |
| ATOM | 475 | O | ALA | A | 76 | −46.417 | 31.794 | −19.378 | 1.00 | 50.18 | A |
| ATOM | 476 | N | TRP | A | 77 | −46.111 | 29.866 | −18.259 | 1.00 | 47.56 | A |
| ATOM | 477 | CA | TRP | A | 77 | −46.387 | 29.063 | −19.438 | 1.00 | 46.48 | A |
| ATOM | 478 | CB | TRP | A | 77 | −45.110 | 28.355 | −19.877 | 1.00 | 44.34 | A |
| ATOM | 479 | CG | TRP | A | 77 | −43.913 | 29.259 | −19.895 | 1.00 | 42.62 | A |
| ATOM | 480 | CD2 | TRP | A | 77 | −43.655 | 30.325 | −20.813 | 1.00 | 40.67 | A |
| ATOM | 481 | CE2 | TRP | A | 77 | −42.422 | 30.902 | −20.448 | 1.00 | 40.13 | A |
| ATOM | 482 | CE3 | TRP | A | 77 | −44.344 | 30.847 | −21.914 | 1.00 | 42.24 | A |
| ATOM | 483 | CD1 | TRP | A | 77 | −42.860 | 29.232 | −19.036 | 1.00 | 40.98 | A |
| ATOM | 484 | NE1 | TRP | A | 77 | −41.958 | 30.213 | −19.360 | 1.00 | 41.31 | A |
| ATOM | 485 | CZ2 | TRP | A | 77 | −41.857 | 31.981 | −21.140 | 1.00 | 41.93 | A |
| ATOM | 486 | CZ3 | TRP | A | 77 | −43.780 | 31.927 | −22.612 | 1.00 | 42.72 | A |
| ATOM | 487 | CH2 | TRP | A | 77 | −42.548 | 32.479 | −22.218 | 1.00 | 40.65 | A |
| ATOM | 488 | C | TRP | A | 77 | −47.499 | 28.044 | −19.317 | 1.00 | 47.54 | A |
| ATOM | 489 | O | TRP | A | 77 | −47.927 | 27.687 | −18.228 | 1.00 | 47.95 | A |
| ATOM | 490 | N | ASP | A | 78 | −47.964 | 27.578 | −20.467 | 1.00 | 50.28 | A |
| ATOM | 491 | CA | ASP | A | 78 | −49.024 | 26.590 | −20.526 | 1.00 | 52.24 | A |
| ATOM | 492 | CB | ASP | A | 78 | −49.376 | 26.310 | −21.986 | 1.00 | 53.78 | A |
| ATOM | 493 | CG | ASP | A | 78 | −50.539 | 25.368 | −22.128 | 1.00 | 55.91 | A |
| ATOM | 494 | OD1 | ASP | A | 78 | −50.307 | 24.144 | −22.238 | 1.00 | 57.57 | A |
| ATOM | 495 | OD2 | ASP | A | 78 | −51.689 | 25.857 | −22.115 | 1.00 | 57.70 | A |
| ATOM | 496 | C | ASP | A | 78 | −48.591 | 25.309 | −19.815 | 1.00 | 53.52 | A |
| ATOM | 497 | O | ASP | A | 78 | −47.633 | 24.638 | −20.217 | 1.00 | 53.27 | A |
| ATOM | 498 | N | ALA | A | 79 | −49.304 | 24.978 | −18.746 | 1.00 | 54.38 | A |
| ATOM | 499 | CA | ALA | A | 79 | −48.983 | 23.797 | −17.961 | 1.00 | 54.80 | A |
| ATOM | 500 | CB | ALA | A | 79 | −50.123 | 23.488 | −16.991 | 1.00 | 54.45 | A |
| ATOM | 501 | C | ALA | A | 79 | −48.692 | 22.594 | −18.843 | 1.00 | 54.31 | A |
| ATOM | 502 | O | ALA | A | 79 | −47.633 | 21.994 | −18.747 | 1.00 | 55.97 | A |
| ATOM | 503 | N | SER | A | 80 | −49.619 | 22.255 | −19.722 | 1.00 | 54.29 | A |
| ATOM | 504 | CA | SER | A | 80 | −49.438 | 21.096 | −20.588 | 1.00 | 54.78 | A |
| ATOM | 505 | CB | SER | A | 80 | −50.677 | 20.900 | −21.471 | 1.00 | 56.80 | A |
| ATOM | 506 | OG | SER | A | 80 | −50.573 | 19.708 | −22.235 | 1.00 | 60.99 | A |
| ATOM | 507 | C | SER | A | 80 | −48.184 | 21.198 | −21.453 | 1.00 | 53.08 | A |
| ATOM | 508 | O | SER | A | 80 | −47.441 | 20.225 | −21.602 | 1.00 | 52.66 | A |
| ATOM | 509 | N | LEU | A | 81 | −47.956 | 22.372 | −22.030 | 1.00 | 51.48 | A |
| ATOM | 510 | CA | LEU | A | 81 | −46.781 | 22.579 | −22.858 | 1.00 | 50.28 | A |
| ATOM | 511 | CB | LEU | A | 81 | −46.848 | 23.939 | −23.567 | 1.00 | 50.13 | A |
| ATOM | 512 | CG | LEU | A | 81 | −47.794 | 24.078 | −24.770 | 1.00 | 52.07 | A |
| ATOM | 513 | CD1 | LEU | A | 81 | −47.823 | 25.523 | −25.274 | 1.00 | 50.96 | A |
| ATOM | 514 | CD2 | LEU | A | 81 | −47.338 | 23.143 | −25.881 | 1.00 | 51.96 | A |
| ATOM | 515 | C | LEU | A | 81 | −45.533 | 22.495 | −21.981 | 1.00 | 49.31 | A |
| ATOM | 516 | O | LEU | A | 81 | −44.655 | 21.673 | −22.231 | 1.00 | 49.33 | A |
| ATOM | 517 | N | LEU | A | 82 | −45.473 | 23.319 | −20.936 | 1.00 | 47.57 | A |
| ATOM | 518 | CA | LEU | A | 82 | −44.323 | 23.330 | −20.033 | 1.00 | 45.33 | A |
| ATOM | 519 | CB | LEU | A | 82 | −44.636 | 24.117 | −18.770 | 1.00 | 46.40 | A |
| ATOM | 520 | CG | LEU | A | 82 | −43.611 | 25.158 | −18.335 | 1.00 | 45.80 | A |
| ATOM | 521 | CD1 | LEU | A | 82 | −43.773 | 25.372 | −16.834 | 1.00 | 43.68 | A |
| ATOM | 522 | CD2 | LEU | A | 82 | −42.207 | 24.705 | −18.670 | 1.00 | 43.36 | A |
| ATOM | 523 | C | LEU | A | 82 | −43.864 | 21.945 | −19.618 | 1.00 | 43.50 | A |

TABLE 7-continued

Atomic coordinates of rSIFN-co (SEQ ID NO: 1)

| ATOM | 524 | O | LEU | A | 82 | −42.689 | 21.626 | −19.728 | 1.00 | 43.15 | A |
|---|---|---|---|---|---|---|---|---|---|---|---|
| ATOM | 525 | N | ALA | A | 83 | −44.785 | 21.114 | −19.146 | 1.00 | 43.10 | A |
| ATOM | 526 | CA | ALA | A | 83 | −44.405 | 19.775 | −18.706 | 1.00 | 43.00 | A |
| ATOM | 527 | CB | ALA | A | 83 | −45.606 | 19.052 | −18.090 | 1.00 | 43.77 | A |
| ATOM | 528 | C | ALA | A | 83 | −43.791 | 18.937 | −19.826 | 1.00 | 42.10 | A |
| ATOM | 529 | O | ALA | A | 83 | −42.857 | 18.179 | −19.591 | 1.00 | 41.05 | A |
| ATOM | 530 | N | LYS | A | 84 | −44.295 | 19.052 | −21.049 | 1.00 | 42.19 | A |
| ATOM | 531 | CA | LYS | A | 84 | −43.688 | 18.251 | −22.101 | 1.00 | 42.91 | A |
| ATOM | 532 | CB | LYS | A | 84 | −44.509 | 18.300 | −23.373 | 1.00 | 44.87 | A |
| ATOM | 533 | CG | LYS | A | 84 | −45.866 | 17.660 | −23.231 | 1.00 | 48.00 | A |
| ATOM | 534 | CD | LYS | A | 84 | −46.263 | 16.952 | −24.500 | 1.00 | 49.01 | A |
| ATOM | 535 | CE | LYS | A | 84 | −47.734 | 17.105 | −24.720 | 1.00 | 51.13 | A |
| ATOM | 536 | NZ | LYS | A | 84 | −48.023 | 18.541 | −24.942 | 1.00 | 52.74 | A |
| ATOM | 537 | C | LYS | A | 84 | −42.285 | 18.763 | −22.359 | 1.00 | 43.12 | A |
| ATOM | 538 | O | LYS | A | 84 | −41.347 | 17.987 | −22.527 | 1.00 | 44.29 | A |
| ATOM | 539 | N | PHE | A | 85 | −42.144 | 20.081 | −22.363 | 1.00 | 42.32 | A |
| ATOM | 540 | CA | PHE | A | 85 | −40.852 | 20.704 | −22.571 | 1.00 | 42.58 | A |
| ATOM | 541 | CB | PHE | A | 85 | −40.964 | 22.222 | −22.450 | 1.00 | 43.25 | A |
| ATOM | 542 | CG | PHE | A | 85 | −39.681 | 22.944 | −22.734 | 1.00 | 42.84 | A |
| ATOM | 543 | CD1 | PHE | A | 85 | −39.076 | 22.847 | −23.982 | 1.00 | 43.39 | A |
| ATOM | 544 | CD2 | PHE | A | 85 | −39.084 | 23.734 | −21.768 | 1.00 | 42.83 | A |
| ATOM | 545 | CE1 | PHE | A | 85 | −37.897 | 23.528 | −24.265 | 1.00 | 42.40 | A |
| ATOM | 546 | CE2 | PHE | A | 85 | −37.904 | 24.417 | −22.043 | 1.00 | 43.37 | A |
| ATOM | 547 | CZ | PHE | A | 85 | −37.312 | 24.313 | −23.295 | 1.00 | 42.70 | A |
| ATOM | 548 | C | PHE | A | 85 | −39.813 | 20.206 | −21.572 | 1.00 | 44.30 | A |
| ATOM | 549 | O | PHE | A | 85 | −38.835 | 19.562 | −21.964 | 1.00 | 45.07 | A |
| ATOM | 550 | N | TYR | A | 86 | −40.014 | 20.482 | −20.282 | 1.00 | 43.21 | A |
| ATOM | 551 | CA | TYR | A | 86 | −39.018 | 20.055 | −19.319 | 1.00 | 44.18 | A |
| ATOM | 552 | CB | TYR | A | 86 | −39.208 | 20.748 | −17.948 | 1.00 | 45.30 | A |
| ATOM | 553 | CG | TYR | A | 86 | −40.455 | 20.448 | −17.144 | 1.00 | 44.10 | A |
| ATOM | 554 | CD1 | TYR | A | 86 | −41.328 | 21.474 | −16.797 | 1.00 | 43.43 | A |
| ATOM | 555 | CE1 | TYR | A | 86 | −42.432 | 21.239 | −15.988 | 1.00 | 45.72 | A |
| ATOM | 556 | CD2 | TYR | A | 86 | −40.720 | 19.163 | −16.662 | 1.00 | 43.84 | A |
| ATOM | 557 | CE2 | TYR | A | 86 | −41.828 | 18.915 | −15.846 | 1.00 | 46.21 | A |
| ATOM | 558 | CZ | TYR | A | 86 | −42.678 | 19.963 | −15.513 | 1.00 | 47.37 | A |
| ATOM | 559 | OH | TYR | A | 86 | −43.764 | 19.756 | −14.691 | 1.00 | 49.38 | A |
| ATOM | 560 | C | TYR | A | 86 | −38.862 | 18.549 | −19.164 | 1.00 | 44.37 | A |
| ATOM | 561 | O | TYR | A | 86 | −37.848 | 18.080 | −18.656 | 1.00 | 44.46 | A |
| ATOM | 562 | N | THR | A | 87 | −39.846 | 17.785 | −19.621 | 1.00 | 44.44 | A |
| ATOM | 563 | CA | THR | A | 87 | −39.752 | 16.330 | −19.537 | 1.00 | 43.78 | A |
| ATOM | 564 | CB | THR | A | 87 | −41.129 | 15.644 | −19.751 | 1.00 | 43.93 | A |
| ATOM | 565 | OG1 | THR | A | 87 | −42.035 | 16.055 | −18.722 | 1.00 | 42.91 | A |
| ATOM | 566 | CG2 | THR | A | 87 | −40.986 | 14.130 | −19.712 | 1.00 | 40.48 | A |
| ATOM | 567 | C | THR | A | 87 | −38.813 | 15.905 | −20.654 | 1.00 | 43.41 | A |
| ATOM | 568 | O | THR | A | 87 | −38.040 | 14.962 | −20.509 | 1.00 | 42.95 | A |
| ATOM | 569 | N | GLU | A | 88 | −38.898 | 16.620 | −21.774 | 1.00 | 43.70 | A |
| ATOM | 570 | CA | GLU | A | 88 | −38.057 | 16.359 | −22.932 | 1.00 | 42.33 | A |
| ATOM | 571 | CB | GLU | A | 88 | −38.503 | 17.245 | −24.098 | 1.00 | 43.68 | A |
| ATOM | 572 | CG | GLU | A | 88 | −37.754 | 17.014 | −25.394 | 1.00 | 48.37 | A |
| ATOM | 573 | CD | GLU | A | 88 | −37.718 | 15.546 | −25.822 | 1.00 | 51.49 | A |
| ATOM | 574 | OE1 | GLU | A | 88 | −38.767 | 14.864 | −25.751 | 1.00 | 51.50 | A |
| ATOM | 575 | OE2 | GLU | A | 88 | −36.634 | 15.083 | −26.242 | 1.00 | 52.60 | A |
| ATOM | 576 | C | GLU | A | 88 | −36.616 | 16.664 | −22.541 | 1.00 | 40.76 | A |
| ATOM | 577 | O | GLU | A | 88 | −35.695 | 15.921 | −22.878 | 1.00 | 40.05 | A |
| ATOM | 578 | N | LEU | A | 89 | −36.428 | 17.756 | −21.809 | 1.00 | 39.65 | A |
| ATOM | 579 | CA | LEU | A | 89 | −35.096 | 18.127 | −21.373 | 1.00 | 40.05 | A |
| ATOM | 580 | CB | LEU | A | 89 | −35.128 | 19.464 | −20.619 | 1.00 | 39.26 | A |
| ATOM | 581 | CG | LEU | A | 89 | −35.580 | 20.688 | −21.432 | 1.00 | 39.90 | A |
| ATOM | 582 | CD1 | LEU | A | 89 | −35.594 | 21.916 | −20.546 | 1.00 | 41.45 | A |
| ATOM | 583 | CD2 | LEU | A | 89 | −34.647 | 20.917 | −22.599 | 1.00 | 37.56 | A |
| ATOM | 584 | C | LEU | A | 89 | −34.555 | 17.030 | −20.481 | 1.00 | 40.50 | A |
| ATOM | 585 | O | LEU | A | 89 | −33.394 | 16.638 | −20.598 | 1.00 | 39.83 | A |
| ATOM | 586 | N | TYR | A | 90 | −35.412 | 16.520 | −19.598 | 1.00 | 42.46 | A |
| ATOM | 587 | CA | TYR | A | 90 | −35.020 | 15.465 | −18.674 | 1.00 | 43.11 | A |
| ATOM | 588 | CB | TYR | A | 90 | −36.154 | 15.134 | −17.711 | 1.00 | 45.71 | A |
| ATOM | 589 | CG | TYR | A | 90 | −35.682 | 14.361 | −16.502 | 1.00 | 49.69 | A |
| ATOM | 590 | CD1 | TYR | A | 90 | −35.034 | 15.013 | −15.447 | 1.00 | 50.12 | A |
| ATOM | 591 | CE1 | TYR | A | 90 | −34.535 | 14.307 | −14.365 | 1.00 | 52.01 | A |
| ATOM | 592 | CD2 | TYR | A | 90 | −35.820 | 12.974 | −16.435 | 1.00 | 50.69 | A |
| ATOM | 593 | CE2 | TYR | A | 90 | −35.326 | 12.256 | −15.349 | 1.00 | 53.04 | A |
| ATOM | 594 | CZ | TYR | A | 90 | −34.680 | 12.929 | −14.321 | 1.00 | 53.92 | A |
| ATOM | 595 | OH | TYR | A | 90 | −34.161 | 12.227 | −13.256 | 1.00 | 56.71 | A |
| ATOM | 596 | C | TYR | A | 90 | −34.643 | 14.217 | −19.446 | 1.00 | 43.97 | A |
| ATOM | 597 | O | TYR | A | 90 | −33.682 | 13.534 | −19.106 | 1.00 | 44.98 | A |
| ATOM | 598 | N | GLN | A | 91 | −35.406 | 13.915 | −20.489 | 1.00 | 45.76 | A |
| ATOM | 599 | CA | GLN | A | 91 | −35.116 | 12.748 | −21.300 | 1.00 | 48.45 | A |
| ATOM | 600 | CB | GLN | A | 91 | −36.126 | 12.616 | −22.440 | 1.00 | 51.91 | A |
| ATOM | 601 | CG | GLN | A | 91 | −36.964 | 11.363 | −22.371 | 1.00 | 56.69 | A |

TABLE 7-continued

Atomic coordinates of rSIFN-co (SEQ ID NO: 1)

| ATOM | 602 | CD | GLN | A | 91 | −36.141 | 10.178 | −21.917 | 1.00 | 61.59 | A |
|---|---|---|---|---|---|---|---|---|---|---|---|
| ATOM | 603 | OE1 | GLN | A | 91 | −36.223 | 9.756 | −20.760 | 1.00 | 63.01 | A |
| ATOM | 604 | NE2 | GLN | A | 91 | −35.322 | 9.648 | −22.816 | 1.00 | 61.97 | A |
| ATOM | 605 | C | GLN | A | 91 | −33.719 | 12.909 | −21.880 | 1.00 | 48.95 | A |
| ATOM | 606 | O | GLN | A | 91 | −32.906 | 11.984 | −21.826 | 1.00 | 48.74 | A |
| ATOM | 607 | N | GLN | A | 92 | −33.451 | 14.098 | −22.419 | 1.00 | 48.30 | A |
| ATOM | 608 | CA | GLN | A | 92 | −32.166 | 14.403 | −23.030 | 1.00 | 49.20 | A |
| ATOM | 609 | CB | GLN | A | 92 | −32.204 | 15.800 | −23.666 | 1.00 | 49.21 | A |
| ATOM | 610 | CG | GLN | A | 92 | −32.906 | 15.825 | −25.020 | 1.00 | 50.13 | A |
| ATOM | 611 | CD | GLN | A | 92 | −33.021 | 17.215 | −25.621 | 1.00 | 51.05 | A |
| ATOM | 612 | OE1 | GLN | A | 92 | −32.087 | 18.010 | −25.566 | 1.00 | 53.57 | A |
| ATOM | 613 | NE2 | GLN | A | 92 | −34.166 | 17.505 | −26.214 | 1.00 | 52.77 | A |
| ATOM | 614 | C | GLN | A | 92 | −30.998 | 14.279 | −22.061 | 1.00 | 49.71 | A |
| ATOM | 615 | O | GLN | A | 92 | −29.895 | 13.902 | −22.462 | 1.00 | 50.06 | A |
| ATOM | 616 | N | LEU | A | 93 | −31.223 | 14.602 | −20.790 | 1.00 | 48.85 | A |
| ATOM | 617 | CA | LEU | A | 93 | −30.148 | 14.463 | −19.820 | 1.00 | 49.45 | A |
| ATOM | 618 | CB | LEU | A | 93 | −30.545 | 15.025 | −18.454 | 1.00 | 47.86 | A |
| ATOM | 619 | CG | LEU | A | 93 | −30.469 | 16.530 | −18.237 | 1.00 | 45.97 | A |
| ATOM | 620 | CD1 | LEU | A | 93 | −30.980 | 16.854 | −16.851 | 1.00 | 45.24 | A |
| ATOM | 621 | CD2 | LEU | A | 93 | −29.042 | 16.997 | −18.410 | 1.00 | 45.80 | A |
| ATOM | 622 | C | LEU | A | 93 | −29.883 | 12.974 | −19.679 | 1.00 | 51.53 | A |
| ATOM | 623 | O | LEU | A | 93 | −28.730 | 12.531 | −19.661 | 1.00 | 49.61 | A |
| ATOM | 624 | N | ALA | A | 94 | −30.974 | 12.212 | −19.585 | 1.00 | 54.03 | A |
| ATOM | 625 | CA | ALA | A | 94 | −30.902 | 10.766 | −19.439 | 1.00 | 56.50 | A |
| ATOM | 626 | CB | ALA | A | 94 | −32.306 | 10.177 | −19.305 | 1.00 | 55.64 | A |
| ATOM | 627 | C | ALA | A | 94 | −30.161 | 10.139 | −20.618 | 1.00 | 58.27 | A |
| ATOM | 628 | O | ALA | A | 94 | −29.383 | 9.208 | −20.431 | 1.00 | 60.16 | A |
| ATOM | 629 | N | ASP | A | 95 | −30.382 | 10.654 | −21.826 | 1.00 | 59.89 | A |
| ATOM | 630 | CA | ASP | A | 95 | −29.696 | 10.115 | −22.998 | 1.00 | 60.86 | A |
| ATOM | 631 | CB | ASP | A | 95 | −30.293 | 10.665 | −24.295 | 1.00 | 61.06 | A |
| ATOM | 632 | CG | ASP | A | 95 | −31.745 | 10.259 | −24.489 | 1.00 | 64.37 | A |
| ATOM | 633 | OD1 | ASP | A | 95 | −32.123 | 9.156 | −24.038 | 1.00 | 65.54 | A |
| ATOM | 634 | OD2 | ASP | A | 95 | −32.513 | 11.034 | −25.101 | 1.00 | 65.80 | A |
| ATOM | 635 | C | ASP | A | 95 | −28.208 | 10.424 | −22.960 | 1.00 | 62.01 | A |
| ATOM | 636 | O | ASP | A | 95 | −27.396 | 9.594 | −23.349 | 1.00 | 62.85 | A |
| ATOM | 637 | N | LEU | A | 96 | −27.840 | 11.612 | −22.492 | 1.00 | 63.44 | A |
| ATOM | 638 | CA | LEU | A | 96 | −26.429 | 11.968 | −22.434 | 1.00 | 65.26 | A |
| ATOM | 639 | CB | LEU | A | 96 | −26.250 | 13.437 | −22.063 | 1.00 | 64.67 | A |
| ATOM | 640 | CG | LEU | A | 96 | −26.228 | 14.431 | −23.223 | 1.00 | 64.38 | A |
| ATOM | 641 | CD1 | LEU | A | 96 | −25.876 | 15.815 | −22.699 | 1.00 | 63.39 | A |
| ATOM | 642 | CD2 | LEU | A | 96 | −25.213 | 13.978 | −24.256 | 1.00 | 62.74 | A |
| ATOM | 643 | C | LEU | A | 96 | −25.665 | 11.115 | −21.444 | 1.00 | 67.97 | A |
| ATOM | 644 | O | LEU | A | 96 | −24.520 | 10.735 | −21.693 | 1.00 | 68.62 | A |
| ATOM | 645 | N | GLU | A | 97 | −26.300 | 10.811 | −20.321 | 1.00 | 70.13 | A |
| ATOM | 646 | CA | GLU | A | 97 | −25.657 | 10.017 | −19.291 | 1.00 | 72.55 | A |
| ATOM | 647 | CB | GLU | A | 97 | −26.488 | 10.075 | −18.019 | 1.00 | 71.72 | A |
| ATOM | 648 | CG | GLU | A | 97 | −26.985 | 11.485 | −17.769 | 1.00 | 74.81 | A |
| ATOM | 649 | CD | GLU | A | 97 | −27.241 | 11.799 | −16.314 | 1.00 | 75.51 | A |
| ATOM | 650 | OE1 | GLU | A | 97 | −27.747 | 12.905 | −16.036 | 1.00 | 74.77 | A |
| ATOM | 651 | OE2 | GLU | A | 97 | −26.931 | 10.953 | −15.451 | 1.00 | 77.73 | A |
| ATOM | 652 | C | GLU | A | 97 | −25.450 | 8.588 | −19.762 | 1.00 | 74.96 | A |
| ATOM | 653 | O | GLU | A | 97 | −24.468 | 7.943 | −19.390 | 1.00 | 76.46 | A |
| ATOM | 654 | N | ALA | A | 98 | −26.366 | 8.089 | −20.586 | 1.00 | 76.86 | A |
| ATOM | 655 | CA | ALA | A | 98 | −26.223 | 6.737 | −21.115 | 1.00 | 78.82 | A |
| ATOM | 656 | CB | ALA | A | 98 | −27.433 | 6.366 | −21.954 | 1.00 | 77.13 | A |
| ATOM | 657 | C | ALA | A | 98 | −24.965 | 6.775 | −21.980 | 1.00 | 81.25 | A |
| ATOM | 658 | O | ALA | A | 98 | −24.070 | 5.941 | −21.838 | 1.00 | 81.55 | A |
| ATOM | 659 | N | CYS | A | 99 | −24.907 | 7.778 | −22.854 | 1.00 | 83.47 | A |
| ATOM | 660 | CA | CYS | A | 99 | −23.786 | 7.987 | −23.759 | 1.00 | 85.46 | A |
| ATOM | 661 | CB | CYS | A | 99 | −23.981 | 9.310 | −24.517 | 1.00 | 86.41 | A |
| ATOM | 662 | SG | CYS | A | 99 | −22.959 | 9.545 | −26.007 | 1.00 | 89.76 | A |
| ATOM | 663 | C | CYS | A | 99 | −22.462 | 8.000 | −22.988 | 1.00 | 86.47 | A |
| ATOM | 664 | O | CYS | A | 99 | −21.478 | 7.415 | −23.436 | 1.00 | 87.19 | A |
| ATOM | 665 | N | VAL | A | 100 | −22.438 | 8.659 | −21.832 | 1.00 | 87.06 | A |
| ATOM | 666 | CA | VAL | A | 100 | −21.221 | 8.718 | −21.018 | 1.00 | 88.28 | A |
| ATOM | 667 | CB | VAL | A | 100 | −21.364 | 9.721 | −19.840 | 1.00 | 87.74 | A |
| ATOM | 668 | CG1 | VAL | A | 100 | −20.109 | 9.704 | −18.980 | 1.00 | 87.01 | A |
| ATOM | 669 | CG2 | VAL | A | 100 | −21.603 | 11.118 | −20.371 | 1.00 | 87.68 | A |
| ATOM | 670 | C | VAL | A | 100 | −20.878 | 7.339 | −20.442 | 1.00 | 89.50 | A |
| ATOM | 671 | O | VAL | A | 100 | −19.728 | 6.899 | −20.506 | 1.00 | 89.46 | A |
| ATOM | 672 | N | ALA | A | 101 | −21.881 | 6.666 | −19.880 | 1.00 | 90.52 | A |
| ATOM | 673 | CA | ALA | A | 101 | −21.696 | 5.340 | −19.294 | 1.00 | 91.37 | A |
| ATOM | 674 | CB | ALA | A | 101 | −22.924 | 4.958 | −18.477 | 1.00 | 90.68 | A |
| ATOM | 675 | C | ALA | A | 101 | −21.448 | 4.305 | −20.390 | 1.00 | 92.11 | A |
| ATOM | 676 | O | ALA | A | 101 | −22.144 | 3.290 | −20.483 | 1.00 | 92.02 | A |
| ATOM | 677 | N | GLY | A | 102 | −20.445 | 4.572 | −21.218 | 1.00 | 92.66 | A |
| ATOM | 678 | CA | GLY | A | 102 | −20.117 | 3.672 | −22.303 | 1.00 | 93.77 | A |
| ATOM | 679 | C | GLY | A | 102 | −19.599 | 4.456 | −23.490 | 1.00 | 94.37 | A |

TABLE 7-continued

Atomic coordinates of rSIFN-co (SEQ ID NO: 1)

| ATOM | 680 | O   | GLY | A | 102 | −20.320 | 4.666  | −24.467 | 1.00 | 94.30 A |
|------|-----|-----|-----|---|-----|---------|--------|---------|------|---------|
| ATOM | 681 | N   | GLY | A | 103 | −18.345 | 4.893  | −23.399 | 1.00 | 94.78 A |
| ATOM | 682 | CA  | GLY | A | 103 | −17.741 | 5.662  | −24.472 | 1.00 | 94.59 A |
| ATOM | 683 | C   | GLY | A | 103 | −17.097 | 6.930  | −23.948 | 1.00 | 94.45 A |
| ATOM | 684 | O   | GLY | A | 103 | −17.324 | 7.326  | −22.804 | 1.00 | 94.32 A |
| ATOM | 685 | N   | ALA | A | 111 | −11.108 | 13.549 | −17.360 | 1.00 | 90.11 A |
| ATOM | 686 | CA  | ALA | A | 111 | −11.032 | 14.851 | −16.699 | 1.00 | 90.12 A |
| ATOM | 687 | CB  | ALA | A | 111 | −9.569  | 15.220 | −16.438 | 1.00 | 89.81 A |
| ATOM | 688 | C   | ALA | A | 111 | −11.713 | 15.942 | −17.530 | 1.00 | 89.66 A |
| ATOM | 689 | O   | ALA | A | 111 | −12.411 | 15.650 | −18.506 | 1.00 | 90.16 A |
| ATOM | 690 | N   | GLY | A | 112 | −11.509 | 17.197 | −17.136 | 1.00 | 88.41 A |
| ATOM | 691 | CA  | GLY | A | 112 | −12.108 | 18.312 | −17.853 | 1.00 | 86.60 A |
| ATOM | 692 | C   | GLY | A | 112 | −11.712 | 19.656 | −17.267 | 1.00 | 85.50 A |
| ATOM | 693 | O   | GLY | A | 112 | −10.617 | 19.797 | −16.709 | 1.00 | 86.67 A |
| ATOM | 694 | N   | ASN | A | 113 | −12.590 | 20.650 | −17.400 | 1.00 | 82.82 A |
| ATOM | 695 | CA  | ASN | A | 113 | −12.309 | 21.975 | −16.860 | 1.00 | 79.24 A |
| ATOM | 696 | CB  | ASN | A | 113 | −11.567 | 22.843 | −17.893 | 1.00 | 81.82 A |
| ATOM | 697 | CG  | ASN | A | 113 | −12.359 | 23.059 | −19.177 | 1.00 | 83.86 A |
| ATOM | 698 | OD1 | ASN | A | 113 | −12.808 | 22.103 | −19.818 | 1.00 | 85.28 A |
| ATOM | 699 | ND2 | ASN | A | 113 | −12.518 | 24.324 | −19.569 | 1.00 | 83.13 A |
| ATOM | 700 | C   | ASN | A | 113 | −13.551 | 22.693 | −16.339 | 1.00 | 75.65 A |
| ATOM | 701 | O   | ASN | A | 113 | −14.603 | 22.722 | −16.985 | 1.00 | 74.61 A |
| ATOM | 702 | N   | ALA | A | 114 | −13.397 | 23.272 | −15.152 | 1.00 | 71.33 A |
| ATOM | 703 | CA  | ALA | A | 114 | −14.456 | 23.986 | −14.447 | 1.00 | 66.25 A |
| ATOM | 704 | CB  | ALA | A | 114 | −14.016 | 24.237 | −13.002 | 1.00 | 65.33 A |
| ATOM | 705 | C   | ALA | A | 114 | −14.901 | 25.299 | −15.078 | 1.00 | 61.91 A |
| ATOM | 706 | O   | ALA | A | 114 | −16.020 | 25.746 | −14.859 | 1.00 | 60.64 A |
| ATOM | 707 | N   | ASP | A | 115 | −14.037 | 25.924 | −15.858 | 1.00 | 58.78 A |
| ATOM | 708 | CA  | ASP | A | 115 | −14.404 | 27.197 | −16.444 | 1.00 | 57.63 A |
| ATOM | 709 | CB  | ASP | A | 115 | −13.170 | 27.864 | −17.050 | 1.00 | 58.76 A |
| ATOM | 710 | CG  | ASP | A | 115 | −12.240 | 28.440 | −15.977 | 1.00 | 60.80 A |
| ATOM | 711 | OD1 | ASP | A | 115 | −12.644 | 29.410 | −15.283 | 1.00 | 58.59 A |
| ATOM | 712 | OD2 | ASP | A | 115 | −11.114 | 27.911 | −15.822 | 1.00 | 60.92 A |
| ATOM | 713 | C   | ASP | A | 115 | −15.553 | 27.143 | −17.441 | 1.00 | 56.69 A |
| ATOM | 714 | O   | ASP | A | 115 | −16.446 | 27.994 | −17.395 | 1.00 | 55.98 A |
| ATOM | 715 | N   | SER | A | 116 | −15.547 | 26.154 | −18.332 | 1.00 | 54.36 A |
| ATOM | 716 | CA  | SER | A | 116 | −16.629 | 26.025 | −19.305 | 1.00 | 51.56 A |
| ATOM | 717 | CB  | SER | A | 116 | −16.464 | 24.749 | −20.132 | 1.00 | 51.85 A |
| ATOM | 718 | OG  | SER | A | 116 | −15.262 | 24.765 | −20.875 | 1.00 | 52.43 A |
| ATOM | 719 | C   | SER | A | 116 | −17.957 | 25.964 | −18.549 | 1.00 | 50.12 A |
| ATOM | 720 | O   | SER | A | 116 | −18.876 | 26.747 | −18.798 | 1.00 | 48.52 A |
| ATOM | 721 | N   | ILE | A | 117 | −18.035 | 25.028 | −17.612 | 1.00 | 48.20 A |
| ATOM | 722 | CA  | ILE | A | 117 | −19.234 | 24.839 | −16.809 | 1.00 | 47.04 A |
| ATOM | 723 | CB  | ILE | A | 117 | −19.056 | 23.654 | −15.843 | 1.00 | 45.89 A |
| ATOM | 724 | CG2 | ILE | A | 117 | −20.128 | 23.680 | −14.771 | 1.00 | 41.04 A |
| ATOM | 725 | CG1 | ILE | A | 117 | −19.086 | 22.351 | −16.645 | 1.00 | 44.74 A |
| ATOM | 726 | CD1 | ILE | A | 117 | −18.727 | 21.139 | −15.847 | 1.00 | 47.83 A |
| ATOM | 727 | C   | ILE | A | 117 | −19.577 | 26.093 | −16.029 | 1.00 | 47.34 A |
| ATOM | 728 | O   | ILE | A | 117 | −20.747 | 26.363 | −15.755 | 1.00 | 47.25 A |
| ATOM | 729 | N   | LEU | A | 118 | −18.549 | 26.857 | −15.676 | 1.00 | 47.11 A |
| ATOM | 730 | CA  | LEU | A | 118 | −18.743 | 28.095 | −14.941 | 1.00 | 46.33 A |
| ATOM | 731 | CB  | LEU | A | 118 | −17.391 | 28.640 | −14.481 | 1.00 | 46.21 A |
| ATOM | 732 | CG  | LEU | A | 118 | −17.207 | 29.082 | −13.023 | 1.00 | 47.56 A |
| ATOM | 733 | CD1 | LEU | A | 118 | −17.864 | 28.110 | −12.045 | 1.00 | 45.29 A |
| ATOM | 734 | CD2 | LEU | A | 118 | −15.717 | 29.169 | −12.742 | 1.00 | 46.63 A |
| ATOM | 735 | C   | LEU | A | 118 | −19.419 | 29.071 | −15.894 | 1.00 | 45.37 A |
| ATOM | 736 | O   | LEU | A | 118 | −20.361 | 29.770 | −15.522 | 1.00 | 45.75 A |
| ATOM | 737 | N   | ALA | A | 119 | −18.947 | 29.095 | −17.135 | 1.00 | 43.53 A |
| ATOM | 738 | CA  | ALA | A | 119 | −19.515 | 29.980 | −18.145 | 1.00 | 44.02 A |
| ATOM | 739 | CB  | ALA | A | 119 | −18.835 | 29.746 | −19.483 | 1.00 | 43.57 A |
| ATOM | 740 | C   | ALA | A | 119 | −21.022 | 29.760 | −18.282 | 1.00 | 44.16 A |
| ATOM | 741 | O   | ALA | A | 119 | −21.802 | 30.707 | −18.185 | 1.00 | 43.43 A |
| ATOM | 742 | N   | VAL | A | 120 | −21.420 | 28.506 | −18.504 | 1.00 | 43.64 A |
| ATOM | 743 | CA  | VAL | A | 120 | −22.826 | 28.157 | −18.653 | 1.00 | 41.82 A |
| ATOM | 744 | CB  | VAL | A | 120 | −23.023 | 26.629 | −18.940 | 1.00 | 41.05 A |
| ATOM | 745 | CG1 | VAL | A | 120 | −24.488 | 26.335 | −19.229 | 1.00 | 38.92 A |
| ATOM | 746 | CG2 | VAL | A | 120 | −22.176 | 26.185 | −20.109 | 1.00 | 35.59 A |
| ATOM | 747 | C   | VAL | A | 120 | −23.582 | 28.530 | −17.378 | 1.00 | 42.89 A |
| ATOM | 748 | O   | VAL | A | 120 | −24.632 | 29.168 | −17.443 | 1.00 | 43.59 A |
| ATOM | 749 | N   | LYS | A | 121 | −23.050 | 28.148 | −16.218 | 1.00 | 43.62 A |
| ATOM | 750 | CA  | LYS | A | 121 | −23.713 | 28.470 | −14.950 | 1.00 | 43.47 A |
| ATOM | 751 | CB  | LYS | A | 121 | −22.938 | 27.909 | −13.757 | 1.00 | 42.82 A |
| ATOM | 752 | CG  | LYS | A | 121 | −23.098 | 26.405 | −13.565 | 1.00 | 42.66 A |
| ATOM | 753 | CD  | LYS | A | 121 | −22.183 | 25.886 | −12.463 | 1.00 | 44.00 A |
| ATOM | 754 | CE  | LYS | A | 121 | −22.464 | 24.418 | −12.136 | 1.00 | 45.31 A |
| ATOM | 755 | NZ  | LYS | A | 121 | −23.826 | 24.200 | −11.551 | 1.00 | 43.66 A |
| ATOM | 756 | C   | LYS | A | 121 | −23.892 | 29.963 | −14.773 | 1.00 | 43.91 A |
| ATOM | 757 | O   | LYS | A | 121 | −24.932 | 30.404 | −14.305 | 1.00 | 45.66 A |

TABLE 7-continued

Atomic coordinates of rSIFN-co (SEQ ID NO: 1)

| ATOM | 758 | N | LYS | A | 122 | −22.889 | 30.746 | −15.156 | 1.00 | 45.29 | A |
|---|---|---|---|---|---|---|---|---|---|---|---|
| ATOM | 759 | CA | LYS | A | 122 | −22.979 | 32.200 | −15.028 | 1.00 | 45.49 | A |
| ATOM | 760 | CB | LYS | A | 122 | −21.584 | 32.824 | −15.117 | 1.00 | 46.13 | A |
| ATOM | 761 | CG | LYS | A | 122 | −20.822 | 32.741 | −13.784 | 1.00 | 49.15 | A |
| ATOM | 762 | CD | LYS | A | 122 | −19.309 | 32.760 | −13.945 | 1.00 | 52.08 | A |
| ATOM | 763 | CE | LYS | A | 122 | −18.822 | 33.994 | −14.692 | 1.00 | 54.97 | A |
| ATOM | 764 | NZ | LYS | A | 122 | −17.332 | 33.997 | −14.825 | 1.00 | 58.31 | A |
| ATOM | 765 | C | LYS | A | 122 | −23.930 | 32.815 | −16.051 | 1.00 | 44.74 | A |
| ATOM | 766 | O | LYS | A | 122 | −24.576 | 33.819 | −15.774 | 1.00 | 44.79 | A |
| ATOM | 767 | N | TYR | A | 123 | −24.035 | 32.201 | −17.226 | 1.00 | 43.85 | A |
| ATOM | 768 | CA | TYR | A | 123 | −24.959 | 32.687 | −18.249 | 1.00 | 41.73 | A |
| ATOM | 769 | CB | TYR | A | 123 | −24.823 | 31.864 | −19.534 | 1.00 | 43.00 | A |
| ATOM | 770 | CG | TYR | A | 123 | −26.012 | 31.914 | −20.483 | 1.00 | 43.26 | A |
| ATOM | 771 | CD1 | TYR | A | 123 | −26.334 | 33.079 | −21.181 | 1.00 | 42.96 | A |
| ATOM | 772 | CE1 | TYR | A | 123 | −27.375 | 33.096 | −22.120 | 1.00 | 43.17 | A |
| ATOM | 773 | CD2 | TYR | A | 123 | −26.768 | 30.761 | −20.739 | 1.00 | 44.34 | A |
| ATOM | 774 | CE2 | TYR | A | 123 | −27.808 | 30.764 | −21.676 | 1.00 | 43.97 | A |
| ATOM | 775 | CZ | TYR | A | 123 | −28.100 | 31.934 | −22.361 | 1.00 | 43.84 | A |
| ATOM | 776 | OH | TYR | A | 123 | −29.106 | 31.942 | −23.289 | 1.00 | 43.65 | A |
| ATOM | 777 | C | TYR | A | 123 | −26.374 | 32.558 | −17.718 | 1.00 | 40.54 | A |
| ATOM | 778 | O | TYR | A | 123 | −27.180 | 33.464 | −17.886 | 1.00 | 40.80 | A |
| ATOM | 779 | N | PHE | A | 124 | −26.667 | 31.429 | −17.076 | 1.00 | 40.17 | A |
| ATOM | 780 | CA | PHE | A | 124 | −27.993 | 31.187 | −16.520 | 1.00 | 42.42 | A |
| ATOM | 781 | CB | PHE | A | 124 | −28.188 | 29.688 | −16.247 | 1.00 | 41.69 | A |
| ATOM | 782 | CG | PHE | A | 124 | −28.617 | 28.909 | −17.462 | 1.00 | 42.10 | A |
| ATOM | 783 | CD1 | PHE | A | 124 | −29.922 | 29.007 | −17.939 | 1.00 | 42.51 | A |
| ATOM | 784 | CD2 | PHE | A | 124 | −27.708 | 28.120 | −18.165 | 1.00 | 40.74 | A |
| ATOM | 785 | CE1 | PHE | A | 124 | −30.317 | 28.332 | −19.106 | 1.00 | 41.41 | A |
| ATOM | 786 | CE2 | PHE | A | 124 | −28.095 | 27.445 | −19.329 | 1.00 | 41.37 | A |
| ATOM | 787 | CZ | PHE | A | 124 | −29.400 | 27.554 | −19.797 | 1.00 | 39.97 | A |
| ATOM | 788 | C | PHE | A | 124 | −28.242 | 32.023 | −15.264 | 1.00 | 43.39 | A |
| ATOM | 789 | O | PHE | A | 124 | −29.378 | 32.322 | −14.922 | 1.00 | 42.59 | A |
| ATOM | 790 | N | GLN | A | 125 | −27.179 | 32.421 | −14.587 | 1.00 | 45.23 | A |
| ATOM | 791 | CA | GLN | A | 125 | −27.343 | 33.251 | −13.415 | 1.00 | 48.87 | A |
| ATOM | 792 | CB | GLN | A | 125 | −25.980 | 33.479 | −12.749 | 1.00 | 52.70 | A |
| ATOM | 793 | CG | GLN | A | 125 | −26.006 | 34.131 | −11.371 | 1.00 | 53.89 | A |
| ATOM | 794 | CD | GLN | A | 125 | −26.959 | 33.442 | −10.402 | 1.00 | 58.25 | A |
| ATOM | 795 | OE1 | GLN | A | 125 | −27.117 | 32.216 | −10.422 | 1.00 | 58.23 | A |
| ATOM | 796 | NE2 | GLN | A | 125 | −27.590 | 34.233 | −9.534 | 1.00 | 58.44 | A |
| ATOM | 797 | C | GLN | A | 125 | −27.942 | 34.565 | −13.920 | 1.00 | 49.60 | A |
| ATOM | 798 | O | GLN | A | 125 | −28.921 | 35.070 | −13.366 | 1.00 | 50.24 | A |
| ATOM | 799 | N | ARG | A | 126 | −27.361 | 35.119 | −14.979 | 1.00 | 50.02 | A |
| ATOM | 800 | CA | ARG | A | 126 | −27.883 | 36.362 | −15.537 | 1.00 | 51.12 | A |
| ATOM | 801 | CB | ARG | A | 126 | −27.070 | 36.766 | −16.753 | 1.00 | 50.74 | A |
| ATOM | 802 | CG | ARG | A | 126 | −25.703 | 37.248 | −16.397 | 1.00 | 51.91 | A |
| ATOM | 803 | CD | ARG | A | 126 | −24.873 | 37.578 | −17.655 | 1.00 | 53.15 | A |
| ATOM | 804 | NE | ARG | A | 126 | −23.567 | 36.942 | −17.591 | 1.00 | 56.26 | A |
| ATOM | 805 | CZ | ARG | A | 126 | −23.143 | 36.070 | −18.500 | 1.00 | 56.88 | A |
| ATOM | 806 | NH1 | ARG | A | 126 | −21.926 | 35.525 | −18.418 | 1.00 | 61.63 | A |
| ATOM | 807 | NH2 | ARG | A | 126 | −23.950 | 35.718 | −19.488 | 1.00 | 57.30 | A |
| ATOM | 808 | C | ARG | A | 126 | −29.365 | 36.270 | −15.891 | 1.00 | 51.99 | A |
| ATOM | 809 | O | ARG | A | 126 | −30.141 | 37.168 | −15.542 | 1.00 | 53.15 | A |
| ATOM | 810 | N | ILE | A | 127 | −29.758 | 35.181 | −16.554 | 1.00 | 51.87 | A |
| ATOM | 811 | CA | ILE | A | 127 | −31.152 | 34.972 | −16.914 | 1.00 | 50.67 | A |
| ATOM | 812 | CB | ILE | A | 127 | −31.403 | 33.556 | −17.498 | 1.00 | 49.15 | A |
| ATOM | 813 | CG2 | ILE | A | 127 | −32.888 | 33.373 | −17.759 | 1.00 | 45.24 | A |
| ATOM | 814 | CG1 | ILE | A | 127 | −30.611 | 33.343 | −18.790 | 1.00 | 49.62 | A |
| ATOM | 815 | CD1 | ILE | A | 127 | −31.121 | 34.119 | −19.945 | 1.00 | 50.32 | A |
| ATOM | 816 | C | ILE | A | 127 | −31.992 | 35.089 | −15.644 | 1.00 | 51.30 | A |
| ATOM | 817 | O | ILE | A | 127 | −32.917 | 35.891 | −15.579 | 1.00 | 50.89 | A |
| ATOM | 818 | N | THR | A | 128 | −31.669 | 34.274 | −14.644 | 1.00 | 52.07 | A |
| ATOM | 819 | CA | THR | A | 128 | −32.412 | 34.277 | −13.391 | 1.00 | 55.06 | A |
| ATOM | 820 | CB | THR | A | 128 | −31.762 | 33.325 | −12.358 | 1.00 | 54.18 | A |
| ATOM | 821 | OG1 | THR | A | 128 | −32.194 | 31.987 | −12.618 | 1.00 | 55.56 | A |
| ATOM | 822 | CG2 | THR | A | 128 | −32.163 | 33.691 | −10.943 | 1.00 | 56.16 | A |
| ATOM | 823 | C | THR | A | 128 | −32.517 | 35.679 | −12.811 | 1.00 | 56.81 | A |
| ATOM | 824 | O | THR | A | 128 | −33.602 | 36.128 | −12.445 | 1.00 | 56.02 | A |
| ATOM | 825 | N | LEU | A | 129 | −31.383 | 36.370 | −12.754 | 1.00 | 59.30 | A |
| ATOM | 826 | CA | LEU | A | 129 | −31.321 | 37.718 | −12.212 | 1.00 | 60.85 | A |
| ATOM | 827 | CB | LEU | A | 129 | −29.863 | 38.176 | −12.166 | 1.00 | 63.37 | A |
| ATOM | 828 | CG | LEU | A | 129 | −29.428 | 39.036 | −10.972 | 1.00 | 67.01 | A |
| ATOM | 829 | CD1 | LEU | A | 129 | −27.937 | 38.819 | −10.757 | 1.00 | 67.40 | A |
| ATOM | 830 | CD2 | LEU | A | 129 | −29.758 | 40.522 | −11.184 | 1.00 | 65.11 | A |
| ATOM | 831 | C | LEU | A | 129 | −32.158 | 38.693 | −13.037 | 1.00 | 61.24 | A |
| ATOM | 832 | O | LEU | A | 129 | −32.768 | 39.610 | −12.491 | 1.00 | 62.01 | A |
| ATOM | 833 | N | TYR | A | 130 | −32.181 | 38.497 | −14.351 | 1.00 | 60.00 | A |
| ATOM | 834 | CA | TYR | A | 130 | −32.953 | 39.357 | −15.243 | 1.00 | 58.99 | A |
| ATOM | 835 | CB | TYR | A | 130 | −32.663 | 38.993 | −16.701 | 1.00 | 58.50 | A |

TABLE 7-continued

Atomic coordinates of rSIFN-co (SEQ ID NO: 1)

| ATOM | 836 | CG | TYR | A | 130 | −33.584 | 39.637 | −17.715 | 1.00 | 57.74 | A |
|---|---|---|---|---|---|---|---|---|---|---|---|
| ATOM | 837 | CD1 | TYR | A | 130 | −33.439 | 40.974 | −18.074 | 1.00 | 58.05 | A |
| ATOM | 838 | CE1 | TYR | A | 130 | −34.279 | 41.560 | −19.020 | 1.00 | 58.22 | A |
| ATOM | 839 | CD2 | TYR | A | 130 | −34.594 | 38.901 | −18.327 | 1.00 | 58.06 | A |
| ATOM | 840 | CE2 | TYR | A | 130 | −35.437 | 39.478 | −19.272 | 1.00 | 57.76 | A |
| ATOM | 841 | CZ | TYR | A | 130 | −35.274 | 40.805 | −19.613 | 1.00 | 58.23 | A |
| ATOM | 842 | OH | TYR | A | 130 | −36.113 | 41.378 | −20.540 | 1.00 | 58.83 | A |
| ATOM | 843 | C | TYR | A | 130 | −34.434 | 39.166 | −14.957 | 1.00 | 59.31 | A |
| ATOM | 844 | O | TYR | A | 130 | −35.183 | 40.134 | −14.814 | 1.00 | 59.29 | A |
| ATOM | 845 | N | LEU | A | 131 | −34.844 | 37.904 | −14.875 | 1.00 | 58.83 | A |
| ATOM | 846 | CA | LEU | A | 131 | −36.233 | 37.558 | −14.617 | 1.00 | 58.58 | A |
| ATOM | 847 | CB | LEU | A | 131 | −36.390 | 36.037 | −14.555 | 1.00 | 55.68 | A |
| ATOM | 848 | CG | LEU | A | 131 | −36.422 | 35.361 | −15.922 | 1.00 | 53.74 | A |
| ATOM | 849 | CD1 | LEU | A | 131 | −36.318 | 33.863 | −15.755 | 1.00 | 54.07 | A |
| ATOM | 850 | CD2 | LEU | A | 131 | −37.699 | 35.742 | −16.649 | 1.00 | 52.53 | A |
| ATOM | 851 | C | LEU | A | 131 | −36.740 | 38.193 | −13.330 | 1.00 | 59.15 | A |
| ATOM | 852 | O | LEU | A | 131 | −37.811 | 38.807 | −13.304 | 1.00 | 57.39 | A |
| ATOM | 853 | N | THR | A | 132 | −35.966 | 38.041 | −12.262 | 1.00 | 60.31 | A |
| ATOM | 854 | CA | THR | A | 132 | −36.342 | 38.608 | −10.982 | 1.00 | 61.04 | A |
| ATOM | 855 | CB | THR | A | 132 | −35.474 | 38.034 | −9.826 | 1.00 | 61.40 | A |
| ATOM | 856 | OG1 | THR | A | 132 | −35.587 | 38.887 | −8.680 | 1.00 | 64.65 | A |
| ATOM | 857 | CG2 | THR | A | 132 | −34.026 | 37.929 | −10.227 | 1.00 | 59.77 | A |
| ATOM | 858 | C | THR | A | 132 | −36.212 | 40.125 | −11.044 | 1.00 | 61.41 | A |
| ATOM | 859 | O | THR | A | 132 | −37.112 | 40.853 | −10.624 | 1.00 | 61.07 | A |
| ATOM | 860 | N | GLY | A | 133 | −35.102 | 40.598 | −11.597 | 1.00 | 62.03 | A |
| ATOM | 861 | CA | GLY | A | 133 | −34.891 | 42.029 | −11.705 | 1.00 | 62.46 | A |
| ATOM | 862 | C | GLY | A | 133 | −35.929 | 42.684 | −12.592 | 1.00 | 62.83 | A |
| ATOM | 863 | O | GLY | A | 133 | −36.032 | 43.905 | −12.634 | 1.00 | 63.96 | A |
| ATOM | 864 | N | LYS | A | 134 | −36.708 | 41.869 | −13.295 | 1.00 | 62.98 | A |
| ATOM | 865 | CA | LYS | A | 134 | −37.729 | 42.375 | −14.205 | 1.00 | 62.76 | A |
| ATOM | 866 | CB | LYS | A | 134 | −37.523 | 41.775 | −15.595 | 1.00 | 63.31 | A |
| ATOM | 867 | CG | LYS | A | 134 | −37.830 | 42.712 | −16.742 | 1.00 | 63.91 | A |
| ATOM | 868 | CD | LYS | A | 134 | −36.734 | 43.744 | −16.932 | 1.00 | 64.03 | A |
| ATOM | 869 | CE | LYS | A | 134 | −37.008 | 44.589 | −18.172 | 1.00 | 65.71 | A |
| ATOM | 870 | NZ | LYS | A | 134 | −35.986 | 45.656 | −18.394 | 1.00 | 66.60 | A |
| ATOM | 871 | C | LYS | A | 134 | −39.122 | 42.026 | −13.694 | 1.00 | 62.52 | A |
| ATOM | 872 | O | LYS | A | 134 | −40.118 | 42.159 | −14.408 | 1.00 | 61.64 | A |
| ATOM | 873 | N | ALA | A | 135 | −39.175 | 41.558 | −12.454 | 1.00 | 62.91 | A |
| ATOM | 874 | CA | ALA | A | 135 | −40.433 | 41.207 | −11.809 | 1.00 | 62.68 | A |
| ATOM | 875 | CB | ALA | A | 135 | −41.307 | 42.469 | −11.671 | 1.00 | 63.48 | A |
| ATOM | 876 | C | ALA | A | 135 | −41.221 | 40.096 | −12.501 | 1.00 | 61.65 | A |
| ATOM | 877 | O | ALA | A | 135 | −42.444 | 40.041 | −12.385 | 1.00 | 61.18 | A |
| ATOM | 878 | N | TYR | A | 136 | −40.525 | 39.215 | −13.213 | 1.00 | 60.39 | A |
| ATOM | 879 | CA | TYR | A | 136 | −41.166 | 38.091 | −13.908 | 1.00 | 60.51 | A |
| ATOM | 880 | CB | TYR | A | 136 | −41.622 | 37.024 | −12.899 | 1.00 | 60.08 | A |
| ATOM | 881 | CG | TYR | A | 136 | −40.547 | 36.596 | −11.924 | 1.00 | 62.10 | A |
| ATOM | 882 | CD1 | TYR | A | 136 | −40.241 | 37.378 | −10.807 | 1.00 | 62.66 | A |
| ATOM | 883 | CE1 | TYR | A | 136 | −39.227 | 37.007 | −9.919 | 1.00 | 63.23 | A |
| ATOM | 884 | CD2 | TYR | A | 136 | −39.811 | 35.424 | −12.131 | 1.00 | 62.49 | A |
| ATOM | 885 | CE2 | TYR | A | 136 | −38.792 | 35.044 | −11.249 | 1.00 | 64.05 | A |
| ATOM | 886 | CZ | TYR | A | 136 | −38.507 | 35.844 | −10.146 | 1.00 | 63.71 | A |
| ATOM | 887 | OH | TYR | A | 136 | −37.495 | 35.495 | −9.280 | 1.00 | 63.34 | A |
| ATOM | 888 | C | TYR | A | 136 | −42.359 | 38.479 | −14.785 | 1.00 | 60.49 | A |
| ATOM | 889 | O | TYR | A | 136 | −43.334 | 37.731 | −14.882 | 1.00 | 60.06 | A |
| ATOM | 890 | N | SER | A | 137 | −42.289 | 39.641 | −15.425 | 1.00 | 61.06 | A |
| ATOM | 891 | CA | SER | A | 137 | −43.383 | 40.088 | −16.284 | 1.00 | 61.14 | A |
| ATOM | 892 | CB | SER | A | 137 | −43.205 | 41.557 | −16.650 | 1.00 | 60.90 | A |
| ATOM | 893 | OG | SER | A | 137 | −42.133 | 41.713 | −17.559 | 1.00 | 63.48 | A |
| ATOM | 894 | C | SER | A | 137 | −43.432 | 39.257 | −17.563 | 1.00 | 61.21 | A |
| ATOM | 895 | O | SER | A | 137 | −42.414 | 38.718 | −18.004 | 1.00 | 59.84 | A |
| ATOM | 896 | N | PRO | A | 138 | −44.624 | 39.150 | −18.178 | 1.00 | 61.71 | A |
| ATOM | 897 | CD | PRO | A | 138 | −45.906 | 39.727 | −17.725 | 1.00 | 60.80 | A |
| ATOM | 898 | CA | PRO | A | 138 | −44.819 | 38.384 | −19.414 | 1.00 | 60.13 | A |
| ATOM | 899 | CB | PRO | A | 138 | −46.238 | 38.773 | −19.831 | 1.00 | 59.80 | A |
| ATOM | 900 | CG | PRO | A | 138 | −46.929 | 38.932 | −18.523 | 1.00 | 58.23 | A |
| ATOM | 901 | C | PRO | A | 138 | −43.783 | 38.661 | −20.506 | 1.00 | 59.03 | A |
| ATOM | 902 | O | PRO | A | 138 | −43.361 | 37.737 | −21.199 | 1.00 | 59.70 | A |
| ATOM | 903 | N | CYS | A | 139 | −43.382 | 39.922 | −20.659 | 1.00 | 57.95 | A |
| ATOM | 904 | CA | CYS | A | 139 | −42.392 | 40.296 | −21.666 | 1.00 | 58.35 | A |
| ATOM | 905 | C | CYS | A | 139 | −41.024 | 39.758 | −21.311 | 1.00 | 57.19 | A |
| ATOM | 906 | O | CYS | A | 139 | −40.267 | 39.329 | −22.185 | 1.00 | 57.07 | A |
| ATOM | 907 | CB | CYS | A | 139 | −42.280 | 41.813 | −21.798 | 1.00 | 60.88 | A |
| ATOM | 908 | SG | CYS | A | 139 | −43.778 | 42.639 | −22.404 | 1.00 | 68.54 | A |
| ATOM | 909 | N | ALA | A | 140 | −40.701 | 39.807 | −20.022 | 1.00 | 55.95 | A |
| ATOM | 910 | CA | ALA | A | 140 | −39.420 | 39.318 | −19.537 | 1.00 | 53.50 | A |
| ATOM | 911 | CB | ALA | A | 140 | −39.307 | 39.547 | −18.039 | 1.00 | 51.95 | A |
| ATOM | 912 | C | ALA | A | 140 | −39.311 | 37.831 | −19.857 | 1.00 | 52.02 | A |
| ATOM | 913 | O | ALA | A | 140 | −38.249 | 37.350 | −20.237 | 1.00 | 52.56 | A |

TABLE 7-continued

Atomic coordinates of rSIFN-co (SEQ ID NO: 1)

| ATOM | 914 | N | TRP | A | 141 | −40.418 | 37.111 | −19.714 | 1.00 | 50.19 | A |
|------|-----|------|-----|---|-----|---------|--------|---------|------|-------|---|
| ATOM | 915 | CA | TRP | A | 141 | −40.429 | 35.685 | −19.990 | 1.00 | 49.75 | A |
| ATOM | 916 | CB | TRP | A | 141 | −41.662 | 35.034 | −19.365 | 1.00 | 48.78 | A |
| ATOM | 917 | CG | TRP | A | 141 | −41.411 | 34.516 | −17.981 | 1.00 | 49.84 | A |
| ATOM | 918 | CD2 | TRP | A | 141 | −40.564 | 33.415 | −17.616 | 1.00 | 48.87 | A |
| ATOM | 919 | CE2 | TRP | A | 141 | −40.649 | 33.274 | −16.212 | 1.00 | 48.13 | A |
| ATOM | 920 | CE3 | TRP | A | 141 | −39.744 | 32.534 | −18.340 | 1.00 | 46.28 | A |
| ATOM | 921 | CD1 | TRP | A | 141 | −41.953 | 34.984 | −16.814 | 1.00 | 47.90 | A |
| ATOM | 922 | NE1 | TRP | A | 141 | −41.501 | 34.243 | −15.754 | 1.00 | 47.02 | A |
| ATOM | 923 | CZ2 | TRP | A | 141 | −39.944 | 32.281 | −15.514 | 1.00 | 46.41 | A |
| ATOM | 924 | CZ3 | TRP | A | 141 | −39.042 | 31.544 | −17.644 | 1.00 | 44.50 | A |
| ATOM | 925 | CH2 | TRP | A | 141 | −39.150 | 31.428 | −16.246 | 1.00 | 46.31 | A |
| ATOM | 926 | C | TRP | A | 141 | −40.373 | 35.394 | −21.487 | 1.00 | 49.99 | A |
| ATOM | 927 | O | TRP | A | 141 | −39.865 | 34.356 | −21.908 | 1.00 | 49.91 | A |
| ATOM | 928 | N | GLU | A | 142 | −40.902 | 36.314 | −22.285 | 1.00 | 49.68 | A |
| ATOM | 929 | CA | GLU | A | 142 | −40.885 | 36.176 | −23.734 | 1.00 | 49.54 | A |
| ATOM | 930 | CB | GLU | A | 142 | −41.879 | 37.161 | −24.359 | 1.00 | 51.93 | A |
| ATOM | 931 | CG | GLU | A | 142 | −42.054 | 37.014 | −25.862 | 1.00 | 55.37 | A |
| ATOM | 932 | CD | GLU | A | 142 | −42.079 | 35.566 | −26.315 | 1.00 | 58.44 | A |
| ATOM | 933 | OE1 | GLU | A | 142 | −42.804 | 34.747 | −25.698 | 1.00 | 59.65 | A |
| ATOM | 934 | OE2 | GLU | A | 142 | −41.371 | 35.252 | −27.296 | 1.00 | 58.89 | A |
| ATOM | 935 | C | GLU | A | 142 | −39.457 | 36.445 | −24.235 | 1.00 | 48.12 | A |
| ATOM | 936 | O | GLU | A | 142 | −38.990 | 35.830 | −25.195 | 1.00 | 46.88 | A |
| ATOM | 937 | N | VAL | A | 143 | −38.766 | 37.363 | −23.569 | 1.00 | 46.47 | A |
| ATOM | 938 | CA | VAL | A | 143 | −37.387 | 37.685 | −23.918 | 1.00 | 46.26 | A |
| ATOM | 939 | CB | VAL | A | 143 | −36.925 | 38.990 | −23.219 | 1.00 | 46.29 | A |
| ATOM | 940 | CG1 | VAL | A | 143 | −35.505 | 39.327 | −23.605 | 1.00 | 43.99 | A |
| ATOM | 941 | CG2 | VAL | A | 143 | −37.855 | 40.124 | −23.594 | 1.00 | 48.07 | A |
| ATOM | 942 | C | VAL | A | 143 | −36.471 | 36.532 | −23.490 | 1.00 | 45.08 | A |
| ATOM | 943 | O | VAL | A | 143 | −35.421 | 36.312 | −24.087 | 1.00 | 46.32 | A |
| ATOM | 944 | N | VAL | A | 144 | −36.861 | 35.800 | −22.451 | 1.00 | 42.03 | A |
| ATOM | 945 | CA | VAL | A | 144 | −36.051 | 34.680 | −22.010 | 1.00 | 40.59 | A |
| ATOM | 946 | CB | VAL | A | 144 | −36.331 | 34.343 | −20.517 | 1.00 | 39.36 | A |
| ATOM | 947 | CG1 | VAL | A | 144 | −35.716 | 32.999 | −20.144 | 1.00 | 38.27 | A |
| ATOM | 948 | CG2 | VAL | A | 144 | −35.722 | 35.421 | −19.626 | 1.00 | 37.69 | A |
| ATOM | 949 | C | VAL | A | 144 | −36.328 | 33.472 | −22.916 | 1.00 | 41.36 | A |
| ATOM | 950 | O | VAL | A | 144 | −35.419 | 32.715 | −23.262 | 1.00 | 39.87 | A |
| ATOM | 951 | N | ARG | A | 145 | −37.584 | 33.304 | −23.311 | 1.00 | 42.03 | A |
| ATOM | 952 | CA | ARG | A | 145 | −37.954 | 32.200 | −24.178 | 1.00 | 43.63 | A |
| ATOM | 953 | CB | ARG | A | 145 | −39.458 | 32.238 | −24.485 | 1.00 | 43.53 | A |
| ATOM | 954 | CG | ARG | A | 145 | −40.010 | 30.975 | −25.172 | 1.00 | 44.12 | A |
| ATOM | 955 | CD | ARG | A | 145 | −41.466 | 31.179 | −25.671 | 1.00 | 47.31 | A |
| ATOM | 956 | NE | ARG | A | 145 | −41.546 | 32.147 | −26.772 | 1.00 | 49.05 | A |
| ATOM | 957 | CZ | ARG | A | 145 | −41.087 | 31.924 | −28.005 | 1.00 | 47.86 | A |
| ATOM | 958 | NH1 | ARG | A | 145 | −40.526 | 30.765 | −28.323 | 1.00 | 47.20 | A |
| ATOM | 959 | NH2 | ARG | A | 145 | −41.141 | 32.882 | −28.910 | 1.00 | 48.43 | A |
| ATOM | 960 | C | ARG | A | 145 | −37.144 | 32.333 | −25.474 | 1.00 | 44.89 | A |
| ATOM | 961 | O | ARG | A | 145 | −36.551 | 31.367 | −25.952 | 1.00 | 44.68 | A |
| ATOM | 962 | N | ALA | A | 146 | −37.098 | 33.542 | −26.024 | 1.00 | 45.26 | A |
| ATOM | 963 | CA | ALA | A | 146 | −36.366 | 33.786 | −27.267 | 1.00 | 44.68 | A |
| ATOM | 964 | CB | ALA | A | 146 | −36.639 | 35.199 | −27.766 | 1.00 | 41.89 | A |
| ATOM | 965 | C | ALA | A | 146 | −34.865 | 33.564 | −27.115 | 1.00 | 44.62 | A |
| ATOM | 966 | O | ALA | A | 146 | −34.214 | 33.063 | −28.028 | 1.00 | 45.73 | A |
| ATOM | 967 | N | GLU | A | 147 | −34.319 | 33.940 | −25.963 | 1.00 | 43.92 | A |
| ATOM | 968 | CA | GLU | A | 147 | −32.894 | 33.772 | −25.697 | 1.00 | 42.58 | A |
| ATOM | 969 | CB | GLU | A | 147 | −32.512 | 34.500 | −24.403 | 1.00 | 40.40 | A |
| ATOM | 970 | CG | GLU | A | 147 | −31.124 | 34.186 | −23.878 | 1.00 | 40.78 | A |
| ATOM | 971 | CD | GLU | A | 147 | −30.021 | 34.667 | −24.802 | 1.00 | 44.78 | A |
| ATOM | 972 | OE1 | GLU | A | 147 | −30.039 | 35.853 | −25.201 | 1.00 | 46.12 | A |
| ATOM | 973 | OE2 | GLU | A | 147 | −29.125 | 33.862 | −25.128 | 1.00 | 46.08 | A |
| ATOM | 974 | C | GLU | A | 147 | −32.526 | 32.288 | −25.600 | 1.00 | 42.73 | A |
| ATOM | 975 | O | GLU | A | 147 | −31.490 | 31.871 | −26.130 | 1.00 | 41.47 | A |
| ATOM | 976 | N | ILE | A | 148 | −33.367 | 31.497 | −24.929 | 1.00 | 41.27 | A |
| ATOM | 977 | CA | ILE | A | 148 | −33.103 | 30.066 | −24.794 | 1.00 | 42.00 | A |
| ATOM | 978 | CB | ILE | A | 148 | −34.031 | 29.409 | −23.715 | 1.00 | 42.87 | A |
| ATOM | 979 | CG2 | ILE | A | 148 | −34.159 | 27.894 | −23.939 | 1.00 | 41.81 | A |
| ATOM | 980 | CG1 | ILE | A | 148 | −33.423 | 29.613 | −22.331 | 1.00 | 42.77 | A |
| ATOM | 981 | CD1 | ILE | A | 148 | −33.158 | 31.046 | −21.993 | 1.00 | 47.88 | A |
| ATOM | 982 | C | ILE | A | 148 | −33.284 | 29.382 | −26.148 | 1.00 | 42.52 | A |
| ATOM | 983 | O | ILE | A | 148 | −32.521 | 28.489 | −26.510 | 1.00 | 40.95 | A |
| ATOM | 984 | N | MET | A | 149 | −34.297 | 29.820 | −26.890 | 1.00 | 43.15 | A |
| ATOM | 985 | CA | MET | A | 149 | −34.594 | 29.288 | −28.210 | 1.00 | 43.66 | A |
| ATOM | 986 | CB | MET | A | 149 | −35.738 | 30.082 | −28.840 | 1.00 | 45.34 | A |
| ATOM | 987 | CG | MET | A | 149 | −36.136 | 29.660 | −30.241 | 1.00 | 47.78 | A |
| ATOM | 988 | SD | MET | A | 149 | −37.331 | 28.311 | −30.248 | 1.00 | 53.42 | A |
| ATOM | 989 | CE | MET | A | 149 | −36.351 | 27.036 | −30.894 | 1.00 | 52.10 | A |
| ATOM | 990 | C | MET | A | 149 | −33.342 | 29.456 | −29.052 | 1.00 | 45.41 | A |
| ATOM | 991 | O | MET | A | 149 | −32.924 | 28.543 | −29.776 | 1.00 | 46.37 | A |

TABLE 7-continued

Atomic coordinates of rSIFN-co (SEQ ID NO: 1)

| ATOM | 992 | N | ARG | A | 150 | −32.733 | 30.629 | −28.945 | 1.00 | 45.61 | A |
|---|---|---|---|---|---|---|---|---|---|---|---|
| ATOM | 993 | CA | ARG | A | 150 | −31.540 | 30.895 | −29.709 | 1.00 | 47.17 | A |
| ATOM | 994 | CB | ARG | A | 150 | −31.254 | 32.389 | −29.720 | 1.00 | 48.49 | A |
| ATOM | 995 | CG | ARG | A | 150 | −30.191 | 32.777 | −30.712 | 1.00 | 53.95 | A |
| ATOM | 996 | CD | ARG | A | 150 | −29.717 | 34.199 | −30.516 | 1.00 | 59.85 | A |
| ATOM | 997 | NE | ARG | A | 150 | −28.745 | 34.560 | −31.546 | 1.00 | 66.19 | A |
| ATOM | 998 | CZ | ARG | A | 150 | −27.975 | 35.644 | −31.513 | 1.00 | 69.41 | A |
| ATOM | 999 | NH1 | ARG | A | 150 | −28.053 | 36.493 | −30.488 | 1.00 | 70.95 | A |
| ATOM | 1000 | NH2 | ARG | A | 150 | −27.129 | 35.882 | −32.510 | 1.00 | 69.33 | A |
| ATOM | 1001 | C | ARG | A | 150 | −30.334 | 30.126 | −29.161 | 1.00 | 48.23 | A |
| ATOM | 1002 | O | ARG | A | 150 | −29.612 | 29.473 | −29.923 | 1.00 | 48.56 | A |
| ATOM | 1003 | N | SER | A | 151 | −30.122 | 30.177 | −27.847 | 1.00 | 47.72 | A |
| ATOM | 1004 | CA | SER | A | 151 | −28.973 | 29.492 | −27.258 | 1.00 | 48.57 | A |
| ATOM | 1005 | CB | SER | A | 151 | −28.714 | 29.993 | −25.837 | 1.00 | 48.92 | A |
| ATOM | 1006 | OG | SER | A | 151 | −29.880 | 29.900 | −25.045 | 1.00 | 54.27 | A |
| ATOM | 1007 | C | SER | A | 151 | −29.090 | 27.979 | −27.253 | 1.00 | 48.50 | A |
| ATOM | 1008 | O | SER | A | 151 | −28.113 | 27.278 | −27.517 | 1.00 | 46.55 | A |
| ATOM | 1009 | N | PHE | A | 152 | −30.277 | 27.468 | −26.953 | 1.00 | 49.05 | A |
| ATOM | 1010 | CA | PHE | A | 152 | −30.463 | 26.024 | −26.938 | 1.00 | 50.72 | A |
| ATOM | 1011 | CB | PHE | A | 152 | −31.808 | 25.667 | −26.301 | 1.00 | 48.90 | A |
| ATOM | 1012 | CG | PHE | A | 152 | −31.872 | 24.270 | −25.772 | 1.00 | 47.92 | A |
| ATOM | 1013 | CD1 | PHE | A | 152 | −31.364 | 23.970 | −24.514 | 1.00 | 48.09 | A |
| ATOM | 1014 | CD2 | PHE | A | 152 | −32.430 | 23.246 | −26.535 | 1.00 | 48.59 | A |
| ATOM | 1015 | CE1 | PHE | A | 152 | −31.406 | 22.667 | −24.010 | 1.00 | 47.02 | A |
| ATOM | 1016 | CE2 | PHE | A | 152 | −32.480 | 21.938 | −26.047 | 1.00 | 49.53 | A |
| ATOM | 1017 | CZ | PHE | A | 152 | −31.964 | 21.649 | −24.775 | 1.00 | 48.38 | A |
| ATOM | 1018 | C | PHE | A | 152 | −30.376 | 25.492 | −28.387 | 1.00 | 52.04 | A |
| ATOM | 1019 | O | PHE | A | 152 | −30.086 | 24.319 | −28.612 | 1.00 | 51.28 | A |
| ATOM | 1020 | N | ALA | A | 153 | −30.628 | 26.359 | −29.366 | 1.00 | 53.53 | A |
| ATOM | 1021 | CA | ALA | A | 153 | −30.521 | 25.960 | −30.771 | 1.00 | 55.59 | A |
| ATOM | 1022 | CB | ALA | A | 153 | −31.077 | 27.049 | −31.698 | 1.00 | 53.76 | A |
| ATOM | 1023 | C | ALA | A | 153 | −29.040 | 25.729 | −31.060 | 1.00 | 55.66 | A |
| ATOM | 1024 | O | ALA | A | 153 | −28.665 | 24.692 | −31.599 | 1.00 | 55.80 | A |
| ATOM | 1025 | N | LEU | A | 154 | −28.205 | 26.699 | −30.696 | 1.00 | 57.44 | A |
| ATOM | 1026 | CA | LEU | A | 154 | −26.756 | 26.584 | −30.891 | 1.00 | 60.09 | A |
| ATOM | 1027 | CB | LEU | A | 154 | −26.045 | 27.854 | −30.407 | 1.00 | 57.36 | A |
| ATOM | 1028 | CG | LEU | A | 154 | −26.306 | 29.106 | −31.239 | 1.00 | 56.81 | A |
| ATOM | 1029 | CD1 | LEU | A | 154 | −25.681 | 30.305 | −30.566 | 1.00 | 54.66 | A |
| ATOM | 1030 | CD2 | LEU | A | 154 | −25.746 | 28.915 | −32.642 | 1.00 | 54.86 | A |
| ATOM | 1031 | C | LEU | A | 154 | −26.212 | 25.376 | −30.122 | 1.00 | 61.78 | A |
| ATOM | 1032 | O | LEU | A | 154 | −25.251 | 24.730 | −30.550 | 1.00 | 62.63 | A |
| ATOM | 1033 | N | SER | A | 155 | −26.840 | 25.084 | −28.986 | 1.00 | 62.76 | A |
| ATOM | 1034 | CA | SER | A | 155 | −26.446 | 23.966 | −28.146 | 1.00 | 63.82 | A |
| ATOM | 1035 | CB | SER | A | 155 | −27.144 | 24.065 | −26.797 | 1.00 | 63.60 | A |
| ATOM | 1036 | OG | SER | A | 155 | −26.966 | 22.869 | −26.066 | 1.00 | 65.69 | A |
| ATOM | 1037 | C | SER | A | 155 | −26.779 | 22.627 | −28.798 | 1.00 | 65.21 | A |
| ATOM | 1038 | O | SER | A | 155 | −25.974 | 21.697 | −28.767 | 1.00 | 65.58 | A |
| ATOM | 1039 | N | THR | A | 156 | −27.976 | 22.531 | −29.371 | 1.00 | 66.30 | A |
| ATOM | 1040 | CA | THR | A | 156 | −28.422 | 21.319 | −30.050 | 1.00 | 67.72 | A |
| ATOM | 1041 | CB | THR | A | 156 | −29.893 | 21.452 | −30.519 | 1.00 | 67.52 | A |
| ATOM | 1042 | OG1 | THR | A | 156 | −30.765 | 21.393 | −29.386 | 1.00 | 69.40 | A |
| ATOM | 1043 | CG2 | THR | A | 156 | −30.262 | 20.339 | −31.479 | 1.00 | 68.25 | A |
| ATOM | 1044 | C | THR | A | 156 | −27.535 | 21.032 | −31.267 | 1.00 | 69.26 | A |
| ATOM | 1045 | O | THR | A | 156 | −27.422 | 19.885 | −31.693 | 1.00 | 69.59 | A |
| ATOM | 1046 | N | ASN | A | 157 | −26.915 | 22.076 | −31.822 | 1.00 | 70.20 | A |
| ATOM | 1047 | CA | ASN | A | 157 | −26.031 | 21.928 | −32.979 | 1.00 | 70.93 | A |
| ATOM | 1048 | CB | ASN | A | 157 | −25.561 | 23.295 | −33.490 | 1.00 | 71.29 | A |
| ATOM | 1049 | CG | ASN | A | 157 | −26.661 | 24.082 | −34.186 | 1.00 | 71.77 | A |
| ATOM | 1050 | OD1 | ASN | A | 157 | −27.846 | 23.776 | −34.054 | 1.00 | 71.35 | A |
| ATOM | 1051 | ND2 | ASN | A | 157 | −26.268 | 25.116 | −34.924 | 1.00 | 72.68 | A |
| ATOM | 1052 | C | ASN | A | 157 | −24.818 | 21.117 | −32.560 | 1.00 | 72.23 | A |
| ATOM | 1053 | O | ASN | A | 157 | −24.347 | 20.254 | −33.302 | 1.00 | 73.06 | A |
| ATOM | 1054 | N | LEU | A | 158 | −24.309 | 21.409 | −31.367 | 1.00 | 73.17 | A |
| ATOM | 1055 | CA | LEU | A | 158 | −23.152 | 20.701 | −30.836 | 1.00 | 73.49 | A |
| ATOM | 1056 | CB | LEU | A | 158 | −22.680 | 21.363 | −29.539 | 1.00 | 73.26 | A |
| ATOM | 1057 | CG | LEU | A | 158 | −21.264 | 21.080 | −29.018 | 1.00 | 74.00 | A |
| ATOM | 1058 | CD1 | LEU | A | 158 | −21.085 | 21.764 | −27.673 | 1.00 | 73.67 | A |
| ATOM | 1059 | CD2 | LEU | A | 158 | −21.025 | 19.591 | −28.866 | 1.00 | 74.47 | A |
| ATOM | 1060 | C | LEU | A | 158 | −23.601 | 19.270 | −30.561 | 1.00 | 73.89 | A |
| ATOM | 1061 | O | LEU | A | 158 | −22.823 | 18.328 | −30.663 | 1.00 | 72.76 | A |
| ATOM | 1062 | N | GLN | A | 159 | −24.875 | 19.120 | −30.220 | 1.00 | 75.65 | A |
| ATOM | 1063 | CA | GLN | A | 159 | −25.439 | 17.811 | −29.926 | 1.00 | 78.32 | A |
| ATOM | 1064 | CB | GLN | A | 159 | −26.861 | 17.972 | −29.374 | 1.00 | 79.21 | A |
| ATOM | 1065 | CG | GLN | A | 159 | −27.392 | 16.753 | −28.635 | 1.00 | 80.98 | A |
| ATOM | 1066 | CD | GLN | A | 159 | −28.629 | 17.063 | −27.811 | 1.00 | 81.67 | A |
| ATOM | 1067 | OE1 | GLN | A | 159 | −29.666 | 17.463 | −28.347 | 1.00 | 82.31 | A |
| ATOM | 1068 | NE2 | GLN | A | 159 | −28.522 | 16.883 | −26.499 | 1.00 | 80.98 | A |
| ATOM | 1069 | C | GLN | A | 159 | −25.446 | 16.967 | −31.198 | 1.00 | 79.66 | A |

TABLE 7-continued

Atomic coordinates of rSIFN-co (SEQ ID NO: 1)

| ATOM | 1070 | O | GLN | A | 159 | −25.157 | 15.769 | −31.165 | 1.00 | 79.48 | A |
|---|---|---|---|---|---|---|---|---|---|---|---|
| ATOM | 1071 | N | GLY | A | 160 | −25.776 | 17.605 | −32.320 | 1.00 | 81.34 | A |
| ATOM | 1072 | CA | GLY | A | 160 | −25.793 | 16.909 | −33.592 | 1.00 | 81.32 | A |
| ATOM | 1073 | C | GLY | A | 160 | −24.383 | 16.471 | −33.944 | 1.00 | 82.28 | A |
| ATOM | 1074 | O | GLY | A | 160 | −24.160 | 15.338 | −34.363 | 1.00 | 82.91 | A |
| ATOM | 1075 | N | ALA | A | 161 | −23.420 | 17.369 | −33.756 | 1.00 | 82.27 | A |
| ATOM | 1076 | CA | ALA | A | 161 | −22.023 | 17.071 | −34.057 | 1.00 | 82.68 | A |
| ATOM | 1077 | CB | ALA | A | 161 | −21.197 | 18.371 | −34.048 | 1.00 | 82.24 | A |
| ATOM | 1078 | C | ALA | A | 161 | −21.435 | 16.061 | −33.067 | 1.00 | 82.41 | A |
| ATOM | 1079 | O | ALA | A | 161 | −20.248 | 15.738 | −33.117 | 1.00 | 82.19 | A |
| ATOM | 1080 | N | LEU | A | 162 | −22.274 | 15.560 | −32.171 | 1.00 | 82.59 | A |
| ATOM | 1081 | CA | LEU | A | 162 | −21.833 | 14.600 | −31.169 | 1.00 | 82.81 | A |
| ATOM | 1082 | CB | LEU | A | 162 | −22.266 | 15.075 | −29.776 | 1.00 | 81.71 | A |
| ATOM | 1083 | CG | LEU | A | 162 | −22.133 | 14.141 | −28.573 | 1.00 | 80.63 | A |
| ATOM | 1084 | CD1 | LEU | A | 162 | −21.690 | 14.939 | −27.359 | 1.00 | 80.31 | A |
| ATOM | 1085 | CD2 | LEU | A | 162 | −23.463 | 13.447 | −28.309 | 1.00 | 79.59 | A |
| ATOM | 1086 | C | LEU | A | 162 | −22.379 | 13.206 | −31.450 | 1.00 | 83.84 | A |
| ATOM | 1087 | O | LEU | A | 162 | −21.694 | 12.207 | −31.222 | 1.00 | 83.86 | A |
| ATOM | 1088 | N | GLY | A | 163 | −23.606 | 13.142 | −31.958 | 1.00 | 84.78 | A |
| ATOM | 1089 | CA | GLY | A | 163 | −24.212 | 11.855 | −32.255 | 1.00 | 85.12 | A |
| ATOM | 1090 | C | GLY | A | 163 | −23.963 | 11.378 | −33.671 | 1.00 | 85.32 | A |
| ATOM | 1091 | O | GLY | A | 163 | −24.939 | 10.958 | −34.330 | 1.00 | 85.87 | A |
| ATOM | 1092 | OXT | GLY | A | 163 | −22.795 | 11.408 | −34.121 | 1.00 | 84.75 | A |
| ATOM | 1093 | CB | ASN | B | 11 | −36.003 | 31.054 | −49.710 | 1.00 | 85.15 | B |
| ATOM | 1094 | CG | ASN | B | 11 | −35.553 | 29.922 | −50.640 | 1.00 | 85.60 | B |
| ATOM | 1095 | OD1 | ASN | B | 11 | −34.661 | 29.139 | −50.297 | 1.00 | 84.41 | B |
| ATOM | 1096 | ND2 | ASN | B | 11 | −36.172 | 29.834 | −51.818 | 1.00 | 84.86 | B |
| ATOM | 1097 | C | ASN | B | 11 | −38.419 | 31.748 | −49.975 | 1.00 | 83.40 | B |
| ATOM | 1098 | O | ASN | B | 11 | −38.848 | 32.106 | −48.869 | 1.00 | 83.24 | B |
| ATOM | 1099 | N | ASN | B | 11 | −36.612 | 33.443 | −50.017 | 1.00 | 85.25 | B |
| ATOM | 1100 | CA | ASN | B | 11 | −36.970 | 32.041 | −50.393 | 1.00 | 84.75 | B |
| ATOM | 1101 | N | ARG | B | 12 | −39.176 | 31.116 | −50.871 | 1.00 | 80.64 | B |
| ATOM | 1102 | CA | ARG | B | 12 | −40.566 | 30.781 | −50.583 | 1.00 | 75.89 | B |
| ATOM | 1103 | CB | ARG | B | 12 | −41.494 | 31.295 | −51.681 | 1.00 | 76.32 | B |
| ATOM | 1104 | CG | ARG | B | 12 | −42.957 | 31.189 | −51.303 | 1.00 | 77.28 | B |
| ATOM | 1105 | CD | ARG | B | 12 | −43.165 | 31.751 | −49.908 | 1.00 | 77.55 | B |
| ATOM | 1106 | NE | ARG | B | 12 | −44.512 | 32.270 | −49.718 | 1.00 | 78.19 | B |
| ATOM | 1107 | CZ | ARG | B | 12 | −44.864 | 33.064 | −48.715 | 1.00 | 77.18 | B |
| ATOM | 1108 | NH1 | ARG | B | 12 | −43.962 | 33.426 | −47.813 | 1.00 | 76.35 | B |
| ATOM | 1109 | NH2 | ARG | B | 12 | −46.113 | 33.503 | −48.622 | 1.00 | 76.77 | B |
| ATOM | 1110 | C | ARG | B | 12 | −40.747 | 29.286 | −50.453 | 1.00 | 72.00 | B |
| ATOM | 1111 | O | ARG | B | 12 | −41.679 | 28.718 | −51.024 | 1.00 | 69.87 | B |
| ATOM | 1112 | N | ARG | B | 13 | −39.860 | 28.652 | −49.694 | 1.00 | 68.53 | B |
| ATOM | 1113 | CA | ARG | B | 13 | −39.940 | 27.215 | −49.514 | 1.00 | 66.86 | B |
| ATOM | 1114 | CB | ARG | B | 13 | −38.635 | 26.669 | −48.944 | 1.00 | 69.00 | B |
| ATOM | 1115 | CG | ARG | B | 13 | −38.279 | 27.157 | −47.572 | 1.00 | 72.00 | B |
| ATOM | 1116 | CD | ARG | B | 13 | −37.016 | 26.456 | −47.145 | 1.00 | 75.81 | B |
| ATOM | 1117 | NE | ARG | B | 13 | −37.112 | 25.019 | −47.396 | 1.00 | 78.98 | B |
| ATOM | 1118 | CZ | ARG | B | 13 | −36.088 | 24.176 | −47.307 | 1.00 | 80.56 | B |
| ATOM | 1119 | NH1 | ARG | B | 13 | −34.886 | 24.632 | −46.971 | 1.00 | 82.00 | B |
| ATOM | 1120 | NH2 | ARG | B | 13 | −36.263 | 22.882 | −47.557 | 1.00 | 78.63 | B |
| ATOM | 1121 | C | ARG | B | 13 | −41.110 | 26.828 | −48.628 | 1.00 | 63.21 | B |
| ATOM | 1122 | O | ARG | B | 13 | −41.297 | 25.660 | −48.296 | 1.00 | 63.10 | B |
| ATOM | 1123 | N | ALA | B | 14 | −41.906 | 27.819 | −48.256 | 1.00 | 58.81 | B |
| ATOM | 1124 | CA | ALA | B | 14 | −43.068 | 27.565 | −47.439 | 1.00 | 56.19 | B |
| ATOM | 1125 | CB | ALA | B | 14 | −43.667 | 28.874 | −46.988 | 1.00 | 57.98 | B |
| ATOM | 1126 | C | ALA | B | 14 | −44.066 | 26.779 | −48.288 | 1.00 | 54.53 | B |
| ATOM | 1127 | O | ALA | B | 14 | −44.438 | 25.651 | −47.958 | 1.00 | 53.40 | B |
| ATOM | 1128 | N | LEU | B | 15 | −44.490 | 27.379 | −49.393 | 1.00 | 53.25 | B |
| ATOM | 1129 | CA | LEU | B | 15 | −45.437 | 26.730 | −50.287 | 1.00 | 51.60 | B |
| ATOM | 1130 | CB | LEU | B | 15 | −45.868 | 27.717 | −51.376 | 1.00 | 53.42 | B |
| ATOM | 1131 | CG | LEU | B | 15 | −46.780 | 28.860 | −50.918 | 1.00 | 54.05 | B |
| ATOM | 1132 | CD1 | LEU | B | 15 | −46.739 | 30.011 | −51.905 | 1.00 | 53.59 | B |
| ATOM | 1133 | CD2 | LEU | B | 15 | −48.192 | 28.335 | −50.780 | 1.00 | 55.07 | B |
| ATOM | 1134 | C | LEU | B | 15 | −44.836 | 25.465 | −50.911 | 1.00 | 49.98 | B |
| ATOM | 1135 | O | LEU | B | 15 | −45.538 | 24.473 | −51.136 | 1.00 | 49.36 | B |
| ATOM | 1136 | N | ILE | B | 16 | −43.535 | 25.491 | −51.178 | 1.00 | 46.77 | B |
| ATOM | 1137 | CA | ILE | B | 16 | −42.883 | 24.334 | −51.765 | 1.00 | 45.58 | B |
| ATOM | 1138 | CB | ILE | B | 16 | −41.435 | 24.679 | −52.164 | 1.00 | 45.17 | B |
| ATOM | 1139 | CG2 | ILE | B | 16 | −40.607 | 23.420 | −52.375 | 1.00 | 42.57 | B |
| ATOM | 1140 | CG1 | ILE | B | 16 | −41.466 | 25.512 | −53.448 | 1.00 | 44.62 | B |
| ATOM | 1141 | CD1 | ILE | B | 16 | −40.094 | 25.930 | −53.945 | 1.00 | 47.42 | B |
| ATOM | 1142 | C | ILE | B | 16 | −42.926 | 23.097 | −50.863 | 1.00 | 46.11 | B |
| ATOM | 1143 | O | ILE | B | 16 | −43.308 | 22.013 | −51.309 | 1.00 | 45.20 | B |
| ATOM | 1144 | N | LEU | B | 17 | −42.548 | 23.246 | −49.596 | 1.00 | 46.19 | B |
| ATOM | 1145 | CA | LEU | B | 17 | −42.584 | 22.105 | −48.676 | 1.00 | 45.40 | B |
| ATOM | 1146 | CB | LEU | B | 17 | −42.067 | 22.519 | −47.303 | 1.00 | 43.77 | B |
| ATOM | 1147 | CG | LEU | B | 17 | −40.618 | 22.983 | −47.397 | 1.00 | 43.17 | B |

TABLE 7-continued

Atomic coordinates of rSIFN-co (SEQ ID NO: 1)

| ATOM | 1148 | CD1 | LEU | B | 17 | −40.256 | 23.847 | −46.210 | 1.00 | 42.11 | B |
|------|------|-----|-----|---|----|---------|--------|---------|------|-------|---|
| ATOM | 1149 | CD2 | LEU | B | 17 | −39.723 | 21.774 | −47.522 | 1.00 | 42.21 | B |
| ATOM | 1150 | C | LEU | B | 17 | −44.007 | 21.566 | −48.567 | 1.00 | 45.21 | B |
| ATOM | 1151 | O | LEU | B | 17 | −44.219 | 20.354 | −48.575 | 1.00 | 45.78 | B |
| ATOM | 1152 | N | LEU | B | 18 | −44.983 | 22.464 | −48.466 | 1.00 | 44.38 | B |
| ATOM | 1153 | CA | LEU | B | 18 | −46.373 | 22.046 | −48.391 | 1.00 | 44.44 | B |
| ATOM | 1154 | CB | LEU | B | 18 | −47.291 | 23.257 | −48.262 | 1.00 | 43.44 | B |
| ATOM | 1155 | CG | LEU | B | 18 | −47.574 | 23.721 | −46.831 | 1.00 | 43.94 | B |
| ATOM | 1156 | CD1 | LEU | B | 18 | −48.104 | 25.149 | −46.842 | 1.00 | 42.55 | B |
| ATOM | 1157 | CD2 | LEU | B | 18 | −48.565 | 22.761 | −46.172 | 1.00 | 40.40 | B |
| ATOM | 1158 | C | LEU | B | 18 | −46.713 | 21.278 | −49.654 | 1.00 | 46.61 | B |
| ATOM | 1159 | O | LEU | B | 18 | −47.504 | 20.332 | −49.628 | 1.00 | 47.62 | B |
| ATOM | 1160 | N | ALA | B | 19 | −46.107 | 21.692 | −50.764 | 1.00 | 47.27 | B |
| ATOM | 1161 | CA | ALA | B | 19 | −46.326 | 21.043 | −52.053 | 1.00 | 47.65 | B |
| ATOM | 1162 | CB | ALA | B | 19 | −45.762 | 21.912 | −53.174 | 1.00 | 47.43 | B |
| ATOM | 1163 | C | ALA | B | 19 | −45.679 | 19.659 | −52.087 | 1.00 | 48.06 | B |
| ATOM | 1164 | O | ALA | B | 19 | −46.257 | 18.715 | −52.620 | 1.00 | 47.48 | B |
| ATOM | 1165 | N | GLN | B | 20 | −44.474 | 19.553 | −51.526 | 1.00 | 49.52 | B |
| ATOM | 1166 | CA | GLN | B | 20 | −43.742 | 18.286 | −51.482 | 1.00 | 50.43 | B |
| ATOM | 1167 | CB | GLN | B | 20 | −42.266 | 18.521 | −51.141 | 1.00 | 50.28 | B |
| ATOM | 1168 | CG | GLN | B | 20 | −41.409 | 19.164 | −52.227 | 1.00 | 48.64 | B |
| ATOM | 1169 | CD | GLN | B | 20 | −40.000 | 19.484 | −51.738 | 1.00 | 49.87 | B |
| ATOM | 1170 | OE1 | GLN | B | 20 | −39.518 | 18.888 | −50.778 | 1.00 | 51.73 | B |
| ATOM | 1171 | NE2 | GLN | B | 20 | −39.333 | 20.418 | −52.403 | 1.00 | 49.40 | B |
| ATOM | 1172 | C | GLN | B | 20 | −44.352 | 17.371 | −50.428 | 1.00 | 51.95 | B |
| ATOM | 1173 | O | GLN | B | 20 | −44.020 | 16.199 | −50.350 | 1.00 | 52.62 | B |
| ATOM | 1174 | N | MET | B | 21 | −45.249 | 17.915 | −49.618 | 1.00 | 54.15 | B |
| ATOM | 1175 | CA | MET | B | 21 | −45.892 | 17.138 | −48.568 | 1.00 | 56.60 | B |
| ATOM | 1176 | CB | MET | B | 21 | −46.325 | 18.064 | −47.420 | 1.00 | 56.38 | B |
| ATOM | 1177 | CG | MET | B | 21 | −45.231 | 18.357 | −46.394 | 1.00 | 57.01 | B |
| ATOM | 1178 | SD | MET | B | 21 | −45.690 | 19.612 | −45.174 | 1.00 | 57.20 | B |
| ATOM | 1179 | CE | MET | B | 21 | −47.211 | 18.885 | −44.499 | 1.00 | 57.95 | B |
| ATOM | 1180 | C | MET | B | 21 | −47.090 | 16.327 | −49.056 | 1.00 | 58.24 | B |
| ATOM | 1181 | O | MET | B | 21 | −47.551 | 15.424 | −48.363 | 1.00 | 58.12 | B |
| ATOM | 1182 | N | ALA | B | 22 | −47.600 | 16.645 | −50.243 | 1.00 | 61.09 | B |
| ATOM | 1183 | CA | ALA | B | 22 | −48.754 | 15.922 | −50.773 | 1.00 | 62.96 | B |
| ATOM | 1184 | CB | ALA | B | 22 | −49.151 | 16.468 | −52.145 | 1.00 | 61.96 | B |
| ATOM | 1185 | C | ALA | B | 22 | −48.415 | 14.446 | −50.872 | 1.00 | 64.38 | B |
| ATOM | 1186 | O | ALA | B | 22 | −47.323 | 14.086 | −51.300 | 1.00 | 64.43 | B |
| ATOM | 1187 | N | ARG | B | 23 | −49.352 | 13.596 | −50.463 | 1.00 | 67.27 | B |
| ATOM | 1188 | CA | ARG | B | 23 | −49.132 | 12.158 | −50.508 | 1.00 | 70.44 | B |
| ATOM | 1189 | CB | ARG | B | 23 | −48.613 | 11.669 | −49.152 | 1.00 | 71.01 | B |
| ATOM | 1190 | CG | ARG | B | 23 | −49.450 | 12.102 | −47.968 | 1.00 | 72.18 | B |
| ATOM | 1191 | CD | ARG | B | 23 | −48.731 | 11.815 | −46.667 | 1.00 | 73.33 | B |
| ATOM | 1192 | NE | ARG | B | 23 | −48.552 | 10.385 | −46.450 | 1.00 | 76.38 | B |
| ATOM | 1193 | CZ | ARG | B | 23 | −47.854 | 9.860 | −45.445 | 1.00 | 78.19 | B |
| ATOM | 1194 | NH1 | ARG | B | 23 | −47.256 | 10.649 | −44.553 | 1.00 | 77.51 | B |
| ATOM | 1195 | NH2 | ARG | B | 23 | −47.760 | 8.538 | −45.329 | 1.00 | 77.90 | B |
| ATOM | 1196 | C | ARG | B | 23 | −50.362 | 11.354 | −50.923 | 1.00 | 72.04 | B |
| ATOM | 1197 | O | ARG | B | 23 | −50.280 | 10.139 | −51.102 | 1.00 | 73.43 | B |
| ATOM | 1198 | N | ALA | B | 24 | −51.500 | 12.023 | −51.077 | 1.00 | 73.32 | B |
| ATOM | 1199 | CA | ALA | B | 24 | −52.721 | 11.340 | −51.489 | 1.00 | 75.11 | B |
| ATOM | 1200 | CB | ALA | B | 24 | −53.947 | 12.016 | −50.872 | 1.00 | 72.05 | B |
| ATOM | 1201 | C | ALA | B | 24 | −52.817 | 11.370 | −53.011 | 1.00 | 77.82 | B |
| ATOM | 1202 | O | ALA | B | 24 | −52.334 | 12.309 | −53.653 | 1.00 | 78.81 | B |
| ATOM | 1203 | N | SER | B | 25 | −53.429 | 10.339 | −53.588 | 1.00 | 79.74 | B |
| ATOM | 1204 | CA | SER | B | 25 | −53.599 | 10.261 | −55.033 | 1.00 | 82.06 | B |
| ATOM | 1205 | CB | SER | B | 25 | −53.912 | 8.827 | −55.442 | 1.00 | 82.21 | B |
| ATOM | 1206 | OG | SER | B | 25 | −55.044 | 8.348 | −54.737 | 1.00 | 83.63 | B |
| ATOM | 1207 | C | SER | B | 25 | −54.746 | 11.178 | −55.459 | 1.00 | 84.39 | B |
| ATOM | 1208 | O | SER | B | 25 | −55.633 | 11.492 | −54.657 | 1.00 | 84.68 | B |
| ATOM | 1209 | N | PRO | B | 26 | −54.749 | 11.614 | −56.730 | 1.00 | 85.80 | B |
| ATOM | 1210 | CD | PRO | B | 26 | −53.769 | 11.287 | −57.779 | 1.00 | 85.92 | B |
| ATOM | 1211 | CA | PRO | B | 26 | −55.793 | 12.500 | −57.254 | 1.00 | 87.16 | B |
| ATOM | 1212 | CB | PRO | B | 26 | −55.212 | 12.950 | −58.588 | 1.00 | 86.58 | B |
| ATOM | 1213 | CG | PRO | B | 26 | −54.482 | 11.736 | −59.038 | 1.00 | 86.26 | B |
| ATOM | 1214 | C | PRO | B | 26 | −57.166 | 11.837 | −57.407 | 1.00 | 88.81 | B |
| ATOM | 1215 | O | PRO | B | 26 | −58.139 | 12.487 | −57.795 | 1.00 | 89.06 | B |
| ATOM | 1216 | N | PHE | B | 27 | −57.242 | 10.544 | −57.108 | 1.00 | 89.93 | B |
| ATOM | 1217 | CA | PHE | B | 27 | −58.507 | 9.823 | −57.207 | 1.00 | 91.46 | B |
| ATOM | 1218 | CB | PHE | B | 27 | −58.359 | 8.550 | −58.053 | 1.00 | 91.94 | B |
| ATOM | 1219 | CG | PHE | B | 27 | −57.967 | 8.801 | −59.482 | 1.00 | 91.42 | B |
| ATOM | 1220 | CD1 | PHE | B | 27 | −56.659 | 9.137 | −59.811 | 1.00 | 91.14 | B |
| ATOM | 1221 | CD2 | PHE | B | 27 | −58.909 | 8.695 | −60.498 | 1.00 | 90.75 | B |
| ATOM | 1222 | CE1 | PHE | B | 27 | −56.294 | 9.361 | −61.131 | 1.00 | 91.14 | B |
| ATOM | 1223 | CE2 | PHE | B | 27 | −58.555 | 8.917 | −61.820 | 1.00 | 91.00 | B |
| ATOM | 1224 | CZ | PHE | B | 27 | −57.245 | 9.252 | −62.139 | 1.00 | 91.47 | B |
| ATOM | 1225 | C | PHE | B | 27 | −58.989 | 9.426 | −55.820 | 1.00 | 92.32 | B |

TABLE 7-continued

Atomic coordinates of rSIFN-co (SEQ ID NO: 1)

| ATOM | 1226 | O | PHE | B | 27 | −60.192 | 9.267 | −55.599 | 1.00 | 93.11 | B |
| --- | --- | --- | --- | --- | --- | --- | --- | --- | --- | --- | --- |
| ATOM | 1227 | N | ALA | B | 28 | −58.035 | 9.269 | −54.900 | 1.00 | 92.92 | B |
| ATOM | 1228 | CA | ALA | B | 28 | −58.295 | 8.864 | −53.516 | 1.00 | 92.18 | B |
| ATOM | 1229 | CB | ALA | B | 28 | −56.996 | 8.915 | −52.706 | 1.00 | 91.40 | B |
| ATOM | 1230 | C | ALA | B | 28 | −59.387 | 9.649 | −52.790 | 1.00 | 91.90 | B |
| ATOM | 1231 | O | ALA | B | 28 | −60.199 | 9.057 | −52.074 | 1.00 | 91.57 | B |
| ATOM | 1232 | N | CYS | B | 29 | −59.416 | 10.969 | −52.963 | 1.00 | 91.32 | B |
| ATOM | 1233 | CA | CYS | B | 29 | −60.433 | 11.772 | −52.288 | 1.00 | 91.47 | B |
| ATOM | 1234 | C | CYS | B | 29 | −61.450 | 12.374 | −53.243 | 1.00 | 92.66 | B |
| ATOM | 1235 | O | CYS | B | 29 | −61.088 | 12.992 | −54.245 | 1.00 | 92.45 | B |
| ATOM | 1236 | CB | CYS | B | 29 | −59.780 | 12.887 | −51.463 | 1.00 | 89.53 | B |
| ATOM | 1237 | SG | CYS | B | 29 | −58.531 | 12.280 | −50.282 | 1.00 | 86.39 | B |
| ATOM | 1238 | N | GLY | B | 30 | −62.727 | 12.178 | −52.926 | 1.00 | 93.98 | B |
| ATOM | 1239 | CA | GLY | B | 30 | −63.784 | 12.716 | −53.758 | 1.00 | 95.70 | B |
| ATOM | 1240 | C | GLY | B | 30 | −63.862 | 14.212 | −53.543 | 1.00 | 96.95 | B |
| ATOM | 1241 | O | GLY | B | 30 | −63.276 | 14.727 | −52.592 | 1.00 | 97.62 | B |
| ATOM | 1242 | N | GLY | B | 31 | −64.577 | 14.908 | −54.420 | 1.00 | 97.39 | B |
| ATOM | 1243 | CA | GLY | B | 31 | −64.707 | 16.349 | −54.296 | 1.00 | 97.58 | B |
| ATOM | 1244 | C | GLY | B | 31 | −65.411 | 16.803 | −53.027 | 1.00 | 97.64 | B |
| ATOM | 1245 | O | GLY | B | 31 | −66.503 | 17.375 | −53.083 | 1.00 | 98.81 | B |
| ATOM | 1246 | N | GLY | B | 32 | −64.787 | 16.546 | −51.880 | 1.00 | 96.79 | B |
| ATOM | 1247 | CA | GLY | B | 32 | −65.360 | 16.951 | −50.609 | 1.00 | 94.95 | B |
| ATOM | 1248 | C | GLY | B | 32 | −64.893 | 18.350 | −50.254 | 1.00 | 93.64 | B |
| ATOM | 1249 | O | GLY | B | 32 | −64.396 | 18.597 | −49.150 | 1.00 | 93.49 | B |
| ATOM | 1250 | N | GLY | B | 33 | −65.052 | 19.265 | −51.207 | 1.00 | 92.18 | B |
| ATOM | 1251 | CA | GLY | B | 33 | −64.646 | 20.645 | −51.009 | 1.00 | 89.82 | B |
| ATOM | 1252 | C | GLY | B | 33 | −65.345 | 21.318 | −49.846 | 1.00 | 88.28 | B |
| ATOM | 1253 | O | GLY | B | 33 | −66.577 | 21.331 | −49.762 | 1.00 | 88.34 | B |
| ATOM | 1254 | N | HIS | B | 34 | −64.544 | 21.878 | −48.943 | 1.00 | 85.84 | B |
| ATOM | 1255 | CA | HIS | B | 34 | −65.053 | 22.571 | −47.762 | 1.00 | 82.36 | B |
| ATOM | 1256 | CB | HIS | B | 34 | −64.630 | 21.808 | −46.496 | 1.00 | 80.60 | B |
| ATOM | 1257 | CG | HIS | B | 34 | −65.146 | 22.398 | −45.220 | 1.00 | 78.05 | B |
| ATOM | 1258 | CD2 | HIS | B | 34 | −65.986 | 21.899 | −44.281 | 1.00 | 76.62 | B |
| ATOM | 1259 | ND1 | HIS | B | 34 | −64.766 | 23.644 | −44.763 | 1.00 | 77.24 | B |
| ATOM | 1260 | CE1 | HIS | B | 34 | −65.346 | 23.883 | −43.603 | 1.00 | 75.05 | B |
| ATOM | 1261 | NE2 | HIS | B | 34 | −66.092 | 22.838 | −43.287 | 1.00 | 75.00 | B |
| ATOM | 1262 | C | HIS | B | 34 | −64.472 | 23.983 | −47.764 | 1.00 | 80.50 | B |
| ATOM | 1263 | O | HIS | B | 34 | −63.349 | 24.198 | −48.226 | 1.00 | 81.27 | B |
| ATOM | 1264 | N | ASP | B | 35 | −65.246 | 24.947 | −47.278 | 1.00 | 77.74 | B |
| ATOM | 1265 | CA | ASP | B | 35 | −64.787 | 26.330 | −47.225 | 1.00 | 75.78 | B |
| ATOM | 1266 | CB | ASP | B | 35 | −65.795 | 27.264 | −47.895 | 1.00 | 76.50 | B |
| ATOM | 1267 | CG | ASP | B | 35 | −65.703 | 28.687 | −47.371 | 1.00 | 77.21 | B |
| ATOM | 1268 | OD1 | ASP | B | 35 | −64.578 | 29.227 | −47.288 | 1.00 | 77.48 | B |
| ATOM | 1269 | OD2 | ASP | B | 35 | −66.759 | 29.266 | −47.040 | 1.00 | 77.57 | B |
| ATOM | 1270 | C | ASP | B | 35 | −64.579 | 26.767 | −45.784 | 1.00 | 73.69 | B |
| ATOM | 1271 | O | ASP | B | 35 | −65.486 | 26.653 | −44.956 | 1.00 | 74.03 | B |
| ATOM | 1272 | N | PHE | B | 36 | −63.390 | 27.282 | −45.484 | 1.00 | 69.71 | B |
| ATOM | 1273 | CA | PHE | B | 36 | −63.097 | 27.707 | −44.125 | 1.00 | 65.47 | B |
| ATOM | 1274 | CB | PHE | B | 36 | −61.694 | 27.260 | −43.724 | 1.00 | 63.29 | B |
| ATOM | 1275 | CG | PHE | B | 36 | −61.484 | 25.780 | −43.842 | 1.00 | 61.40 | B |
| ATOM | 1276 | CD1 | PHE | B | 36 | −61.068 | 25.218 | −45.040 | 1.00 | 60.82 | B |
| ATOM | 1277 | CD2 | PHE | B | 36 | −61.722 | 24.942 | −42.762 | 1.00 | 59.30 | B |
| ATOM | 1278 | CE1 | PHE | B | 36 | −60.896 | 23.840 | −45.157 | 1.00 | 59.96 | B |
| ATOM | 1279 | CE2 | PHE | B | 36 | −61.554 | 23.568 | −42.873 | 1.00 | 58.76 | B |
| ATOM | 1280 | CZ | PHE | B | 36 | −61.139 | 23.018 | −44.071 | 1.00 | 57.07 | B |
| ATOM | 1281 | C | PHE | B | 36 | −63.254 | 29.195 | −43.882 | 1.00 | 63.46 | B |
| ATOM | 1282 | O | PHE | B | 36 | −62.813 | 29.701 | −42.860 | 1.00 | 63.36 | B |
| ATOM | 1283 | N | GLY | B | 37 | −63.892 | 29.889 | −44.816 | 1.00 | 61.85 | B |
| ATOM | 1284 | CA | GLY | B | 37 | −64.105 | 31.317 | −44.657 | 1.00 | 60.22 | B |
| ATOM | 1285 | C | GLY | B | 37 | −62.860 | 32.105 | −44.299 | 1.00 | 59.45 | B |
| ATOM | 1286 | O | GLY | B | 37 | −62.897 | 32.984 | −43.436 | 1.00 | 59.52 | B |
| ATOM | 1287 | N | PHE | B | 38 | −61.757 | 31.785 | −44.965 | 1.00 | 58.21 | B |
| ATOM | 1288 | CA | PHE | B | 38 | −60.496 | 32.467 | −44.735 | 1.00 | 57.09 | B |
| ATOM | 1289 | CB | PHE | B | 38 | −59.465 | 32.035 | −45.776 | 1.00 | 55.16 | B |
| ATOM | 1290 | CG | PHE | B | 38 | −58.169 | 32.774 | −45.684 | 1.00 | 52.52 | B |
| ATOM | 1291 | CD1 | PHE | B | 38 | −57.409 | 32.728 | −44.523 | 1.00 | 51.16 | B |
| ATOM | 1292 | CD2 | PHE | B | 38 | −57.704 | 33.517 | −46.760 | 1.00 | 52.45 | B |
| ATOM | 1293 | CE1 | PHE | B | 38 | −56.201 | 33.414 | −44.433 | 1.00 | 50.89 | B |
| ATOM | 1294 | CE2 | PHE | B | 38 | −56.492 | 34.207 | −46.681 | 1.00 | 52.43 | B |
| ATOM | 1295 | CZ | PHE | B | 38 | −55.741 | 34.152 | −45.511 | 1.00 | 51.93 | B |
| ATOM | 1296 | C | PHE | B | 38 | −60.729 | 33.958 | −44.844 | 1.00 | 57.08 | B |
| ATOM | 1297 | O | PHE | B | 38 | −61.224 | 34.434 | −45.853 | 1.00 | 56.69 | B |
| ATOM | 1298 | N | PRO | B | 39 | −60.369 | 34.716 | −43.802 | 1.00 | 58.27 | B |
| ATOM | 1299 | CD | PRO | B | 39 | −59.687 | 34.259 | −42.581 | 1.00 | 58.11 | B |
| ATOM | 1300 | CA | PRO | B | 39 | −60.542 | 36.168 | −43.776 | 1.00 | 60.08 | B |
| ATOM | 1301 | CB | PRO | B | 39 | −60.253 | 36.511 | −42.323 | 1.00 | 59.19 | B |
| ATOM | 1302 | CG | PRO | B | 39 | −59.163 | 35.556 | −41.999 | 1.00 | 58.94 | B |
| ATOM | 1303 | C | PRO | B | 39 | −59.596 | 36.875 | −44.742 | 1.00 | 62.95 | B |

TABLE 7-continued

Atomic coordinates of rSIFN-co (SEQ ID NO: 1)

| ATOM | 1304 | O | PRO | B | 39 | −58.544 | 37.387 | −44.344 | 1.00 | 63.46 | B |
|---|---|---|---|---|---|---|---|---|---|---|---|
| ATOM | 1305 | N | GLN | B | 40 | −59.982 | 36.908 | −46.014 | 1.00 | 65.02 | B |
| ATOM | 1306 | CA | GLN | B | 40 | −59.163 | 37.545 | −47.031 | 1.00 | 66.34 | B |
| ATOM | 1307 | CB | GLN | B | 40 | −59.705 | 37.224 | −48.412 | 1.00 | 66.89 | B |
| ATOM | 1308 | CG | GLN | B | 40 | −58.720 | 37.527 | −49.510 | 1.00 | 69.39 | B |
| ATOM | 1309 | CD | GLN | B | 40 | −59.274 | 37.201 | −50.872 | 1.00 | 71.14 | B |
| ATOM | 1310 | OE1 | GLN | B | 40 | −59.732 | 36.084 | −51.121 | 1.00 | 71.05 | B |
| ATOM | 1311 | NE2 | GLN | B | 40 | −59.235 | 38.174 | −51.769 | 1.00 | 72.52 | B |
| ATOM | 1312 | C | GLN | B | 40 | −59.085 | 39.056 | −46.856 | 1.00 | 67.85 | B |
| ATOM | 1313 | O | GLN | B | 40 | −58.107 | 39.678 | −47.260 | 1.00 | 67.07 | B |
| ATOM | 1314 | N | GLU | B | 41 | −60.110 | 39.643 | −46.248 | 1.00 | 70.00 | B |
| ATOM | 1315 | CA | GLU | B | 41 | −60.135 | 41.085 | −46.029 | 1.00 | 73.07 | B |
| ATOM | 1316 | CB | GLU | B | 41 | −61.390 | 41.506 | −45.255 | 1.00 | 73.73 | B |
| ATOM | 1317 | CG | GLU | B | 41 | −62.623 | 40.648 | −45.473 | 1.00 | 75.45 | B |
| ATOM | 1318 | CD | GLU | B | 41 | −62.636 | 39.399 | −44.604 | 1.00 | 76.40 | B |
| ATOM | 1319 | OE1 | GLU | B | 41 | −62.528 | 39.534 | −43.363 | 1.00 | 75.97 | B |
| ATOM | 1320 | OE2 | GLU | B | 41 | −62.764 | 38.285 | −45.162 | 1.00 | 76.54 | B |
| ATOM | 1321 | C | GLU | B | 41 | −58.914 | 41.562 | −45.241 | 1.00 | 74.88 | B |
| ATOM | 1322 | O | GLU | B | 41 | −58.437 | 42.675 | −45.439 | 1.00 | 75.45 | B |
| ATOM | 1323 | N | GLU | B | 42 | −58.414 | 40.722 | −44.342 | 1.00 | 76.27 | B |
| ATOM | 1324 | CA | GLU | B | 42 | −57.272 | 41.091 | −43.515 | 1.00 | 76.77 | B |
| ATOM | 1325 | CB | GLU | B | 42 | −57.154 | 40.118 | −42.341 | 1.00 | 77.03 | B |
| ATOM | 1326 | CG | GLU | B | 42 | −58.484 | 39.812 | −41.670 | 1.00 | 76.96 | B |
| ATOM | 1327 | CD | GLU | B | 42 | −59.135 | 41.036 | −41.062 | 1.00 | 77.01 | B |
| ATOM | 1328 | OE1 | GLU | B | 42 | −60.354 | 40.980 | −40.783 | 1.00 | 76.54 | B |
| ATOM | 1329 | OE2 | GLU | B | 42 | −58.428 | 42.047 | −40.855 | 1.00 | 77.00 | B |
| ATOM | 1330 | C | GLU | B | 42 | −55.953 | 41.136 | −44.276 | 1.00 | 77.34 | B |
| ATOM | 1331 | O | GLU | B | 42 | −54.978 | 41.721 | −43.797 | 1.00 | 76.70 | B |
| ATOM | 1332 | N | PHE | B | 43 | −55.927 | 40.523 | −45.460 | 1.00 | 78.79 | B |
| ATOM | 1333 | CA | PHE | B | 43 | −54.716 | 40.481 | −46.282 | 1.00 | 79.57 | B |
| ATOM | 1334 | CB | PHE | B | 43 | −54.354 | 39.030 | −46.614 | 1.00 | 76.30 | B |
| ATOM | 1335 | CG | PHE | B | 43 | −54.174 | 38.158 | −45.407 | 1.00 | 73.38 | B |
| ATOM | 1336 | CD1 | PHE | B | 43 | −55.259 | 37.518 | −44.827 | 1.00 | 72.32 | B |
| ATOM | 1337 | CD2 | PHE | B | 43 | −52.918 | 37.982 | −44.846 | 1.00 | 72.34 | B |
| ATOM | 1338 | CE1 | PHE | B | 43 | −55.093 | 36.716 | −43.708 | 1.00 | 71.63 | B |
| ATOM | 1339 | CE2 | PHE | B | 43 | −52.743 | 37.182 | −43.727 | 1.00 | 71.80 | B |
| ATOM | 1340 | CZ | PHE | B | 43 | −53.832 | 36.547 | −43.158 | 1.00 | 71.86 | B |
| ATOM | 1341 | C | PHE | B | 43 | −54.830 | 41.274 | −47.584 | 1.00 | 81.78 | B |
| ATOM | 1342 | O | PHE | B | 43 | −54.032 | 42.171 | −47.855 | 1.00 | 82.37 | B |
| ATOM | 1343 | N | GLY | B | 44 | −55.825 | 40.932 | −48.391 | 1.00 | 84.35 | B |
| ATOM | 1344 | CA | GLY | B | 44 | −56.013 | 41.619 | −49.654 | 1.00 | 86.86 | B |
| ATOM | 1345 | C | GLY | B | 44 | −56.880 | 42.859 | −49.557 | 1.00 | 88.99 | B |
| ATOM | 1346 | O | GLY | B | 44 | −58.085 | 42.785 | −49.304 | 1.00 | 88.66 | B |
| ATOM | 1347 | N | GLY | B | 45 | −56.259 | 44.011 | −49.766 | 1.00 | 90.98 | B |
| ATOM | 1348 | CA | GLY | B | 45 | −56.995 | 45.256 | −49.708 | 1.00 | 93.31 | B |
| ATOM | 1349 | C | GLY | B | 45 | −56.073 | 46.453 | −49.679 | 1.00 | 95.02 | B |
| ATOM | 1350 | O | GLY | B | 45 | −54.874 | 46.323 | −49.413 | 1.00 | 95.65 | B |
| ATOM | 1351 | N | GLY | B | 46 | −56.633 | 47.624 | −49.967 | 1.00 | 95.75 | B |
| ATOM | 1352 | CA | GLY | B | 46 | −55.846 | 48.839 | −49.947 | 1.00 | 96.64 | B |
| ATOM | 1353 | C | GLY | B | 46 | −55.513 | 49.204 | −48.513 | 1.00 | 97.19 | B |
| ATOM | 1354 | O | GLY | B | 46 | −55.188 | 50.354 | −48.212 | 1.00 | 97.50 | B |
| ATOM | 1355 | N | GLY | B | 47 | −55.602 | 48.218 | −47.623 | 1.00 | 97.06 | B |
| ATOM | 1356 | CA | GLY | B | 47 | −55.307 | 48.454 | −46.223 | 1.00 | 97.22 | B |
| ATOM | 1357 | C | GLY | B | 47 | −54.088 | 49.337 | −46.029 | 1.00 | 97.43 | B |
| ATOM | 1358 | O | GLY | B | 47 | −54.193 | 50.430 | −45.463 | 1.00 | 97.59 | B |
| ATOM | 1359 | N | GLY | B | 48 | −52.935 | 48.868 | −46.508 | 1.00 | 96.90 | B |
| ATOM | 1360 | CA | GLY | B | 48 | −51.700 | 49.623 | −46.371 | 1.00 | 95.31 | B |
| ATOM | 1361 | C | GLY | B | 48 | −51.429 | 50.049 | −44.937 | 1.00 | 94.30 | B |
| ATOM | 1362 | O | GLY | B | 48 | −51.772 | 51.165 | −44.541 | 1.00 | 94.67 | B |
| ATOM | 1363 | N | ALA | B | 49 | −50.817 | 49.163 | −44.155 | 1.00 | 92.52 | B |
| ATOM | 1364 | CA | ALA | B | 49 | −50.508 | 49.455 | −42.756 | 1.00 | 90.44 | B |
| ATOM | 1365 | CB | ALA | B | 49 | −51.795 | 49.488 | −41.929 | 1.00 | 90.39 | B |
| ATOM | 1366 | C | ALA | B | 49 | −49.536 | 48.424 | −42.182 | 1.00 | 88.31 | B |
| ATOM | 1367 | O | ALA | B | 49 | −49.944 | 47.366 | −41.697 | 1.00 | 87.77 | B |
| ATOM | 1368 | N | GLY | B | 50 | −48.249 | 48.753 | −42.241 | 1.00 | 85.76 | B |
| ATOM | 1369 | CA | GLY | B | 50 | −47.214 | 47.865 | −41.742 | 1.00 | 82.69 | B |
| ATOM | 1370 | C | GLY | B | 50 | −47.476 | 47.214 | −40.396 | 1.00 | 80.16 | B |
| ATOM | 1371 | O | GLY | B | 50 | −46.976 | 46.125 | −40.130 | 1.00 | 80.60 | B |
| ATOM | 1372 | N | ALA | B | 51 | −48.256 | 47.867 | −39.543 | 1.00 | 77.39 | B |
| ATOM | 1373 | CA | ALA | B | 51 | −48.548 | 47.319 | −38.223 | 1.00 | 74.09 | B |
| ATOM | 1374 | CB | ALA | B | 51 | −48.967 | 48.433 | −37.273 | 1.00 | 74.25 | B |
| ATOM | 1375 | C | ALA | B | 51 | −49.631 | 46.252 | −38.287 | 1.00 | 71.65 | B |
| ATOM | 1376 | O | ALA | B | 51 | −49.622 | 45.307 | −37.499 | 1.00 | 70.67 | B |
| ATOM | 1377 | N | ALA | B | 52 | −50.568 | 46.412 | −39.220 | 1.00 | 68.72 | B |
| ATOM | 1378 | CA | ALA | B | 52 | −51.652 | 45.450 | −39.392 | 1.00 | 65.82 | B |
| ATOM | 1379 | CB | ALA | B | 52 | −52.784 | 46.066 | −40.204 | 1.00 | 65.58 | B |
| ATOM | 1380 | C | ALA | B | 52 | −51.102 | 44.226 | −40.111 | 1.00 | 63.64 | B |
| ATOM | 1381 | O | ALA | B | 52 | −51.346 | 43.086 | −39.713 | 1.00 | 63.09 | B |

TABLE 7-continued

| | | | | | | | | | | |
|---|---|---|---|---|---|---|---|---|---|---|
| Atomic coordinates of rSIFN-co (SEQ ID NO: 1) | | | | | | | | | | |
| ATOM | 1382 | N | ALA | B | 53 | −50.351 | 44.472 | −41.175 | 1.00 | 60.70 B |
| ATOM | 1383 | CA | ALA | B | 53 | −49.758 | 43.390 | −41.942 | 1.00 | 58.62 B |
| ATOM | 1384 | CB | ALA | B | 53 | −48.812 | 43.959 | −42.994 | 1.00 | 57.63 B |
| ATOM | 1385 | C | ALA | B | 53 | −49.003 | 42.443 | −41.014 | 1.00 | 56.79 B |
| ATOM | 1386 | O | ALA | B | 53 | −49.350 | 41.271 | −40.897 | 1.00 | 56.46 B |
| ATOM | 1387 | N | ILE | B | 54 | −47.977 | 42.971 | −40.350 | 1.00 | 55.35 B |
| ATOM | 1388 | CA | ILE | B | 54 | −47.139 | 42.197 | −39.440 | 1.00 | 53.78 B |
| ATOM | 1389 | CB | ILE | B | 54 | −46.178 | 43.100 | −38.678 | 1.00 | 53.66 B |
| ATOM | 1390 | CG2 | ILE | B | 54 | −45.360 | 42.267 | −37.708 | 1.00 | 53.50 B |
| ATOM | 1391 | CG1 | ILE | B | 54 | −45.275 | 43.848 | −39.665 | 1.00 | 54.89 B |
| ATOM | 1392 | CD1 | ILE | B | 54 | −44.430 | 44.947 | −39.029 | 1.00 | 53.54 B |
| ATOM | 1393 | C | ILE | B | 54 | −47.913 | 41.393 | −38.412 | 1.00 | 53.50 B |
| ATOM | 1394 | O | ILE | B | 54 | −47.529 | 40.280 | −38.074 | 1.00 | 53.63 B |
| ATOM | 1395 | N | SER | B | 55 | −48.999 | 41.965 | −37.916 | 1.00 | 53.54 B |
| ATOM | 1396 | CA | SER | B | 55 | −49.820 | 41.306 | −36.922 | 1.00 | 53.69 B |
| ATOM | 1397 | CB | SER | B | 55 | −50.764 | 42.312 | −36.277 | 1.00 | 55.26 B |
| ATOM | 1398 | OG | SER | B | 55 | −50.023 | 43.376 | −35.708 | 1.00 | 58.90 B |
| ATOM | 1399 | C | SER | B | 55 | −50.615 | 40.161 | −37.515 | 1.00 | 52.96 B |
| ATOM | 1400 | O | SER | B | 55 | −50.797 | 39.142 | −36.867 | 1.00 | 54.85 B |
| ATOM | 1401 | N | VAL | B | 56 | −51.098 | 40.307 | −38.738 | 1.00 | 51.44 B |
| ATOM | 1402 | CA | VAL | B | 56 | −51.849 | 39.210 | −39.318 | 1.00 | 51.64 B |
| ATOM | 1403 | CB | VAL | B | 56 | −52.798 | 39.692 | −40.431 | 1.00 | 51.99 B |
| ATOM | 1404 | CG1 | VAL | B | 56 | −53.812 | 40.643 | −39.846 | 1.00 | 50.15 B |
| ATOM | 1405 | CG2 | VAL | B | 56 | −52.020 | 40.360 | −41.536 | 1.00 | 51.94 B |
| ATOM | 1406 | C | VAL | B | 56 | −50.924 | 38.115 | −39.849 | 1.00 | 51.00 B |
| ATOM | 1407 | O | VAL | B | 56 | −51.165 | 36.937 | −39.613 | 1.00 | 50.59 B |
| ATOM | 1408 | N | LEU | B | 57 | −49.867 | 38.489 | −40.560 | 1.00 | 50.84 B |
| ATOM | 1409 | CA | LEU | B | 57 | −48.943 | 37.479 | −41.061 | 1.00 | 51.20 B |
| ATOM | 1410 | CB | LEU | B | 57 | −47.755 | 38.107 | −41.798 | 1.00 | 51.55 B |
| ATOM | 1411 | CG | LEU | B | 57 | −47.820 | 38.373 | −43.304 | 1.00 | 52.66 B |
| ATOM | 1412 | CD1 | LEU | B | 57 | −48.796 | 37.400 | −43.946 | 1.00 | 52.07 B |
| ATOM | 1413 | CD2 | LEU | B | 57 | −48.221 | 39.805 | −43.569 | 1.00 | 52.06 B |
| ATOM | 1414 | C | LEU | B | 57 | −48.410 | 36.699 | −39.871 | 1.00 | 50.92 B |
| ATOM | 1415 | O | LEU | B | 57 | −48.392 | 35.462 | −39.879 | 1.00 | 51.14 B |
| ATOM | 1416 | N | HIS | B | 58 | −47.983 | 37.427 | −38.841 | 1.00 | 48.84 B |
| ATOM | 1417 | CA | HIS | B | 58 | −47.433 | 36.786 | −37.649 | 1.00 | 48.56 B |
| ATOM | 1418 | CB | HIS | B | 58 | −47.033 | 37.837 | −36.593 | 1.00 | 45.06 B |
| ATOM | 1419 | CG | HIS | B | 58 | −46.150 | 37.292 | −35.510 | 1.00 | 41.60 B |
| ATOM | 1420 | CD2 | HIS | B | 58 | −44.811 | 37.390 | −35.322 | 1.00 | 40.97 B |
| ATOM | 1421 | ND1 | HIS | B | 58 | −46.620 | 36.470 | −34.511 | 1.00 | 41.10 B |
| ATOM | 1422 | CE1 | HIS | B | 58 | −45.605 | 36.077 | −33.754 | 1.00 | 39.76 B |
| ATOM | 1423 | NE2 | HIS | B | 58 | −44.500 | 36.619 | −34.225 | 1.00 | 38.18 B |
| ATOM | 1424 | C | HIS | B | 58 | −48.405 | 35.769 | −37.035 | 1.00 | 47.89 B |
| ATOM | 1425 | O | HIS | B | 58 | −48.000 | 34.667 | −36.652 | 1.00 | 47.61 B |
| ATOM | 1426 | N | GLU | B | 59 | −49.682 | 36.125 | −36.955 | 1.00 | 44.67 B |
| ATOM | 1427 | CA | GLU | B | 59 | −50.649 | 35.215 | −36.376 | 1.00 | 44.65 B |
| ATOM | 1428 | CB | GLU | B | 59 | −51.992 | 35.911 | −36.156 | 1.00 | 45.09 B |
| ATOM | 1429 | CG | GLU | B | 59 | −52.996 | 35.078 | −35.377 | 1.00 | 46.22 B |
| ATOM | 1430 | CD | GLU | B | 59 | −52.491 | 34.750 | −33.994 | 1.00 | 48.75 B |
| ATOM | 1431 | OE1 | GLU | B | 59 | −51.714 | 35.571 | −33.474 | 1.00 | 50.15 B |
| ATOM | 1432 | OE2 | GLU | B | 59 | −52.860 | 33.696 | −33.422 | 1.00 | 48.92 B |
| ATOM | 1433 | C | GLU | B | 59 | −50.857 | 33.998 | −37.257 | 1.00 | 44.41 B |
| ATOM | 1434 | O | GLU | B | 59 | −51.033 | 32.892 | −36.757 | 1.00 | 44.67 B |
| ATOM | 1435 | N | MET | B | 60 | −50.842 | 34.196 | −38.571 | 1.00 | 44.37 B |
| ATOM | 1436 | CA | MET | B | 60 | −51.055 | 33.079 | −39.471 | 1.00 | 45.11 B |
| ATOM | 1437 | CB | MET | B | 60 | −51.331 | 33.559 | −40.897 | 1.00 | 48.89 B |
| ATOM | 1438 | CG | MET | B | 60 | −51.721 | 32.415 | −41.821 | 1.00 | 53.44 B |
| ATOM | 1439 | SD | MET | B | 60 | −51.754 | 32.856 | −43.555 | 1.00 | 61.98 B |
| ATOM | 1440 | CE | MET | B | 60 | −50.021 | 33.361 | −43.846 | 1.00 | 58.01 B |
| ATOM | 1441 | C | MET | B | 60 | −49.864 | 32.128 | −39.465 | 1.00 | 43.04 B |
| ATOM | 1442 | O | MET | B | 60 | −50.039 | 30.909 | −39.449 | 1.00 | 40.32 B |
| ATOM | 1443 | N | ILE | B | 61 | −48.655 | 32.671 | −39.481 | 1.00 | 40.71 B |
| ATOM | 1444 | CA | ILE | B | 61 | −47.500 | 31.802 | −39.457 | 1.00 | 42.41 B |
| ATOM | 1445 | CB | ILE | B | 61 | −46.170 | 32.608 | −39.520 | 1.00 | 43.92 B |
| ATOM | 1446 | CG2 | ILE | B | 61 | −44.975 | 31.667 | −39.434 | 1.00 | 44.05 B |
| ATOM | 1447 | CG1 | ILE | B | 61 | −46.094 | 33.395 | −40.823 | 1.00 | 41.85 B |
| ATOM | 1448 | CD1 | ILE | B | 61 | −46.283 | 32.551 | −42.028 | 1.00 | 45.99 B |
| ATOM | 1449 | C | ILE | B | 61 | −47.557 | 30.991 | −38.153 | 1.00 | 43.11 B |
| ATOM | 1450 | O | ILE | B | 61 | −47.413 | 29.762 | −38.158 | 1.00 | 43.91 B |
| ATOM | 1451 | N | GLN | B | 62 | −47.795 | 31.690 | −37.049 | 1.00 | 42.04 B |
| ATOM | 1452 | CA | GLN | B | 62 | −47.863 | 31.082 | −35.726 | 1.00 | 43.22 B |
| ATOM | 1453 | CB | GLN | B | 62 | −48.229 | 32.140 | −34.685 | 1.00 | 46.41 B |
| ATOM | 1454 | CG | GLN | B | 62 | −48.049 | 31.713 | −33.245 | 1.00 | 46.91 B |
| ATOM | 1455 | CD | GLN | B | 62 | −46.596 | 31.663 | −32.837 | 1.00 | 52.53 B |
| ATOM | 1456 | OE1 | GLN | B | 62 | −45.904 | 30.665 | −33.070 | 1.00 | 55.84 B |
| ATOM | 1457 | NE2 | GLN | B | 62 | −46.113 | 32.748 | −32.228 | 1.00 | 54.09 B |
| ATOM | 1458 | C | GLN | B | 62 | −48.880 | 29.960 | −35.663 | 1.00 | 43.47 B |
| ATOM | 1459 | O | GLN | B | 62 | −48.587 | 28.870 | −35.152 | 1.00 | 44.07 B |

TABLE 7-continued

Atomic coordinates of rSIFN-co (SEQ ID NO: 1)

| ATOM | 1460 | N | GLN | B | 63 | −50.083 | 30.228 | −36.163 | 1.00 | 42.32 | B |
|------|------|------|-----|---|----|---------|--------|---------|------|-------|---|
| ATOM | 1461 | CA | GLN | B | 63 | −51.140 | 29.221 | −36.158 | 1.00 | 43.14 | B |
| ATOM | 1462 | CB | GLN | B | 63 | −52.456 | 29.812 | −36.653 | 1.00 | 43.36 | B |
| ATOM | 1463 | CG | GLN | B | 63 | −53.088 | 30.810 | −35.702 | 1.00 | 45.90 | B |
| ATOM | 1464 | CD | GLN | B | 63 | −53.432 | 30.220 | −34.339 | 1.00 | 44.57 | B |
| ATOM | 1465 | OE1 | GLN | B | 63 | −53.643 | 30.956 | −33.386 | 1.00 | 44.63 | B |
| ATOM | 1466 | NE2 | GLN | B | 63 | −53.497 | 28.896 | −34.250 | 1.00 | 44.30 | B |
| ATOM | 1467 | C | GLN | B | 63 | −50.796 | 28.018 | −37.017 | 1.00 | 43.72 | B |
| ATOM | 1468 | O | GLN | B | 63 | −51.089 | 26.880 | −36.649 | 1.00 | 44.40 | B |
| ATOM | 1469 | N | THR | B | 64 | −50.177 | 28.277 | −38.164 | 1.00 | 42.86 | B |
| ATOM | 1470 | CA | THR | B | 64 | −49.811 | 27.211 | −39.073 | 1.00 | 42.63 | B |
| ATOM | 1471 | CB | THR | B | 64 | −49.271 | 27.777 | −40.409 | 1.00 | 42.59 | B |
| ATOM | 1472 | OG1 | THR | B | 64 | −50.275 | 28.599 | −41.012 | 1.00 | 40.41 | B |
| ATOM | 1473 | CG2 | THR | B | 64 | −48.910 | 26.649 | −41.368 | 1.00 | 39.23 | B |
| ATOM | 1474 | C | THR | B | 64 | −48.762 | 26.343 | −38.405 | 1.00 | 43.08 | B |
| ATOM | 1475 | O | THR | B | 64 | −48.801 | 25.118 | −38.509 | 1.00 | 45.34 | B |
| ATOM | 1476 | N | PHE | B | 65 | −47.820 | 26.980 | −37.724 | 1.00 | 41.85 | B |
| ATOM | 1477 | CA | PHE | B | 65 | −46.781 | 26.245 | −37.026 | 1.00 | 41.65 | B |
| ATOM | 1478 | CB | PHE | B | 65 | −45.890 | 27.210 | −36.231 | 1.00 | 39.65 | B |
| ATOM | 1479 | CG | PHE | B | 65 | −44.753 | 26.533 | −35.514 | 1.00 | 37.50 | B |
| ATOM | 1480 | CD1 | PHE | B | 65 | −43.503 | 26.448 | −36.095 | 1.00 | 38.07 | B |
| ATOM | 1481 | CD2 | PHE | B | 65 | −44.952 | 25.931 | −34.285 | 1.00 | 38.71 | B |
| ATOM | 1482 | CE1 | PHE | B | 65 | −42.463 | 25.766 | −35.473 | 1.00 | 38.97 | B |
| ATOM | 1483 | CE2 | PHE | B | 65 | −43.927 | 25.247 | −33.651 | 1.00 | 40.75 | B |
| ATOM | 1484 | CZ | PHE | B | 65 | −42.674 | 25.163 | −34.252 | 1.00 | 41.00 | B |
| ATOM | 1485 | C | PHE | B | 65 | −47.459 | 25.268 | −36.062 | 1.00 | 42.95 | B |
| ATOM | 1486 | O | PHE | B | 65 | −47.199 | 24.067 | −36.077 | 1.00 | 41.78 | B |
| ATOM | 1487 | N | ASN | B | 66 | −48.346 | 25.797 | −35.228 | 1.00 | 44.10 | B |
| ATOM | 1488 | CA | ASN | B | 66 | −49.036 | 24.976 | −34.244 | 1.00 | 45.15 | B |
| ATOM | 1489 | CB | ASN | B | 66 | −50.014 | 25.836 | −33.444 | 1.00 | 45.22 | B |
| ATOM | 1490 | CG | ASN | B | 66 | −49.309 | 26.882 | −32.588 | 1.00 | 45.60 | B |
| ATOM | 1491 | OD1 | ASN | B | 66 | −49.917 | 27.866 | −32.179 | 1.00 | 47.81 | B |
| ATOM | 1492 | ND2 | ASN | B | 66 | −48.026 | 26.667 | −32.310 | 1.00 | 45.74 | B |
| ATOM | 1493 | C | ASN | B | 66 | −49.758 | 23.802 | −34.874 | 1.00 | 45.93 | B |
| ATOM | 1494 | O | ASN | B | 66 | −49.592 | 22.661 | −34.443 | 1.00 | 46.70 | B |
| ATOM | 1495 | N | LEU | B | 67 | −50.545 | 24.087 | −35.906 | 1.00 | 46.78 | B |
| ATOM | 1496 | CA | LEU | B | 67 | −51.314 | 23.072 | −36.614 | 1.00 | 45.25 | B |
| ATOM | 1497 | CB | LEU | B | 67 | −52.027 | 23.708 | −37.802 | 1.00 | 44.17 | B |
| ATOM | 1498 | CG | LEU | B | 67 | −52.943 | 22.848 | −38.673 | 1.00 | 44.83 | B |
| ATOM | 1499 | CD1 | LEU | B | 67 | −54.221 | 22.524 | −37.908 | 1.00 | 43.33 | B |
| ATOM | 1500 | CD2 | LEU | B | 67 | −53.269 | 23.609 | −39.950 | 1.00 | 43.75 | B |
| ATOM | 1501 | C | LEU | B | 67 | −50.465 | 21.914 | −37.109 | 1.00 | 46.02 | B |
| ATOM | 1502 | O | LEU | B | 67 | −50.888 | 20.763 | −37.037 | 1.00 | 47.59 | B |
| ATOM | 1503 | N | PHE | B | 68 | −49.270 | 22.209 | −37.606 | 1.00 | 45.93 | B |
| ATOM | 1504 | CA | PHE | B | 68 | −48.407 | 21.165 | −38.142 | 1.00 | 48.01 | B |
| ATOM | 1505 | CB | PHE | B | 68 | −47.690 | 21.674 | −39.400 | 1.00 | 47.07 | B |
| ATOM | 1506 | CG | PHE | B | 68 | −48.573 | 21.725 | −40.623 | 1.00 | 47.28 | B |
| ATOM | 1507 | CD1 | PHE | B | 68 | −49.374 | 22.834 | −40.879 | 1.00 | 47.40 | B |
| ATOM | 1508 | CD2 | PHE | B | 68 | −48.629 | 20.643 | −41.497 | 1.00 | 45.54 | B |
| ATOM | 1509 | CE1 | PHE | B | 68 | −50.217 | 22.863 | −41.985 | 1.00 | 45.20 | B |
| ATOM | 1510 | CE2 | PHE | B | 68 | −49.463 | 20.660 | −42.598 | 1.00 | 45.58 | B |
| ATOM | 1511 | CZ | PHE | B | 68 | −50.261 | 21.772 | −42.843 | 1.00 | 45.21 | B |
| ATOM | 1512 | C | PHE | B | 68 | −47.385 | 20.564 | −37.174 | 1.00 | 50.56 | B |
| ATOM | 1513 | O | PHE | B | 68 | −46.660 | 19.625 | −37.519 | 1.00 | 50.22 | B |
| ATOM | 1514 | N | SER | B | 69 | −47.333 | 21.093 | −35.959 | 1.00 | 52.03 | B |
| ATOM | 1515 | CA | SER | B | 69 | −46.397 | 20.592 | −34.963 | 1.00 | 51.91 | B |
| ATOM | 1516 | CB | SER | B | 69 | −45.844 | 21.762 | −34.145 | 1.00 | 50.79 | B |
| ATOM | 1517 | OG | SER | B | 69 | −46.861 | 22.698 | −33.850 | 1.00 | 50.68 | B |
| ATOM | 1518 | C | SER | B | 69 | −47.098 | 19.559 | −34.071 | 1.00 | 52.49 | B |
| ATOM | 1519 | O | SER | B | 69 | −46.471 | 18.877 | −33.263 | 1.00 | 51.65 | B |
| ATOM | 1520 | N | THR | B | 70 | −48.406 | 19.437 | −34.256 | 1.00 | 53.35 | B |
| ATOM | 1521 | CA | THR | B | 70 | −49.220 | 18.485 | −33.519 | 1.00 | 54.95 | B |
| ATOM | 1522 | CB | THR | B | 70 | −50.715 | 18.667 | −33.892 | 1.00 | 54.32 | B |
| ATOM | 1523 | OG1 | THR | B | 70 | −51.292 | 19.672 | −33.051 | 1.00 | 53.43 | B |
| ATOM | 1524 | CG2 | THR | B | 70 | −51.491 | 17.378 | −33.749 | 1.00 | 53.28 | B |
| ATOM | 1525 | C | THR | B | 70 | −48.816 | 17.024 | −33.764 | 1.00 | 57.60 | B |
| ATOM | 1526 | O | THR | B | 70 | −48.196 | 16.683 | −34.775 | 1.00 | 56.59 | B |
| ATOM | 1527 | N | ARG | B | 71 | −49.183 | 16.177 | −32.806 | 1.00 | 60.45 | B |
| ATOM | 1528 | CA | ARG | B | 71 | −48.931 | 14.739 | −32.839 | 1.00 | 63.09 | B |
| ATOM | 1529 | CB | ARG | B | 71 | −49.445 | 14.131 | −31.527 | 1.00 | 66.17 | B |
| ATOM | 1530 | CG | ARG | B | 71 | −50.748 | 14.806 | −31.033 | 1.00 | 71.66 | B |
| ATOM | 1531 | CD | ARG | B | 71 | −50.651 | 15.471 | −29.626 | 1.00 | 74.28 | B |
| ATOM | 1532 | NE | ARG | B | 71 | −49.626 | 16.519 | −29.495 | 1.00 | 75.60 | B |
| ATOM | 1533 | CZ | ARG | B | 71 | −48.406 | 16.325 | −28.982 | 1.00 | 76.64 | B |
| ATOM | 1534 | NH1 | ARG | B | 71 | −48.039 | 15.122 | −28.548 | 1.00 | 76.04 | B |
| ATOM | 1535 | NH2 | ARG | B | 71 | −47.551 | 17.338 | −28.891 | 1.00 | 75.84 | B |
| ATOM | 1536 | C | ARG | B | 71 | −49.654 | 14.119 | −34.046 | 1.00 | 62.93 | B |
| ATOM | 1537 | O | ARG | B | 71 | −49.156 | 13.186 | −34.684 | 1.00 | 62.66 | B |

TABLE 7-continued

Atomic coordinates of rSIFN-co (SEQ ID NO: 1)

| ATOM | 1538 | N | ASP | B | 72 | −50.834 | 14.654 | −34.344 | 1.00 | 62.27 | B |
|---|---|---|---|---|---|---|---|---|---|---|---|
| ATOM | 1539 | CA | ASP | B | 72 | −51.642 | 14.201 | −35.465 | 1.00 | 61.32 | B |
| ATOM | 1540 | CB | ASP | B | 72 | −53.017 | 14.844 | −35.398 | 1.00 | 63.05 | B |
| ATOM | 1541 | CG | ASP | B | 72 | −53.745 | 14.517 | −34.121 | 1.00 | 65.14 | B |
| ATOM | 1542 | OD1 | ASP | B | 72 | −54.164 | 13.350 | −33.973 | 1.00 | 66.97 | B |
| ATOM | 1543 | OD2 | ASP | B | 72 | −53.894 | 15.425 | −33.270 | 1.00 | 65.14 | B |
| ATOM | 1544 | C | ASP | B | 72 | −50.973 | 14.600 | −36.768 | 1.00 | 60.42 | B |
| ATOM | 1545 | O | ASP | B | 72 | −51.034 | 13.882 | −37.762 | 1.00 | 61.00 | B |
| ATOM | 1546 | N | SER | B | 73 | −50.341 | 15.762 | −36.758 | 1.00 | 59.06 | B |
| ATOM | 1547 | CA | SER | B | 73 | −49.657 | 16.238 | −37.938 | 1.00 | 58.72 | B |
| ATOM | 1548 | CB | SER | B | 73 | −49.126 | 17.654 | −37.704 | 1.00 | 57.83 | B |
| ATOM | 1549 | OG | SER | B | 73 | −48.578 | 18.194 | −38.892 | 1.00 | 58.48 | B |
| ATOM | 1550 | C | SER | B | 73 | −48.509 | 15.281 | −38.262 | 1.00 | 58.75 | B |
| ATOM | 1551 | O | SER | B | 73 | −48.355 | 14.859 | −39.408 | 1.00 | 58.86 | B |
| ATOM | 1552 | N | SER | B | 74 | −47.718 | 14.927 | −37.250 | 1.00 | 57.50 | B |
| ATOM | 1553 | CA | SER | B | 74 | −46.582 | 14.026 | −37.443 | 1.00 | 56.83 | B |
| ATOM | 1554 | CB | SER | B | 74 | −45.849 | 13.794 | −36.127 | 1.00 | 55.68 | B |
| ATOM | 1555 | OG | SER | B | 74 | −45.131 | 14.949 | −35.737 | 1.00 | 59.88 | B |
| ATOM | 1556 | C | SER | B | 74 | −47.000 | 12.686 | −38.020 | 1.00 | 55.92 | B |
| ATOM | 1557 | O | SER | B | 74 | −46.286 | 12.097 | −38.837 | 1.00 | 54.81 | B |
| ATOM | 1558 | N | ALA | B | 75 | −48.154 | 12.201 | −37.583 | 1.00 | 54.52 | B |
| ATOM | 1559 | CA | ALA | B | 75 | −48.658 | 10.929 | −38.069 | 1.00 | 54.44 | B |
| ATOM | 1560 | CB | ALA | B | 75 | −49.870 | 10.520 | −37.268 | 1.00 | 53.67 | B |
| ATOM | 1561 | C | ALA | B | 75 | −49.029 | 11.043 | −39.540 | 1.00 | 54.05 | B |
| ATOM | 1562 | O | ALA | B | 75 | −48.835 | 10.114 | −40.323 | 1.00 | 53.83 | B |
| ATOM | 1563 | N | ALA | B | 76 | −49.542 | 12.211 | −39.905 | 1.00 | 53.41 | B |
| ATOM | 1564 | CA | ALA | B | 76 | −49.996 | 12.477 | −41.255 | 1.00 | 52.31 | B |
| ATOM | 1565 | CB | ALA | B | 76 | −51.042 | 13.580 | −41.208 | 1.00 | 52.11 | B |
| ATOM | 1566 | C | ALA | B | 76 | −48.946 | 12.810 | −42.315 | 1.00 | 52.55 | B |
| ATOM | 1567 | O | ALA | B | 76 | −49.114 | 12.443 | −43.477 | 1.00 | 52.41 | B |
| ATOM | 1568 | N | TRP | B | 77 | −47.862 | 13.481 | −41.941 | 1.00 | 51.98 | B |
| ATOM | 1569 | CA | TRP | B | 77 | −46.879 | 13.868 | −42.947 | 1.00 | 51.34 | B |
| ATOM | 1570 | CB | TRP | B | 77 | −46.887 | 15.391 | −43.126 | 1.00 | 50.88 | B |
| ATOM | 1571 | CG | TRP | B | 77 | −48.248 | 15.994 | −43.099 | 1.00 | 52.09 | B |
| ATOM | 1572 | CD2 | TRP | B | 77 | −49.187 | 16.052 | −44.178 | 1.00 | 53.10 | B |
| ATOM | 1573 | CE2 | TRP | B | 77 | −50.347 | 16.691 | −43.689 | 1.00 | 53.99 | B |
| ATOM | 1574 | CE3 | TRP | B | 77 | −49.163 | 15.624 | −45.512 | 1.00 | 52.69 | B |
| ATOM | 1575 | CD1 | TRP | B | 77 | −48.858 | 16.579 | −42.032 | 1.00 | 53.81 | B |
| ATOM | 1576 | NE1 | TRP | B | 77 | −50.119 | 17.002 | −42.375 | 1.00 | 54.33 | B |
| ATOM | 1577 | CZ2 | TRP | B | 77 | −51.476 | 16.916 | −44.490 | 1.00 | 54.45 | B |
| ATOM | 1578 | CZ3 | TRP | B | 77 | −50.287 | 15.845 | −46.309 | 1.00 | 50.90 | B |
| ATOM | 1579 | CH2 | TRP | B | 77 | −51.427 | 16.486 | −45.794 | 1.00 | 51.54 | B |
| ATOM | 1580 | C | TRP | B | 77 | −45.450 | 13.425 | −42.722 | 1.00 | 50.67 | B |
| ATOM | 1581 | O | TRP | B | 77 | −45.053 | 13.094 | −41.620 | 1.00 | 49.80 | B |
| ATOM | 1582 | N | ASP | B | 78 | −44.672 | 13.436 | −43.796 | 1.00 | 52.39 | B |
| ATOM | 1583 | CA | ASP | B | 78 | −43.278 | 13.064 | −43.711 | 1.00 | 53.40 | B |
| ATOM | 1584 | CB | ASP | B | 78 | −42.578 | 13.257 | −45.050 | 1.00 | 55.50 | B |
| ATOM | 1585 | CG | ASP | B | 78 | −41.104 | 12.936 | −44.966 | 1.00 | 59.62 | B |
| ATOM | 1586 | OD1 | ASP | B | 78 | −40.273 | 13.875 | −45.018 | 1.00 | 62.42 | B |
| ATOM | 1587 | OD2 | ASP | B | 78 | −40.777 | 11.738 | −44.820 | 1.00 | 59.99 | B |
| ATOM | 1588 | C | ASP | B | 78 | −42.602 | 13.933 | −42.663 | 1.00 | 53.04 | B |
| ATOM | 1589 | O | ASP | B | 78 | −42.706 | 15.160 | −42.700 | 1.00 | 53.12 | B |
| ATOM | 1590 | N | ALA | B | 79 | −41.901 | 13.287 | −41.738 | 1.00 | 52.08 | B |
| ATOM | 1591 | CA | ALA | B | 79 | −41.220 | 13.983 | −40.662 | 1.00 | 52.01 | B |
| ATOM | 1592 | CB | ALA | B | 79 | −40.643 | 12.968 | −39.675 | 1.00 | 50.85 | B |
| ATOM | 1593 | C | ALA | B | 79 | −40.128 | 14.917 | −41.179 | 1.00 | 51.80 | B |
| ATOM | 1594 | O | ALA | B | 79 | −40.008 | 16.050 | −40.723 | 1.00 | 52.56 | B |
| ATOM | 1595 | N | SER | B | 80 | −39.341 | 14.453 | −42.138 | 1.00 | 51.82 | B |
| ATOM | 1596 | CA | SER | B | 80 | −38.273 | 15.277 | −42.687 | 1.00 | 51.59 | B |
| ATOM | 1597 | CB | SER | B | 80 | −37.511 | 14.507 | −43.764 | 1.00 | 53.55 | B |
| ATOM | 1598 | OG | SER | B | 80 | −36.317 | 15.188 | −44.120 | 1.00 | 57.70 | B |
| ATOM | 1599 | C | SER | B | 80 | −38.818 | 16.577 | −43.280 | 1.00 | 50.52 | B |
| ATOM | 1600 | O | SER | B | 80 | −38.223 | 17.649 | −43.113 | 1.00 | 51.02 | B |
| ATOM | 1601 | N | LEU | B | 81 | −39.937 | 16.487 | −43.990 | 1.00 | 47.40 | B |
| ATOM | 1602 | CA | LEU | B | 81 | −40.521 | 17.684 | −44.574 | 1.00 | 46.68 | B |
| ATOM | 1603 | CB | LEU | B | 81 | −41.665 | 17.327 | −45.531 | 1.00 | 44.63 | B |
| ATOM | 1604 | CG | LEU | B | 81 | −41.253 | 16.605 | −46.824 | 1.00 | 43.12 | B |
| ATOM | 1605 | CD1 | LEU | B | 81 | −42.433 | 16.565 | −47.792 | 1.00 | 40.61 | B |
| ATOM | 1606 | CD2 | LEU | B | 81 | −40.080 | 17.329 | −47.467 | 1.00 | 38.50 | B |
| ATOM | 1607 | C | LEU | B | 81 | −41.021 | 18.607 | −43.464 | 1.00 | 47.01 | B |
| ATOM | 1608 | O | LEU | B | 81 | −40.806 | 19.823 | −43.507 | 1.00 | 46.43 | B |
| ATOM | 1609 | N | LEU | B | 82 | −41.668 | 18.019 | −42.462 | 1.00 | 45.79 | B |
| ATOM | 1610 | CA | LEU | B | 82 | −42.184 | 18.790 | −41.344 | 1.00 | 44.38 | B |
| ATOM | 1611 | CB | LEU | B | 82 | −42.915 | 17.881 | −40.355 | 1.00 | 43.65 | B |
| ATOM | 1612 | CG | LEU | B | 82 | −44.350 | 17.506 | −40.712 | 1.00 | 42.39 | B |
| ATOM | 1613 | CD1 | LEU | B | 82 | −44.969 | 16.779 | −39.542 | 1.00 | 41.48 | B |
| ATOM | 1614 | CD2 | LEU | B | 82 | −45.148 | 18.764 | −41.040 | 1.00 | 40.02 | B |
| ATOM | 1615 | C | LEU | B | 82 | −41.106 | 19.579 | −40.608 | 1.00 | 43.60 | B |

TABLE 7-continued

Atomic coordinates of rSIFN-co (SEQ ID NO: 1)

| ATOM | 1616 | O | LEU | B | 82 | −41.306 | 20.748 | −40.294 | 1.00 | 43.44 | B |
|---|---|---|---|---|---|---|---|---|---|---|---|
| ATOM | 1617 | N | ALA | B | 83 | −39.968 | 18.958 | −40.326 | 1.00 | 41.84 | B |
| ATOM | 1618 | CA | ALA | B | 83 | −38.920 | 19.686 | −39.617 | 1.00 | 42.47 | B |
| ATOM | 1619 | CB | ALA | B | 83 | −37.732 | 18.749 | −39.241 | 1.00 | 42.87 | B |
| ATOM | 1620 | C | ALA | B | 83 | −38.442 | 20.857 | −40.466 | 1.00 | 40.93 | B |
| ATOM | 1621 | O | ALA | B | 83 | −38.074 | 21.898 | −39.930 | 1.00 | 41.51 | B |
| ATOM | 1622 | N | LYS | B | 84 | −38.458 | 20.693 | −41.785 | 1.00 | 39.80 | B |
| ATOM | 1623 | CA | LYS | B | 84 | −38.041 | 21.770 | −42.680 | 1.00 | 40.20 | B |
| ATOM | 1624 | CB | LYS | B | 84 | −37.916 | 21.257 | −44.121 | 1.00 | 42.21 | B |
| ATOM | 1625 | CG | LYS | B | 84 | −36.919 | 20.117 | −44.326 | 1.00 | 44.38 | B |
| ATOM | 1626 | CD | LYS | B | 84 | −36.542 | 20.019 | −45.799 | 1.00 | 45.90 | B |
| ATOM | 1627 | CE | LYS | B | 84 | −35.545 | 18.920 | −46.068 | 1.00 | 45.47 | B |
| ATOM | 1628 | NZ | LYS | B | 84 | −36.209 | 17.606 | −45.922 | 1.00 | 49.90 | B |
| ATOM | 1629 | C | LYS | B | 84 | −39.076 | 22.902 | −42.631 | 1.00 | 39.06 | B |
| ATOM | 1630 | O | LYS | B | 84 | −38.743 | 24.087 | −42.678 | 1.00 | 39.36 | B |
| ATOM | 1631 | N | PHE | B | 85 | −40.338 | 22.512 | −42.539 | 1.00 | 37.58 | B |
| ATOM | 1632 | CA | PHE | B | 85 | −41.449 | 23.442 | −42.475 | 1.00 | 38.00 | B |
| ATOM | 1633 | CB | PHE | B | 85 | −42.749 | 22.644 | −42.492 | 1.00 | 38.99 | B |
| ATOM | 1634 | CG | PHE | B | 85 | −43.959 | 23.458 | −42.811 | 1.00 | 39.63 | B |
| ATOM | 1635 | CD1 | PHE | B | 85 | −43.942 | 24.366 | −43.866 | 1.00 | 38.44 | B |
| ATOM | 1636 | CD2 | PHE | B | 85 | −45.137 | 23.276 | −42.099 | 1.00 | 38.81 | B |
| ATOM | 1637 | CE1 | PHE | B | 85 | −45.076 | 25.079 | −44.211 | 1.00 | 39.59 | B |
| ATOM | 1638 | CE2 | PHE | B | 85 | −46.288 | 23.986 | −42.439 | 1.00 | 41.20 | B |
| ATOM | 1639 | CZ | PHE | B | 85 | −46.255 | 24.891 | −43.501 | 1.00 | 41.17 | B |
| ATOM | 1640 | C | PHE | B | 85 | −41.387 | 24.331 | −41.223 | 1.00 | 38.99 | B |
| ATOM | 1641 | O | PHE | B | 85 | −41.419 | 25.557 | −41.334 | 1.00 | 39.44 | B |
| ATOM | 1642 | N | TYR | B | 86 | −41.299 | 23.709 | −40.044 | 1.00 | 38.21 | B |
| ATOM | 1643 | CA | TYR | B | 86 | −41.217 | 24.435 | −38.769 | 1.00 | 37.40 | B |
| ATOM | 1644 | CB | TYR | B | 86 | −40.998 | 23.493 | −37.574 | 1.00 | 35.90 | B |
| ATOM | 1645 | CG | TYR | B | 86 | −41.920 | 22.311 | −37.450 | 1.00 | 33.12 | B |
| ATOM | 1646 | CD1 | TYR | B | 86 | −43.276 | 22.428 | −37.721 | 1.00 | 32.96 | B |
| ATOM | 1647 | CE1 | TYR | B | 86 | −44.138 | 21.343 | −37.563 | 1.00 | 35.08 | B |
| ATOM | 1648 | CD2 | TYR | B | 86 | −41.435 | 21.077 | −37.019 | 1.00 | 30.36 | B |
| ATOM | 1649 | CE2 | TYR | B | 86 | −42.276 | 19.992 | −36.861 | 1.00 | 30.76 | B |
| ATOM | 1650 | CZ | TYR | B | 86 | −43.628 | 20.133 | −37.129 | 1.00 | 34.57 | B |
| ATOM | 1651 | OH | TYR | B | 86 | −44.491 | 19.085 | −36.932 | 1.00 | 37.86 | B |
| ATOM | 1652 | C | TYR | B | 86 | −40.044 | 25.403 | −38.776 | 1.00 | 38.65 | B |
| ATOM | 1653 | O | TYR | B | 86 | −40.156 | 26.527 | −38.300 | 1.00 | 40.78 | B |
| ATOM | 1654 | N | THR | B | 87 | −38.905 | 24.948 | −39.289 | 1.00 | 38.79 | B |
| ATOM | 1655 | CA | THR | B | 87 | −37.712 | 25.778 | −39.347 | 1.00 | 38.38 | B |
| ATOM | 1656 | CB | THR | B | 87 | −36.538 | 25.026 | −39.984 | 1.00 | 35.81 | B |
| ATOM | 1657 | OG1 | THR | B | 87 | −36.316 | 23.803 | −39.276 | 1.00 | 35.27 | B |
| ATOM | 1658 | CG2 | THR | B | 87 | −35.280 | 25.870 | −39.946 | 1.00 | 28.02 | B |
| ATOM | 1659 | C | THR | B | 87 | −37.976 | 27.029 | −40.165 | 1.00 | 40.34 | B |
| ATOM | 1660 | O | THR | B | 87 | −37.600 | 28.136 | −39.768 | 1.00 | 42.58 | B |
| ATOM | 1661 | N | GLU | B | 88 | −38.629 | 26.849 | −41.308 | 1.00 | 41.62 | B |
| ATOM | 1662 | CA | GLU | B | 88 | −38.948 | 27.962 | −42.196 | 1.00 | 41.56 | B |
| ATOM | 1663 | CB | GLU | B | 88 | −39.541 | 27.428 | −43.498 | 1.00 | 41.09 | B |
| ATOM | 1664 | CG | GLU | B | 88 | −39.850 | 28.487 | −44.526 | 1.00 | 43.87 | B |
| ATOM | 1665 | CD | GLU | B | 88 | −38.622 | 29.295 | −44.906 | 1.00 | 47.13 | B |
| ATOM | 1666 | OE1 | GLU | B | 88 | −37.542 | 28.689 | −45.046 | 1.00 | 48.15 | B |
| ATOM | 1667 | OE2 | GLU | B | 88 | −38.728 | 30.528 | −45.078 | 1.00 | 48.87 | B |
| ATOM | 1668 | C | GLU | B | 88 | −39.941 | 28.907 | −41.523 | 1.00 | 41.37 | B |
| ATOM | 1669 | O | GLU | B | 88 | −39.719 | 30.120 | −41.441 | 1.00 | 42.84 | B |
| ATOM | 1670 | N | LEU | B | 89 | −41.037 | 28.342 | −41.032 | 1.00 | 39.06 | B |
| ATOM | 1671 | CA | LEU | B | 89 | −42.049 | 29.144 | −40.380 | 1.00 | 38.27 | B |
| ATOM | 1672 | CB | LEU | B | 89 | −43.214 | 28.255 | −39.938 | 1.00 | 34.88 | B |
| ATOM | 1673 | CG | LEU | B | 89 | −43.971 | 27.575 | −41.087 | 1.00 | 32.56 | B |
| ATOM | 1674 | CD1 | LEU | B | 89 | −45.074 | 26.700 | −40.540 | 1.00 | 29.69 | B |
| ATOM | 1675 | CD2 | LEU | B | 89 | −44.519 | 28.629 | −42.014 | 1.00 | 29.86 | B |
| ATOM | 1676 | C | LEU | B | 89 | −41.475 | 29.923 | −39.199 | 1.00 | 39.22 | B |
| ATOM | 1677 | O | LEU | B | 89 | −41.707 | 31.125 | −39.070 | 1.00 | 38.24 | B |
| ATOM | 1678 | N | TYR | B | 90 | −40.703 | 29.257 | −38.351 | 1.00 | 39.74 | B |
| ATOM | 1679 | CA | TYR | B | 90 | −40.153 | 29.951 | −37.214 | 1.00 | 41.05 | B |
| ATOM | 1680 | CB | TYR | B | 90 | −39.453 | 28.987 | −36.256 | 1.00 | 43.39 | B |
| ATOM | 1681 | CG | TYR | B | 90 | −39.363 | 29.572 | −34.863 | 1.00 | 45.73 | B |
| ATOM | 1682 | CD1 | TYR | B | 90 | −40.479 | 29.577 | −34.019 | 1.00 | 44.72 | B |
| ATOM | 1683 | CE1 | TYR | B | 90 | −40.446 | 30.218 | −32.789 | 1.00 | 46.68 | B |
| ATOM | 1684 | CD2 | TYR | B | 90 | −38.203 | 30.219 | −34.429 | 1.00 | 45.13 | B |
| ATOM | 1685 | CE2 | TYR | B | 90 | −38.160 | 30.863 | −33.193 | 1.00 | 46.07 | B |
| ATOM | 1686 | CZ | TYR | B | 90 | −39.287 | 30.863 | −32.379 | 1.00 | 46.81 | B |
| ATOM | 1687 | OH | TYR | B | 90 | −39.272 | 31.538 | −31.177 | 1.00 | 46.41 | B |
| ATOM | 1688 | C | TYR | B | 90 | −39.193 | 31.047 | −37.639 | 1.00 | 42.36 | B |
| ATOM | 1689 | O | TYR | B | 90 | −39.092 | 32.086 | −36.986 | 1.00 | 43.93 | B |
| ATOM | 1690 | N | GLN | B | 91 | −38.487 | 30.831 | −38.738 | 1.00 | 43.52 | B |
| ATOM | 1691 | CA | GLN | B | 91 | −37.557 | 31.844 | −39.217 | 1.00 | 45.08 | B |
| ATOM | 1692 | CB | GLN | B | 91 | −36.684 | 31.262 | −40.330 | 1.00 | 44.47 | B |
| ATOM | 1693 | CG | GLN | B | 91 | −35.262 | 31.826 | −40.377 | 1.00 | 48.72 | B |

TABLE 7-continued

Atomic coordinates of rSIFN-co (SEQ ID NO: 1)

| ATOM | 1694 | CD | GLN | B | 91 | −34.471 | 31.656 | −39.068 | 1.00 | 49.14 | B |
|---|---|---|---|---|---|---|---|---|---|---|---|
| ATOM | 1695 | OE1 | GLN | B | 91 | −34.568 | 30.634 | −38.385 | 1.00 | 49.61 | B |
| ATOM | 1696 | NE2 | GLN | B | 91 | −33.669 | 32.660 | −38.735 | 1.00 | 49.34 | B |
| ATOM | 1697 | C | GLN | B | 91 | −38.382 | 33.040 | −39.721 | 1.00 | 45.99 | B |
| ATOM | 1698 | O | GLN | B | 91 | −38.042 | 34.204 | −39.472 | 1.00 | 44.12 | B |
| ATOM | 1699 | N | GLN | B | 92 | −39.482 | 32.753 | −40.412 | 1.00 | 45.91 | B |
| ATOM | 1700 | CA | GLN | B | 92 | −40.340 | 33.821 | −40.904 | 1.00 | 47.21 | B |
| ATOM | 1701 | CB | GLN | B | 92 | −41.514 | 33.244 | −41.698 | 1.00 | 47.99 | B |
| ATOM | 1702 | CG | GLN | B | 92 | −41.191 | 32.841 | −43.123 | 1.00 | 51.32 | B |
| ATOM | 1703 | CD | GLN | B | 92 | −42.447 | 32.523 | −43.905 | 1.00 | 55.62 | B |
| ATOM | 1704 | OE1 | GLN | B | 92 | −43.411 | 33.290 | −43.885 | 1.00 | 57.55 | B |
| ATOM | 1705 | NE2 | GLN | B | 92 | −42.448 | 31.390 | −44.602 | 1.00 | 56.89 | B |
| ATOM | 1706 | C | GLN | B | 92 | −40.873 | 34.654 | −39.733 | 1.00 | 47.67 | B |
| ATOM | 1707 | O | GLN | B | 92 | −41.157 | 35.838 | −39.880 | 1.00 | 48.06 | B |
| ATOM | 1708 | N | LEU | B | 93 | −41.011 | 34.017 | −38.575 | 1.00 | 48.22 | B |
| ATOM | 1709 | CA | LEU | B | 93 | −41.502 | 34.663 | −37.366 | 1.00 | 46.33 | B |
| ATOM | 1710 | CB | LEU | B | 93 | −41.793 | 33.606 | −36.312 | 1.00 | 44.07 | B |
| ATOM | 1711 | CG | LEU | B | 93 | −43.211 | 33.418 | −35.790 | 1.00 | 42.19 | B |
| ATOM | 1712 | CD1 | LEU | B | 93 | −44.271 | 33.719 | −36.855 | 1.00 | 40.20 | B |
| ATOM | 1713 | CD2 | LEU | B | 93 | −43.303 | 31.992 | −35.296 | 1.00 | 38.45 | B |
| ATOM | 1714 | C | LEU | B | 93 | −40.454 | 35.629 | −36.848 | 1.00 | 47.84 | B |
| ATOM | 1715 | O | LEU | B | 93 | −40.772 | 36.740 | −36.439 | 1.00 | 47.68 | B |
| ATOM | 1716 | N | ASN | B | 94 | −39.196 | 35.201 | −36.857 | 1.00 | 49.68 | B |
| ATOM | 1717 | CA | ASN | B | 94 | −38.118 | 36.067 | −36.396 | 1.00 | 50.86 | B |
| ATOM | 1718 | CB | ASN | B | 94 | −36.797 | 35.295 | −36.302 | 1.00 | 49.93 | B |
| ATOM | 1719 | CG | ASN | B | 94 | −36.741 | 34.372 | −35.097 | 1.00 | 49.12 | B |
| ATOM | 1720 | OD1 | ASN | B | 94 | −37.613 | 34.402 | −34.228 | 1.00 | 48.85 | B |
| ATOM | 1721 | ND2 | ASN | B | 94 | −35.699 | 33.555 | −35.035 | 1.00 | 50.25 | B |
| ATOM | 1722 | C | ASN | B | 94 | −37.957 | 37.256 | −37.339 | 1.00 | 52.00 | B |
| ATOM | 1723 | O | ASN | B | 94 | −37.673 | 38.362 | −36.902 | 1.00 | 52.28 | B |
| ATOM | 1724 | N | ASP | B | 95 | −38.144 | 37.038 | −38.635 | 1.00 | 54.31 | B |
| ATOM | 1725 | CA | ASP | B | 95 | −38.016 | 38.147 | −39.574 | 1.00 | 55.94 | B |
| ATOM | 1726 | CB | ASP | B | 95 | −38.055 | 37.651 | −41.021 | 1.00 | 56.73 | B |
| ATOM | 1727 | CG | ASP | B | 95 | −36.892 | 36.737 | −41.344 | 1.00 | 59.74 | B |
| ATOM | 1728 | OD1 | ASP | B | 95 | −35.823 | 36.923 | −40.721 | 1.00 | 60.29 | B |
| ATOM | 1729 | OD2 | ASP | B | 95 | −37.037 | 35.844 | −42.216 | 1.00 | 60.62 | B |
| ATOM | 1730 | C | ASP | B | 95 | −39.114 | 39.167 | −39.340 | 1.00 | 55.97 | B |
| ATOM | 1731 | O | ASP | B | 95 | −38.849 | 40.357 | −39.328 | 1.00 | 55.88 | B |
| ATOM | 1732 | N | LEU | B | 96 | −40.343 | 38.701 | −39.145 | 1.00 | 57.37 | B |
| ATOM | 1733 | CA | LEU | B | 96 | −41.460 | 39.602 | −38.898 | 1.00 | 59.48 | B |
| ATOM | 1734 | CB | LEU | B | 96 | −42.762 | 38.813 | −38.735 | 1.00 | 57.57 | B |
| ATOM | 1735 | CG | LEU | B | 96 | −43.302 | 38.114 | −39.984 | 1.00 | 56.36 | B |
| ATOM | 1736 | CD1 | LEU | B | 96 | −44.553 | 37.313 | −39.654 | 1.00 | 53.91 | B |
| ATOM | 1737 | CD2 | LEU | B | 96 | −43.607 | 39.163 | −41.034 | 1.00 | 57.46 | B |
| ATOM | 1738 | C | LEU | B | 96 | −41.201 | 40.436 | −37.644 | 1.00 | 62.45 | B |
| ATOM | 1739 | O | LEU | B | 96 | −41.511 | 41.628 | −37.601 | 1.00 | 62.77 | B |
| ATOM | 1740 | N | GLU | B | 97 | −40.628 | 39.812 | −36.622 | 1.00 | 65.05 | B |
| ATOM | 1741 | CA | GLU | B | 97 | −40.338 | 40.528 | −35.392 | 1.00 | 68.23 | B |
| ATOM | 1742 | CB | GLU | B | 97 | −39.952 | 39.540 | −34.277 | 1.00 | 68.89 | B |
| ATOM | 1743 | CG | GLU | B | 97 | −41.097 | 38.626 | −33.830 | 1.00 | 71.87 | B |
| ATOM | 1744 | CD | GLU | B | 97 | −40.668 | 37.539 | −32.849 | 1.00 | 73.15 | B |
| ATOM | 1745 | OE1 | GLU | B | 97 | −40.181 | 37.886 | −31.756 | 1.00 | 76.25 | B |
| ATOM | 1746 | OE2 | GLU | B | 97 | −40.820 | 36.337 | −33.164 | 1.00 | 72.83 | B |
| ATOM | 1747 | C | GLU | B | 97 | −39.214 | 41.532 | −35.651 | 1.00 | 70.40 | B |
| ATOM | 1748 | O | GLU | B | 97 | −39.135 | 42.571 | −34.998 | 1.00 | 71.54 | B |
| ATOM | 1749 | N | ALA | B | 98 | −38.349 | 41.229 | −36.614 | 1.00 | 73.00 | B |
| ATOM | 1750 | CA | ALA | B | 98 | −37.248 | 42.128 | −36.952 | 1.00 | 75.20 | B |
| ATOM | 1751 | CB | ALA | B | 98 | −36.322 | 41.474 | −37.970 | 1.00 | 75.82 | B |
| ATOM | 1752 | C | ALA | B | 98 | −37.808 | 43.423 | −37.523 | 1.00 | 76.99 | B |
| ATOM | 1753 | O | ALA | B | 98 | −37.160 | 44.467 | −37.448 | 1.00 | 77.06 | B |
| ATOM | 1754 | N | CYS | B | 99 | −39.015 | 43.337 | −38.088 | 1.00 | 79.24 | B |
| ATOM | 1755 | CA | CYS | B | 99 | −39.711 | 44.478 | −38.691 | 1.00 | 81.14 | B |
| ATOM | 1756 | CB | CYS | B | 99 | −40.765 | 44.002 | −39.695 | 1.00 | 81.56 | B |
| ATOM | 1757 | SG | CYS | B | 99 | −40.126 | 43.247 | −41.210 | 1.00 | 84.65 | B |
| ATOM | 1758 | C | CYS | B | 99 | −40.397 | 45.359 | −37.658 | 1.00 | 82.14 | B |
| ATOM | 1759 | O | CYS | B | 99 | −40.290 | 46.582 | −37.715 | 1.00 | 82.34 | B |
| ATOM | 1760 | N | VAL | B | 100 | −41.116 | 44.740 | −36.725 | 1.00 | 83.70 | B |
| ATOM | 1761 | CA | VAL | B | 100 | −41.814 | 45.493 | −35.684 | 1.00 | 85.68 | B |
| ATOM | 1762 | CB | VAL | B | 100 | −42.619 | 44.556 | −34.740 | 1.00 | 85.07 | B |
| ATOM | 1763 | CG1 | VAL | B | 100 | −41.688 | 43.602 | −34.020 | 1.00 | 84.36 | B |
| ATOM | 1764 | CG2 | VAL | B | 100 | −43.405 | 45.381 | −33.741 | 1.00 | 85.62 | B |
| ATOM | 1765 | C | VAL | B | 100 | −40.801 | 46.287 | −34.863 | 1.00 | 87.06 | B |
| ATOM | 1766 | O | VAL | B | 100 | −41.162 | 47.202 | −34.115 | 1.00 | 87.20 | B |
| ATOM | 1767 | N | ALA | B | 101 | −39.529 | 45.927 | −35.023 | 1.00 | 88.22 | B |
| ATOM | 1768 | CA | ALA | B | 101 | −38.434 | 46.582 | −34.323 | 1.00 | 89.09 | B |
| ATOM | 1769 | CB | ALA | B | 101 | −37.497 | 45.533 | −33.730 | 1.00 | 88.54 | B |
| ATOM | 1770 | C | ALA | B | 101 | −37.666 | 47.498 | −35.276 | 1.00 | 89.84 | B |
| ATOM | 1771 | O | ALA | B | 101 | −37.324 | 48.626 | −34.925 | 1.00 | 90.61 | B |

TABLE 7-continued

Atomic coordinates of rSIFN-co (SEQ ID NO: 1)

| ATOM | 1772 | N   | GLY | B | 102 | −37.401 | 47.010 | −36.484 | 1.00 | 90.46 | B |
| ---- | ---- | --- | --- | - | --- | ------- | ------ | ------- | ---- | ----- | - |
| ATOM | 1773 | CA  | GLY | B | 102 | −36.678 | 47.808 | −37.457 | 1.00 | 91.07 | B |
| ATOM | 1774 | C   | GLY | B | 102 | −37.577 | 48.761 | −38.223 | 1.00 | 92.05 | B |
| ATOM | 1775 | O   | GLY | B | 102 | −37.266 | 49.135 | −39.351 | 1.00 | 92.33 | B |
| ATOM | 1776 | N   | GLY | B | 103 | −38.692 | 49.157 | −37.612 | 1.00 | 92.84 | B |
| ATOM | 1777 | CA  | GLY | B | 103 | −39.616 | 50.069 | −38.266 | 1.00 | 92.74 | B |
| ATOM | 1778 | C   | GLY | B | 103 | −40.887 | 50.291 | −37.465 | 1.00 | 92.62 | B |
| ATOM | 1779 | O   | GLY | B | 103 | −41.047 | 51.321 | −36.807 | 1.00 | 92.47 | B |
| ATOM | 1780 | N   | ALA | B | 111 | −51.414 | 47.696 | −31.869 | 1.00 | 93.96 | B |
| ATOM | 1781 | CA  | ALA | B | 111 | −51.666 | 47.368 | −33.267 | 1.00 | 93.85 | B |
| ATOM | 1782 | CB  | ALA | B | 111 | −51.378 | 45.889 | −33.516 | 1.00 | 92.71 | B |
| ATOM | 1783 | C   | ALA | B | 111 | −53.105 | 47.697 | −33.661 | 1.00 | 93.95 | B |
| ATOM | 1784 | O   | ALA | B | 111 | −53.906 | 46.792 | −33.916 | 1.00 | 94.29 | B |
| ATOM | 1785 | N   | GLY | B | 112 | −53.424 | 48.993 | −33.708 | 1.00 | 92.98 | B |
| ATOM | 1786 | CA  | GLY | B | 112 | −54.760 | 49.429 | −34.080 | 1.00 | 91.20 | B |
| ATOM | 1787 | C   | GLY | B | 112 | −55.854 | 48.615 | −33.416 | 1.00 | 90.66 | B |
| ATOM | 1788 | O   | GLY | B | 112 | −56.271 | 48.924 | −32.298 | 1.00 | 91.11 | B |
| ATOM | 1789 | N   | ASN | B | 113 | −56.328 | 47.575 | −34.101 | 1.00 | 88.98 | B |
| ATOM | 1790 | CA  | ASN | B | 113 | −57.368 | 46.715 | −33.546 | 1.00 | 86.63 | B |
| ATOM | 1791 | CB  | ASN | B | 113 | −58.702 | 46.922 | −34.275 | 1.00 | 88.02 | B |
| ATOM | 1792 | CG  | ASN | B | 113 | −58.597 | 46.693 | −35.770 | 1.00 | 88.87 | B |
| ATOM | 1793 | OD1 | ASN | B | 113 | −57.973 | 45.729 | −36.226 | 1.00 | 88.93 | B |
| ATOM | 1794 | ND2 | ASN | B | 113 | −59.225 | 47.573 | −36.545 | 1.00 | 89.31 | B |
| ATOM | 1795 | C   | ASN | B | 113 | −56.988 | 45.237 | −33.586 | 1.00 | 84.10 | B |
| ATOM | 1796 | O   | ASN | B | 113 | −56.396 | 44.750 | −34.559 | 1.00 | 82.68 | B |
| ATOM | 1797 | N   | ALA | B | 114 | −57.333 | 44.538 | −32.507 | 1.00 | 80.69 | B |
| ATOM | 1798 | CA  | ALA | B | 114 | −57.053 | 43.117 | −32.365 | 1.00 | 77.04 | B |
| ATOM | 1799 | CB  | ALA | B | 114 | −57.060 | 42.734 | −30.885 | 1.00 | 74.97 | B |
| ATOM | 1800 | C   | ALA | B | 114 | −58.094 | 42.307 | −33.129 | 1.00 | 75.04 | B |
| ATOM | 1801 | O   | ALA | B | 114 | −58.167 | 41.092 | −32.987 | 1.00 | 75.09 | B |
| ATOM | 1802 | N   | ASP | B | 115 | −58.898 | 42.993 | −33.935 | 1.00 | 73.04 | B |
| ATOM | 1803 | CA  | ASP | B | 115 | −59.940 | 42.354 | −34.739 | 1.00 | 71.39 | B |
| ATOM | 1804 | CB  | ASP | B | 115 | −60.755 | 43.408 | −35.493 | 1.00 | 75.02 | B |
| ATOM | 1805 | CG  | ASP | B | 115 | −61.440 | 44.387 | −34.573 | 1.00 | 77.51 | B |
| ATOM | 1806 | OD1 | ASP | B | 115 | −61.719 | 45.520 | −35.022 | 1.00 | 77.99 | B |
| ATOM | 1807 | OD2 | ASP | B | 115 | −61.707 | 44.019 | −33.408 | 1.00 | 80.45 | B |
| ATOM | 1808 | C   | ASP | B | 115 | −59.318 | 41.429 | −35.766 | 1.00 | 68.05 | B |
| ATOM | 1809 | O   | ASP | B | 115 | −59.626 | 40.245 | −35.834 | 1.00 | 67.22 | B |
| ATOM | 1810 | N   | SER | B | 116 | −58.451 | 42.002 | −36.585 | 1.00 | 65.47 | B |
| ATOM | 1811 | CA  | SER | B | 116 | −57.775 | 41.259 | −37.628 | 1.00 | 62.95 | B |
| ATOM | 1812 | CB  | SER | B | 116 | −56.707 | 42.137 | −38.277 | 1.00 | 63.58 | B |
| ATOM | 1813 | OG  | SER | B | 116 | −57.268 | 43.350 | −38.753 | 1.00 | 63.46 | B |
| ATOM | 1814 | C   | SER | B | 116 | −57.140 | 39.998 | −37.062 | 1.00 | 61.42 | B |
| ATOM | 1815 | O   | SER | B | 116 | −57.296 | 38.917 | −37.626 | 1.00 | 62.05 | B |
| ATOM | 1816 | N   | ILE | B | 117 | −56.430 | 40.137 | −35.946 | 1.00 | 58.31 | B |
| ATOM | 1817 | CA  | ILE | B | 117 | −55.772 | 38.999 | −35.313 | 1.00 | 54.83 | B |
| ATOM | 1818 | CB  | ILE | B | 117 | −54.966 | 39.423 | −34.076 | 1.00 | 53.03 | B |
| ATOM | 1819 | CG2 | ILE | B | 117 | −54.366 | 38.202 | −33.414 | 1.00 | 51.47 | B |
| ATOM | 1820 | CG1 | ILE | B | 117 | −53.871 | 40.404 | −34.477 | 1.00 | 52.17 | B |
| ATOM | 1821 | CD1 | ILE | B | 117 | −53.280 | 41.161 | −33.307 | 1.00 | 50.94 | B |
| ATOM | 1822 | C   | ILE | B | 117 | −56.772 | 37.944 | −34.870 | 1.00 | 54.11 | B |
| ATOM | 1823 | O   | ILE | B | 117 | −56.565 | 36.761 | −35.091 | 1.00 | 56.60 | B |
| ATOM | 1824 | N   | LEU | B | 118 | −57.854 | 38.370 | −34.235 | 1.00 | 52.88 | B |
| ATOM | 1825 | CA  | LEU | B | 118 | −58.862 | 37.430 | −33.766 | 1.00 | 50.60 | B |
| ATOM | 1826 | CB  | LEU | B | 118 | −59.955 | 38.167 | −32.984 | 1.00 | 51.65 | B |
| ATOM | 1827 | CG  | LEU | B | 118 | −61.046 | 37.271 | −32.391 | 1.00 | 54.03 | B |
| ATOM | 1828 | CD1 | LEU | B | 118 | −60.591 | 36.760 | −31.040 | 1.00 | 54.61 | B |
| ATOM | 1829 | CD2 | LEU | B | 118 | −62.343 | 38.044 | −32.249 | 1.00 | 53.11 | B |
| ATOM | 1830 | C   | LEU | B | 118 | −59.470 | 36.716 | −34.966 | 1.00 | 49.21 | B |
| ATOM | 1831 | O   | LEU | B | 118 | −59.797 | 35.534 | −34.900 | 1.00 | 47.90 | B |
| ATOM | 1832 | N   | ALA | B | 119 | −59.611 | 37.436 | −36.072 | 1.00 | 48.72 | B |
| ATOM | 1833 | CA  | ALA | B | 119 | −60.183 | 36.852 | −37.278 | 1.00 | 49.24 | B |
| ATOM | 1834 | CB  | ALA | B | 119 | −60.323 | 37.916 | −38.343 | 1.00 | 48.04 | B |
| ATOM | 1835 | C   | ALA | B | 119 | −59.339 | 35.674 | −37.793 | 1.00 | 50.65 | B |
| ATOM | 1836 | O   | ALA | B | 119 | −59.884 | 34.667 | −38.270 | 1.00 | 51.27 | B |
| ATOM | 1837 | N   | VAL | B | 120 | −58.016 | 35.795 | −37.691 | 1.00 | 49.50 | B |
| ATOM | 1838 | CA  | VAL | B | 120 | −57.130 | 34.727 | −38.130 | 1.00 | 50.37 | B |
| ATOM | 1839 | CB  | VAL | B | 120 | −55.657 | 35.188 | −38.178 | 1.00 | 49.79 | B |
| ATOM | 1840 | CG1 | VAL | B | 120 | −54.746 | 33.979 | −38.348 | 1.00 | 47.60 | B |
| ATOM | 1841 | CG2 | VAL | B | 120 | −55.455 | 36.190 | −39.315 | 1.00 | 47.48 | B |
| ATOM | 1842 | C   | VAL | B | 120 | −57.235 | 33.546 | −37.170 | 1.00 | 52.26 | B |
| ATOM | 1843 | O   | VAL | B | 120 | −57.177 | 32.377 | −37.582 | 1.00 | 51.97 | B |
| ATOM | 1844 | N   | LYS | B | 121 | −57.382 | 33.855 | −35.883 | 1.00 | 53.62 | B |
| ATOM | 1845 | CA  | LYS | B | 121 | −57.501 | 32.811 | −34.875 | 1.00 | 54.59 | B |
| ATOM | 1846 | CB  | LYS | B | 121 | −57.508 | 33.413 | −33.475 | 1.00 | 54.64 | B |
| ATOM | 1847 | CG  | LYS | B | 121 | −56.148 | 33.911 | −33.017 | 1.00 | 58.06 | B |
| ATOM | 1848 | CD  | LYS | B | 121 | −56.232 | 34.584 | −31.650 | 1.00 | 60.35 | B |
| ATOM | 1849 | CE  | LYS | B | 121 | −54.864 | 35.021 | −31.140 | 1.00 | 60.35 | B |

TABLE 7-continued

Atomic coordinates of rSIFN-co (SEQ ID NO: 1)

| ATOM | 1850 | NZ | LYS | B | 121 | −53.990 | 33.861 | −30.842 | 1.00 | 61.51 | B |
|------|------|-----|-----|---|-----|---------|--------|---------|------|-------|---|
| ATOM | 1851 | C | LYS | B | 121 | −58.769 | 32.005 | −35.108 | 1.00 | 55.58 | B |
| ATOM | 1852 | O | LYS | B | 121 | −58.744 | 30.780 | −35.065 | 1.00 | 55.57 | B |
| ATOM | 1853 | N | LYS | B | 122 | −59.876 | 32.689 | −35.378 | 1.00 | 56.77 | B |
| ATOM | 1854 | CA | LYS | B | 122 | −61.140 | 31.997 | −35.618 | 1.00 | 58.18 | B |
| ATOM | 1855 | CB | LYS | B | 122 | −62.275 | 33.014 | −35.811 | 1.00 | 60.88 | B |
| ATOM | 1856 | CG | LYS | B | 122 | −62.628 | 33.807 | −34.545 | 1.00 | 63.85 | B |
| ATOM | 1857 | CD | LYS | B | 122 | −63.785 | 34.770 | −34.784 | 1.00 | 67.04 | B |
| ATOM | 1858 | CE | LYS | B | 122 | −65.079 | 34.020 | −35.089 | 1.00 | 70.23 | B |
| ATOM | 1859 | NZ | LYS | B | 122 | −66.260 | 34.925 | −35.259 | 1.00 | 71.84 | B |
| ATOM | 1860 | C | LYS | B | 122 | −61.036 | 31.078 | −36.835 | 1.00 | 57.34 | B |
| ATOM | 1861 | O | LYS | B | 122 | −61.588 | 29.975 | −36.846 | 1.00 | 57.39 | B |
| ATOM | 1862 | N | TYR | B | 123 | −60.316 | 31.540 | −37.852 | 1.00 | 55.98 | B |
| ATOM | 1863 | CA | TYR | B | 123 | −60.117 | 30.774 | −39.080 | 1.00 | 54.34 | B |
| ATOM | 1864 | CB | TYR | B | 123 | −59.252 | 31.593 | −40.050 | 1.00 | 54.18 | B |
| ATOM | 1865 | CG | TYR | B | 123 | −58.689 | 30.830 | −41.226 | 1.00 | 53.30 | B |
| ATOM | 1866 | CD1 | TYR | B | 123 | −59.524 | 30.175 | −42.130 | 1.00 | 53.39 | B |
| ATOM | 1867 | CE1 | TYR | B | 123 | −59.001 | 29.474 | −43.217 | 1.00 | 53.48 | B |
| ATOM | 1868 | CD2 | TYR | B | 123 | −57.315 | 30.767 | −41.436 | 1.00 | 53.09 | B |
| ATOM | 1869 | CE2 | TYR | B | 123 | −56.781 | 30.069 | −42.518 | 1.00 | 53.78 | B |
| ATOM | 1870 | CZ | TYR | B | 123 | −57.627 | 29.426 | −43.404 | 1.00 | 53.93 | B |
| ATOM | 1871 | OH | TYR | B | 123 | −57.097 | 28.736 | −44.471 | 1.00 | 52.16 | B |
| ATOM | 1872 | C | TYR | B | 123 | −59.458 | 29.430 | −38.773 | 1.00 | 53.07 | B |
| ATOM | 1873 | O | TYR | B | 123 | −59.994 | 28.369 | −39.100 | 1.00 | 51.67 | B |
| ATOM | 1874 | N | PHE | B | 124 | −58.296 | 29.487 | −38.133 | 1.00 | 52.86 | B |
| ATOM | 1875 | CA | PHE | B | 124 | −57.555 | 28.283 | −37.775 | 1.00 | 53.45 | B |
| ATOM | 1876 | CB | PHE | B | 124 | −56.200 | 28.665 | −37.186 | 1.00 | 50.18 | B |
| ATOM | 1877 | CG | PHE | B | 124 | −55.177 | 29.018 | −38.228 | 1.00 | 48.40 | B |
| ATOM | 1878 | CD1 | PHE | B | 124 | −54.460 | 28.019 | −38.880 | 1.00 | 43.87 | B |
| ATOM | 1879 | CD2 | PHE | B | 124 | −54.958 | 30.345 | −38.590 | 1.00 | 46.73 | B |
| ATOM | 1880 | CE1 | PHE | B | 124 | −53.553 | 28.327 | −39.865 | 1.00 | 41.12 | B |
| ATOM | 1881 | CE2 | PHE | B | 124 | −54.040 | 30.659 | −39.587 | 1.00 | 44.49 | B |
| ATOM | 1882 | CZ | PHE | B | 124 | −53.338 | 29.641 | −40.223 | 1.00 | 41.38 | B |
| ATOM | 1883 | C | PHE | B | 124 | −58.336 | 27.440 | −36.796 | 1.00 | 55.05 | B |
| ATOM | 1884 | O | PHE | B | 124 | −58.134 | 26.234 | −36.695 | 1.00 | 54.37 | B |
| ATOM | 1885 | N | GLN | B | 125 | −59.238 | 28.094 | −36.076 | 1.00 | 59.25 | B |
| ATOM | 1886 | CA | GLN | B | 125 | −60.081 | 27.421 | −35.106 | 1.00 | 60.57 | B |
| ATOM | 1887 | CB | GLN | B | 125 | −60.883 | 28.445 | −34.307 | 1.00 | 64.50 | B |
| ATOM | 1888 | CG | GLN | B | 125 | −61.759 | 27.839 | −33.227 | 1.00 | 70.78 | B |
| ATOM | 1889 | CD | GLN | B | 125 | −60.960 | 27.038 | −32.212 | 1.00 | 74.51 | B |
| ATOM | 1890 | OE1 | GLN | B | 125 | −60.071 | 27.575 | −31.540 | 1.00 | 76.71 | B |
| ATOM | 1891 | NE2 | GLN | B | 125 | −61.272 | 25.744 | −32.095 | 1.00 | 75.37 | B |
| ATOM | 1892 | C | GLN | B | 125 | −61.014 | 26.525 | −35.894 | 1.00 | 59.74 | B |
| ATOM | 1893 | O | GLN | B | 125 | −61.124 | 25.336 | −35.608 | 1.00 | 60.48 | B |
| ATOM | 1894 | N | ARG | B | 126 | −61.672 | 27.096 | −36.901 | 1.00 | 58.55 | B |
| ATOM | 1895 | CA | ARG | B | 126 | −62.591 | 26.332 | −37.740 | 1.00 | 58.45 | B |
| ATOM | 1896 | CB | ARG | B | 126 | −63.192 | 27.230 | −38.819 | 1.00 | 58.22 | B |
| ATOM | 1897 | CG | ARG | B | 126 | −64.322 | 28.135 | −38.334 | 1.00 | 56.82 | B |
| ATOM | 1898 | CD | ARG | B | 126 | −64.632 | 29.227 | −39.348 | 1.00 | 55.96 | B |
| ATOM | 1899 | NE | ARG | B | 126 | −64.100 | 30.523 | −38.925 | 1.00 | 56.75 | B |
| ATOM | 1900 | CZ | ARG | B | 126 | −63.490 | 31.379 | −39.738 | 1.00 | 57.05 | B |
| ATOM | 1901 | NH1 | ARG | B | 126 | −63.333 | 31.072 | −41.013 | 1.00 | 56.86 | B |
| ATOM | 1902 | NH2 | ARG | B | 126 | −63.039 | 32.541 | −39.282 | 1.00 | 57.49 | B |
| ATOM | 1903 | C | ARG | B | 126 | −61.874 | 25.151 | −38.384 | 1.00 | 59.08 | B |
| ATOM | 1904 | O | ARG | B | 126 | −62.406 | 24.043 | −38.425 | 1.00 | 58.89 | B |
| ATOM | 1905 | N | ILE | B | 127 | −60.667 | 25.396 | −38.888 | 1.00 | 59.70 | B |
| ATOM | 1906 | CA | ILE | B | 127 | −59.862 | 24.351 | −39.514 | 1.00 | 59.95 | B |
| ATOM | 1907 | CB | ILE | B | 127 | −58.472 | 24.891 | −39.914 | 1.00 | 59.73 | B |
| ATOM | 1908 | CG2 | ILE | B | 127 | −57.508 | 23.745 | −40.190 | 1.00 | 57.13 | B |
| ATOM | 1909 | CG1 | ILE | B | 127 | −58.609 | 25.809 | −41.126 | 1.00 | 60.37 | B |
| ATOM | 1910 | CD1 | ILE | B | 127 | −57.338 | 26.563 | −41.468 | 1.00 | 62.06 | B |
| ATOM | 1911 | C | ILE | B | 127 | −59.675 | 23.199 | −38.538 | 1.00 | 60.89 | B |
| ATOM | 1912 | O | ILE | B | 127 | −59.904 | 22.041 | −38.884 | 1.00 | 60.80 | B |
| ATOM | 1913 | N | THR | B | 128 | −59.264 | 23.543 | −37.319 | 1.00 | 61.84 | B |
| ATOM | 1914 | CA | THR | B | 128 | −59.012 | 22.583 | −36.241 | 1.00 | 63.43 | B |
| ATOM | 1915 | CB | THR | B | 128 | −58.598 | 23.320 | −34.940 | 1.00 | 64.67 | B |
| ATOM | 1916 | OG1 | THR | B | 128 | −57.481 | 24.172 | −35.212 | 1.00 | 67.07 | B |
| ATOM | 1917 | CG2 | THR | B | 128 | −58.204 | 22.331 | −33.853 | 1.00 | 65.28 | B |
| ATOM | 1918 | C | THR | B | 128 | −60.209 | 21.690 | −35.918 | 1.00 | 63.22 | B |
| ATOM | 1919 | O | THR | B | 128 | −60.045 | 20.515 | −35.585 | 1.00 | 61.95 | B |
| ATOM | 1920 | N | LEU | B | 129 | −61.407 | 22.256 | −36.008 | 1.00 | 64.24 | B |
| ATOM | 1921 | CA | LEU | B | 129 | −62.630 | 21.524 | −35.716 | 1.00 | 66.29 | B |
| ATOM | 1922 | CB | LEU | B | 129 | −63.771 | 22.505 | −35.454 | 1.00 | 66.59 | B |
| ATOM | 1923 | CG | LEU | B | 129 | −64.722 | 22.138 | −34.313 | 1.00 | 67.84 | B |
| ATOM | 1924 | CD1 | LEU | B | 129 | −65.736 | 23.255 | −34.140 | 1.00 | 67.06 | B |
| ATOM | 1925 | CD2 | LEU | B | 129 | −65.409 | 20.796 | −34.595 | 1.00 | 67.62 | B |
| ATOM | 1926 | C | LEU | B | 129 | −62.986 | 20.619 | −36.886 | 1.00 | 68.37 | B |
| ATOM | 1927 | O | LEU | B | 129 | −63.672 | 19.613 | −36.720 | 1.00 | 70.05 | B |

TABLE 7-continued

Atomic coordinates of rSIFN-co (SEQ ID NO: 1)

| ATOM | 1928 | N | TYR | B | 130 | −62.530 | 20.994 | −38.077 | 1.00 | 69.17 | B |
|---|---|---|---|---|---|---|---|---|---|---|---|
| ATOM | 1929 | CA | TYR | B | 130 | −62.780 | 20.208 | −39.273 | 1.00 | 68.74 | B |
| ATOM | 1930 | CB | TYR | B | 130 | −62.296 | 20.973 | −40.507 | 1.00 | 69.94 | B |
| ATOM | 1931 | CG | TYR | B | 130 | −62.397 | 20.200 | −41.803 | 1.00 | 71.43 | B |
| ATOM | 1932 | CD1 | TYR | B | 130 | −63.627 | 19.990 | −42.425 | 1.00 | 71.95 | B |
| ATOM | 1933 | CE1 | TYR | B | 130 | −63.719 | 19.273 | −43.624 | 1.00 | 72.25 | B |
| ATOM | 1934 | CD2 | TYR | B | 130 | −61.258 | 19.671 | −42.409 | 1.00 | 72.21 | B |
| ATOM | 1935 | CE2 | TYR | B | 130 | −61.340 | 18.950 | −43.607 | 1.00 | 72.56 | B |
| ATOM | 1936 | CZ | TYR | B | 130 | −62.571 | 18.756 | −44.207 | 1.00 | 72.07 | B |
| ATOM | 1937 | OH | TYR | B | 130 | −62.649 | 18.044 | −45.383 | 1.00 | 71.77 | B |
| ATOM | 1938 | C | TYR | B | 130 | −61.996 | 18.911 | −39.115 | 1.00 | 69.00 | B |
| ATOM | 1939 | O | TYR | B | 130 | −62.556 | 17.821 | −39.175 | 1.00 | 68.44 | B |
| ATOM | 1940 | N | LEU | B | 131 | −60.691 | 19.044 | −38.896 | 1.00 | 68.64 | B |
| ATOM | 1941 | CA | LEU | B | 131 | −59.821 | 17.890 | −38.724 | 1.00 | 68.04 | B |
| ATOM | 1942 | CB | LEU | B | 131 | −58.422 | 18.345 | −38.310 | 1.00 | 66.02 | B |
| ATOM | 1943 | CG | LEU | B | 131 | −57.471 | 18.856 | −39.391 | 1.00 | 65.04 | B |
| ATOM | 1944 | CD1 | LEU | B | 131 | −56.264 | 19.481 | −38.719 | 1.00 | 63.94 | B |
| ATOM | 1945 | CD2 | LEU | B | 131 | −57.043 | 17.716 | −40.313 | 1.00 | 63.38 | B |
| ATOM | 1946 | C | LEU | B | 131 | −60.347 | 16.891 | −37.698 | 1.00 | 68.93 | B |
| ATOM | 1947 | O | LEU | B | 131 | −60.523 | 15.714 | −38.006 | 1.00 | 68.61 | B |
| ATOM | 1948 | N | THR | B | 132 | −60.594 | 17.363 | −36.478 | 1.00 | 70.61 | B |
| ATOM | 1949 | CA | THR | B | 132 | −61.083 | 16.495 | −35.406 | 1.00 | 71.92 | B |
| ATOM | 1950 | CB | THR | B | 132 | −60.841 | 17.131 | −34.008 | 1.00 | 71.89 | B |
| ATOM | 1951 | OG1 | THR | B | 132 | −61.250 | 16.214 | −32.987 | 1.00 | 70.43 | B |
| ATOM | 1952 | CG2 | THR | B | 132 | −61.623 | 18.429 | −33.860 | 1.00 | 72.59 | B |
| ATOM | 1953 | C | THR | B | 132 | −62.565 | 16.161 | −35.562 | 1.00 | 72.74 | B |
| ATOM | 1954 | O | THR | B | 132 | −63.170 | 15.549 | −34.683 | 1.00 | 73.16 | B |
| ATOM | 1955 | N | GLY | B | 133 | −63.141 | 16.576 | −36.687 | 1.00 | 73.71 | B |
| ATOM | 1956 | CA | GLY | B | 133 | −64.539 | 16.301 | −36.968 | 1.00 | 73.91 | B |
| ATOM | 1957 | C | GLY | B | 133 | −64.582 | 15.208 | −38.019 | 1.00 | 74.32 | B |
| ATOM | 1958 | O | GLY | B | 133 | −65.606 | 14.556 | −38.236 | 1.00 | 74.32 | B |
| ATOM | 1959 | N | LYS | B | 134 | −63.442 | 15.015 | −38.676 | 1.00 | 74.07 | B |
| ATOM | 1960 | CA | LYS | B | 134 | −63.296 | 14.001 | −39.708 | 1.00 | 73.57 | B |
| ATOM | 1961 | CB | LYS | B | 134 | −62.847 | 14.629 | −41.028 | 1.00 | 72.93 | B |
| ATOM | 1962 | CG | LYS | B | 134 | −63.976 | 14.926 | −42.004 | 1.00 | 73.33 | B |
| ATOM | 1963 | CD | LYS | B | 134 | −64.905 | 16.035 | −41.525 | 1.00 | 74.01 | B |
| ATOM | 1964 | CE | LYS | B | 134 | −65.972 | 16.349 | −42.583 | 1.00 | 74.15 | B |
| ATOM | 1965 | NZ | LYS | B | 134 | −66.745 | 17.600 | −42.317 | 1.00 | 72.79 | B |
| ATOM | 1966 | C | LYS | B | 134 | −62.282 | 12.962 | −39.262 | 1.00 | 73.93 | B |
| ATOM | 1967 | O | LYS | B | 134 | −61.676 | 12.278 | −40.082 | 1.00 | 72.76 | B |
| ATOM | 1968 | N | LYS | B | 135 | −62.093 | 12.867 | −37.951 | 1.00 | 75.07 | B |
| ATOM | 1969 | CA | LYS | B | 135 | −61.184 | 11.890 | −37.367 | 1.00 | 76.77 | B |
| ATOM | 1970 | CB | LYS | B | 135 | −61.808 | 10.496 | −37.485 | 1.00 | 77.37 | B |
| ATOM | 1971 | CG | LYS | B | 135 | −63.245 | 10.428 | −36.990 | 1.00 | 78.83 | B |
| ATOM | 1972 | CD | LYS | B | 135 | −63.856 | 9.057 | −37.231 | 1.00 | 81.28 | B |
| ATOM | 1973 | CE | LYS | B | 135 | −63.278 | 8.000 | −36.295 | 1.00 | 83.54 | B |
| ATOM | 1974 | NZ | LYS | B | 135 | −63.708 | 8.200 | −34.876 | 1.00 | 84.34 | B |
| ATOM | 1975 | C | LYS | B | 135 | −59.773 | 11.878 | −37.967 | 1.00 | 77.31 | B |
| ATOM | 1976 | O | LYS | B | 135 | −59.174 | 10.815 | −38.135 | 1.00 | 78.04 | B |
| ATOM | 1977 | N | TYR | B | 136 | −59.246 | 13.056 | −38.283 | 1.00 | 77.23 | B |
| ATOM | 1978 | CA | TYR | B | 136 | −57.902 | 13.181 | −38.845 | 1.00 | 76.63 | B |
| ATOM | 1979 | CB | TYR | B | 136 | −56.861 | 12.989 | −37.748 | 1.00 | 78.09 | B |
| ATOM | 1980 | CG | TYR | B | 136 | −57.053 | 13.907 | −36.564 | 1.00 | 82.10 | B |
| ATOM | 1981 | CD1 | TYR | B | 136 | −58.076 | 13.685 | −35.638 | 1.00 | 83.03 | B |
| ATOM | 1982 | CE1 | TYR | B | 136 | −58.244 | 14.522 | −34.529 | 1.00 | 84.37 | B |
| ATOM | 1983 | CD2 | TYR | B | 136 | −56.204 | 14.992 | −36.359 | 1.00 | 83.46 | B |
| ATOM | 1984 | CE2 | TYR | B | 136 | −56.362 | 15.837 | −35.255 | 1.00 | 85.30 | B |
| ATOM | 1985 | CZ | TYR | B | 136 | −57.382 | 15.596 | −34.341 | 1.00 | 85.81 | B |
| ATOM | 1986 | OH | TYR | B | 136 | −57.524 | 16.419 | −33.237 | 1.00 | 85.88 | B |
| ATOM | 1987 | C | TYR | B | 136 | −57.615 | 12.202 | −39.980 | 1.00 | 75.70 | B |
| ATOM | 1988 | O | TYR | B | 136 | −56.528 | 11.625 | −40.057 | 1.00 | 74.43 | B |
| ATOM | 1989 | N | SER | B | 137 | −58.592 | 12.039 | −40.867 | 1.00 | 75.24 | B |
| ATOM | 1990 | CA | SER | B | 137 | −58.477 | 11.131 | −42.001 | 1.00 | 74.25 | B |
| ATOM | 1991 | CB | SER | B | 137 | −59.860 | 10.845 | −42.580 | 1.00 | 73.68 | B |
| ATOM | 1992 | OG | SER | B | 137 | −60.451 | 12.033 | −43.072 | 1.00 | 73.31 | B |
| ATOM | 1993 | C | SER | B | 137 | −57.578 | 11.668 | −43.106 | 1.00 | 74.57 | B |
| ATOM | 1994 | O | SER | B | 137 | −57.476 | 12.880 | −43.312 | 1.00 | 73.85 | B |
| ATOM | 1995 | N | PRO | B | 138 | −56.921 | 10.758 | −43.842 | 1.00 | 74.56 | B |
| ATOM | 1996 | CD | PRO | B | 138 | −56.984 | 9.296 | −43.668 | 1.00 | 74.19 | B |
| ATOM | 1997 | CA | PRO | B | 138 | −56.021 | 11.103 | −44.940 | 1.00 | 74.13 | B |
| ATOM | 1998 | CB | PRO | B | 138 | −55.832 | 9.771 | −45.643 | 1.00 | 73.66 | B |
| ATOM | 1999 | CG | PRO | B | 138 | −55.810 | 8.822 | −44.486 | 1.00 | 73.91 | B |
| ATOM | 2000 | C | PRO | B | 138 | −56.579 | 12.177 | −45.859 | 1.00 | 74.15 | B |
| ATOM | 2001 | O | PRO | B | 138 | −55.832 | 13.016 | −46.362 | 1.00 | 74.48 | B |
| ATOM | 2002 | N | CYS | B | 139 | −57.887 | 12.156 | −46.081 | 1.00 | 74.19 | B |
| ATOM | 2003 | CA | CYS | B | 139 | −58.488 | 13.163 | −46.943 | 1.00 | 75.46 | B |
| ATOM | 2004 | C | CYS | B | 139 | −58.702 | 14.457 | −46.178 | 1.00 | 74.04 | B |
| ATOM | 2005 | O | CYS | B | 139 | −58.472 | 15.545 | −46.705 | 1.00 | 73.77 | B |

TABLE 7-continued

Atomic coordinates of rSIFN-co (SEQ ID NO: 1)

| ATOM | 2006 | CB | CYS | B | 139 | −59.814 | 12.665 | −47.538 | 1.00 | 79.16 | B |
|---|---|---|---|---|---|---|---|---|---|---|---|
| ATOM | 2007 | SG | CYS | B | 139 | −59.600 | 11.373 | −48.809 | 1.00 | 82.68 | B |
| ATOM | 2008 | N | ALA | B | 140 | −59.136 | 14.342 | −44.930 | 1.00 | 72.55 | B |
| ATOM | 2009 | CA | ALA | B | 140 | −59.346 | 15.529 | −44.115 | 1.00 | 71.12 | B |
| ATOM | 2010 | CB | ALA | B | 140 | −59.704 | 15.128 | −42.704 | 1.00 | 71.98 | B |
| ATOM | 2011 | C | ALA | B | 140 | −58.063 | 16.364 | −44.117 | 1.00 | 70.40 | B |
| ATOM | 2012 | O | ALA | B | 140 | −58.104 | 17.576 | −44.354 | 1.00 | 70.21 | B |
| ATOM | 2013 | N | TRP | B | 141 | −56.929 | 15.706 | −43.862 | 1.00 | 68.06 | B |
| ATOM | 2014 | CA | TRP | B | 141 | −55.630 | 16.379 | −43.839 | 1.00 | 66.09 | B |
| ATOM | 2015 | CB | TRP | B | 141 | −54.511 | 15.405 | −43.429 | 1.00 | 65.31 | B |
| ATOM | 2016 | CG | TRP | B | 141 | −54.188 | 15.447 | −41.954 | 1.00 | 64.66 | B |
| ATOM | 2017 | CD2 | TRP | B | 141 | −53.698 | 16.570 | −41.215 | 1.00 | 63.91 | B |
| ATOM | 2018 | CE2 | TRP | B | 141 | −53.587 | 16.171 | −39.868 | 1.00 | 63.61 | B |
| ATOM | 2019 | CE3 | TRP | B | 141 | −53.333 | 17.879 | −41.564 | 1.00 | 63.30 | B |
| ATOM | 2020 | CD1 | TRP | B | 141 | −54.351 | 14.438 | −41.046 | 1.00 | 64.31 | B |
| ATOM | 2021 | NE1 | TRP | B | 141 | −53.995 | 14.864 | −39.793 | 1.00 | 63.47 | B |
| ATOM | 2022 | CZ2 | TRP | B | 141 | −53.140 | 17.031 | −38.864 | 1.00 | 63.01 | B |
| ATOM | 2023 | CZ3 | TRP | B | 141 | −52.887 | 18.735 | −40.566 | 1.00 | 63.15 | B |
| ATOM | 2024 | CH2 | TRP | B | 141 | −52.792 | 18.305 | −39.231 | 1.00 | 62.58 | B |
| ATOM | 2025 | C | TRP | B | 141 | −55.293 | 16.999 | −45.190 | 1.00 | 65.08 | B |
| ATOM | 2026 | O | TRP | B | 141 | −54.775 | 18.118 | −45.263 | 1.00 | 64.05 | B |
| ATOM | 2027 | N | GLU | B | 142 | −55.592 | 16.268 | −46.259 | 1.00 | 63.17 | B |
| ATOM | 2028 | CA | GLU | B | 142 | −55.324 | 16.750 | −47.603 | 1.00 | 60.88 | B |
| ATOM | 2029 | CB | GLU | B | 142 | −55.801 | 15.725 | −48.635 | 1.00 | 59.86 | B |
| ATOM | 2030 | CG | GLU | B | 142 | −55.595 | 16.126 | −50.094 | 1.00 | 58.69 | B |
| ATOM | 2031 | CD | GLU | B | 142 | −54.176 | 16.583 | −50.414 | 1.00 | 57.82 | B |
| ATOM | 2032 | OE1 | GLU | B | 142 | −53.198 | 15.912 | −50.004 | 1.00 | 58.06 | B |
| ATOM | 2033 | OE2 | GLU | B | 142 | −54.045 | 17.617 | −51.096 | 1.00 | 54.99 | B |
| ATOM | 2034 | C | GLU | B | 142 | −56.005 | 18.092 | −47.825 | 1.00 | 60.14 | B |
| ATOM | 2035 | O | GLU | B | 142 | −55.367 | 19.042 | −48.265 | 1.00 | 61.06 | B |
| ATOM | 2036 | N | VAL | B | 143 | −57.288 | 18.184 | −47.505 | 1.00 | 58.83 | B |
| ATOM | 2037 | CA | VAL | B | 143 | −58.006 | 19.437 | −47.692 | 1.00 | 60.46 | B |
| ATOM | 2038 | CB | VAL | B | 143 | −59.473 | 19.312 | −47.217 | 1.00 | 63.38 | B |
| ATOM | 2039 | CG1 | VAL | B | 143 | −60.189 | 20.652 | −47.353 | 1.00 | 64.93 | B |
| ATOM | 2040 | CG2 | VAL | B | 143 | −60.194 | 18.259 | −48.044 | 1.00 | 62.82 | B |
| ATOM | 2041 | C | VAL | B | 143 | −57.324 | 20.584 | −46.937 | 1.00 | 60.05 | B |
| ATOM | 2042 | O | VAL | B | 143 | −57.199 | 21.703 | −47.453 | 1.00 | 60.09 | B |
| ATOM | 2043 | N | VAL | B | 144 | −56.881 | 20.301 | −45.716 | 1.00 | 58.84 | B |
| ATOM | 2044 | CA | VAL | B | 144 | −56.207 | 21.307 | −44.905 | 1.00 | 56.80 | B |
| ATOM | 2045 | CB | VAL | B | 144 | −55.901 | 20.779 | −43.475 | 1.00 | 56.37 | B |
| ATOM | 2046 | CG1 | VAL | B | 144 | −54.933 | 21.720 | −42.756 | 1.00 | 53.83 | B |
| ATOM | 2047 | CG2 | VAL | B | 144 | −57.195 | 20.655 | −42.688 | 1.00 | 53.78 | B |
| ATOM | 2048 | C | VAL | B | 144 | −54.907 | 21.723 | −45.570 | 1.00 | 55.71 | B |
| ATOM | 2049 | O | VAL | B | 144 | −54.580 | 22.907 | −45.619 | 1.00 | 56.30 | B |
| ATOM | 2050 | N | ARG | B | 145 | −54.166 | 20.748 | −46.083 | 1.00 | 54.57 | B |
| ATOM | 2051 | CA | ARG | B | 145 | −52.904 | 21.039 | −46.746 | 1.00 | 53.98 | B |
| ATOM | 2052 | CB | ARG | B | 145 | −52.290 | 19.755 | −47.301 | 1.00 | 54.48 | B |
| ATOM | 2053 | CG | ARG | B | 145 | −50.776 | 19.805 | −47.398 | 1.00 | 57.53 | B |
| ATOM | 2054 | CD | ARG | B | 145 | −50.189 | 18.656 | −48.226 | 1.00 | 59.32 | B |
| ATOM | 2055 | NE | ARG | B | 145 | −50.007 | 19.028 | −49.627 | 1.00 | 60.85 | B |
| ATOM | 2056 | CZ | ARG | B | 145 | −51.000 | 19.146 | −50.497 | 1.00 | 61.21 | B |
| ATOM | 2057 | NH1 | ARG | B | 145 | −52.245 | 18.912 | −50.113 | 1.00 | 63.40 | B |
| ATOM | 2058 | NH2 | ARG | B | 145 | −50.750 | 19.516 | −51.741 | 1.00 | 61.96 | B |
| ATOM | 2059 | C | ARG | B | 145 | −53.163 | 22.034 | −47.884 | 1.00 | 53.44 | B |
| ATOM | 2060 | O | ARG | B | 145 | −52.508 | 23.072 | −47.982 | 1.00 | 51.98 | B |
| ATOM | 2061 | N | ALA | B | 146 | −54.141 | 21.724 | −48.729 | 1.00 | 52.37 | B |
| ATOM | 2062 | CA | ALA | B | 146 | −54.474 | 22.596 | −49.844 | 1.00 | 52.73 | B |
| ATOM | 2063 | CB | ALA | B | 146 | −55.476 | 21.927 | −50.752 | 1.00 | 53.23 | B |
| ATOM | 2064 | C | ALA | B | 146 | −55.013 | 23.937 | −49.375 | 1.00 | 52.70 | B |
| ATOM | 2065 | O | ALA | B | 146 | −54.678 | 24.964 | −49.964 | 1.00 | 53.35 | B |
| ATOM | 2066 | N | GLU | B | 147 | −55.841 | 23.937 | −48.328 | 1.00 | 52.05 | B |
| ATOM | 2067 | CA | GLU | B | 147 | −56.401 | 25.191 | −47.799 | 1.00 | 51.29 | B |
| ATOM | 2068 | CB | GLU | B | 147 | −57.351 | 24.913 | −46.626 | 1.00 | 52.80 | B |
| ATOM | 2069 | CG | GLU | B | 147 | −57.846 | 26.161 | −45.865 | 1.00 | 56.59 | B |
| ATOM | 2070 | CD | GLU | B | 147 | −58.780 | 27.066 | −46.685 | 1.00 | 60.42 | B |
| ATOM | 2071 | OE1 | GLU | B | 147 | −59.760 | 26.554 | −47.274 | 1.00 | 63.21 | B |
| ATOM | 2072 | OE2 | GLU | B | 147 | −58.546 | 28.294 | −46.732 | 1.00 | 61.56 | B |
| ATOM | 2073 | C | GLU | B | 147 | −55.295 | 26.129 | −47.325 | 1.00 | 50.23 | B |
| ATOM | 2074 | O | GLU | B | 147 | −55.338 | 27.332 | −47.575 | 1.00 | 48.90 | B |
| ATOM | 2075 | N | ILE | B | 148 | −54.308 | 25.561 | −46.638 | 1.00 | 49.88 | B |
| ATOM | 2076 | CA | ILE | B | 148 | −53.187 | 26.320 | −46.099 | 1.00 | 48.21 | B |
| ATOM | 2077 | CB | ILE | B | 148 | −52.368 | 25.443 | −45.110 | 1.00 | 47.14 | B |
| ATOM | 2078 | CG2 | ILE | B | 148 | −51.030 | 26.118 | −44.755 | 1.00 | 44.12 | B |
| ATOM | 2079 | CG1 | ILE | B | 148 | −53.223 | 25.162 | −43.870 | 1.00 | 44.09 | B |
| ATOM | 2080 | CD1 | ILE | B | 148 | −53.734 | 26.429 | −43.164 | 1.00 | 42.93 | B |
| ATOM | 2081 | C | ILE | B | 148 | −52.292 | 26.883 | −47.196 | 1.00 | 48.42 | B |
| ATOM | 2082 | O | ILE | B | 148 | −51.653 | 27.925 | −47.014 | 1.00 | 47.29 | B |
| ATOM | 2083 | N | MET | B | 149 | −52.243 | 26.199 | −48.335 | 1.00 | 49.13 | B |

TABLE 7-continued

Atomic coordinates of rSIFN-co (SEQ ID NO: 1)

| ATOM | 2084 | CA | MET | B | 149 | −51.442 | 26.686 | −49.452 | 1.00 | 51.23 | B |
| ATOM | 2085 | CB | MET | B | 149 | −51.230 | 25.600 | −50.494 | 1.00 | 51.00 | B |
| ATOM | 2086 | CG | MET | B | 149 | −49.910 | 24.895 | −50.350 | 1.00 | 53.30 | B |
| ATOM | 2087 | SD | MET | B | 149 | −49.527 | 23.955 | −51.813 | 1.00 | 56.01 | B |
| ATOM | 2088 | CE | MET | B | 149 | −50.453 | 22.505 | −51.485 | 1.00 | 54.85 | B |
| ATOM | 2089 | C | MET | B | 149 | −52.176 | 27.855 | −50.082 | 1.00 | 51.95 | B |
| ATOM | 2090 | O | MET | B | 149 | −51.568 | 28.851 | −50.492 | 1.00 | 52.45 | B |
| ATOM | 2091 | N | ARG | B | 150 | −53.495 | 27.724 | −50.150 | 1.00 | 51.47 | B |
| ATOM | 2092 | CA | ARG | B | 150 | −54.333 | 28.767 | −50.707 | 1.00 | 52.51 | B |
| ATOM | 2093 | CB | ARG | B | 150 | −55.790 | 28.312 | −50.658 | 1.00 | 55.92 | B |
| ATOM | 2094 | CG | ARG | B | 150 | −56.784 | 29.125 | −51.454 | 1.00 | 60.87 | B |
| ATOM | 2095 | CD | ARG | B | 150 | −58.038 | 28.271 | −51.662 | 1.00 | 67.39 | B |
| ATOM | 2096 | NE | ARG | B | 150 | −59.207 | 29.025 | −52.117 | 1.00 | 73.67 | B |
| ATOM | 2097 | CZ | ARG | B | 150 | −59.231 | 29.827 | −53.180 | 1.00 | 76.78 | B |
| ATOM | 2098 | NH1 | ARG | B | 150 | −58.140 | 30.001 | −53.922 | 1.00 | 78.58 | B |
| ATOM | 2099 | NH2 | ARG | B | 150 | −60.354 | 30.456 | −53.506 | 1.00 | 77.37 | B |
| ATOM | 2100 | C | ARG | B | 150 | −54.109 | 30.009 | −49.851 | 1.00 | 51.57 | B |
| ATOM | 2101 | O | ARG | B | 150 | −53.689 | 31.046 | −50.355 | 1.00 | 52.44 | B |
| ATOM | 2102 | N | SER | B | 151 | −54.354 | 29.887 | −48.549 | 1.00 | 50.14 | B |
| ATOM | 2103 | CA | SER | B | 151 | −54.168 | 30.999 | −47.633 | 1.00 | 49.46 | B |
| ATOM | 2104 | CB | SER | B | 151 | −54.458 | 30.559 | −46.207 | 1.00 | 48.27 | B |
| ATOM | 2105 | OG | SER | B | 151 | −55.742 | 29.986 | −46.112 | 1.00 | 48.71 | B |
| ATOM | 2106 | C | SER | B | 151 | −52.760 | 31.574 | −47.705 | 1.00 | 50.79 | B |
| ATOM | 2107 | O | SER | B | 151 | −52.584 | 32.791 | −47.687 | 1.00 | 50.33 | B |
| ATOM | 2108 | N | PHE | B | 152 | −51.749 | 30.716 | −47.778 | 1.00 | 52.18 | B |
| ATOM | 2109 | CA | PHE | B | 152 | −50.380 | 31.225 | −47.861 | 1.00 | 55.34 | B |
| ATOM | 2110 | CB | PHE | B | 152 | −49.365 | 30.087 | −47.739 | 1.00 | 55.53 | B |
| ATOM | 2111 | CG | PHE | B | 152 | −48.768 | 29.954 | −46.366 | 1.00 | 54.12 | B |
| ATOM | 2112 | CD1 | PHE | B | 152 | −49.502 | 29.406 | −45.320 | 1.00 | 54.49 | B |
| ATOM | 2113 | CD2 | PHE | B | 152 | −47.476 | 30.391 | −46.114 | 1.00 | 53.65 | B |
| ATOM | 2114 | CE1 | PHE | B | 152 | −48.954 | 29.297 | −44.039 | 1.00 | 53.70 | B |
| ATOM | 2115 | CE2 | PHE | B | 152 | −46.925 | 30.286 | −44.834 | 1.00 | 55.29 | B |
| ATOM | 2116 | CZ | PHE | B | 152 | −47.668 | 29.737 | −43.799 | 1.00 | 53.15 | B |
| ATOM | 2117 | C | PHE | B | 152 | −50.095 | 32.024 | −49.145 | 1.00 | 55.94 | B |
| ATOM | 2118 | O | PHE | B | 152 | −49.423 | 33.062 | −49.115 | 1.00 | 54.62 | B |
| ATOM | 2119 | N | ALA | B | 153 | −50.603 | 31.541 | −50.271 | 1.00 | 57.38 | B |
| ATOM | 2120 | CA | ALA | B | 153 | −50.381 | 32.238 | −51.526 | 1.00 | 59.97 | B |
| ATOM | 2121 | CB | ALA | B | 153 | −50.910 | 31.408 | −52.700 | 1.00 | 59.69 | B |
| ATOM | 2122 | C | ALA | B | 153 | −51.083 | 33.587 | −51.460 | 1.00 | 61.25 | B |
| ATOM | 2123 | O | ALA | B | 153 | −50.514 | 34.607 | −51.841 | 1.00 | 62.94 | B |
| ATOM | 2124 | N | LEU | B | 154 | −52.312 | 33.588 | −50.953 | 1.00 | 62.12 | B |
| ATOM | 2125 | CA | LEU | B | 154 | −53.112 | 34.804 | −50.833 | 1.00 | 63.13 | B |
| ATOM | 2126 | CB | LEU | B | 154 | −54.510 | 34.437 | −50.340 | 1.00 | 60.76 | B |
| ATOM | 2127 | CG | LEU | B | 154 | −55.360 | 33.639 | −51.331 | 1.00 | 59.42 | B |
| ATOM | 2128 | CD1 | LEU | B | 154 | −56.627 | 33.136 | −50.660 | 1.00 | 58.68 | B |
| ATOM | 2129 | CD2 | LEU | B | 154 | −55.698 | 34.523 | −52.513 | 1.00 | 57.64 | B |
| ATOM | 2130 | C | LEU | B | 154 | −52.518 | 35.899 | −49.932 | 1.00 | 65.86 | B |
| ATOM | 2131 | O | LEU | B | 154 | −52.951 | 37.052 | −49.982 | 1.00 | 65.99 | B |
| ATOM | 2132 | N | SER | B | 155 | −51.525 | 35.546 | −49.121 | 1.00 | 68.63 | B |
| ATOM | 2133 | CA | SER | B | 155 | −50.899 | 36.509 | −48.219 | 1.00 | 71.66 | B |
| ATOM | 2134 | CB | SER | B | 155 | −50.675 | 35.871 | −46.845 | 1.00 | 71.59 | B |
| ATOM | 2135 | OG | SER | B | 155 | −49.726 | 34.820 | −46.920 | 1.00 | 71.04 | B |
| ATOM | 2136 | C | SER | B | 155 | −49.562 | 37.032 | −48.750 | 1.00 | 74.34 | B |
| ATOM | 2137 | O | SER | B | 155 | −48.873 | 37.802 | −48.071 | 1.00 | 74.13 | B |
| ATOM | 2138 | N | THR | B | 156 | −49.193 | 36.611 | −49.958 | 1.00 | 76.74 | B |
| ATOM | 2139 | CA | THR | B | 156 | −47.930 | 37.037 | −50.556 | 1.00 | 78.25 | B |
| ATOM | 2140 | CB | THR | B | 156 | −47.659 | 36.302 | −51.909 | 1.00 | 78.41 | B |
| ATOM | 2141 | OG1 | THR | B | 156 | −48.703 | 36.602 | −52.847 | 1.00 | 78.59 | B |
| ATOM | 2142 | CG2 | THR | B | 156 | −47.600 | 34.791 | −51.697 | 1.00 | 77.83 | B |
| ATOM | 2143 | C | THR | B | 156 | −47.930 | 38.547 | −50.784 | 1.00 | 78.96 | B |
| ATOM | 2144 | O | THR | B | 156 | −46.955 | 39.233 | −50.479 | 1.00 | 77.97 | B |
| ATOM | 2145 | N | ASN | B | 157 | −49.035 | 39.062 | −51.313 | 1.00 | 80.60 | B |
| ATOM | 2146 | CA | ASN | B | 157 | −49.146 | 40.489 | −51.576 | 1.00 | 82.39 | B |
| ATOM | 2147 | CB | ASN | B | 157 | −50.574 | 40.847 | −52.011 | 1.00 | 83.54 | B |
| ATOM | 2148 | CG | ASN | B | 157 | −50.923 | 40.286 | −53.382 | 1.00 | 85.98 | B |
| ATOM | 2149 | OD1 | ASN | B | 157 | −50.166 | 40.449 | −54.344 | 1.00 | 86.88 | B |
| ATOM | 2150 | ND2 | ASN | B | 157 | −52.075 | 39.628 | −53.481 | 1.00 | 87.40 | B |
| ATOM | 2151 | C | ASN | B | 157 | −48.752 | 41.307 | −50.351 | 1.00 | 82.41 | B |
| ATOM | 2152 | O | ASN | B | 157 | −48.015 | 42.290 | −50.459 | 1.00 | 83.08 | B |
| ATOM | 2153 | N | LEU | B | 158 | −49.234 | 40.889 | −49.185 | 1.00 | 81.77 | B |
| ATOM | 2154 | CA | LEU | B | 158 | −48.936 | 41.585 | −47.941 | 1.00 | 80.56 | B |
| ATOM | 2155 | CB | LEU | B | 158 | −49.732 | 40.974 | −46.785 | 1.00 | 80.09 | B |
| ATOM | 2156 | CG | LEU | B | 158 | −50.412 | 41.950 | −45.821 | 1.00 | 79.10 | B |
| ATOM | 2157 | CD1 | LEU | B | 158 | −51.452 | 42.765 | −46.569 | 1.00 | 79.09 | B |
| ATOM | 2158 | CD2 | LEU | B | 158 | −51.078 | 41.183 | −44.702 | 1.00 | 79.49 | B |
| ATOM | 2159 | C | LEU | B | 158 | −47.447 | 41.501 | −47.647 | 1.00 | 80.15 | B |
| ATOM | 2160 | O | LEU | B | 158 | −46.772 | 42.520 | −47.568 | 1.00 | 80.43 | B |
| ATOM | 2161 | N | GLN | B | 159 | −46.935 | 40.286 | −47.494 | 1.00 | 80.14 | B |

TABLE 7-continued

Atomic coordinates of rSIFN-co (SEQ ID NO: 1)

| ATOM | 2162 | CA | GLN | B | 159 | −45.519 | 40.095 | −47.210 | 1.00 | 81.12 | B |
|---|---|---|---|---|---|---|---|---|---|---|---|
| ATOM | 2163 | CB | GLN | B | 159 | −45.171 | 38.603 | −47.275 | 1.00 | 81.69 | B |
| ATOM | 2164 | CG | GLN | B | 159 | −45.683 | 37.807 | −46.067 | 1.00 | 83.74 | B |
| ATOM | 2165 | CD | GLN | B | 159 | −45.782 | 36.306 | −46.320 | 1.00 | 84.02 | B |
| ATOM | 2166 | OE1 | GLN | B | 159 | −46.586 | 35.853 | −47.141 | 1.00 | 84.95 | B |
| ATOM | 2167 | NE2 | GLN | B | 159 | −44.969 | 35.531 | −45.611 | 1.00 | 81.86 | B |
| ATOM | 2168 | C | GLN | B | 159 | −44.662 | 40.899 | −48.189 | 1.00 | 81.34 | B |
| ATOM | 2169 | O | GLN | B | 159 | −43.627 | 41.459 | −47.813 | 1.00 | 80.91 | B |
| ATOM | 2170 | N | GLY | B | 160 | −45.115 | 40.973 | −49.438 | 1.00 | 81.50 | B |
| ATOM | 2171 | CA | GLY | B | 160 | −44.389 | 41.716 | −50.453 | 1.00 | 82.03 | B |
| ATOM | 2172 | C | GLY | B | 160 | −44.444 | 43.224 | −50.261 | 1.00 | 82.52 | B |
| ATOM | 2173 | O | GLY | B | 160 | −43.401 | 43.875 | −50.197 | 1.00 | 83.21 | B |
| ATOM | 2174 | N | ALA | B | 161 | −45.652 | 43.783 | −50.174 | 1.00 | 82.63 | B |
| ATOM | 2175 | CA | ALA | B | 161 | −45.832 | 45.225 | −49.989 | 1.00 | 82.61 | B |
| ATOM | 2176 | CB | ALA | B | 161 | −47.318 | 45.575 | −49.991 | 1.00 | 81.89 | B |
| ATOM | 2177 | C | ALA | B | 161 | −45.193 | 45.672 | −48.681 | 1.00 | 82.81 | B |
| ATOM | 2178 | O | ALA | B | 161 | −44.989 | 46.865 | −48.444 | 1.00 | 82.18 | B |
| ATOM | 2179 | N | LEU | B | 162 | −44.892 | 44.691 | −47.836 | 1.00 | 83.61 | B |
| ATOM | 2180 | CA | LEU | B | 162 | −44.262 | 44.918 | −46.542 | 1.00 | 83.73 | B |
| ATOM | 2181 | CB | LEU | B | 162 | −44.569 | 43.741 | −45.608 | 1.00 | 81.75 | B |
| ATOM | 2182 | CG | LEU | B | 162 | −44.375 | 43.877 | −44.097 | 1.00 | 80.23 | B |
| ATOM | 2183 | CD1 | LEU | B | 162 | −44.889 | 42.617 | −43.433 | 1.00 | 79.72 | B |
| ATOM | 2184 | CD2 | LEU | B | 162 | −42.912 | 44.096 | −43.755 | 1.00 | 80.03 | B |
| ATOM | 2185 | C | LEU | B | 162 | −42.760 | 45.014 | −46.802 | 1.00 | 84.64 | B |
| ATOM | 2186 | O | LEU | B | 162 | −42.053 | 45.804 | −46.167 | 1.00 | 84.99 | B |
| ATOM | 2187 | N | GLY | B | 163 | −42.288 | 44.206 | −47.752 | 1.00 | 84.65 | B |
| ATOM | 2188 | CA | GLY | B | 163 | −40.881 | 44.207 | −48.107 | 1.00 | 84.77 | B |
| ATOM | 2189 | C | GLY | B | 163 | −40.469 | 45.480 | −48.828 | 1.00 | 85.10 | B |
| ATOM | 2190 | O | GLY | B | 163 | −39.592 | 46.201 | −48.300 | 1.00 | 84.53 | B |
| ATOM | 2191 | OXT | GLY | B | 163 | −41.021 | 45.762 | −49.918 | 1.00 | 84.32 | B |
| ATOM | 2192 | S | CXS | $ | 1001 | −37.007 | 7.286 | −12.909 | 1.00 | 89.60 | $ |
| ATOM | 2193 | O1 | CXS | $ | 1001 | −37.722 | 7.642 | −11.758 | 1.00 | 90.92 | $ |
| ATOM | 2194 | O2 | CXS | $ | 1001 | −37.206 | 7.283 | −14.330 | 1.00 | 90.52 | $ |
| ATOM | 2195 | O3 | CXS | $ | 1001 | −35.476 | 7.404 | −12.678 | 1.00 | 90.21 | $ |
| ATOM | 2196 | C1 | CXS | $ | 1001 | −36.878 | 9.113 | −13.140 | 1.00 | 86.35 | $ |
| ATOM | 2197 | C2 | CXS | $ | 1001 | −38.280 | 9.714 | −13.449 | 1.00 | 82.21 | $ |
| ATOM | 2198 | C3 | CXS | $ | 1001 | −38.308 | 11.211 | −13.660 | 1.00 | 78.87 | $ |
| ATOM | 2199 | N | CXS | $ | 1001 | −39.730 | 11.610 | −13.907 | 1.00 | 74.83 | $ |
| ATOM | 2200 | C4 | CXS | $ | 1001 | −39.806 | 13.069 | −14.118 | 1.00 | 72.04 | $ |
| ATOM | 2201 | C5 | CXS | $ | 1001 | −38.946 | 13.813 | −13.094 | 1.00 | 71.28 | $ |
| ATOM | 2202 | C6 | CXS | $ | 1001 | −38.989 | 15.336 | −13.308 | 1.00 | 70.38 | $ |
| ATOM | 2203 | C7 | CXS | $ | 1001 | −38.608 | 15.704 | −14.767 | 1.00 | 70.92 | $ |
| ATOM | 2204 | C8 | CXS | $ | 1001 | −39.501 | 14.945 | −15.785 | 1.00 | 69.52 | $ |
| ATOM | 2205 | C9 | CXS | $ | 1001 | −39.379 | 13.417 | −15.567 | 1.00 | 71.02 | $ |
| ATOM | 2206 | S | CXS | $ | 1002 | −33.172 | 31.213 | −33.664 | 1.00 | 59.12 | $ |
| ATOM | 2207 | O1 | CXS | $ | 1002 | −33.303 | 31.719 | −34.982 | 1.00 | 61.00 | $ |
| ATOM | 2208 | O2 | CXS | $ | 1002 | −31.915 | 30.813 | −33.130 | 1.00 | 59.84 | $ |
| ATOM | 2209 | O3 | CXS | $ | 1002 | −33.679 | 32.294 | −32.738 | 1.00 | 61.33 | $ |
| ATOM | 2210 | C1 | CXS | $ | 1002 | −34.407 | 29.954 | −33.375 | 1.00 | 56.21 | $ |
| ATOM | 2211 | C2 | CXS | $ | 1002 | −34.146 | 28.753 | −34.253 | 1.00 | 51.82 | $ |
| ATOM | 2212 | C3 | CXS | $ | 1002 | −35.236 | 27.757 | −33.951 | 1.00 | 52.23 | $ |
| ATOM | 2213 | N | CXS | $ | 1002 | −35.098 | 26.561 | −34.782 | 1.00 | 53.07 | $ |
| ATOM | 2214 | C4 | CXS | $ | 1002 | −36.180 | 25.616 | −34.422 | 1.00 | 50.12 | $ |
| ATOM | 2215 | C5 | CXS | $ | 1002 | −37.574 | 26.289 | −34.439 | 1.00 | 47.85 | $ |
| ATOM | 2216 | C6 | CXS | $ | 1002 | −38.645 | 25.266 | −34.045 | 1.00 | 47.93 | $ |
| ATOM | 2217 | C7 | CXS | $ | 1002 | −38.644 | 24.095 | −35.046 | 1.00 | 49.65 | $ |
| ATOM | 2218 | C8 | CXS | $ | 1002 | −37.263 | 23.410 | −35.077 | 1.00 | 49.27 | $ |
| ATOM | 2219 | C9 | CXS | $ | 1002 | −36.157 | 24.435 | −35.413 | 1.00 | 50.51 | $ |
| ATOM | 2220 | O | HOH | S | 1 | −55.089 | 30.721 | −29.788 | 1.00 | 42.32 | S |
| ATOM | 2221 | O | HOH | S | 2 | −51.354 | 16.117 | −54.214 | 1.00 | 66.49 | S |
| ATOM | 2222 | O | HOH | S | 3 | −35.292 | 43.228 | −45.412 | 1.00 | 70.66 | S |
| ATOM | 2223 | O | HOH | S | 6 | −36.194 | 33.341 | −31.023 | 1.00 | 62.49 | S |
| ATOM | 2224 | O | HOH | S | 8 | −42.460 | 34.031 | −31.211 | 1.00 | 52.51 | S |
| ATOM | 2225 | O | HOH | S | 11 | −51.117 | 14.500 | −24.316 | 1.00 | 63.19 | S |
| ATOM | 2226 | O | HOH | S | 13 | −34.186 | 35.241 | −31.749 | 1.00 | 69.73 | S |
| ATOM | 2227 | O | HOH | S | 14 | −46.886 | 23.354 | −15.063 | 1.00 | 62.91 | S |
| ATOM | 2228 | O | HOH | S | 15 | −67.379 | 16.745 | −38.051 | 1.00 | 74.92 | S |
| ATOM | 2229 | O | HOH | S | 16 | −48.149 | 52.600 | −41.809 | 1.00 | 65.55 | S |
| ATOM | 2230 | O | HOH | S | 20 | −37.533 | 46.814 | −44.158 | 1.00 | 63.62 | S |
| ATOM | 2231 | O | HOH | S | 23 | −26.090 | 20.564 | −40.954 | 1.00 | 64.92 | S |
| ATOM | 2232 | O | HOH | S | 33 | −66.641 | 27.143 | −35.990 | 1.00 | 64.70 | S |
| ATOM | 2233 | O | HOH | S | 34 | −34.278 | 43.389 | −42.980 | 1.00 | 66.36 | S |
| ATOM | 2234 | O | HOH | S | 35 | −40.575 | 14.233 | −23.786 | 1.00 | 68.23 | S |
| ATOM | 2235 | O | HOH | S | 36 | −26.941 | 28.813 | −12.491 | 1.00 | 61.13 | S |
| ATOM | 2236 | O | HOH | S | 37 | −30.827 | 27.593 | −14.316 | 1.00 | 59.11 | S |
| ATOM | 2237 | O | HOH | S | 39 | −44.040 | 36.979 | −30.178 | 1.00 | 56.62 | S |
| ATOM | 2238 | O | HOH | S | 40 | −33.347 | 44.688 | −11.256 | 1.00 | 77.43 | S |
| ATOM | 2239 | O | HOH | S | 42 | −64.966 | 36.711 | −39.384 | 1.00 | 64.46 | S |

TABLE 7-continued

Atomic coordinates of rSIFN-co (SEQ ID NO: 1)

| ATOM | 2240 | O | HOH | S | 43 | −14.994 | 28.360 | −34.554 | 1.00 | 79.56 | S |
|---|---|---|---|---|---|---|---|---|---|---|---|
| ATOM | 2241 | O | HOH | S | 45 | −58.115 | 31.298 | −30.300 | 1.00 | 73.59 | S |
| ATOM | 2242 | O | HOH | S | 46 | −36.924 | 25.549 | −50.937 | 1.00 | 62.92 | S |
| ATOM | 2243 | O | HOH | S | 49 | −20.930 | 37.291 | −14.901 | 1.00 | 62.70 | S |
| ATOM | 2244 | O | HOH | S | 55 | −35.088 | 9.503 | −41.169 | 1.00 | 56.66 | S |
| ATOM | 2245 | O | HOH | S | 58 | −45.523 | 36.927 | −10.019 | 1.00 | 53.41 | S |
| ATOM | 2246 | O | HOH | S | 60 | −24.940 | 43.426 | −34.908 | 1.00 | 64.11 | S |
| ATOM | 2247 | O | HOH | S | 61 | −43.094 | 16.769 | −33.268 | 1.00 | 88.80 | S |
| ATOM | 2248 | O | HOH | S | 64 | −52.392 | 52.632 | −34.025 | 1.00 | 92.27 | S |
| ATOM | 2249 | O | HOH | S | 66 | −14.474 | 29.522 | −20.678 | 1.00 | 73.76 | S |
| ATOM | 2250 | O | HOH | S | 67 | −61.923 | 12.568 | −56.894 | 1.00 | 71.78 | S |
| ATOM | 2251 | O | HOH | S | 68 | −17.930 | 11.026 | −27.010 | 1.00 | 57.62 | S |
| ATOM | 2252 | O | HOH | S | 69 | −26.009 | 23.821 | −38.215 | 1.00 | 56.83 | S |
| ATOM | 2253 | O | HOH | S | 70 | −34.979 | 17.848 | −41.915 | 1.00 | 57.66 | S |
| ATOM | 2254 | O | HOH | S | 73 | −53.375 | 25.113 | −34.332 | 1.00 | 67.17 | S |
| ATOM | 2255 | O | HOH | S | 78 | −3.369 | 14.903 | −39.536 | 1.00 | 76.47 | S |
| ATOM | 2256 | O | HOH | S | 79 | −49.809 | 52.012 | −53.024 | 1.00 | 74.16 | S |
| ATOM | 2257 | O | HOH | S | 80 | −52.873 | 32.569 | −23.870 | 1.00 | 59.72 | S |
| ATOM | 2258 | O | HOH | S | 81 | −69.907 | 24.040 | −37.219 | 1.00 | 59.30 | S |
| ATOM | 2259 | O | HOH | S | 82 | −42.669 | 56.555 | −30.390 | 1.00 | 65.30 | S |
| ATOM | 2260 | O | HOH | S | 85 | −29.842 | 34.315 | −33.948 | 1.00 | 62.56 | S |
| ATOM | 2261 | O | HOH | S | 96 | −54.795 | 49.118 | −60.472 | 1.00 | 72.94 | S |
| ATOM | 2262 | O | HOH | S | 100 | −16.120 | 34.824 | −29.084 | 1.00 | 73.72 | S |
| ATOM | 2263 | O | HOH | S | 103 | −41.801 | 10.188 | −41.652 | 1.00 | 59.23 | S |
| ATOM | 2264 | O | HOH | S | 108 | −72.826 | 20.167 | −44.484 | 1.00 | 75.51 | S |
| ATOM | 2265 | O | HOH | S | 111 | −31.210 | 25.257 | −37.321 | 1.00 | 71.53 | S |
| ATOM | 2266 | O | HOH | S | 113 | −35.456 | 11.432 | −29.314 | 1.00 | 64.29 | S |
| ATOM | 2267 | O | HOH | S | 114 | −14.615 | 14.030 | −42.236 | 1.00 | 64.98 | S |
| ATOM | 2268 | O | HOH | S | 116 | −30.150 | 46.628 | −35.936 | 1.00 | 67.88 | S |
| ATOM | 2269 | O | HOH | S | 117 | −33.711 | 52.716 | −21.422 | 1.00 | 75.50 | S |
| ATOM | 2270 | O | HOH | S | 122 | −42.524 | 31.582 | −56.165 | 1.00 | 60.35 | S |
| ATOM | 2271 | O | HOH | S | 124 | −57.788 | 19.390 | −20.057 | 1.00 | 80.05 | S |
| ATOM | 2272 | O | HOH | S | 127 | −8.352 | 21.156 | −33.703 | 1.00 | 72.60 | S |
| ATOM | 2273 | O | HOH | S | 131 | −65.658 | 4.703 | −48.301 | 1.00 | 67.75 | S |
| ATOM | 2274 | O | HOH | S | 136 | −31.961 | 29.091 | −37.073 | 1.00 | 65.98 | S |
| ATOM | 2275 | O | HOH | S | 144 | −32.295 | 17.761 | −36.053 | 1.00 | 61.82 | S |
| ATOM | 2276 | O | HOH | S | 145 | −16.099 | 20.782 | −27.246 | 1.00 | 62.57 | S |
| ATOM | 2277 | O | HOH | S | 152 | −40.098 | 47.171 | −61.867 | 1.00 | 70.18 | S |
| ATOM | 2278 | O | HOH | S | 153 | −16.949 | 16.723 | −30.701 | 1.00 | 72.82 | S |
| ATOM | 2279 | O | HOH | S | 154 | −49.102 | 54.760 | −44.857 | 1.00 | 74.87 | S |
| ATOM | 2280 | O | HOH | S | 155 | −33.241 | 36.181 | −28.893 | 1.00 | 53.26 | S |
| ATOM | 2281 | O | HOH | S | 157 | −28.846 | 4.566 | −28.970 | 1.00 | 65.48 | S |
| ATOM | 2282 | O | HOH | S | 159 | −18.078 | 6.979 | −32.388 | 1.00 | 62.25 | S |
| ATOM | 2283 | O | HOH | S | 160 | −49.927 | 12.224 | −25.999 | 1.00 | 83.57 | S |
| ATOM | 2284 | O | HOH | S | 161 | −35.384 | 38.748 | −45.921 | 1.00 | 78.38 | S |
| ATOM | 2285 | O | HOH | S | 164 | −19.431 | 9.631 | −42.561 | 1.00 | 83.75 | S |
| ATOM | 2286 | O | HOH | S | 165 | −24.757 | 7.452 | −28.428 | 1.00 | 62.83 | S |
| ATOM | 2287 | O | HOH | S | 166 | −26.095 | 40.110 | −19.029 | 1.00 | 71.51 | S |
| ATOM | 2288 | O | HOH | S | 167 | −33.517 | 28.875 | −11.950 | 1.00 | 65.15 | S |
| ATOM | 2289 | O | HOH | S | 169 | −23.559 | 26.637 | −34.978 | 1.00 | 69.82 | S |
| ATOM | 2290 | O | HOH | S | 171 | −35.911 | 32.089 | −11.426 | 1.00 | 70.81 | S |
| ATOM | 2291 | O | HOH | S | 173 | −29.541 | 39.675 | −27.861 | 1.00 | 73.58 | S |
| ATOM | 2292 | O | HOH | S | 174 | −42.366 | 9.773 | −12.564 | 1.00 | 75.10 | S |
| ATOM | 2293 | O | HOH | S | 179 | −37.615 | 36.321 | −6.575 | 1.00 | 60.84 | S |
| ATOM | 2294 | O | HOH | S | 185 | −37.396 | 54.966 | −35.497 | 1.00 | 66.51 | S |
| ATOM | 2295 | O | HOH | S | 186 | −34.811 | 40.197 | −42.025 | 1.00 | 78.57 | S |
| ATOM | 2296 | O | HOH | S | 189 | −41.472 | 38.031 | −56.357 | 1.00 | 76.56 | S |
| ATOM | 2297 | O | HOH | S | 193 | −31.145 | 43.929 | −38.718 | 1.00 | 64.82 | S |
| ATOM | 2298 | O | HOH | S | 197 | −44.621 | 37.091 | −53.919 | 1.00 | 74.57 | S |
| ATOM | 2299 | O | HOH | S | 200 | −26.601 | 47.858 | −27.412 | 1.00 | 73.60 | S |
| ATOM | 2300 | O | HOH | S | 204 | −34.070 | 22.759 | −42.394 | 1.00 | 64.86 | S |
| ATOM | 2301 | O | HOH | S | 206 | −56.104 | 23.451 | −54.858 | 1.00 | 63.95 | S |
| ATOM | 2302 | O | HOH | S | 207 | −42.623 | 14.939 | −36.850 | 1.00 | 58.12 | S |
| ATOM | 2303 | O | HOH | S | 215 | −57.916 | 20.611 | −53.534 | 1.00 | 65.65 | S |
| ATOM | 2304 | O | HOH | S | 217 | −68.703 | 19.492 | −32.308 | 1.00 | 66.71 | S |
| ATOM | 2305 | O | HOH | S | 218 | −34.288 | 47.462 | −17.190 | 1.00 | 87.83 | S |
| ATOM | 2306 | O | HOH | S | 219 | −47.023 | 49.480 | −49.463 | 1.00 | 80.36 | S |
| ATOM | 2307 | O | HOH | S | 221 | −36.167 | 35.091 | −46.526 | 1.00 | 82.36 | S |
| ATOM | 2308 | O | HOH | S | 229 | −5.120 | 14.056 | −34.382 | 1.00 | 80.88 | S |
| ATOM | 2309 | O | HOH | S | 234 | −61.102 | 28.009 | −56.501 | 1.00 | 73.87 | S |
| ATOM | 2310 | O | HOH | S | 236 | −50.038 | 53.208 | −31.379 | 1.00 | 80.66 | S |
| ATOM | 2311 | O | HOH | S | 238 | −63.210 | 5.594 | −33.656 | 1.00 | 73.31 | S |
| ATOM | 2312 | O | HOH | S | 239 | −18.979 | 25.474 | −40.262 | 1.00 | 65.13 | S |
| ATOM | 2313 | O | HOH | S | 241 | −9.247 | 22.473 | −40.473 | 1.00 | 62.01 | S |
| ATOM | 2314 | O | HOH | S | 242 | −23.581 | 0.874 | −22.639 | 1.00 | 79.48 | S |
| ATOM | 2315 | O | HOH | S | 244 | −37.921 | 9.795 | −41.267 | 1.00 | 71.07 | S |
| ATOM | 2316 | O | HOH | S | 245 | −68.213 | 16.294 | −47.338 | 1.00 | 66.37 | S |
| ATOM | 2317 | O | HOH | S | 259 | −54.297 | 15.702 | −29.864 | 1.00 | 69.25 | S |

TABLE 7-continued

Atomic coordinates of rSIFN-co (SEQ ID NO: 1)

| ATOM | 2318 | O | HOH | S | 260 | −53.332 | 29.741 | −10.004 | 1.00 | 79.52 | S |
|---|---|---|---|---|---|---|---|---|---|---|---|
| ATOM | 2319 | O | HOH | S | 261 | −58.281 | 47.179 | −58.668 | 1.00 | 71.63 | S |
| ATOM | 2320 | O | HOH | S | 262 | −61.633 | 19.952 | −25.923 | 1.00 | 74.21 | S |
| ATOM | 2321 | O | HOH | S | 264 | −59.854 | 24.019 | −57.410 | 1.00 | 84.87 | S |
| ATOM | 2322 | O | HOH | S | 265 | −34.910 | 13.726 | −35.043 | 1.00 | 75.92 | S |
| ATOM | 2323 | O | HOH | S | 266 | −65.206 | −1.041 | −22.378 | 1.00 | 67.71 | S |
| ATOM | 2324 | O | HOH | S | 267 | −30.825 | 12.386 | −15.339 | 1.00 | 53.22 | S |
| ATOM | 2325 | O | HOH | S | 268 | −23.141 | 25.046 | −40.085 | 1.00 | 77.62 | S |
| ATOM | 2326 | O | HOH | S | 273 | −64.261 | 24.028 | −29.410 | 1.00 | 61.30 | S |
| ATOM | 2327 | O | HOH | S | 281 | −45.175 | 18.432 | −30.051 | 1.00 | 88.80 | S |
| ATOM | 2328 | O | HOH | S | 285 | −44.514 | 56.451 | −43.099 | 1.00 | 73.84 | S |
| ATOM | 2329 | O | HOH | S | 298 | −41.747 | 37.900 | −7.567 | 1.00 | 67.96 | S |
| ATOM | 2330 | O | HOH | S | 301 | −51.187 | 22.922 | −27.202 | 1.00 | 59.87 | S |
| ATOM | 2331 | O | HOH | S | 308 | −56.697 | 51.798 | −45.311 | 1.00 | 76.39 | S |
| ATOM | 2332 | O | HOH | S | 310 | −30.921 | 48.271 | −19.130 | 1.00 | 67.15 | S |
| ATOM | 2333 | O | HOH | S | 315 | −26.247 | 3.171 | −24.345 | 1.00 | 70.11 | S |
| ATOM | 2334 | O | HOH | S | 317 | −7.989 | 11.928 | −10.219 | 1.00 | 69.93 | S |
| ATOM | 2335 | O | HOH | S | 323 | −67.469 | 1.840 | −28.352 | 1.00 | 73.34 | S |
| ATOM | 2336 | O | HOH | S | 327 | −1.519 | 7.683 | −30.620 | 1.00 | 68.63 | S |
| ATOM | 2337 | O | HOH | S | 330 | −13.341 | 11.540 | −27.689 | 1.00 | 66.95 | S |
| ATOM | 2338 | O | HOH | S | 334 | −31.782 | 46.438 | −31.042 | 1.00 | 84.75 | S |
| ATOM | 2339 | O | HOH | S | 337 | −14.963 | 25.917 | −41.978 | 1.00 | 64.34 | S |
| ATOM | 2340 | O | HOH | S | 341 | −55.975 | 23.392 | −31.423 | 1.00 | 74.05 | S |
| ATOM | 2341 | O | HOH | S | 347 | −30.795 | 46.682 | −44.519 | 1.00 | 85.03 | S |
| ATOM | 2342 | O | HOH | S | 348 | −40.398 | 44.400 | −17.941 | 1.00 | 78.54 | S |
| ATOM | 2343 | O | HOH | S | 351 | −63.588 | 34.580 | −53.000 | 1.00 | 64.83 | S |
| ATOM | 2344 | O | HOH | S | 352 | −52.859 | 26.925 | −10.393 | 1.00 | 76.36 | S |
| ATOM | 2345 | O | HOH | S | 360 | −66.994 | 13.614 | −58.601 | 1.00 | 80.08 | S |
| ATOM | 2346 | O | HOH | S | 362 | −6.728 | 7.392 | −14.487 | 1.00 | 66.11 | S |
| ATOM | 2347 | O | HOH | S | 363 | −45.315 | 52.345 | −44.599 | 1.00 | 70.94 | S |
| ATOM | 2348 | O | HOH | S | 364 | −27.723 | 55.681 | −25.949 | 1.00 | 80.92 | S |
| ATOM | 2349 | O | HOH | S | 365 | −0.192 | 8.761 | −14.858 | 1.00 | 65.43 | S |
| ATOM | 2350 | O | HOH | S | 366 | −33.943 | 48.435 | −9.023 | 1.00 | 73.21 | S |
| ATOM | 2351 | O | HOH | S | 369 | −23.185 | 39.615 | −20.816 | 1.00 | 75.14 | S |
| ATOM | 2352 | O | HOH | S | 371 | −47.369 | 8.811 | −24.333 | 1.00 | 90.58 | S |
| ATOM | 2353 | O | HOH | S | 378 | −72.215 | 16.093 | −37.276 | 1.00 | 79.02 | S |
| ATOM | 2354 | O | HOH | S | 382 | −62.101 | 39.118 | −53.345 | 1.00 | 91.47 | S |
| ATOM | 2355 | O | HOH | S | 399 | −5.346 | 7.993 | −18.480 | 1.00 | 82.98 | S |
| ATOM | 2356 | O | HOH | S | 404 | −48.898 | 52.763 | −34.937 | 1.00 | 79.67 | S |
| ATOM | 2357 | O | HOH | S | 408 | −58.332 | 50.605 | −57.798 | 1.00 | 73.84 | S |
| ATOM | 2358 | O | HOH | S | 414 | −16.594 | 33.677 | −18.292 | 1.00 | 67.72 | S |
| ATOM | 2359 | O | HOH | S | 421 | −14.075 | 7.273 | −31.446 | 1.00 | 75.74 | S |
| ATOM | 2360 | O | HOH | S | 425 | −52.456 | 25.670 | −30.099 | 1.00 | 68.36 | S |
| ATOM | 2361 | O | HOH | S | 429 | −34.829 | 54.773 | −17.284 | 1.00 | 73.77 | S |
| ATOM | 2362 | O | HOH | S | 438 | −25.176 | 29.403 | −40.958 | 1.00 | 77.48 | S |
| ATOM | 2363 | O | HOH | S | 444 | −42.956 | 49.806 | −10.829 | 1.00 | 87.00 | S |
| ATOM | 2364 | O | HOH | S | 458 | −70.377 | 23.808 | −46.086 | 1.00 | 78.30 | S |
| ATOM | 2365 | O | HOH | S | 476 | −33.612 | 35.694 | −43.631 | 1.00 | 66.61 | S |
| ATOM | 2366 | O | HOH | S | 488 | −43.909 | 38.988 | −59.269 | 1.00 | 90.04 | S |
| ATOM | 2367 | O | HOH | S | 490 | −55.112 | 12.025 | −28.305 | 1.00 | 69.08 | S |
| ATOM | 2368 | O | HOH | S | 497 | −52.018 | 36.590 | −59.300 | 1.00 | 73.00 | S |
| ATOM | 2369 | O | HOH | S | 498 | −67.080 | 8.456 | −47.025 | 1.00 | 77.54 | S |
| ATOM | 2370 | O | HOH | S | 501 | −33.375 | 45.638 | −46.606 | 1.00 | 67.04 | S |
| ATOM | 2371 | O | HOH | S | 504 | −17.519 | 40.287 | −29.824 | 1.00 | 75.48 | S |
| ATOM | 2372 | O | HOH | S | 508 | −38.469 | 54.630 | −22.566 | 1.00 | 81.92 | S |
| ATOM | 2373 | O | HOH | S | 548 | −7.619 | 13.490 | −18.323 | 1.00 | 80.70 | S |
| ATOM | 2374 | O | HOH | S | 562 | −52.127 | 9.380 | −31.442 | 1.00 | 93.77 | S |
| ATOM | 2375 | O | HOH | S | 574 | −71.476 | 15.001 | −51.047 | 1.00 | 83.08 | S |
| ATOM | 2376 | O | HOH | S | 581 | −35.133 | 54.715 | −54.265 | 1.00 | 79.21 | S |
| ATOM | 2377 | O | HOH | S | 598 | −38.686 | 54.511 | −51.645 | 1.00 | 83.16 | S |
| END | | | | | | | | | | | |

What is claimed is:

1. A method of treating a tumor in a subject, comprising the step of administering to said subject an effective amount of an interferon crystal, wherein said interferon consisting of the amino acid sequence of SEQ ID NO: 1, said crystal has a space group of $P3_121$ and unit cell parameters of a=b=77.92 Å, c=125.935 Å, $\alpha=\beta=90°$, and $\gamma=120°$.

2. The method of claim 1, wherein said interferon crystal contains two molecules in an asymmetric unit.

3. The method of claim 1, wherein said interferon crystal comprises covalently or non-covalently bound metal ions.

4. The method of claim 1, wherein said tumor is a solid tumor.

5. The method of claim 1, wherein said tumor is selected from: skin cancer, basal cell carcinoma, malignant melanoma, renal cell carcinoma, liver cancer, thyroid cancer, nasopharyngeal cancer, solid tumors, prostate cancer, stomach/abdominal cancer, esophageal cancer, rectal cancer, pancreatic cancer, breast cancer, ovarian cancer, superficial bladder cancer, hemangioma, epidermoid cancer, cervical cancer, non-small cell lung cancer, small cell lung cancer, glial stromal tumors, leukemia, acute leukemia, chronic leukemia, chronic myelogenous leukemia, hairy cell leukemia, lymphadenoma, multiple myeloma, polycythemia and Kaposi's sarcoma.

* * * * *

UNITED STATES PATENT AND TRADEMARK OFFICE
CERTIFICATE OF CORRECTION

PATENT NO. : 9,273,109 B2  
APPLICATION NO. : 14/461360  
DATED : March 1, 2016  
INVENTOR(S) : Guangwen Wei and Dacheng Wang It is certified that error appears in the above-identified patent and that said Letters Patent is hereby corrected as shown below:

Title Page

On page 1 of the patent, under (30) Foreign Application Priority Data:
"Dec. 18, 2009 (CN) ............ 2009 1 0259339" should be
"Dec. 18, 2009 (CN) ............ 200910259339.2".

On page 2 of the patent, under (56) References Cited, left column, line 4 from the bottom:
"Jul. 9, 2013 U.S. Office Action for U.S. Appl. No. 13/490,719, filed" should be
"Sept. 9, 2013 U.S. Office Action for U.S. Appl. No. 13/490,719, filed".

Signed and Sealed this  
Third Day of May, 2016

Michelle K. Lee  
*Director of the United States Patent and Trademark Office*

SEQUENCE LISTING

<160> NUMBER OF SEQ ID NOS: 15

<210> SEQ ID NO 1
<211> LENGTH: 167
<212> TYPE: PRT
<213> ORGANISM: Artificial Sequence
<220> FEATURE:
<223> OTHER INFORMATION: Amino acid sequence of recombinant interferon

<400> SEQUENCE: 1

```
Met Cys Asp Leu Pro Gln Thr His Ser Leu Gly Asn Arg Arg Ala Leu
1               5                   10                  15

Ile Leu Leu Ala Gln Met Arg Arg Ile Ser Pro Phe Ser Cys Leu Lys
            20                  25                  30

Asp Arg His Asp Phe Gly Phe Pro Gln Glu Glu Phe Asp Gly Asn Gln
        35                  40                  45

Phe Gln Lys Ala Gln Ala Ile Ser Val Leu His Glu Met Ile Gln Gln
    50                  55                  60

Thr Phe Asn Leu Phe Ser Thr Lys Asp Ser Ser Ala Ala Trp Asp Glu
65                  70                  75                  80

Ser Leu Leu Glu Lys Phe Tyr Thr Glu Leu Tyr Gln Gln Leu Asn Asp
                85                  90                  95

Leu Glu Ala Cys Val Ile Gln Glu Val Gly Val Glu Thr Pro Leu
            100                 105                 110

Met Asn Val Asp Ser Ile Leu Ala Val Lys Lys Tyr Phe Gln Arg Ile
            115                 120                 125

Thr Leu Tyr Leu Thr Glu Lys Lys Tyr Ser Pro Cys Ala Trp Glu Val
    130                 135                 140

Val Arg Ala Glu Ile Met Arg Ser Phe Ser Leu Ser Thr Asn Leu Gln
145                 150                 155                 160

Glu Arg Leu Arg Arg Lys Glu
                165
```

<210> SEQ ID NO 2
<211> LENGTH: 504
<212> TYPE: DNA
<213> ORGANISM: Artificial Sequence
<220> FEATURE:
<223> OTHER INFORMATION: Nucleotide sequence encoding recombinant interferon

<400> SEQUENCE: 2

```
atgtgcgacc tgccgcagac ccactccctg ggtaaccgtc gtgctctgat cctgctggct    60
cagatgcgtc gtatctcccc gttctcctgc ctgaaagacc gtcacgactt cggtttcccg   120
caggaagaat tcgacggtaa ccagttccag aaagctcagg ctatctccgt tctgcacgaa   180
atgatccagc agaccttcaa cctgttctcc accaaagact cctccgctgc ttgggacgaa   240
tccctgctgg aaaaattcta caccgaactg taccagcagc tgaacgacct ggaagcttgc   300
gttatccagg aagttggtgt tgaagaaacc ccgctgatga acgttgactc catcctggct   360
gttaaaaaat acttccagcg tatcaccctg tacctgaccg aaaaaaaata ctccccgtgc   420
gcttgggaag ttgttcgtgc tgaaatcatg cgttccttct ccctgtccac caacctgcag   480
gaacgtctgc gtcgtaaaga ataa                                         504
```

<210> SEQ ID NO 3
<211> LENGTH: 504
<212> TYPE: DNA
<213> ORGANISM: Artificial Sequence
<220> FEATURE:
<223> OTHER INFORMATION: Nucleotide sequence encoding recombinant interferon

<400> SEQUENCE: 3

```
tacacgctgg acggcgtctg ggtgagggac ccattggcag cacgagacta ggacgaccga    60
gtctacgcag catagagggg caagaggacg gactttctgg cagtgctgaa gccaaagggc   120
```

```
gtccttctta agctgccatt ggtcaaggtc tttcgagtcc gatagaggca agacgtgctt      180
tactaggtcg tctggaagtt ggacaagagg tggtttctga ggaggcgacg aaccctgctt      240
agggacgacc ttttttaagat gtggcttgac atggtcgtcg acttgctgga ccttcgaacg     300
caataggtcc ttcaaccaca acttctttgg ggcgactact tgcaactgag gtaggaccga     360
caatttttta tgaaggtcgc atagtgggac atggactggc ttttttttat gagggggcacg    420 cgaacccttc aacaagcacg actttagtac gcaaggaaga gggacaggtg gttggacgtc     480
cttgcagacg cagcatttct tatt                                            504

<210> SEQ ID NO 4
<211> LENGTH: 9
<212> TYPE: PRT
<213> ORGANISM: Artificial Sequence
<220> FEATURE:
<223> OTHER INFORMATION: Amino acid sequence of AB loop

<400> SEQUENCE: 4

Ser Pro Phe Ser Cys Leu Lys Asp Arg
1               5

<210> SEQ ID NO 5
<211> LENGTH: 9
<212> TYPE: PRT
<213> ORGANISM: Artificial Sequence
<220> FEATURE:
<223> OTHER INFORMATION: Amino acid sequence of BC loop

<400> SEQUENCE: 5

Asp Gly Asn Gln Phe Gln Lys Ala Gln
1               5

<210> SEQ ID NO 6
<211> LENGTH: 108
<212> TYPE: DNA
<213> ORGANISM: Artificial Sequence
<220> FEATURE:
<223> OTHER INFORMATION: Chemically synthesized

<400> SEQUENCE: 6
atgtgcgacc tgccgcagac ccactccctg ggtaaccgtc gtgctctgat cctgctggct      60
cagatgcgtc gtatctcccc gttctcctgc ctgaaagacc gtcacgac                  108

<210> SEQ ID NO 7
<211> LENGTH: 108
<212> TYPE: DNA
<213> ORGANISM: Artificial Sequence
<220> FEATURE:
<223> OTHER INFORMATION: Chemically synthesized

<400> SEQUENCE: 7
ctgaaagacc gtcacgactt cggtttcccg caggaagaat cgacggtaa ccagttccag       60 aaagctcagg ctatctccgt tctgcacgaa atgatccagc agaccttc                  108

<210> SEQ ID NO 8
<211> LENGTH: 103
<212> TYPE: DNA
<213> ORGANISM: Artificial Sequence
<220> FEATURE:
<223> OTHER INFORMATION: Chemically synthesized

<400> SEQUENCE: 8
gctgctggta cagttcggtg tagaattttt ccagcaggga ttcgtcccaa gcagcggagg      60
```

```
agtctttggt ggagaacagg ttgaaggtct gctggatcat ttc                         103
```

<210> SEQ ID NO 9
<211> LENGTH: 103
<212> TYPE: DNA
<213> ORGANISM: Artificial Sequence
<220> FEATURE:
<223> OTHER INFORMATION: Chemically synthesized

<400> SEQUENCE: 9

```
atccctgctg gaaaaattct acaccgaact gtaccagcag ctgaacgacc tggaagcttg       60
cgttatccag gaagttggtg ttgaagaaac cccgctgatg aac                         103
```

<210> SEQ ID NO 10
<211> LENGTH: 106
<212> TYPE: DNA
<213> ORGANISM: Artificial Sequence
<220> FEATURE:
<223> OTHER INFORMATION: Chemically synthesized

<400> SEQUENCE: 10

```
gaagaaaccc cgctgatgaa cgttgactcc atcctggctg ttaaaaaata cttccagcgt       60
atcaccctgt acctgaccga aaaaaaatac tccccgtgcg cttggg                     106
```

<210> SEQ ID NO 11
<211> LENGTH: 112
<212> TYPE: DNA
<213> ORGANISM: Artificial Sequence
<220> FEATURE:
<223> OTHER INFORMATION: Chemically synthesized

<400> SEQUENCE: 11

```
ttattcttta cgacgcagac gttcctgcag gttggtggac agggagaagg aacgcatgat       60
ttcagcacga caacttccc aagcgcacgg ggagtatttt ttttcggtca gg               112
```

<210> SEQ ID NO 12
<211> LENGTH: 31
<212> TYPE: DNA
<213> ORGANISM: Artificial Sequence
<220> FEATURE:
<223> OTHER INFORMATION: Chemically synthesized

<400> SEQUENCE: 12

```
atcggccata tgtgcgacct gccgcagacc c                                      31
```

<210> SEQ ID NO 13
<211> LENGTH: 40
<212> TYPE: DNA
<213> ORGANISM: Artificial Sequence
<220> FEATURE:
<223> OTHER INFORMATION: Chemically synthesized

<400> SEQUENCE: 13

```
actgccaggc tgcagttatt ctttacgacg cagacgttcc                             40
```

<210> SEQ ID NO 14
<211> LENGTH: 15
<212> TYPE: PRT
<213> ORGANISM: Artificial Sequence
<220> FEATURE:
<223> OTHER INFORMATION: Synthetic Construct

<400> SEQUENCE: 14

-continued

```
Cys Asp Leu Pro Gln Thr His Ser Leu Gly Asn Arg Arg Ala Leu
1               5                   10                  15
```

<210> SEQ ID NO 15
<211> LENGTH: 4
<212> TYPE: PRT
<213> ORGANISM: Artificial Sequence
<220> FEATURE:
<223> OTHER INFORMATION: Synthetic Construct

<400> SEQUENCE: 15

```
Arg Arg Lys Glu
1
```